(12) United States Patent
Horwitz et al.

(10) Patent No.: US 10,626,418 B2
(45) Date of Patent: Apr. 21, 2020

(54) METHODS FOR GENOMIC INTEGRATION

(71) Applicant: Amyris, Inc., Emeryville, CA (US)

(72) Inventors: Andrew Horwitz, Emeryville, CA (US); Kristy Michelle Hawkins, Emeryville, CA (US); Max Schubert, Emeryville, CA (US); Wayne Szeto, Emeryville, CA (US)

(73) Assignee: AMYRIS, INC., Emeryville, CA (US)

( * ) Notice: Subject to any disclaimer, the term of this patent is extended or adjusted under 35 U.S.C. 154(b) by 0 days.

(21) Appl. No.: 16/044,381

(22) Filed: Jul. 24, 2018

(65) Prior Publication Data

US 2019/0017074 A1 Jan. 17, 2019

Related U.S. Application Data

(63) Continuation of application No. 15/261,727, filed on Sep. 9, 2016, now Pat. No. 10,041,092, which is a continuation of application No. 14/577,997, filed on Dec. 19, 2014, now Pat. No. 9,476,065.

(60) Provisional application No. 61/937,444, filed on Feb. 7, 2014, provisional application No. 61/918,625, filed on Dec. 19, 2013.

(51) Int. Cl.
*C12N 9/22* (2006.01)
*C12N 15/90* (2006.01)
*C12Q 1/6897* (2018.01)
*C12N 15/11* (2006.01)

(52) U.S. Cl.
CPC .......... *C12N 15/907* (2013.01); *C12N 15/111* (2013.01); *C12N 15/902* (2013.01); *C12Q 1/6897* (2013.01); *C12N 2310/20* (2017.05)

(58) Field of Classification Search
CPC ................................ C12N 9/22; C12N 15/111
See application file for complete search history.

(56) References Cited

U.S. PATENT DOCUMENTS

| 8,685,737 B2 | 4/2014 | Serber et al. |
| 2013/0171657 A1 | 7/2013 | Doyon et al. |

FOREIGN PATENT DOCUMENTS

| WO | WO 2011/002503 A1 | 1/2011 |
| WO | WO 2013/098244 A1 | 7/2013 |
| WO | WO 2013/141680 A1 | 9/2013 |
| WO | WO 2013/142578 A1 | 9/2013 |

OTHER PUBLICATIONS

Ma et al., "Plasmid construction by homologous recombination in yeast", Gene, vol. 58, 1987, pp. 201-216.
Adar et al. "Repair of gaps opposite lesions by homologous recombination in mammalian cells," Nucleic Acids Research, 2009, vol. 37, No. 17, pp. 5737-5748.
Belhaj et al. "Plant genome editing made easy: targeted mutagenesis in model and crop plants using the CRISPR/Cas system," Plant Methods, 2013, vol. 9, No. 39, pp. 1-10.
Beloglazova et al. "Structure and activity of the Cas3 HD nuclease M J0384, an effector enzyme e of the CRISPR interference," The EMBO Journal, 2011, vol. 30, No. 22, pp. 4616-4627.
Bessa et al. "Improved gap repair cloning in yeast: treatment of the gapped vector with *Taq* DNA polymerase avoids vector self-ligation," Yeast, 2012, vol. 29, pp. 419-423.
Bhaya et al. "CRISPR-Cas Systems in Bacteria and Archaea: Versatile Small RNAs for Adaptive Defense and Regulation," Annu. Rev. Genet., 2011, vol. 45, pp. 273-297.
Brouns et al. "Small CRISPR RNAs Guide Antiviral Defense in Prokaryotes," Science, 2008, vol. 321, pp. 960-964.
Carreira-Rosario et al. "Recombineering Homologous Recombination Constructs in *Drosophila*,"J. Vis. Exp., 2013, vol. 77, DOI: 10.3791/50346, pp. 1-10.
Chang et al. "Genome editing with RNA-guided Cas9 nuclease in Zebrafish embryos," Cell Research, 2013, vol. 23, pp. 465-472.
Chen et al. "High-frequency genome editing using ssDNA oligonucleotides with zinc-finger nucleases," Nat Methods, 2013, vol. 8, No. 9, pp. 753-755.
Cho et al. "Targeted genome engineering in human cells with the Cas9 RNA-guided endonuclease," Nature Biotechnology, 2013, vol. 31, No. 3, pp. 230-232.
Cong et al. "Multiplex Genome Engineering Using CRISPR/Cas Systems," Science, 2013, vol. 339, pp. 819-823.
Datta et al. "A set of recombineering plasmids for gram-negative bacteria," Gene, 2006, vol. 379, pp. 109-115.
Deltcheva et al. "CRISPR RNA maturation by trans-encoded small RNA and host factor RNase III," Nature, 2011, vol. 471, No. 7340, pp. 602-607.
DiCarlo et al. "Genome engineering in *Saccharomyces* cerevisiae using CRISPR-Cas systems," Nucleic Acids Research, 2013, doi:10.1093/nar/gkt135, pp. 1-8.
Fu et al. "High frequency off-target mutagenesis induced by CRISPR-Cas nuclease in human cells," Nat Biotechnol., 2013, vol. 31, No. 9, pp. 822-826.
Gaj et al. "ZFN TALEN and CRISPR/Cas-based methods for genome engineering," Trends in Biotechnology, 2013, vol. 31, No. 7, pp. 397-405.
Gasiunas et al. "Cas9-crRNA ribonucleoprotein complex mediates specific DNA cleavage for adaptive immunity in bacteria," PNAS, 2012, pp. E2579-E2586.

(Continued)

*Primary Examiner* — Karen Cochrane Carlson
(74) *Attorney, Agent, or Firm* — Squire Patton Boggs (US) LLP

(57) ABSTRACT

Provided herein are methods of integrating one or more exogenous nucleic acids into one or more selected target sites of a host cell genome. In certain embodiments, the methods comprise contacting the host cell genome with one or more integration polynucleotides comprising an exogenous nucleic acid to be integrated into a genomic target site, a nuclease capable of causing a break at the genomic target site, and a linear nucleic acid capable of homologous recombination with itself or with one or more additional linear nucleic acids contacted with the population of cells, whereupon said homologous recombination results in formation of a circular extrachromosomal nucleic acid comprising a coding sequence for a selectable marker. In some embodiments, the methods further comprise selecting a host cell that expresses the selectable marker.

Figure 1:
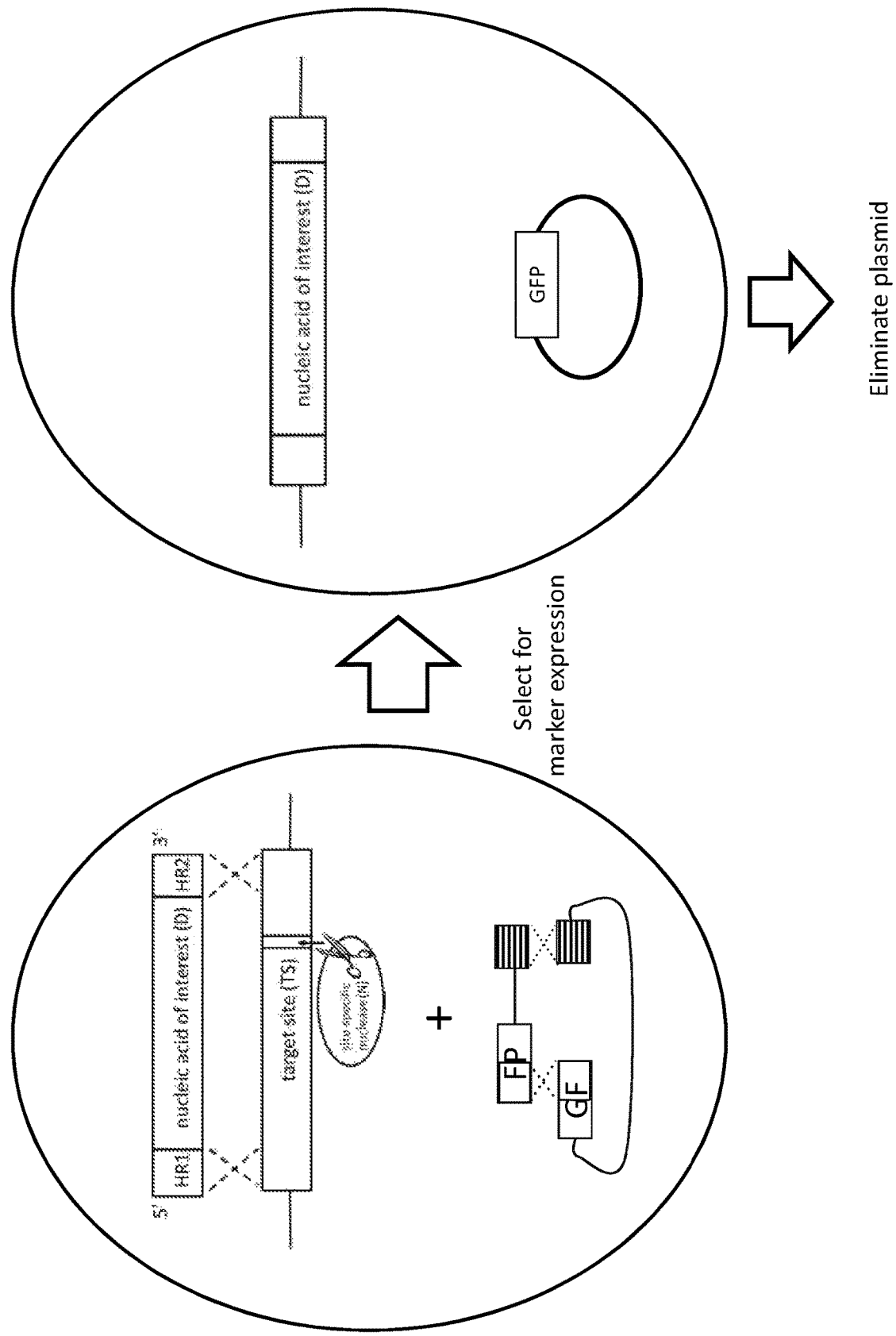

17 Claims, 34 Drawing Sheets
Specification includes a Sequence Listing.

(56) References Cited

OTHER PUBLICATIONS

Gratz et al. "Genome Engineering of Drosophila with the CRISPR RNA-Guided Cas9 Nuclease," Genetics, 2013, vol. 194, pp. 1029-1035.
Hale et al. "Essential features and rational design of CRISPR RNAs that function with the Cas RAMP module complex to cleave RNAs," Mol Cell, 2012, vol. 45, No. 43, pp. 292-302.
Hasty et al. "The Length of Homology Required for Gene Targeting in Embryonic Stem Cells," Molecular and Cellular Biology, 1991, vol. 11, No. 11, pp. 5586-5591.
Horvath et al. "CRISPR/Cas, the Immune System of Bacteria and Archaea," Science, 2010, vol. 327, pp. 167-170.
Horvath et al. "RNA-guided genome editing à la carte,"Cell Research, 2013, vol. 23, pp. 733-734.
Hwang et al. "Efficient in Vivo Genome Editing Using RNA-Guided Nucleases," Nat Biotechnol., 2013, vol. 31, No. 3, pp. 227-229.
International Search Report for related PCT Application No. PCT/US2014/071693, dated May 7, 2015, 6 pages.
Jasin et al. "Genetic manipulation of genomes with rare-cutting endonucleases," TIG Jun. 1996, vol. 12, No. 6, pp. 224-228.
Jiang et al. "CRISPR-assisted editing of bacterial genomes," Nat Biotechnol., 2013, vol. 31, No. 3, pp. 233-239.
Jiang et al. "Demonstration of CRISPR/Cas9/sgRNA-mediated targeted gene modification in *Arabidopsis*, tobacco, sorghum and rice," Nucleic Acids Research, 2013, vol. 41, No. 20, e188, pp. 1-12.
Jinek et al. "A Programmable Dual-RNA-Guided DNA Endonuclease in Adaptive Bacterial Immunity," Science, 2012, vol. 337, pp. 816-821.
Jinek et al. "RNA-programmed genome editing in human cells," eLife, 2013, DOI: 10.7554/eLife.00471, pp. 1-9.
Kass et al. "Double-strand break repair by homologous recombination in primary mouse somatic cells requires BRCA1 but no the ATM kinase," PNAS, 2013, vol. 110, No. 14, pp. 5564-5569.
Li et al. "Mutiplex and homologous recombination-mediated plant genome editing via guide RNA/Cas9," Nat Biotechnol., 2013, vol. 31. No. 8, pp. 688-691.
Makarova et al. "Evolution and classification of the CRISPR-Cas systems," Nat Rev. Microbiol., 2011, vol. 9, No. 6, vol. 467-477.
Mali et al. "RNA-Guided Human Genome Engineering via Cas9," Science, 2013, vol. 339, No. 6121, pp. 823-826.
Marraffini et al."CRISPR Interference Limits Horizontal Gene Transfer in *Staphylococci* by Targeting DNA," Science, 2008, vol. 322, No. 5909, pp. 1843-1845.
Matsuo et al. "Simple and Effective Gap-Repair Cloning Using Short Tracts of Flanking Homology in Fission Yeast," Bioscience, Biotechnology, and Biochemistry, 2010, vol. 74, No. 3, pp. 685-689.
Moehle et al. "Targeted gene addition into a specified location in the human genome using designed zinc finger nucleases," PNAS, vol. 104, No. 9, pp. 3055-3060.
Orr-Weaver et al. "[14] Genetic Applications of Yeast Transformation with Linear and Gapped Plasmids," Methods in Enzymology, 1983, vol. 101, pp. 228-245.
Pride et al. "Analysis of *Streptococcal* CRISPRs from human saliva reveals substantial sequence diversity within and between subjects over time," Genome Research, 2011, vol. 21, pp. 126-136.
Qi, et al. "Repurposing CRISPR as an RNA-Guided Platform for Sequence-Specific Control of Gene Expression," Cell, 2013, vol. 152, No. 5, pp. 1173-1183.
Ran et al. "Genome engineering using the CRISPR-Cas9 system," Nature Protocols, 2013, vol. 8, No. 11, pp. 2281-2308.
Rho et al. "Diverse CRISPRs Evolving in Human Microbiomes," PLoS Genetics, 2012, vol. 8, No. 6, e1002441, pp. 1-12.
Sinkunas et al. "Cas3 is a single-stranded DNA nuclease and ATP-dependent helicase in the CRISPR/Cas immune system," The EMBO Journal, 2011, vol. 30, pp. 1335-1342.
Terns et al. "CRISPR-Based Adaptive Immune Systems," Curr Opin Microbiol, 2011, vol. 14, No. 3, pp. 321-327.
Urnov et al. "Highly efficient endogenous human gene correction using designed zinc-finger nucleases," Nature, 2005, vol. 435, No. 2, pp. 646-651.
Wang et al. "One-Step Generation of Mice Carrying Mutations in Multiple Genes by CRISPR/Cas-Mediated Genome Engineering," Cell, 2013. vol. 153, No. 4, pp. 910-918.
Wiedenheft et al. "RNA-guided genetic silencing systems in bacteria and archaea," Nature, 2012, vol. 482, pp. 331-338.
Written Opinion of the International Searching Authority for related PCT Application No. PCT/US2014/071693, dated May 7, 2015, 7 pages.
Zhang et al. "Structure and mechanism of the CMR complex for CRISPR-mediated antiviral immunity," Mol. Cell., 2012, vol. 45, No. 3, pp. 303-313.

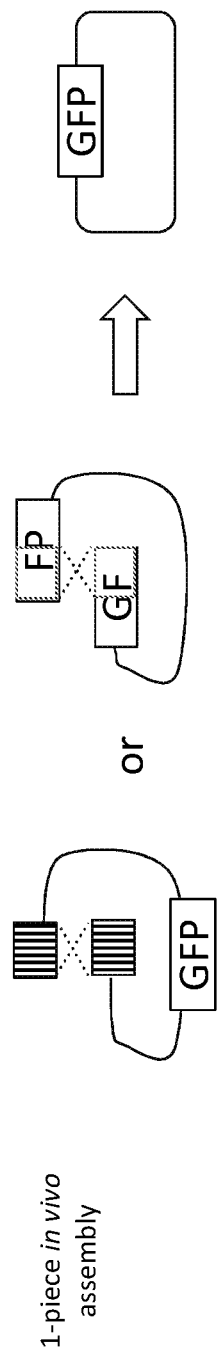
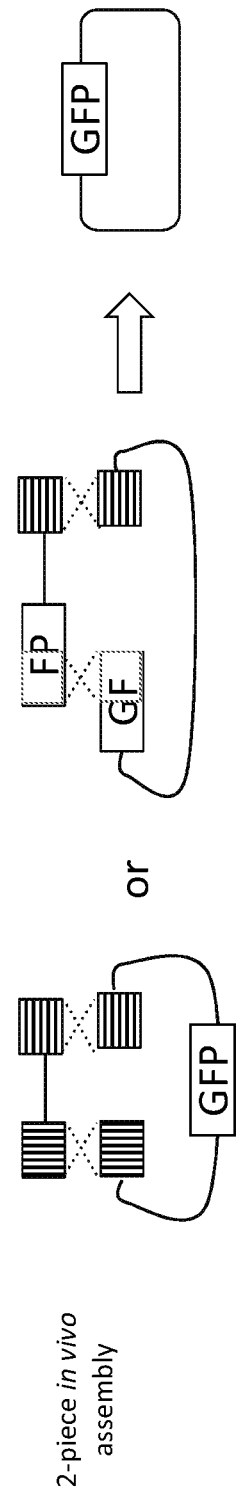
FIGURE 4A
FIGURE 4B 1-piece in vivo assembly 2-piece in vivo assembly

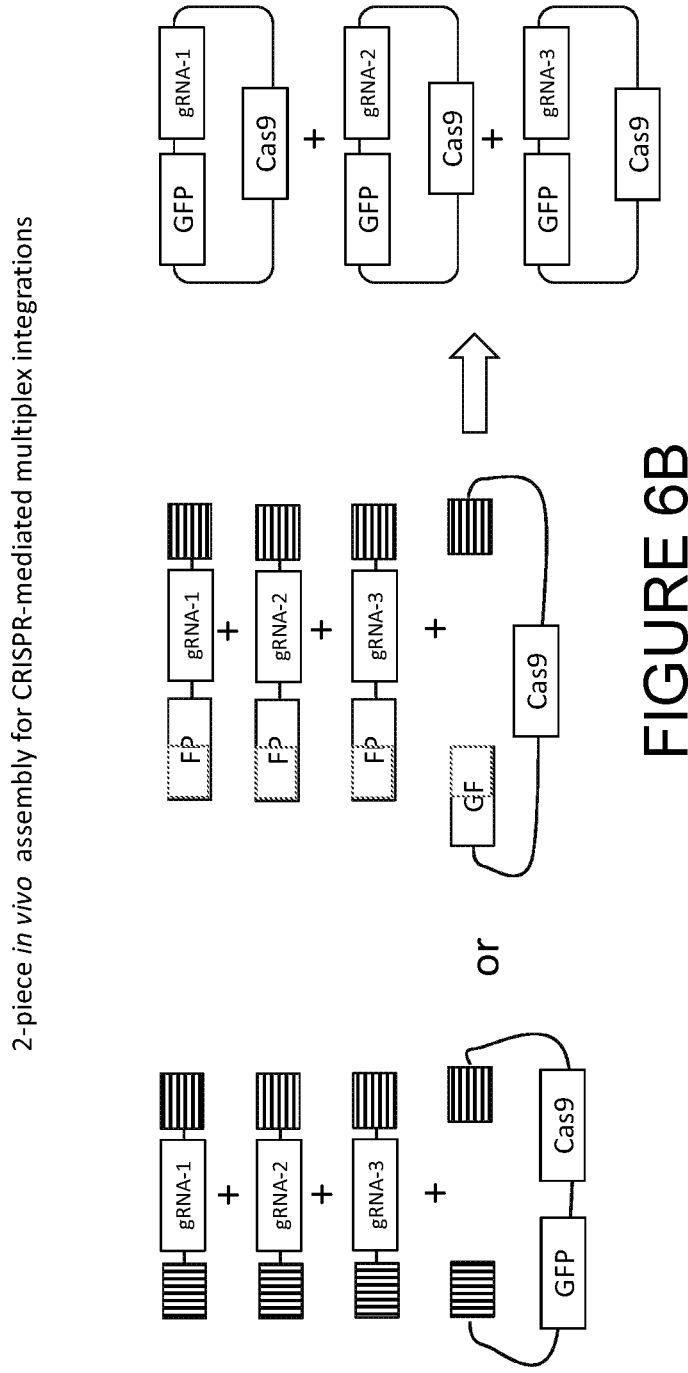

|  |  | 1st Expt | | 2nd Expt | | 3rd Expt | | |
| --- | --- | --- | --- | --- | --- | --- | --- | --- |
| gRNA | marker vector | #positive / #screened | fold increase | #positive / #screened | fold increase | #positive / #screened | fold increase | avg. fold increase |
| RHR2 | Closed | 34.80% |  | 4.30% |  | 26.10% |  |  |
| RHR2 | Gap repair vector | 34.80% | 0 | 30.40% | 7.07 | 65.20% | 2.50 | 3.19 |
| HO | Closed | 13.00% |  | 4.30% |  | 17.40% |  |  |
| HO | Gap repair vector | 43.50% | 3.35 | 34.80% | 8.09 | 43.50% | 2.50 | 4.65 |
| ADH5 | Closed | 34.80% |  | 17.40% |  | 8.70% |  |  |
| ADH5 | Gap repair vector | 60.90% | 1.75 | 47.80% | 2.75 | 56.50% | 6.49 | 3.66 |

FIGURE 10

METHODS FOR GENOMIC INTEGRATION

CROSS-REFERENCE TO RELATED APPLICATIONS

This application is a continuation of U.S. application Ser. No. 15/261,727, filed Sep. 9, 2016, which is a continuation of U.S. application Ser. No. 14/577,997, filed Dec. 19, 2014, and now issued as U.S. Pat. No. 9,476,065, which claims the benefit of U.S. Provisional Application No. 61/918,625, filed Dec. 19, 2013 and U.S. Provisional Application No. 61/937,444, filed Feb. 7, 2014. Each of the foregoing applications is incorporated by reference in its entirety.

GOVERNMENT LICENSE RIGHTS

This invention was made with Government support under Agreement HR0011-12-3-0006, awarded by the Defense Advanced Research Projects Agency (DARPA). The Government has certain rights in the invention.

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "Sequence_Listing.txt," created Aug. 19, 2016, and is 161 KB in size. The sequence listing contained in this .txt file is part of the specification and is incorporated herein by reference in its entirety.

1. FIELD OF THE INVENTION

The methods and compositions provided herein generally relate to the fields of molecular biology and genetic engineering.

2. BACKGROUND

Genetic engineering techniques to introduce targeted modifications into a host cell genome find use in a variety of fields. Fundamentally, the determination of how genotype influences phenotype relies on the ability to introduce targeted insertions or deletions to impair or abolish native gene function. In the field of synthetic biology, the fabrication of genetically modified microbes capable of producing compounds of interest requires the insertion of customized DNA sequences into a chromosome of the host cell; industrial scale production generally requires the introduction of dozens of genes, e.g., whole biosynthetic pathways, into a single host genome. In a therapeutic context, the ability to introduce precise genome modifications has enormous potential to address diseases resulting from single-gene defects, e.g., X-linked severe combined immune deficiency (SCID), hemophilia B, beta-thalassemia, cystic fibrosis, muscular dystrophy and sickle-cell disease.

Recent advances in genome engineering have enabled the manipulation and/or introduction of virtually any gene across a diverse range of cell types and organisms. In particular, the advent of site-specific designer nucleases has enabled site-specific genetic modifications by introducing targeted breaks into a host cell genome, i.e., genome editing. These nucleases include zinc finger nucleases (ZFNs), transcription activator-like effector nucleases (TALENs), and clustered regulatory interspaced short palindromic repeats CRISPR/Cas (CRISPR-associated)-based RNA-guided endonucleases. ZFNs have been utilized, inter alia, to modify target loci in crops (Wright et al., *Plant J* 44:693-705 (2005)), to improve mammalian cell culture lines expressing therapeutic antibodies (Malphettes et al., *Biotechnol Bioeng* 106(5):774-783 (2010)), and to edit the human genome to evoke resistance to HIV (Urnov et al., *Nat Rev Genet* 11(9):636-646 (2010)). Similarly, TALENs have been utilized to modify a variety of genomes, including those of crop plants (Li, et al., *Nat. Biotechnol.* 30: 390-392 (2012)), human, cattle, and mouse (Xu et al., *Molecular Therapy—Nucleic Acids* 2, e112 (2013)). More recently, CRISPRs have been successfully utilized to edit the genomes of bacteria (e.g., Jiang et al., *Nature Biotechnology* 31(3):233-239 (2013); Qi et al., *Cell,* 5, 1173-1183 (2013)); yeast (e.g., DiCarlo et al., *Nucleic Acids Res.,* 7, 4336-4343 (2013)); zebrafish (e.g. Hwang et al., *Nat. Biotechnol.,* 3, 227-229 (2013)); fruit flies (e.g., Gratz et al., *Genetics,* 194, 1029-1035 (2013)); human cells (e.g., Cong et al., *Science* 6121, 819-823, (2013); Mali et al., *Science,* 6121, 823-826 (2013); Cho et al., *Nat. Biotechnol.,* 3, 230-232 (2013)); and plants (e.g., Jiang et al., *Nucleic Acids Research* 41(20):e188 (2013)); Belhaj et al., *Plant Methods* 9(39) (2013)).

Site-specific nucleases induce breaks in chromosomal DNA that stimulate the host cell's cellular DNA repair mechanisms, including non-homologous end joining (NHEJ), single-strand annealing (SSA), and homology-directed repair (HDR). NHEJ-mediated repair of a nuclease-induced double-strand break (DSB) leads to the introduction of small deletions or insertions at the targeted site, leading to impairment or abolishment of gene function, e.g., via frameshift mutations. The broken ends of the same molecule are rejoined by a multi-step enzymatic process that does not involve another DNA molecule. NHEJ is error prone and imprecise, producing mutant alleles with different and unpredictable insertions and deletions of variable size at the break-site during the repair. Similarly, SSA occurs when complementary strands from sequence repeats flanking the DSB anneal to each other, resulting in repair of the DSB but deletion of the intervening sequence. In contrast, HDR typically leads to an accurately restored molecule, as it relies on a separate undamaged molecule with homologous sequence to help repair the break. There are two major sources of homologous donor sequence native to the cell: the homologous chromosome, available throughout the cell cycle, and the sister chromatid of the broken molecule (which is only available after the DNA is replicated). However, genome engineering techniques routinely introduce exogenous donor DNAs that comprise regions homologous with the target site of the DSB, and can recombine with the target site. By including desired modifications to the target sequence within the exogenous donor, these modifications can be integrated into and replace the original target sequence via HDR.

Upon nuclease-induced breakage of DNA, the host cell's choice of repair pathways depends on a number of factors, and the outcome can dictate the precision of a desired genomic modification. Such factors include the DNA damage signaling pathways of the host cell, the nature of the break, chromatin remodeling, transcription of specific repair proteins, and cyclin-dependent kinase activities present in later phases of the cell cycle. See, e.g., Beucher et al., *EMBO J* 28:3413-27(2009); Sorensen et al., *Nat Cell Biol* 7:195-201 (2005); Jazayeri et al., *Nat Cell Biol* 8:37-45 (2006); Huertas et al., Nature 455:689-92 (2008); Moyal et al., *Mol Cell* 41:529-42 (2011); and Chemikova et al., *Radiat Res* 174:558-65 (2010). If a donor DNA with strong homology to the cleaved DNA is present, the chances of integration of the donor by homologous recombination increase significantly. See, e.g., Moehle et al., *Proc. Natl Acad. Sci. USA,* 9:3055-3060 (2007); Chen et al., *Nat. Methods,* 9, 753-755 (2011). However, the overall frequency at which a homologous donor DNA is integrated via HDR into a cleaved target site, as opposed to non-integrative repair of the target site via NHEJ, can still be quite low. Recent studies suggest that HDR-mediated editing is generally a low efficiency event, and the less precise NHEJ can predominate as the mechanism of repair for DSBs.

For example, Mali et al. (*Science* 339:823-826 (2013)) attempted gene modification in human K562 cells using CRISPR (guide RNA and Cas9 endonuclease) and a concurrently supplied single-stranded donor DNA, and observed an HDR-mediated gene modification at the AAVS1 locus at a frequency of 2.0%, whereas NHEJ-mediated targeted mutagenesis at the same locus was observed at a frequency of 38%. Li et al. (*Nat Biotechnol.* (8):688-91 (2013)) attempted gene replacement in the plant *Nicotiana benthamiana* using CRISPR (guide RNA and Cas9 endonuclease) and a concurrently supplied double-stranded donor DNA, and observed an HDR-mediated gene replacement at a frequency of 9.0%, whereas NHEJ-mediated targeted mutagenesis was observed at a frequency of 14.2%. Kass et al. (*Proc Natl Acad Sci USA.* 110(14): 5564-5569 (2013)) studied HDR in primary normal somatic cell types derived from diverse lineages, and observed that mouse embryonic and adult fibroblasts as well as cells derived from mammary epithelium, ovary, and neonatal brain underwent HDR at I-SceI endonuclease-induced DSBs at frequencies of approximately 1% (0.65-1.7%). Kass and others have reported higher HDR activity when cells are in S and G2 phases of the cell cycle. Li et al. (*Nat Biotechnol.* (8):688-91 (2013)) tested the possibility of enhancing HDR in *Nicotiana benthamiana* by triggering ectopic cell division, via co-expression of *Arabidopsis* CYCD3 (Cyclin D-Type 3), a master activator of the cell cycle; however, this hardly promoted the rate of HDR (up to 11.1% from 9% minus CYCD3). Strategies to improve HDR rates have also included knocking out the antagonistic NHEJ repair mechanism. For example, Qi et al. (*Genome Res* 23:547-554 (2013)) reported an increase of 5-16 fold in HDR-mediated gene targeting in *Arabidopsis* for the ku70 mutant and 3-4 fold for the lig4 mutant. However, the overall rates were observed to be no higher than ~5%, with most less than 1%. Furthermore, once the desired gene-targeting event was produced, the ku70 or lig4 mutations had to be crossed out of the mutant plants.

Given the relatively low rate of HDR-mediated integration in most cell types, insertion of exogenous DNA into the chromosome typically requires the concomitant integration of a selectable marker, which enables enrichment for transformed cells that have undergone the desired integration event. However, this introduces extraneous sequences into the genome which may not be compatible with downstream applications, and prolonged expression of the marker may also have deleterious effects. For example, integration of the neomycin resistance gene into human cell genomes, followed by extended culturing times in G418, has been reported to cause changes to the cell's characteristics, and expression of enhanced green fluorescent protein (EGFP) and other fluorescent proteins has been reported to cause immunogenicity and toxicity. See, e.g., Barese et al., *Human Gene Therapy* 22:659-668 (2011); Morris et al., *Blood* 103:492-499 (2004); and Hanazono et al., *Human Gene Therapy* 8:1313-1319 (1997). Additionally, the integration of selectable-marker genes in genetically modified (GM) plants has raised concerns of horizontal transfer to other organisms; in the case of antibiotic resistance markers, there is particular concern that these markers could lead to an increase in antibiotic resistant bacterial strains. A similar concern relates to the integration of herbicide-resistance markers and the possible creation of new aggressive weeds. At a minimum, removal of integrated marker sequences at later stages is time and labor intensive. This is particularly problematic where only a limited cache of selectable markers are available in a given host, and markers must be recycled to enable additional engineering steps. Thus, certain applications warrant introducing only the minimum exogenous sequences needed to effect a desired phenotype, e.g., for safety and/or regulatory compliance, and may ultimately require the avoidance of marker integration altogether.

Thus, there exists a need for methods and compositions that improve the efficiency and/or selection of HDR-mediated integration of one or more exogenous nucleic acids into a host cell genome. Moreover, there exists a need for genome engineering strategies that do not require co-integration of coding sequences for selectable markers. These and other needs are met by the compositions and methods provided herein.

3. SUMMARY

The methods and compositions provided herein relate to methods for selecting a homologous recombination (HR)-competent host cell. Without being bound by theory of operation, it is believed that HR-competence among a cell population can be selected for by selecting for a host cell that can homologously recombine one or more linear fragment(s), introduced into the host cell, to form a circular vector expressing a selectable marker. Here, this feature is exploited to enhance the identification of host cells that have site-specifically integrated, via HR, of one or more exogenous nucleic acids into the host cell's genome. In some embodiments, site-specific integration is enhanced by contacting the host cell genome with a site-specific nuclease that is capable of creating a break at the intended site of integration. Thus, by introducing to a host cell:

(i) one or more exogenous nucleic acids having homologous regions to one or more target sites of the host cell genome;

(ii) one or more nucleases capable of selectively creating a break at the intended target site(s); and (iii) a linear nucleic acid that can homologously recombine by itself, or with one or more additional linear DNA fragments introduced into the host cell, to form a circular, functional expression vector from which the selectable marker is expressed, and selecting for expression of the selectable marker, co-selection of cells that have integrated the one or more exogenous nucleic acids into their respective target site(s) is also achieved. The increased frequency of recovering host cells that have performed the desired integrations provided by the methods and compositions provided herein enables genetic engineering of otherwise difficult to engineer or intractable host cells, and improves the efficiency of higher order engineering designs, such as multiplex integrations.

Thus, in one aspect, provided herein is a method for integrating one or more exogenous nucleic acids into one or more target sites of a host cell genome, the method comprising contacting one or more host cells with one or more exogenous nucleic acids (ES) capable of recombining, via homologous recombination, at one or more target sites (TS)

of the host cell genome; and one or more nucleases (N) capable of generating a break at each TS; and selecting a host cell competent for homologous recombination. In some embodiments, the selecting comprises selecting a host cell in which an exogenous nucleic acid has homologously recombined. In some embodiments, the nucleic acid that has homologously recombined is a linear nucleic acid capable of homologous recombination with itself or with one or more additional linear nucleic acids. In some embodiments, the linear nucleic acid(s) form a circular nucleic acid upon homologous recombination. In some embodiments, the nucleic acid that has homologously recombined encodes a selectable marker. In some embodiments homologous recombination of the linear nucleic acid to form a circular nucleic acid forms a coding sequence for the selectable marker.

In another aspect, provided herein a method of selecting a host cell competent for homologous recombination, comprising:

(a) contacting one or more host cells with a linear nucleic acid capable of homologous recombination with itself or with one or more additional linear nucleic acids contacted with the population of cells, whereupon said homologous recombination results in formation of a circular extrachromosomal nucleic acid comprising a coding sequence for a selectable marker; and (b) selecting a host cell that expresses the selectable marker.

In another aspect, provided herein is a method for integrating an exogenous nucleic acid into a target site of a host cell genome, the method comprising:

(a) contacting one or more host cells with:
   (i) an exogenous nucleic acid (ES) capable of recombining, via homologous recombination, at the target site (TS) of the host cell genome;
   (ii) a nuclease (N) capable of generating a break at TS; and
   (iii) a linear nucleic acid capable of homologous recombination with itself or with one or more additional linear nucleic acids contacted with the host cell, whereupon said homologous recombination results in formation of a circular extrachromosomal nucleic acid comprising a coding sequence for a selectable marker;
and (b) selecting a host cell that expresses the selectable marker.

In some embodiments, the linear nucleic acid comprises two internal homology regions that are capable of homologously recombining with each other, whereupon homologous recombination of the internal homology regions results in formation of the circular extrachromosomal nucleic acid expressing the selectable marker. In some embodiments, the linear nucleic acid comprises a homology region that is capable of recombining with a homology region of an additional linear nucleic acid contacted with the host cell, whereupon homologous recombination of the two linear nucleic acids results in formation of the circular extrachromosomal nucleic acid expressing the selectable marker. In some embodiments, the linear nucleic acid comprises a partial, interrupted and/or non-contiguous coding sequence for the selectable marker, wherein the selectable marker cannot be expressed from the linear nucleic acid, whereupon said formation of the circular extrachromosomal nucleic acid results in formation of a complete coding sequence of the selectable marker, wherein the selectable marker can be expressed from the circular extrachromosomal nucleic acid.

In some embodiments, the contacted host cell(s) are cultured for a period of at least about 12, 24, 36, 48, 72 or more than 72 hours prior to said selecting. In some embodiments, the contacted cells are cultured under culturing conditions that select against the survival of cells not expressing the selectable marker. In some embodiments, said selecting of step (b) comprises detecting the expression of the selectable marker via visual, colorimetric or fluorescent detection methods. In some embodiments, the method further comprises the step of recovering a host cell wherein ES has homologously recombined at TS. In some embodiments, said recovering does not require integration of a selectable marker into the host cell genome. In some embodiments, said recovering occurs at a frequency of at least about one every 10, 9, 8, 7, 6, 5, 4, 3, or 2 contacted host cells, or clonal populations thereof, screened. In some embodiments, the method further comprises the step of eliminating the circular extrachromasomal nucleic acid from the selected host cell.

In some embodiments, the method comprises integrating a plurality of (n) exogenous nucleic acids into a plurality of (n) target sites of the host cell genome, wherein n is at least two, wherein step (a) comprises contacting the host cell with said plurality of exogenous nucleic acids, wherein x is an integer that varies from 1 to n, and for each integer x, each exogenous nucleic acid $(ES)_x$ is capable of recombining, via homologous recombination, at a target site $(TS)_x$ selected from said plurality of (n) target sites of said host cell genome; and for each said target site $(TS)_x$, the cell is also contacted with a nuclease $(N)_x$ capable of generating a break at $(TS)_x$. In some embodiments, a single nuclease is capable of cleaving each $(TS)_x$. In some embodiments, n=3, 4, 5, 6, 7, 8, 9 or 10. In some embodiments, $(ES)_x$ comprises a first homology region $(HR1)_x$ and a second homology region $(HR2)_x$, wherein $(HR1)_x$ and $(HR2)_x$ are capable of recombining, via homologous recombination, with a third homology region $(HR3)_x$ and a fourth homology region $(HR4)_x$, respectively, wherein $(HR3)_x$ and $(HR4)_x$ are each at TS. In some embodiments, $(N)_x$ is capable of generating a single stranded break or a double stranded break at $(TS)_x$. In some embodiments, $(ES)_x$ further comprises a nucleic acid of interest $(D)_x$. In some embodiments, $(D)_x$ is selected from the group consisting of a selectable marker, a promoter, a nucleic acid sequence encoding an epitope tag, a gene of interest, a reporter gene, and a nucleic acid sequence encoding a termination codon. In some embodiments, $(ES)_x$ is linear.

In some embodiments, the circular extrachromasomal nucleic acid further comprises a coding sequence for the nuclease. In some embodiments, the nuclease is an RNA-guided DNA endonuclease. In some embodiments, the RNA-guided DNA endonuclease is a Cas9 endonuclease. In some embodiments, the circular extrachromosomal nucleic acid further comprises a sequence that encodes a crRNA activity and a tracrRNA activity that enables site-specific recognition and cleavage of TS by the RNA-guided DNA endonuclease. In some embodiments, the crRNA activity and the tracrRNA activity are expressed as a single contiguous RNA molecule.

In some embodiments, the nuclease is selected from the group consisting of an endonuclease, a zinc finger nuclease, a TAL-effector DNA binding domain-nuclease fusion protein (TALEN), a transposase, and a site-specific recombinase. In some embodiments, the zinc finger nuclease is a fusion protein comprising the cleavage domain of a TypeIIS restriction endonuclease fused to an engineered zinc finger binding domain. In some embodiments, the TypeIIS restriction endonuclease is selected from the group consisting of HO endonuclease and Fok I endonuclease. In some embodiments, the zinc finger binding domain comprises 3, 5 or 6 zinc fingers.

In some embodiments, the endonuclease is a homing endonuclease selected from the group consisting of: an LAGLIDADG (SEQ ID NO: 1) homing endonuclease, an HNH homing endonuclease, a His-Cys box homing endonuclease, a GIY-YIG (SEQ ID NO:2) homing endonuclease, and a cyanobacterial homing endonuclease. In some embodiments, the endonuclease is selected from the group consisting of: H-DreI, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, Pi-PspI, F-SceI, F-SceII, F-SuvI, F-CphI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIIP, I-SquIP, I-Ssp68031, I-SthPhiJP, I-SthPhiST3P, I-SthPhiSTe3bP, I-TdeIP, I-TevI, I-TevII, I-TevIII, i-UarAP, i-UarHGPAIP, I-UarHGPA13P, I-VinIP, I-ZbiIP, PI-MgaI, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, or PI-TliII. In some embodiments, the endonuclease is modified to specifically bind an endogenous genomic sequence, wherein the modified endonuclease no longer binds to its wild type endonuclease recognition sequence. In some embodiments, the modified endonuclease is derived from a homing endonuclease selected from the group consisting of: an LAGLIDADG (SEQ ID NO: 1) homing endonuclease, an HNH homing endonuclease, a His-Cys box homing endonuclease, a GIY-YIG (SEQ ID NO:2) homing endonuclease, and a cyanobacterial homing endonuclease. In some embodiments, the modified endonuclease is derived from an endonuclease selected from the group consisting of: H-DreI, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, Pi-PspI, F-SceI, F-SceII, F-SuvI, F-CphI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIIP, I-SquIP, I-Ssp68031, I-SthPhiJP, I-SthPhiST3P, I-SthPhiSTe3bP, I-TdeIP, I-TevI, I-TevII, I-TevIII, i-UarAP, i-UarHGPAIP, I-UarHGPA13P, I-VinIP, I-ZbiIP, PI-MgaI, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, or PI-TliII.

In some embodiments, the host cell is a prokaryotic cell. In some embodiments, the host cell is a eukaryotic cell. In some embodiments, the host cell is selected from the group consisting of a fungal cell, a bacterial cell, a plant cell, an insect cell, an avian cell, a fish cell and a mammalian cell. In some embodiments, the host cell is a mammalian cell selected from the group consisting of a rodent cell, a primate cell and a human cell. In some embodiments, the host cell is a yeast cell. In some embodiments, the yeast is *Saccharomyces cerevisiae*.

In another aspect, provided herein is a host cell comprising: an exogenous nucleic acid (ES) capable of recombining, via homologous recombination, at a target site (TS) of the host cell genome; a nuclease (N) capable of generating a break at TS; and a linear nucleic acid capable of homologous recombination with itself or with one or more additional linear nucleic acid within the host cell, whereupon said homologous recombination results in formation of a circular extrachromosomal nucleic acid comprising a coding sequence for a selectable marker. In some embodiments, the linear nucleic acid comprises two internal homology regions that are capable of homologously recombining with each other, whereupon homologous recombination of the internal homology regions results in formation of the circular extrachromosomal nucleic acid expressing the selectable marker. In some embodiments, the linear nucleic acid comprises a homology region that is capable of recombining with a homology region of an additional linear nucleic acid within the host cell, whereupon homologous recombination of the two linear nucleic acids results in formation of the circular extrachromosomal nucleic acid expressing the selectable marker. In some embodiments, the linear nucleic acid comprises a partial, interrupted and/or non-contiguous coding sequence for the selectable marker, wherein the selectable marker cannot be expressed from the linear nucleic acid, whereupon said formation of the circular extrachromosomal nucleic acid results in formation of a complete coding sequence of the selectable marker, wherein the selectable marker can be expressed from the circular extrachromosomal nucleic acid.

In another aspect, provided herein is a composition comprising: a site-specific nuclease, or a nucleic acid comprising a coding sequence for a site-specific nuclease; and a linear nucleic acid comprising two internal homology regions that are capable of homologously recombining with each other in a host cell, whereupon homologous recombination of the internal homology regions results in formation of a circular nucleic acid comprising a coding sequence for a selectable marker. In some embodiments, the linear nucleic acid comprises a partial, interrupted and/or non-contiguous coding sequence for the selectable marker, wherein the selectable marker cannot be expressed from the linear nucleic acid in a host cell, whereupon said formation of the circular nucleic acid results in formation of a complete coding sequence of the selectable marker, wherein the selectable marker can be expressed from the circular nucleic acid in a host cell.

In another aspect, provided herein is a composition comprising a site-specific nuclease, or a nucleic acid comprising a coding sequence for a site-specific nuclease; and a first linear nucleic acid and one or more additional linear nucleic acids, wherein the first and second linear nucleic acids are capable of homologously recombining with each other in a host cell, whereupon said homologous recombination results in formation of a circular nucleic acid comprising a coding sequence for a selectable marker. In some embodiments, each linear nucleic acid comprises a partial, interrupted and/or non-contiguous coding sequence for the selectable marker, wherein the selectable marker cannot be expressed from each linear nucleic acid in a host cell, whereupon said formation of the circular nucleic acid results in formation of a complete coding sequence of the selectable marker, wherein the selectable marker can be expressed from the circular nucleic acid in a host cell. In some embodiments, the circular nucleic acid further comprises a coding sequence for a site-specific nuclease. In some embodiments, the site-specific nuclease is an RNA-guided DNA endonuclease. In some embodiments, the RNA-guided DNA endonuclease is a Cas9 endonuclease. In some embodiments, the compositions further comprise a ribonucleic acid comprising a crRNA activity and a ribonucleic acid comprising a tracrRNA activity; or a deoxyribonucleic acid that encodes a ribonucleic acid comprising a crRNA activity and a deoxyribonucleic acid that encodes a ribonucleic acid comprising a tracrRNA activity. In some embodiments, the circular nucleic acid further comprises a deoxyribonucleic acid that encodes a ribonucleic acid comprising a crRNA activity and a deoxyribonucleic acid that encodes a ribonucleic acid comprising a tracrRNA activity. In some embodiments, the deoxyribonucleic acid that encodes the crRNA activity and the tracrRNA activity encodes said activities on a single contiguous RNA molecule. In other embodiments, the site-specific nuclease is selected from the group consisting of an endonuclease, a zinc finger nuclease, a TAL-effector DNA binding domain-nuclease fusion protein (TALEN), a transposase, and a site-specific recombinase. Also provided herein is a host cell comprising any of the aforementioned compositions. Also provided herein is a cell culture composition comprising a cell culture medium and any of the host cells described herein. In some embodiments, the cell culture composition further comprises a compound that selects for expression of the selectable marker.

In another aspect, also provided herein is a linear nucleic acid comprising a first homology region (HR1) and a second homology region (HR2), wherein HR1 and HR2 are capable of recombining with each other via homologous recombination, whereupon homologous recombination of HR1 with HR2 results in formation of a circular nucleic acid comprising a coding sequence for a selectable marker. In some embodiments, HR1 comprises a first incomplete coding sequence of the selectable marker and HR2 comprises a second incomplete coding sequence of the selectable marker, and homologous recombination of HR1 with HR2 results in reconstitution of a complete coding sequence for the selectable marker. In some embodiments, the linear nucleic acid further comprises a coding sequence for a site-specific nuclease described herein.

Also provided herein are methods and compositions for genomic integration of one or more donor DNAs into a host cell genome mediated by site-specific RNA guided endonucleases (RGEN), for example, CRISPR/Cas9. In one aspect, provided herein is a method for integrating one or more exogenous nucleic acids into one or more target sites of a host cell genome, the method comprising:
(a) contacting one or more host cells with:
   (i) one or more exogenous donor nucleic acids (ES) capable of recombining, via homologous recombination, at one or more target sites (TS) of the host cell genome;
   (ii) an RNA-guided endonuclease (RGEN);
   (iii) one or more ribonucleic acids that enable site-specific recognition and cleavage of the one or more TS by the RGEN; and
   (iv) a linear pre-recombination nucleic acid capable of homologous recombination with itself or with one or more additional linear pre-recombination nucleic acids contacted with the host cell, whereupon said homologous recombination results in formation of a circular extrachromosomal nucleic acid comprising a coding sequence for a selectable marker; and
(b) selecting a host cell that expresses the selectable marker, thereby selecting for a cell that has integrated the one or more exogenous nucleic acids into the one or more target sites of a host cell genome.

In some embodiments, the homologous recombination results in formation of a complete coding sequence of the selectable marker within the circular extrachromosomal nucleic acid. In some embodiments, at least one linear pre-recombination nucleic acid comprises a sequence that encodes the one or more ribonucleic acids that enables site-specific recognition and cleavage of TS by the RNA-guided DNA endonuclease. In some embodiments, the one or more ribonucleic acids comprise a crRNA activity and a tracrRNA on a single contiguous guide RNA (gRNA) molecule. In some embodiments, at least one linear pre-recombination nucleic acid comprises a sequence that encodes the RNA-guided DNA endonuclease. In some embodiments, the RNA-guided DNA endonuclease is Cas9.

In some embodiments, the formation of the circular extrachromosomal nucleic acid results from homologous recombination of two or three linear pre-recombination nucleic acids. In some embodiments, the one or more linear pre-recombination nucleic acids are generated in vivo by RGEN cleavage of one or more circular nucleic acids comprising the one or more pre-recombination nucleic acids. In some embodiments, a plurality of (n) exogenous nucleic acids is integrated into a plurality of (n) target sites of the host cell genome, wherein n is at least two, wherein step (a) comprises contacting the host cell with:
   (i) said plurality of exogenous nucleic acids, wherein x is an integer that varies from 1 to n, and for each integer x, each exogenous nucleic acid $(ES)_x$ is capable of recombining, via homologous recombination, at a target site $(TS)_x$ selected from said plurality of (n) target sites of said host cell genome;
   (ii) for each said target site $(TS)_x$, a guide RNA $(gRNA)_x$ that enables site-specific recognition and cleavage of $(TS)_x$ by the RGEN.

In some embodiments, the selectable marker is a drug resistance marker, a fluorescent protein or a protein detectable by colorimetric or fluorescent detection methods. In some embodiments, ES further comprises a nucleic acid of interest D. In some embodiments, D is selected from the group consisting of a selectable marker, a promoter, a nucleic acid sequence encoding an epitope tag, a gene of interest, a reporter gene, and a nucleic acid sequence encoding a termination codon. In some embodiments, the host cell is selected from the group consisting of a fungal cell, a bacterial cell, a plant cell, an insect cell, an avian cell, a fish cell and a mammalian cell. In some embodiments, the contacted host cell(s) are cultured for a period of at least about 12, 24, 36, 48, 72 or more than 72 hours prior to said selecting. In some embodiments, the contacted cells are cultured under culturing conditions that select against the survival of cells not expressing the selectable marker. In some embodiments, the selecting of step (b) comprises detecting the expression of the selectable marker via visual, colorimetric or fluorescent detection methods.

In another aspect, provided herein is a composition for integrating one or more exogenous nucleic acids into one or more target sites of a host cell genome, the composition comprising:
(a) one or more exogenous donor nucleic acids (ES) capable of recombining, via homologous recombination, at one or more target sites (TS) of a host cell genome;
(b) an RNA-guided endonuclease (RGEN), or a nucleic acid encoding said RGEN;
(c) one or more ribonucleic acids that enable site-specific recognition and cleavage of the one or more TS by the RGEN, or one or more nucleic acids encoding said one or more ribonucleic acids; and (d) a linear pre-recombination nucleic acid capable of in vivo homologous recombination with itself or with one or more additional linear pre-recombination nucleic acids in the composition, whereupon said in vivo homologous recombination results in formation of a circular extrachromosomal nucleic acid comprising a coding sequence for a selectable marker.

In some embodiments, said homologous recombination results in formation of a complete coding sequence of the selectable marker within the circular extrachromosomal nucleic acid. In some embodiments, at least one linear pre-recombination nucleic acid comprises a sequence that encodes the one or more ribonucleic acids that enables site-specific recognition and cleavage of TS by the RNA-guided DNA endonuclease. In some embodiments, the one or more ribonucleic acid molecules comprise a crRNA activity and a tracrRNA activity on a single contiguous guide RNA (gRNA) molecule. In some embodiments, at least one linear pre-recombination nucleic acid comprises a sequence that encodes the RNA-guided DNA endonuclease. In some embodiments, the RNA-guided DNA endonuclease is Cas9. In some embodiments, the composition comprises two or three linear pre-recombination nucleic acids capable of homologously recombining to form the circular extrachromosomal nucleic acid. In some embodiments, the one or more linear pre-recombination nucleic acids are generated in vivo by RGEN cleavage of one or more circular nucleic acids comprising the one or more pre-recombination nucleic acids.

In some embodiments, the composition comprises:
(a) a plurality of (n) exogenous nucleic acids capable of integrating into a plurality of (n) target sites of the host cell genome, wherein n is at least two, wherein x is an integer that varies from 1 to n, and for each integer x, each exogenous nucleic acid $(ES)_x$ is capable of recombining, via homologous recombination, at a target site $(TS)_x$ selected from said plurality of (n) target sites of said host cell genome; and
(b) for each said target site $(TS)_x$, a guide RNA $(gRNA)_x$ that enables site-specific recognition and cleavage of $(TS)_x$ by the RGEN.

In some embodiments, the selectable marker is a drug resistance marker, a fluorescent protein or a protein detectable by colorimetric or fluorescent detection methods. In some embodiments, ES further comprises a nucleic acid of interest D. In some embodiments, D is selected from the group consisting of a selectable marker, a promoter, a nucleic acid sequence encoding an epitope tag, a gene of interest, a reporter gene, and a nucleic acid sequence encoding a termination codon.

In another aspect, provided herein is a host cell comprising any of the compositions for the RGEN-mediated integration of one or more exogenous nucleic acids into one or more target sites of a host cell genome described herein. In some embodiments, the host cell is selected from the group consisting of a fungal cell, a bacterial cell, a plant cell, an insect cell, an avian cell, a fish cell and a mammalian cell.

4. BRIEF DESCRIPTION OF THE FIGURES

FIG. 1 provides an exemplary embodiment of genomic integration in a host cell of an exogenous nucleic acid (D) using a site-specific nuclease (N) and two pre-recombination molecules capable of homologous recombination (HR) with each other to form a circular plasmid comprising a coding sequence for a selectable marker (GFP). In this example, the coding sequence for green fluorescent protein (GFP) is split among the two pre-recombination molecules, and the coding sequence is reconstituted in vivo upon HR of overlapping homology regions between the two molecules. Selection for expression of the selectable marker also selects for cells which have integrated the exogenous nucleic acid into its target site, and following selection, the plasmid comprising the selectable marker can be eliminated. HR1—upstream homology region; HR2—downstream homology region; TS—target site; N—site-specific nuclease; D—nucleic acid of interest.

Figure 2:
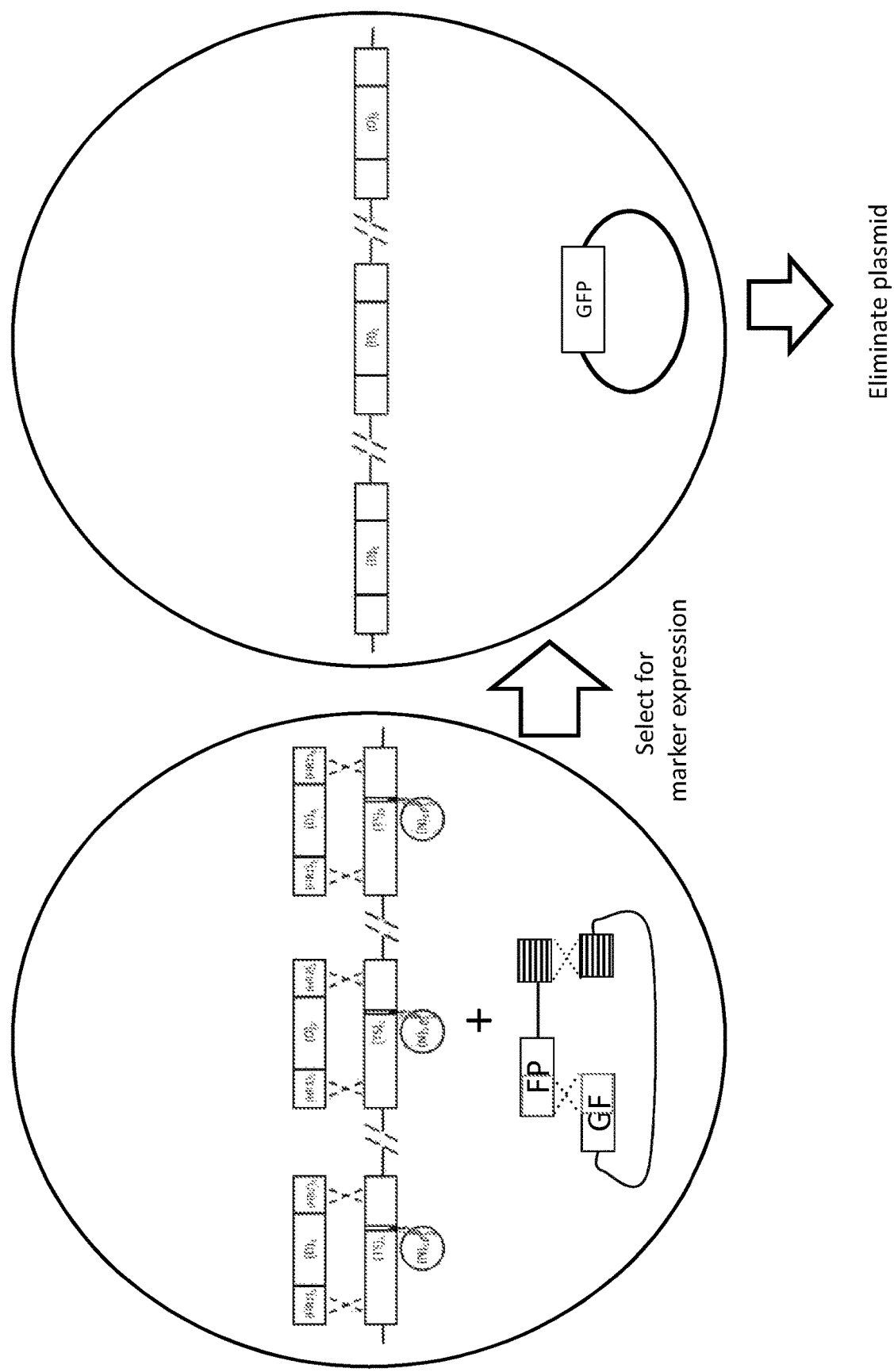

FIG. 2 provides an exemplary embodiment of simultaneous genomic integration in a host cell of a plurality of exogenous nucleic acids using a plurality of site-specific nucleases and two pre-recombination molecules capable of homologous recombination with each other to form a circular plasmid comprising a coding sequence for a selectable marker (GFP). In this example, two pre-recombination molecules are simultaneously introduced with three exogenous donor DNAs, each having homology regions specific to a unique target site in the host cell genome, and one or more nucleases capable of cleaving at the three target sites. Selection for expression of the selectable marker also selects for cells which have integrated each exogenous nucleic acid into its respective target site. HR1—upstream homology region; HR2—downstream homology region; TS—target site; N—site-specific nuclease; D—nucleic acid of interest.

Figure 3A:
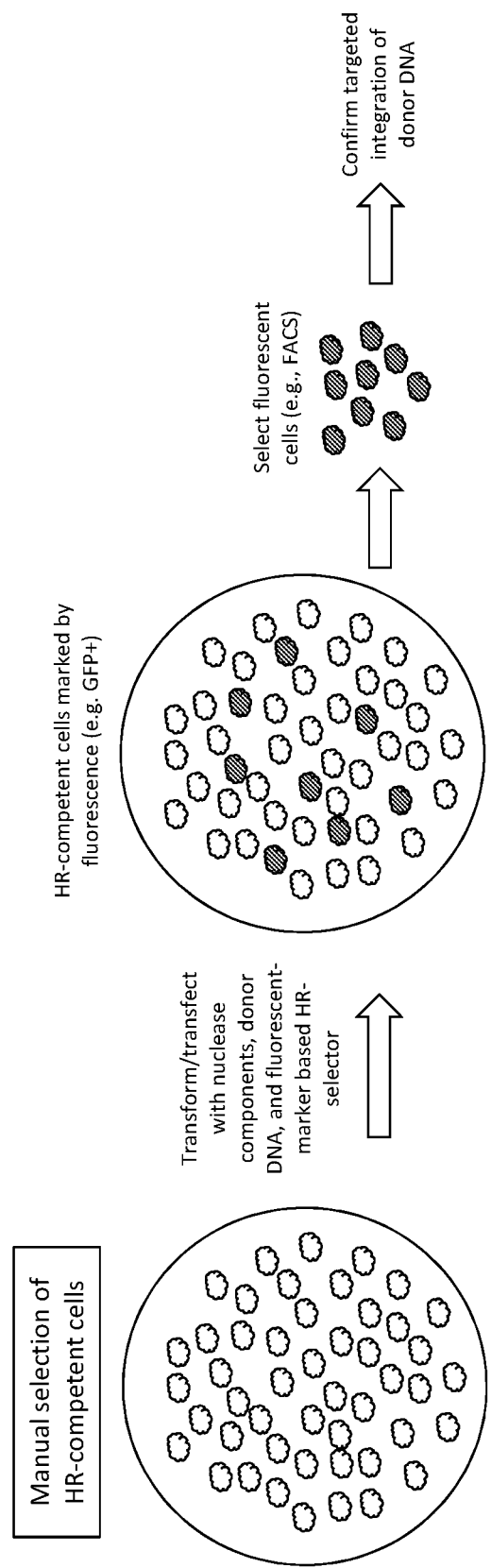
Figure 3B:
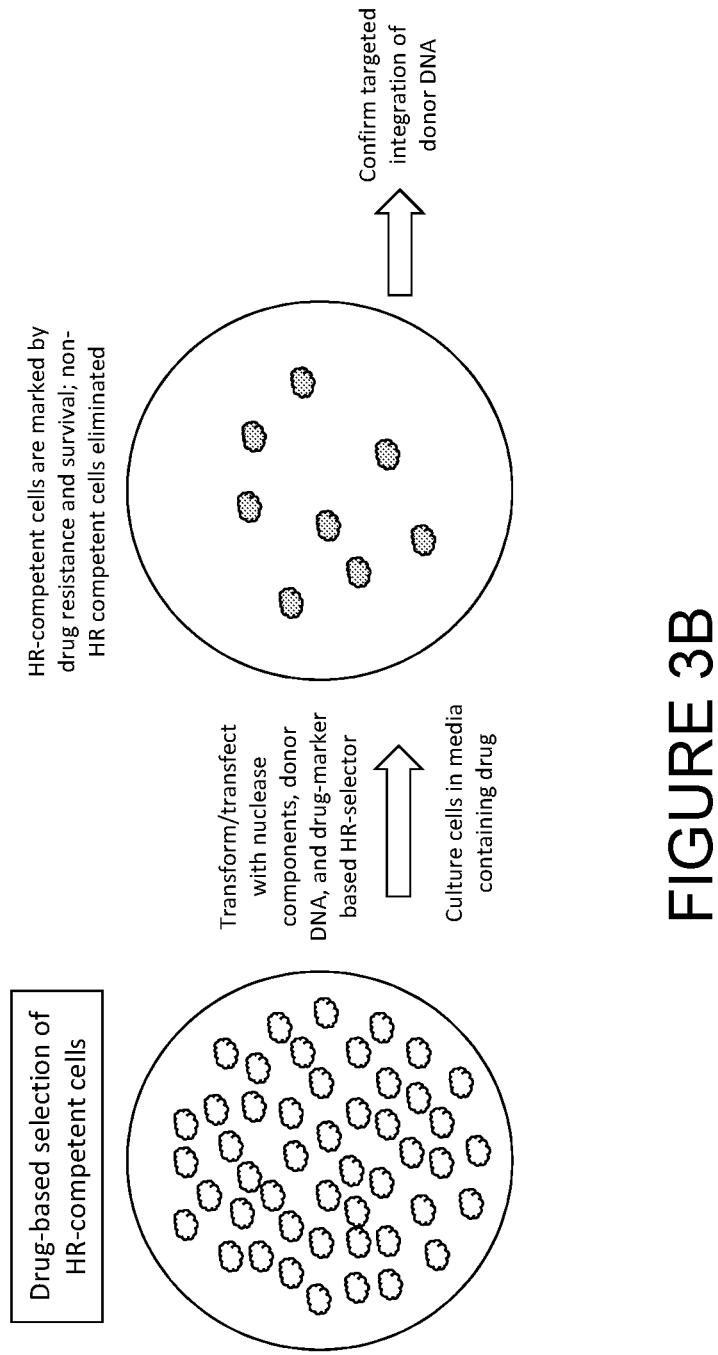

FIG. 3 (A, B) provides two exemplary embodiments for selecting cells capable of HR-mediated assembly of pre-recombination molecules and targeted genomic integration of exogenous donor DNA. FIG. 3A depicts a selection strategy based on HR-mediated formation of a plasmid comprising a fluorescence-based selectable marker. Host cells are transformed with one or more exogenous donor DNAs, one or more pre-recombination molecules, which upon in vivo HR-mediated assembly, forms a circular plasmid comprising a fluorescence-based selectable marker (e.g., GFP), and optionally, one or more site-specific nucleases capable of cleaving one or more target sites of the host cell genome. HR competent cells are marked by fluorescence, and can be isolated from the host cell population using standard techniques such as flow cytometry. FIG. 3B depicts a selection strategy based on HR-mediated formation of a drug-based selectable marker. In this embodiment, HR-competent cells are marked by drug resistance and survival when cultured in media containing the appropriate selective agent, whereas non-HR competent drug-sensitive cells are eliminated. Cells or clonal cell populations isolated under either selection scheme can be expanded and confirmed for harboring the targeted integration of one or more exogenous donor DNAs, for example, by PCR and/or sequencing of the genomic target regions.

FIG. 4 (A, B, C) provides exemplary pre-recombination compositions useful in the methods of genomic integration provided herein. For any of the pre-recombination compositions described herein, the compositions can be transformed directly into a host cell as linear nucleic acid molecules, or alternatively, parental circular molecules comprising the pre-recombination molecules can be introduced into the host cell and cleaved in vivo by one or more nucleases to liberate the pre-recombination molecules. In an HR-competent host cell, the linear pre-recombination molecule(s) homologously recombine to form a circular vector comprising a selectable marker. FIG. 4A depicts two exemplary embodiments of a pre-recombination molecule for 1-piece in vivo assembly of the marker plasmid. (L) A single linear pre-recombination molecule can comprise two overlapping homology regions (represented by vertical striped boxes) outside of, i.e., non-inclusive of an intact coding sequence of the selectable marker (represented by GFP). (C) Alternatively, the single linear pre-recombination molecule can comprise two overlapping homology regions which each comprise a partial coding sequence of a selectable marker (GF and FP, respectively; overlap shaded in gray). (R) For both embodiments, in vivo homologous recombination of the single linear pre-recombination molecule with itself results in the formation of a circular plasmid comprising the complete coding sequence of the selectable marker. In some embodiments, the single linear pre-recombination molecule can further comprise a coding sequence for a site-specific nuclease (not shown).

FIG. 4B depicts two exemplary embodiments of pre-recombination molecule compositions for 2-piece in vivo assembly of the marker plasmid. Two linear pre-recombination molecules can each comprise two non-overlapping homology regions (represented by vertically and horizontally striped boxes, respectively), with each homology region being homologous to a homology region of the other pre-recombination molecule. (L) One of the two linear pre-recombination molecules can comprise an intact coding sequence of a selectable marker (represented by GFP) separate from the two non-overlapping homology regions. (C) Alternatively, each of the two pre-recombination molecules can comprise a partial coding sequence of the selectable marker having homology to a partial marker coding sequence on the other pre-recombination molecule (GF and FP, respectively; overlap shaded in gray). (R) For both embodiments, in vivo homologous recombination of the two linear pre-recombination molecules with each other results in formation of a circular plasmid comprising the complete coding sequence of the selectable marker. In some embodiments, one of the linear pre-recombination molecules can further comprise a complete coding sequence for a site-specific nuclease, or alternatively, each of the two pre-recombination molecules can comprise a partial nuclease coding sequence having homology to a partial nuclease coding sequence on the other pre-recombination molecule (not shown). Such an embodiment may be useful where nuclease expression is desired only in HR-competent cells, for example, to reduce the incidence of nuclease-mediated NHEJ in non-HR-competent cells.

Figure 4C:
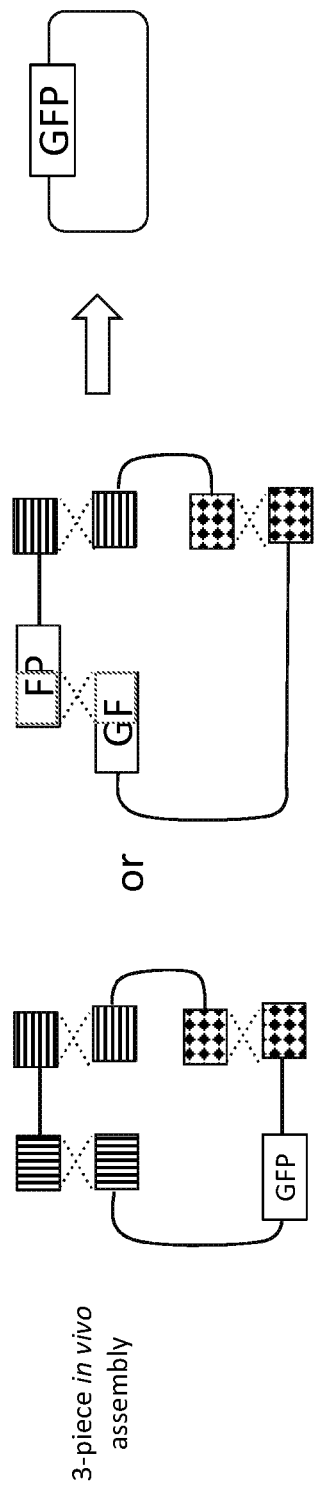

FIG. 4C depicts two exemplary embodiments of pre-recombination molecule compositions for 3-piece in vivo assembly of the marker plasmid. The three linear pre-recombination molecules can each comprise two non-overlapping homology regions (represented by vertically and horizontally striped boxes; a vertically striped box and a diamond-filled box; and a horizontally striped box and a diamond-filled box, respectively), with each homology region being homologous to a homology region on one of the other pre-recombination molecules. (L) One of the three linear pre-recombination molecules can comprise an intact coding sequence of a selectable marker (represented by GFP) separate from the two non-overlapping homology regions. (C) Alternatively, each of at least two pre-recombination molecules can comprise a partial coding sequence of the selectable marker having homology to a partial marker coding sequence on one other pre-recombination molecule (GF and FP, respectively). (R) For both embodiments, homologous recombination of the three linear pre-recombination molecules with each other results in the formation of a circular plasmid comprising the complete coding sequence of the selectable marker. In some embodiments, as in 2-piece assembly, one of the linear pre-recombination molecules can further comprise a complete coding sequence for a site-specific nuclease, or alternatively, each of at least two pre-recombination molecules can comprise a partial nuclease coding sequence having homology to a partial nuclease coding sequence on one other pre-recombination molecule (not shown).

Figure 5A:
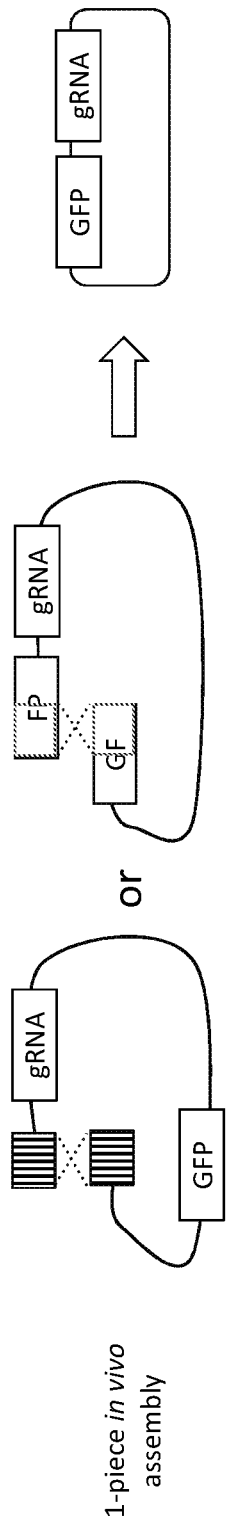
Figure 5B:
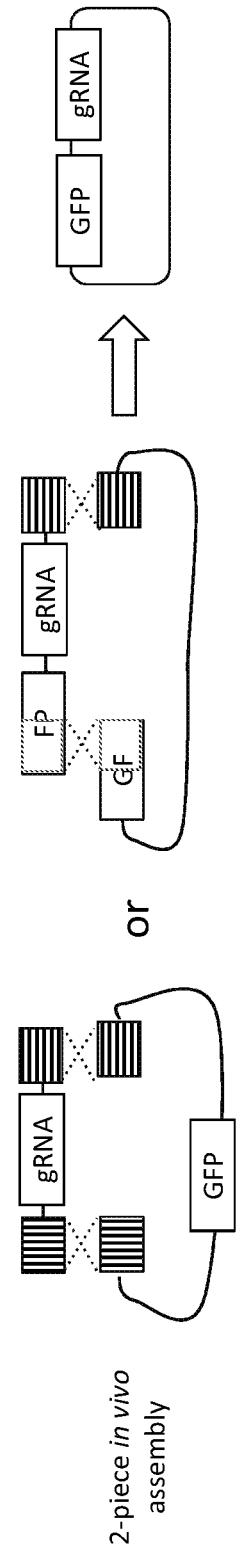
Figure 5C:
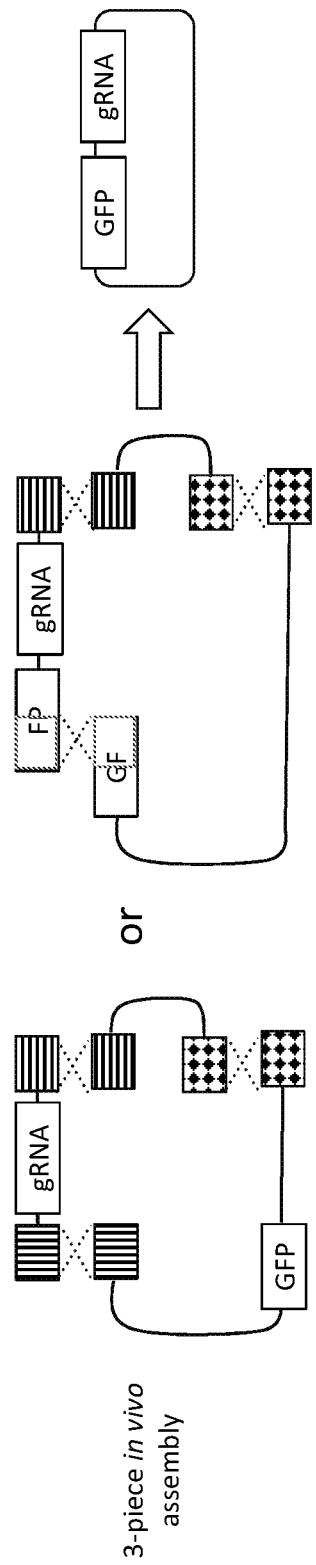

FIG. 5 (A, B, C) provides exemplary pre-recombination compositions useful in RNA-guided DNA endonuclease (RGEN) specific embodiments of the methods of genomic integration provided herein. FIG. 5A: In some embodiments of a 1-piece in vivo assembly depicted in FIG. 4A, the single pre-recombination molecule can further comprise one or more sequences that encode a crRNA activity and a tracr-RNA activity (e.g. a guide RNA (gRNA) sequence) that enables site-specific recognition and cleavage of a genomic target site by an RGEN (e.g., CRISPR/Cas9). In some embodiments, the pre-recombination molecule can further comprise a coding sequence for the RGEN (e.g., Cas9; not shown). FIG. 5B: In some embodiments of a 2-piece in vivo assembly depicted in FIG. 4B, one of the two pre-recombination molecules can further comprise a gRNA sequence. In other embodiments, one of the two pre-recombination molecules can further comprise a complete coding sequence of an RGEN, or alternatively, one of the two pre-recombination molecules can comprise a partial nuclease coding sequence having homology to a partial nuclease coding sequence on the other pre-recombination molecule (not shown). FIG. 5C: In some embodiments of a 3-piece in vivo assembly, one of the three pre-recombination molecules can further comprise a gRNA sequence. In other embodiments, one of the three pre-recombination molecules can further comprise a complete coding sequence of an RGEN, or alternatively, each of at least two pre-recombination molecules can comprise a partial nuclease coding sequence having homology to a partial nuclease coding sequence on one other pre-recombination molecule (not shown).

Figure 6A:
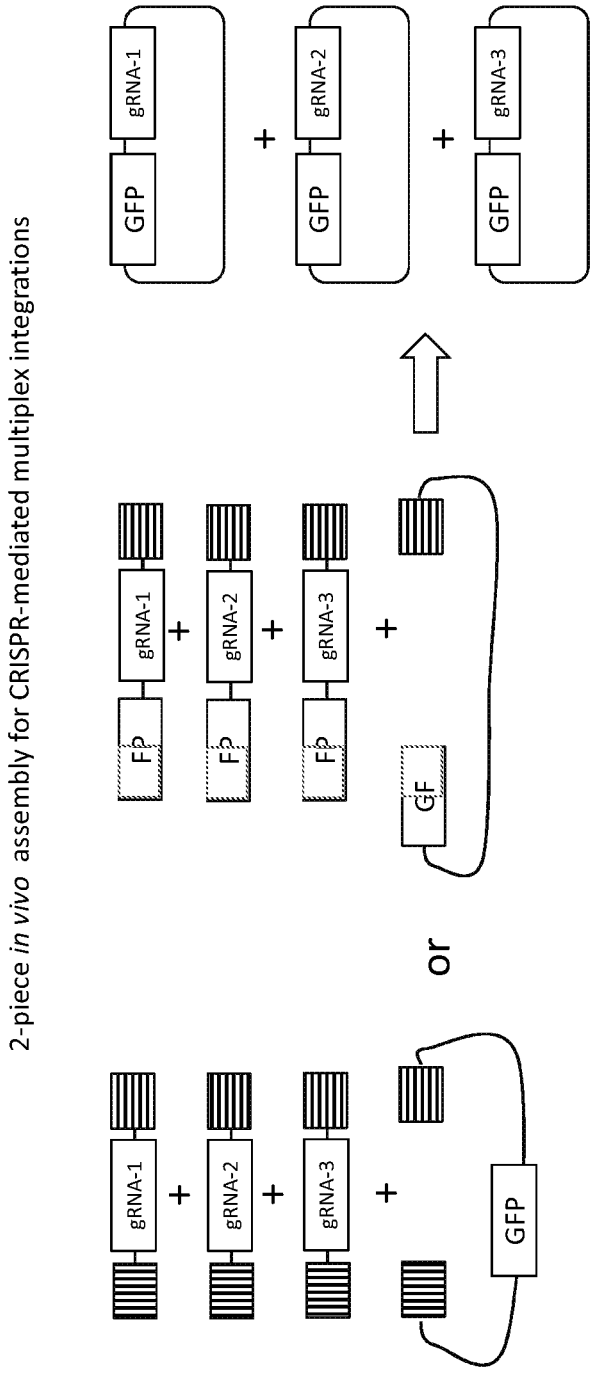

FIG. 6 (A, B) provides exemplary linear pre-recombination compositions useful in RGEN-mediated multiplex genomic integration. FIG. 6A: In some embodiments of a 2-piece in vivo assembly where one of the two pre-recombination molecules participating in the assembly comprises a gRNA sequence, several of these molecules can be provided at once (e.g., 3: gRNA-1, gRNA-2, gRNA-3), each comprising a unique gRNA sequence that targets a different genomic target site. In this embodiment, the other pre-recombination molecule represents a common vector backbone that may comprise a complete coding sequence for a selectable marker (L), or a partial marker coding sequence that is homologous with a partial coding sequence common to each of the gRNA containing fragments (C). (R) HR-competent cells are able to recombine each unique gRNA containing fragment with the common vector backbone to reconstitute three different marker plasmids each comprising a unique gRNA sequence. FIG. 6B: In other embodiments, one of the two linear pre-recombination molecules can further comprise a complete coding sequence of an RGEN (e.g. Cas9). Alternatively, each of the two pre-recombination molecules can comprise a partial nuclease coding sequence having homology to a partial nuclease coding sequence on the other pre-recombination molecule (not shown). Multiplex genomic integrations can be performed with 2-piece, 3-piece, or higher order pre-recombination compositions, in combination with a plurality of unique gRNA cassettes positioned within one or more of the pre-recombination molecules of the composition.

Figure 7:
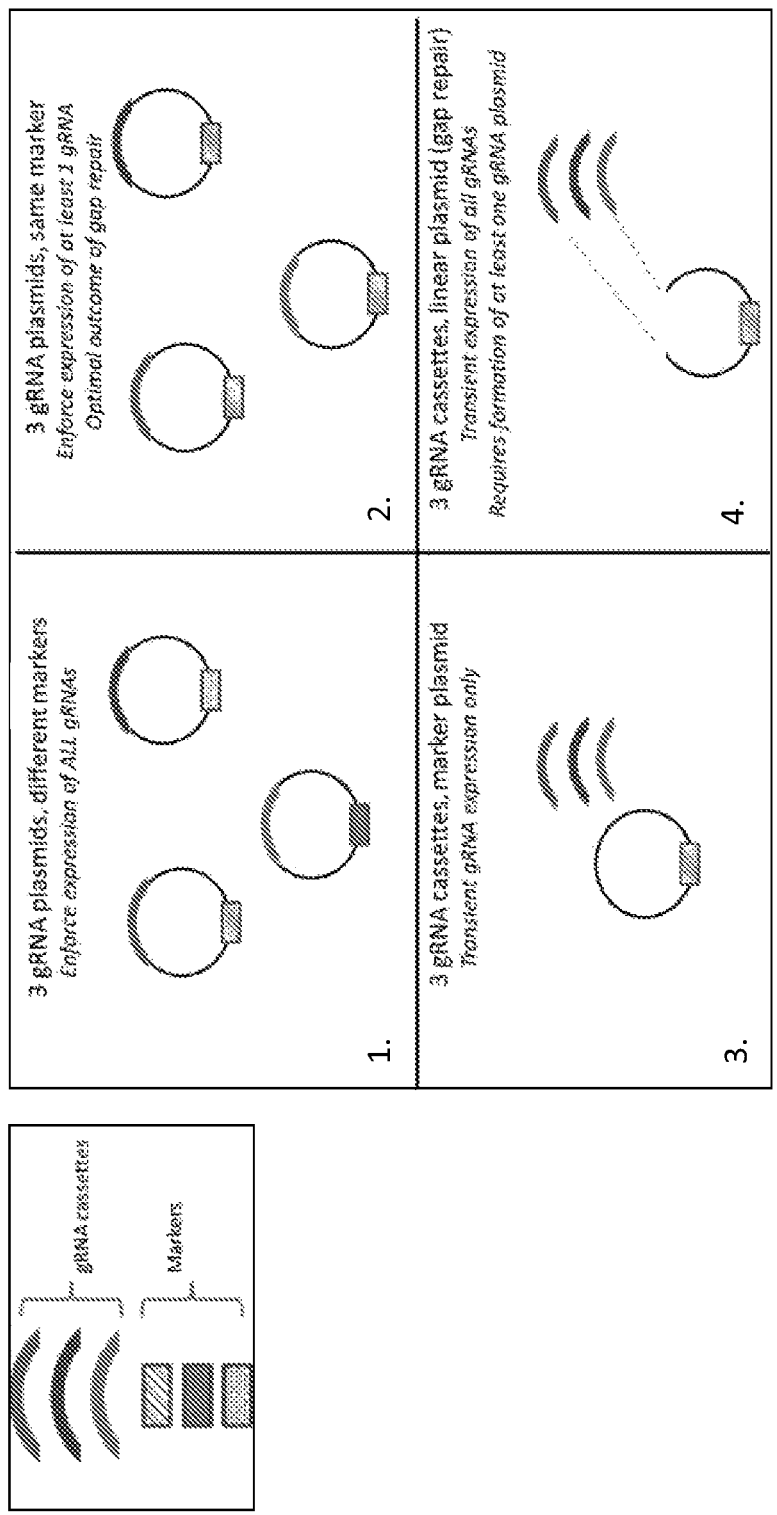

FIG. 7 depicts compositions used in determining optimal modes of gRNA delivery for CRISPR/Cas-9 mediated multiplex donor DNA integrations as described in Example 1.

(L) Unique gRNA cassettes are depicted as crescents, and unique drug selectable markers as depicted as rectangles. (R) gRNA cassettes were introduced to host cells as: (1) circular vectors, wherein each of three unique gRNA cassettes was cloned into a plasmid comprising a unique selectable marker; (2) circular vectors, wherein each of three unique gRNA cassettes was cloned into a plasmid comprising the same selectable marker; (3) linear expression cassettes, wherein the three linear gRNA cassettes were co-transformed with a circular plasmid comprising a selectable marker; and (4) linear expression cassettes, each having ends that are homologous with the ends of a co-transformed linear plasmid comprising a selectable marker, thus allowing for HR-mediated in vivo assembly of circular plasmids comprising each gRNA and a common selectable marker.

Figure 8:
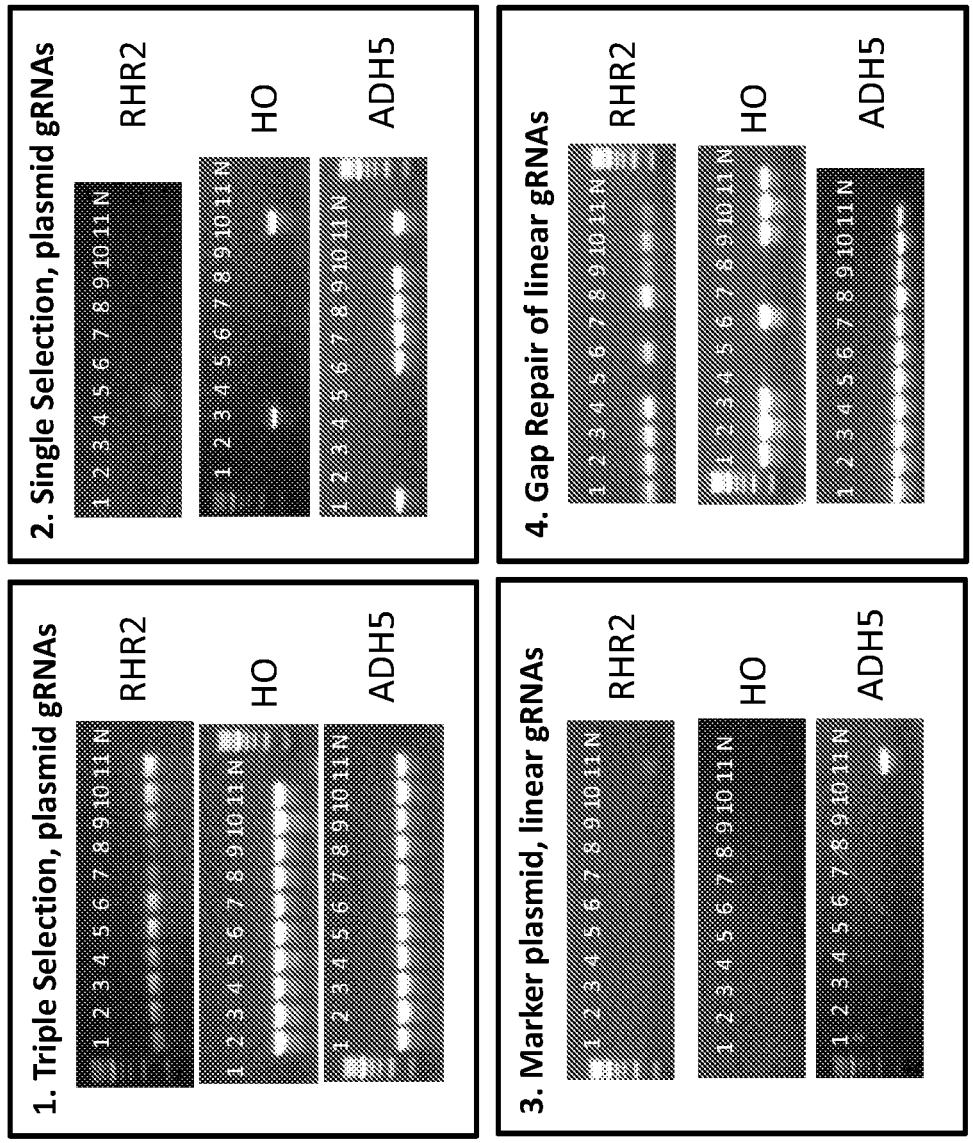

FIG. 8 provides the results of an experiment to determine optimal modes of gRNA delivery as described in Example 1. Cas9-expressing host cells (*S. cerevisiae*) were transformed with donor DNAs for simultaneous, marker-less integration/deletion of RHR2, HO and ADH5 open reading frames and gRNA constructs targeting each locus. Modes of gRNA delivery were 1) three plasmids with three different selectable markers, 2) three plasmids with the same marker, 3) a single marker plasmid, with three linear gRNA cassettes, and 4) a single linearized marker plasmid with flanking sequences for gap repair of three linear gRNA cassettes. Colonies were assayed by cPCR using an upstream forward primer outside of the deletion construct, and a reverse primer binding to a short linker sequence integrated in place of each open reading frame. 11 colonies were assayed for each delivery mode, as well as a parent colony that serves as a negative control ("N").

Figure 9:
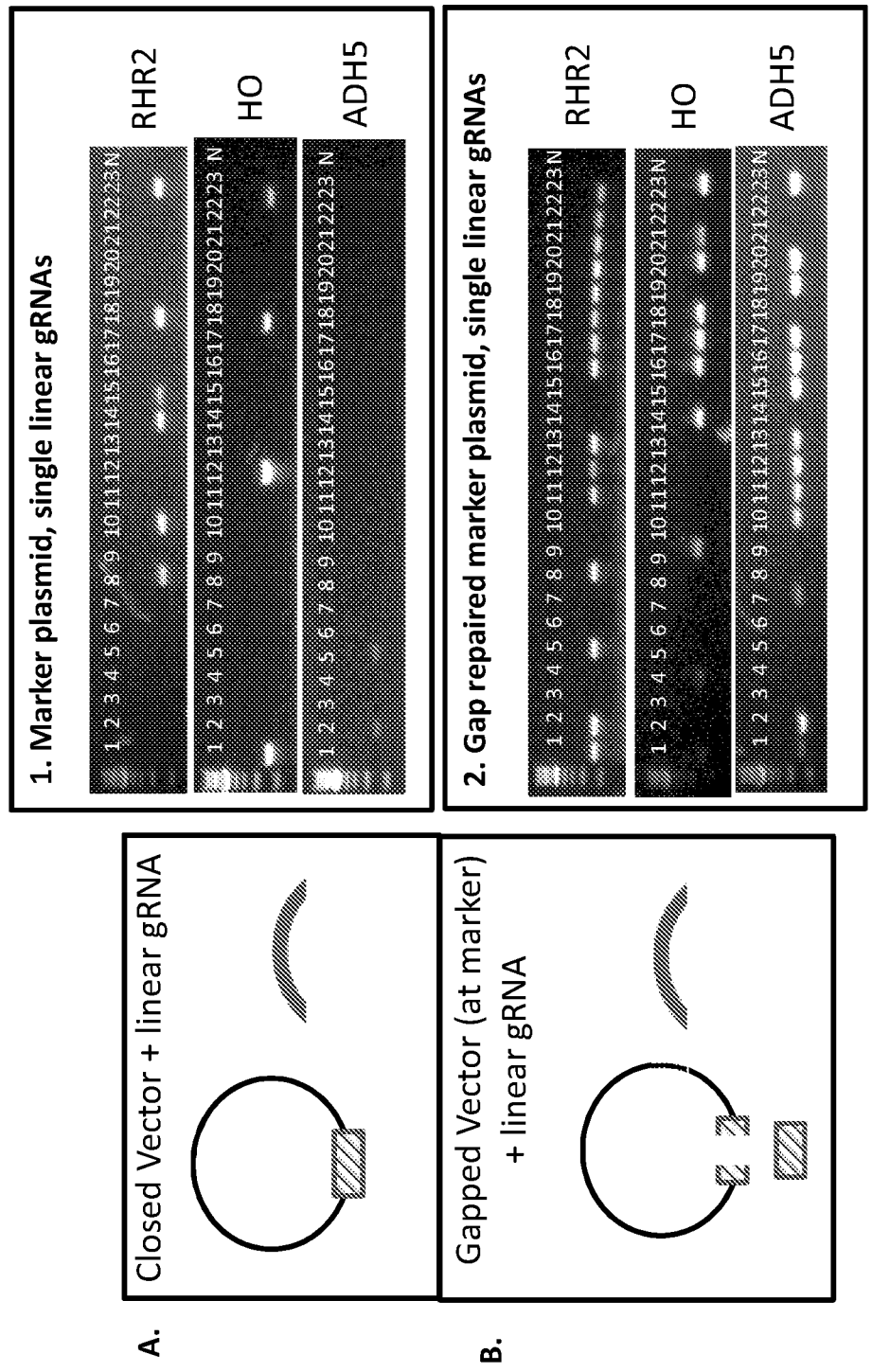

FIG. 9 provides results of an experiment (described in Example 2) to determine the benefit of gap repair of a marker vector, uncoupled from the benefit of selecting for gRNA expression, towards CRISPR/Cas-9 mediated single integration of a donor DNA into the RHR2, HO and ADH5 locus, respectively. Cas9-expressing host cells (*S. cerevisiae*) were transformed with a donor DNA for marker-less deletion of RHR2, HO or ADH5 open reading frames and gRNA constructs targeting each locus. In addition to the appropriate donor DNA, linear gRNA cassettes were co-transformed with 1) a closed marker vector (A), or 2) the same vector, but linearized and truncated such that gap repair of an additional supplied fragment is required to close the vector and reconstitute the marker cassette (B). Colonies were assayed by PCR using an upstream forward primer outside of the deletion construct, and a reverse primer binding to a short linker sequence integrated in place of each open reading frame. 23 colonies were assayed for each delivery mode, as well as a parent colony that serves as a negative control ("N"). The experiment was repeated 3 times; results from a single experiment are shown.

FIG. 10 provides a summation of three gap repair experiments results demonstrated in FIG. 9. For each of three experiments, 23 colonies were assayed.

Figure 11:
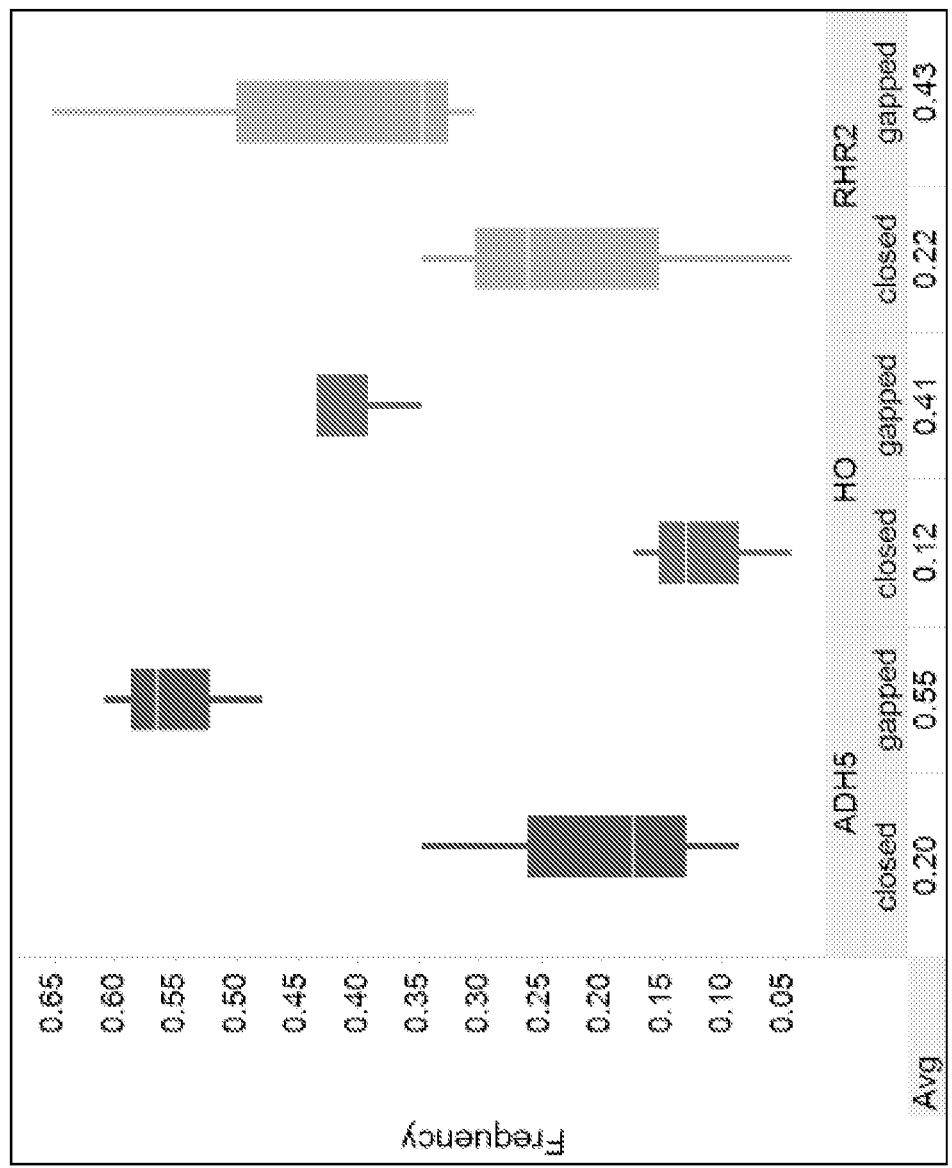

FIG. 11 provides a box plot summation of three gap repair experiments demonstrated in FIG. 9.

Figure 12:
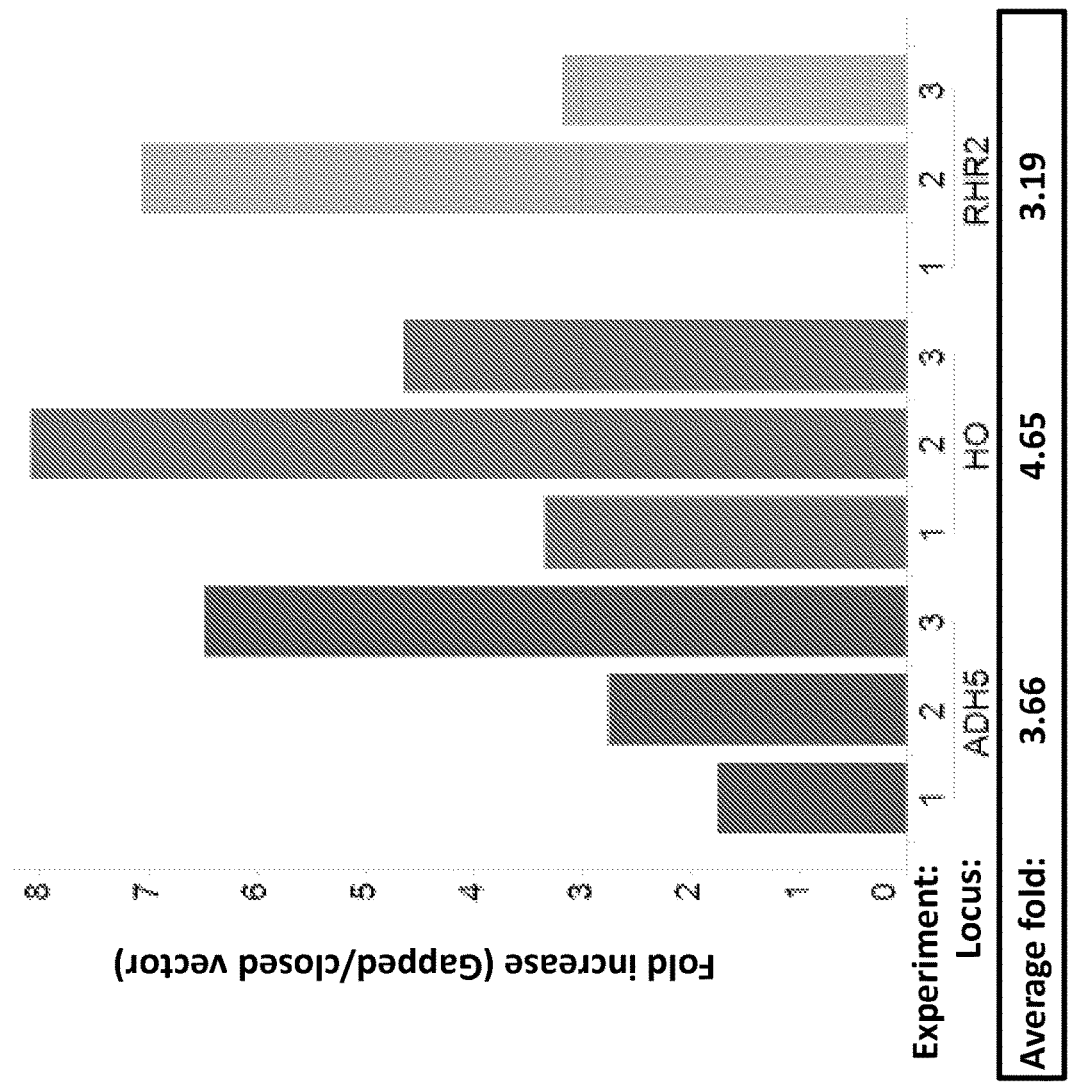

FIG. 12: provides the fold-increase via gap-repair assembly of the marker plasmid; summation of three gap repair experiments demonstrated in FIG. 9.

Figure 13:
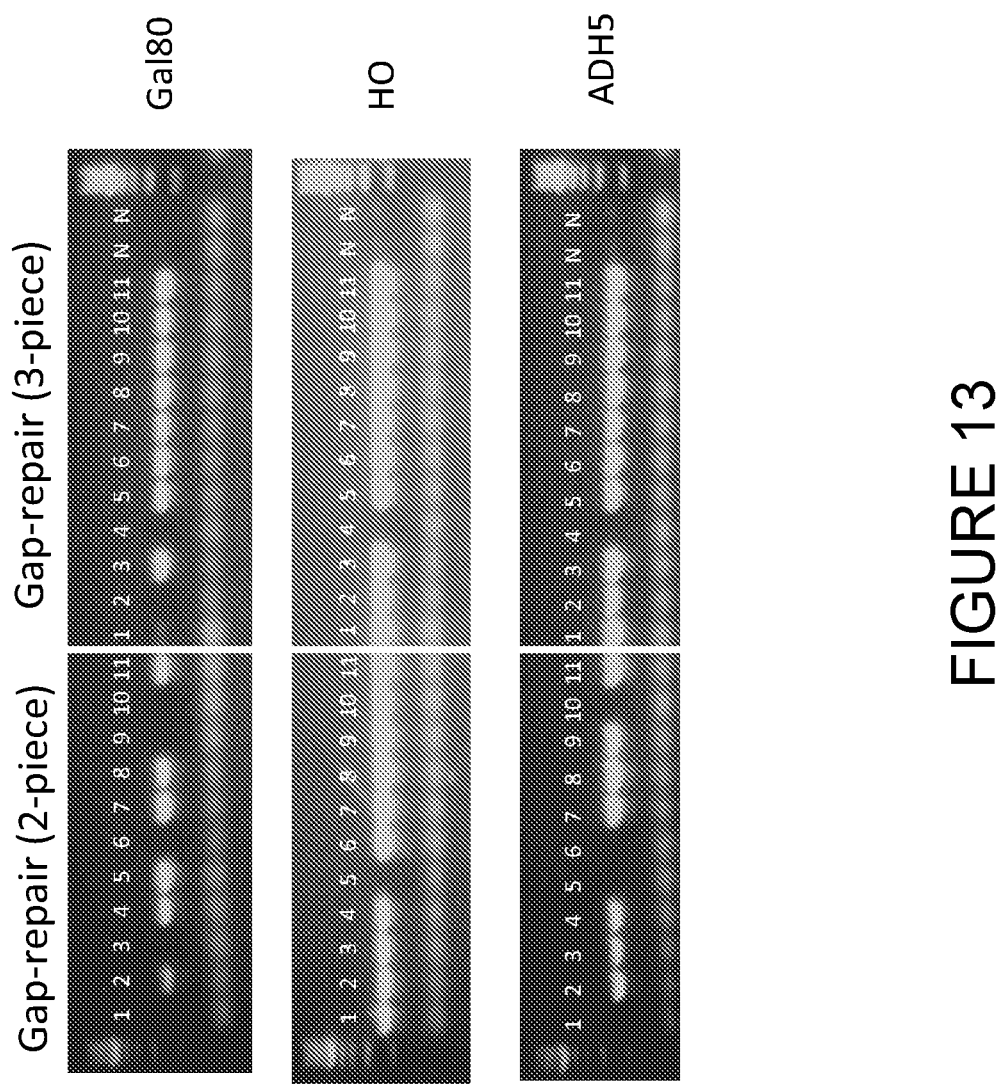

FIG. 13 provides the results of an experiment to determine the benefit of 2-piece in vivo assembly versus 3-piece in vivo assembly of a marker/gRNA vector towards CRISPR/Cas-9 mediated simultaneous integration of three donor DNAs into the Gal80, HO and ADH5 locus, respectively. Cas9-expressing host cells (haploid *S. cerevisiae*) were transformed with donor DNAs for simultaneous, marker-less deletion of Gal80, HO and ADH5 open reading frames, gRNA constructs targeting each locus, and pre-recombination molecules for either 2 or 3 piece marker/gRNA vector assembly. Colonies were assayed by cPCR using an upstream forward primer outside of the deletion construct, and a reverse primer binding to a short linker sequence integrated in place of each open reading frame. 11 colonies were assayed for each delivery mode, as well as a parent colony that serves as a negative control ("N").

Figure 14:
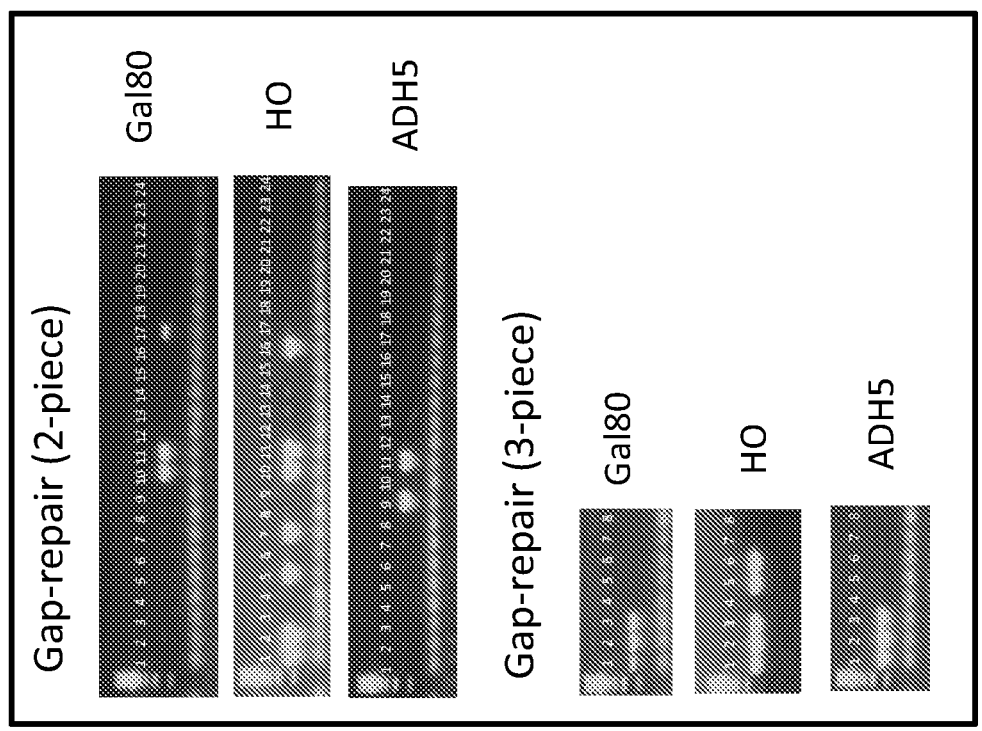

FIG. 14 provides the results of an experiment to determine the benefit of 2-piece in vivo assembly versus 3-piece in vivo assembly of a marker/gRNA vector towards CRISPR/Cas-9 mediated simultaneous integration of three donor DNAs into the Gal80, HO and ADH5 locus, respectively. Cas9-expressing cells of the Diploid yeast strain CAT-1 (*S. cerevisiae*) were transformed with donor DNAs for simultaneous, pan-allelic, marker-less deletion of Gal80, HO and ADH5 open reading frames, gRNA constructs targeting each locus, and pre-recombination molecules for either 2 or 3 piece marker/gRNA vector assembly. Colonies were assayed by PCR using an upstream forward primer outside of the deletion construct, and a reverse primer binding to a short linker sequence integrated in place of each open reading frame. The experiment used a selection scheme in which cells must process transformed DNA reagents using 2 or 3 homologous recombination events to create a selective plasmid. The rate of simultaneous, pan-allelic triple integration was nearly ten-fold higher when 3 events were required. The number of colonies recovered from the experiment was also roughly ten-fold fewer when 3 events were required (not shown), indicating that the selection scheme was responsible for the increased rate of triple integration.

Figure 15:
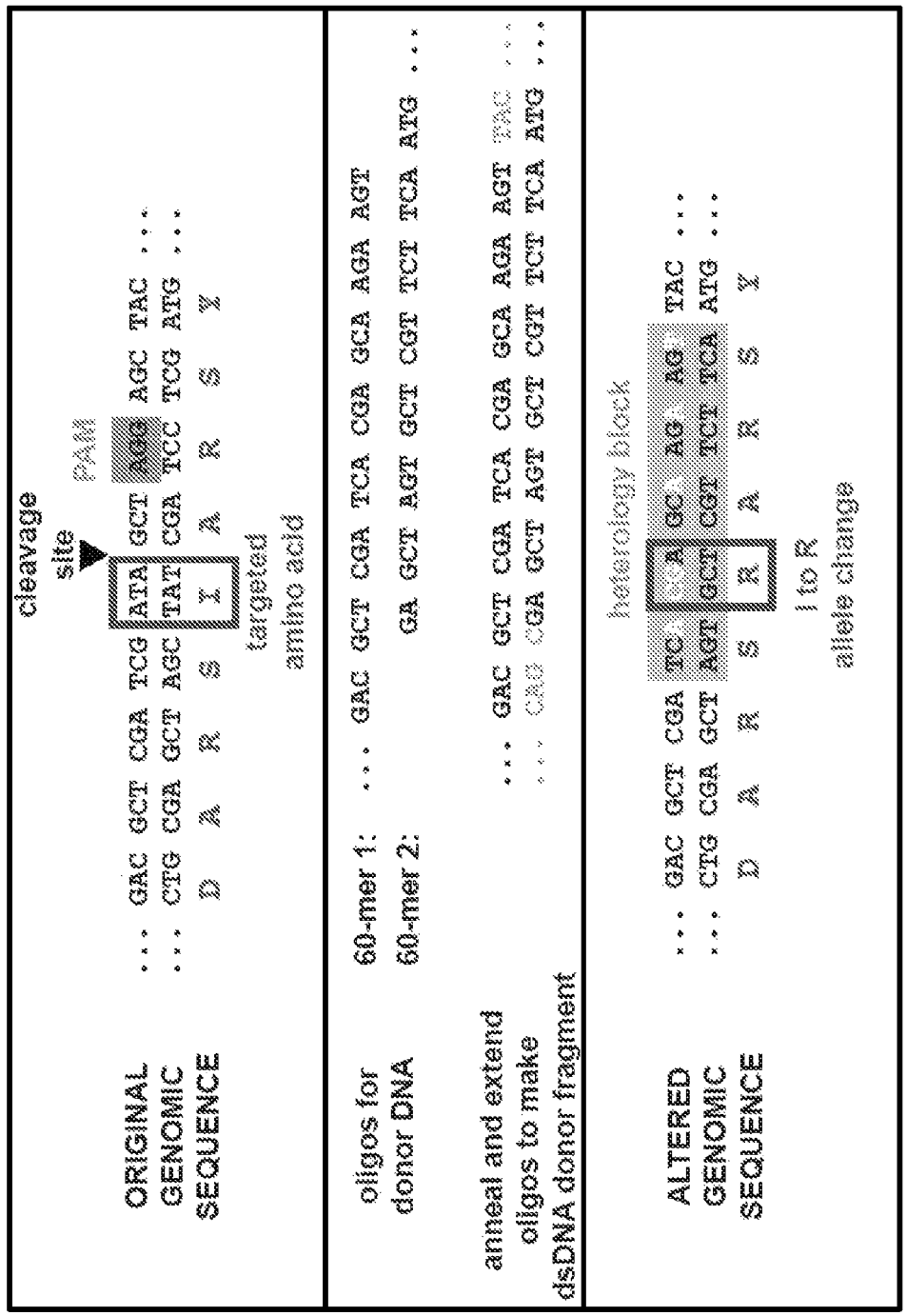

FIG. 15 provides a schematic for introduction of a point mutation in the context of a "heterology block." A targeted amino acid is boxed, and an adjacent cleavage site is annotated with cleavage site and PAM sequence (Top panel). A donor DNA containing the desired point mutation in the context of a heterology block of silent codon changes and flanking homology can be generated synthetically by annealing and extending 60-mer oligos (Middle panel) or with larger cloned constructs. Integration of the donor DNA yields the desired point mutation (Lower panel).

Figure 16:
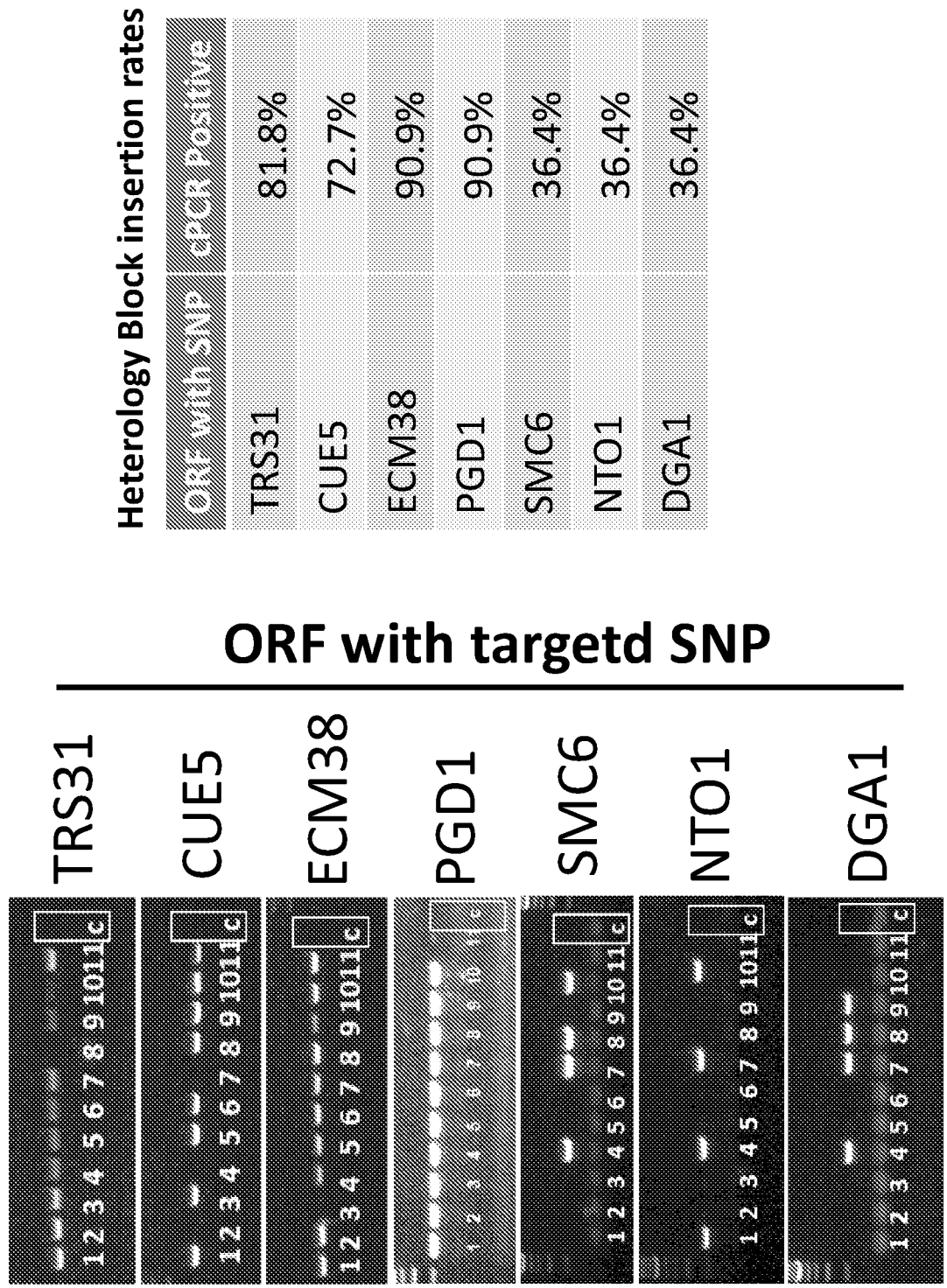

FIG. 16 provides results of an experiment to introduce single point mutations encoded in donor DNA using CRISPR in combination with 2-piece in vivo assembly of a marker/gRNA vector. Candidate colonies (1-11) and parent negative control (c) were assayed by colony PCR against the heterology block and flanking sequence (Left panel, and table). Selected positive colonies were confirmed by sequencing a larger PCR product spanning the integration locus.

Figure 17:
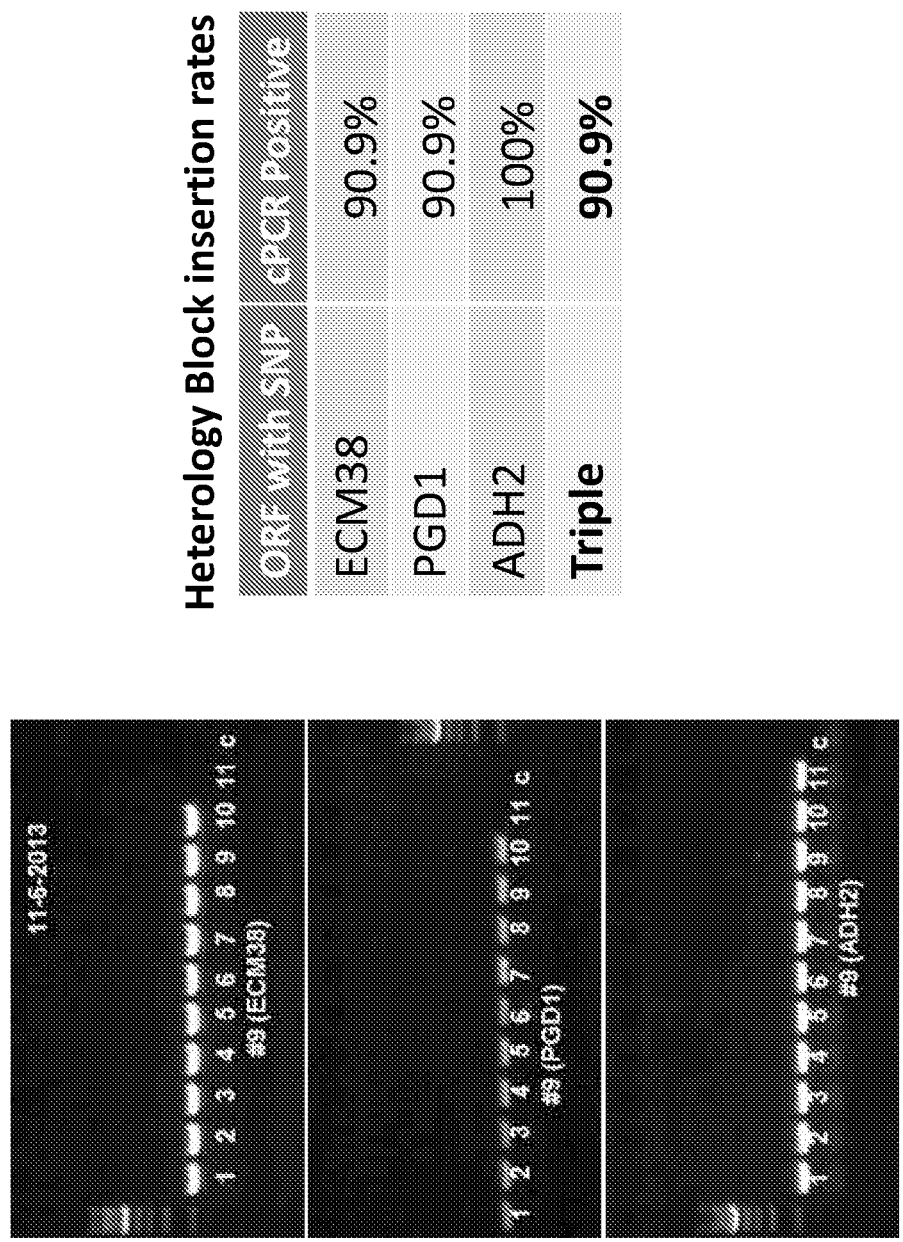

FIG. 17 provides the results of an experiment to introduce in multiplex fashion point mutations encoded in donor DNA using CRISPR in combination with 2-piece in vivo assembly of a marker/gRNA vector. The ECM38, PGD1, and ADH2 loci were targeted for the simultaneous introduction of three point mutations. Donor DNAs were cloned, with 500 bp of upstream and downstream homology flanking each target site. Candidate colonies were identified by colony PCR against the heterology block and flanking sequence (Left panel, and table). 10/11 colonies (90.9%) were positive for integration of all three heterology blocks.

Figure 18:
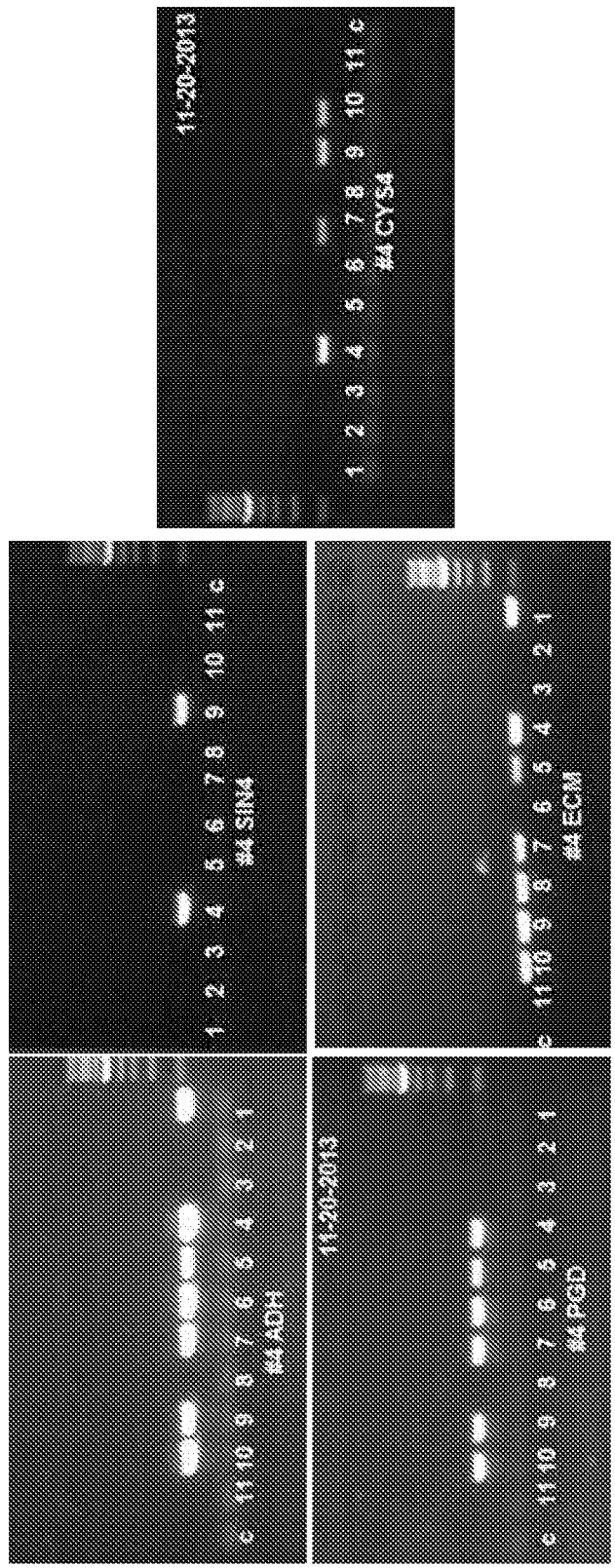

FIG. 18 provides the results of an experiment to introduce in multiplex fashion point mutations encoded in donor DNA using CRISPR in combination with 2-piece in vivo assembly of a marker/gRNA vector. The ADH2, PGD1, ECM38, SIN4 and CYS4 loci were targeted for the simultaneous introduction of five point mutations. Donor DNAs were cloned in this case, with 500 bp of upstream and downstream homology flanking each target site. Candidate colonies were identified by colony PCR against the heterology block and flanking sequence (Left panel, and table). 2/11 colonies (18.2%) were positive for integration of all five heterology blocks (clone #'s 4 and 9).

Figure 19:
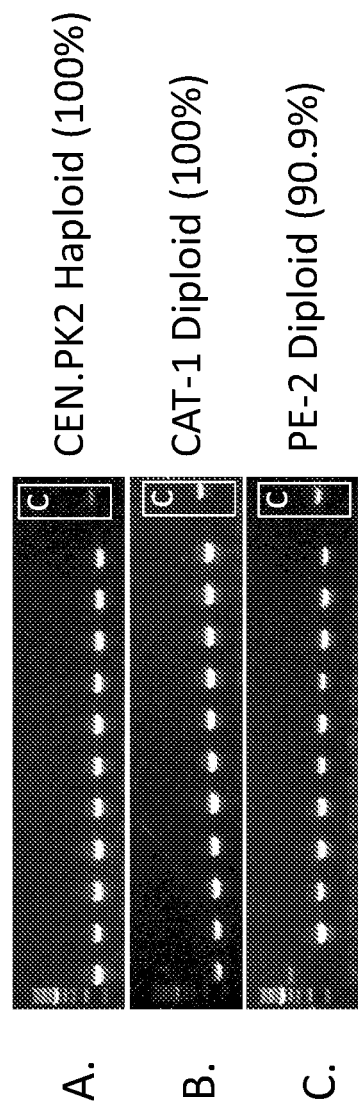

FIG. 19 provides the results of an experiment demonstrating integration of a short linker sequence at the GAL80 locus in haploid CENPK2 (A), and pan-allelic integration of the same construct of the GAL80 locus in diploid industrial strain CAT-1 (B) and diploid industrial strain PE-2 (C). Each colony was assayed for integration of the short linker sequence (odd numbered lanes) as well as for the presence of the wild type allele (even numbered lanes). The final two lanes on each gel are a parental (negative) control.

Figure 20:
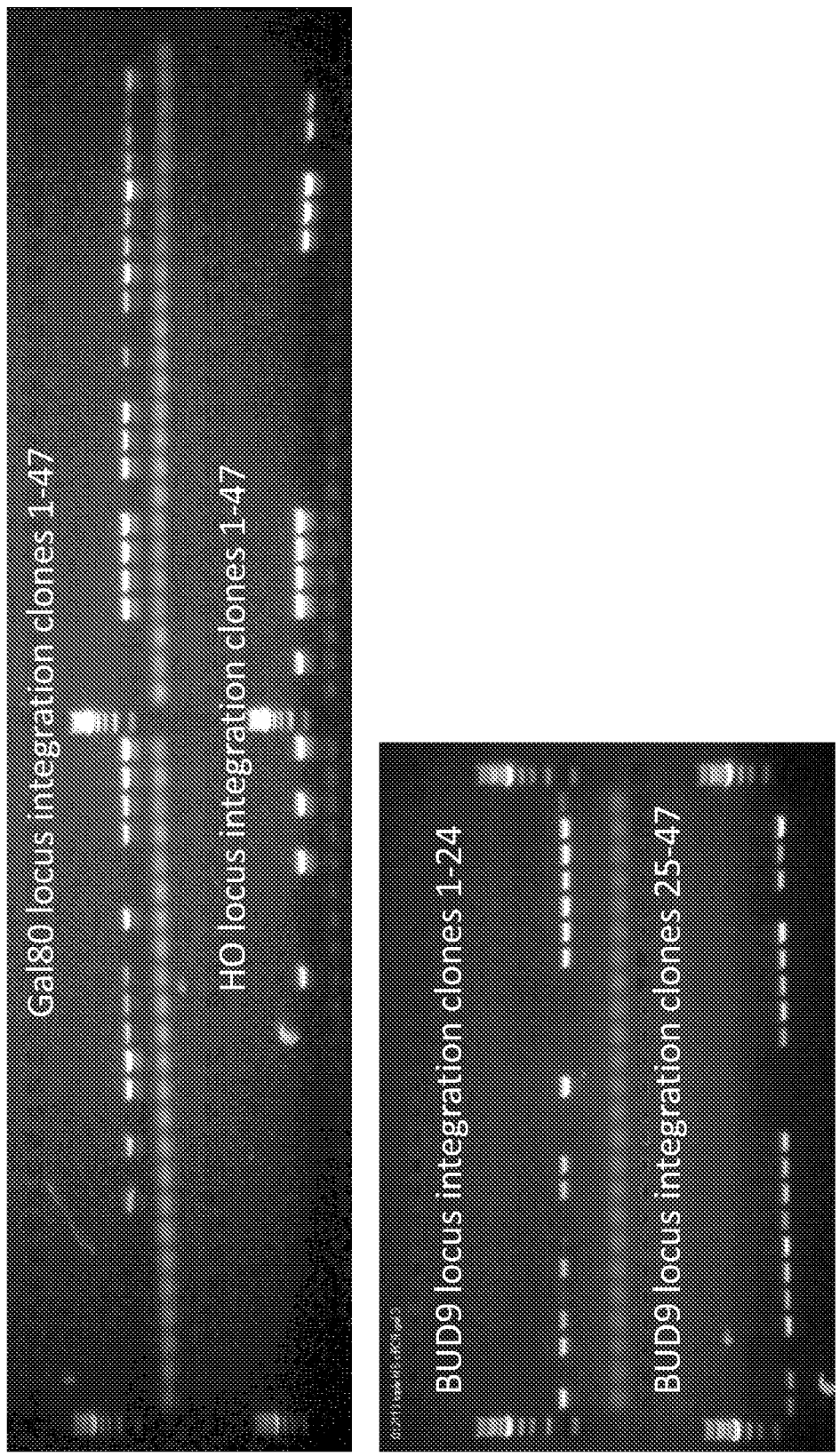

FIG. 20 provides the results of an experiment to introduce in multiplex fashion a 12-gene biosynthetic pathway (totaling ~30 kb) for the production of the isoprenoid famesene, using CRISPR in combination with 2-piece in vivo assembly of a marker/gRNA vector. The Gal80, HO and BUD9 loci were targeted for the simultaneous introduction of 3 donor DNAs comprising coding sequences for the famesene pathway components (donor 1: the transcriptional regulator GAL4; famesene synthase (2 copies) from *Artemisia annua*; ERG10, encoding acetyl-CoA thiolase; and ERG13, encoding HMG-CoA synthase; donor 2: tHMG1 (2 copies) encoding HMG-CoA reductase; and donor 3: ERG12, encoding mevalonate kinase; ERG8, encoding phosphomevalonate kinase; ERG19, encoding mevalonate pyrophosphate decarboxylase; IDI1, encoding isopentenyl pyrophosphate isomerase; and ERG20, encoding farnesyl pyrophosphate synthetase). Donor DNAs were cloned with 500 bp of upstream and downstream homology flanking each target site. Candidate colonies were identified by colony PCR against an internal linker sequence and sequence flanking the integration target sites. 11/47 colonies (23.4%) were positive for integration of the entire pathway.

Figure 21:
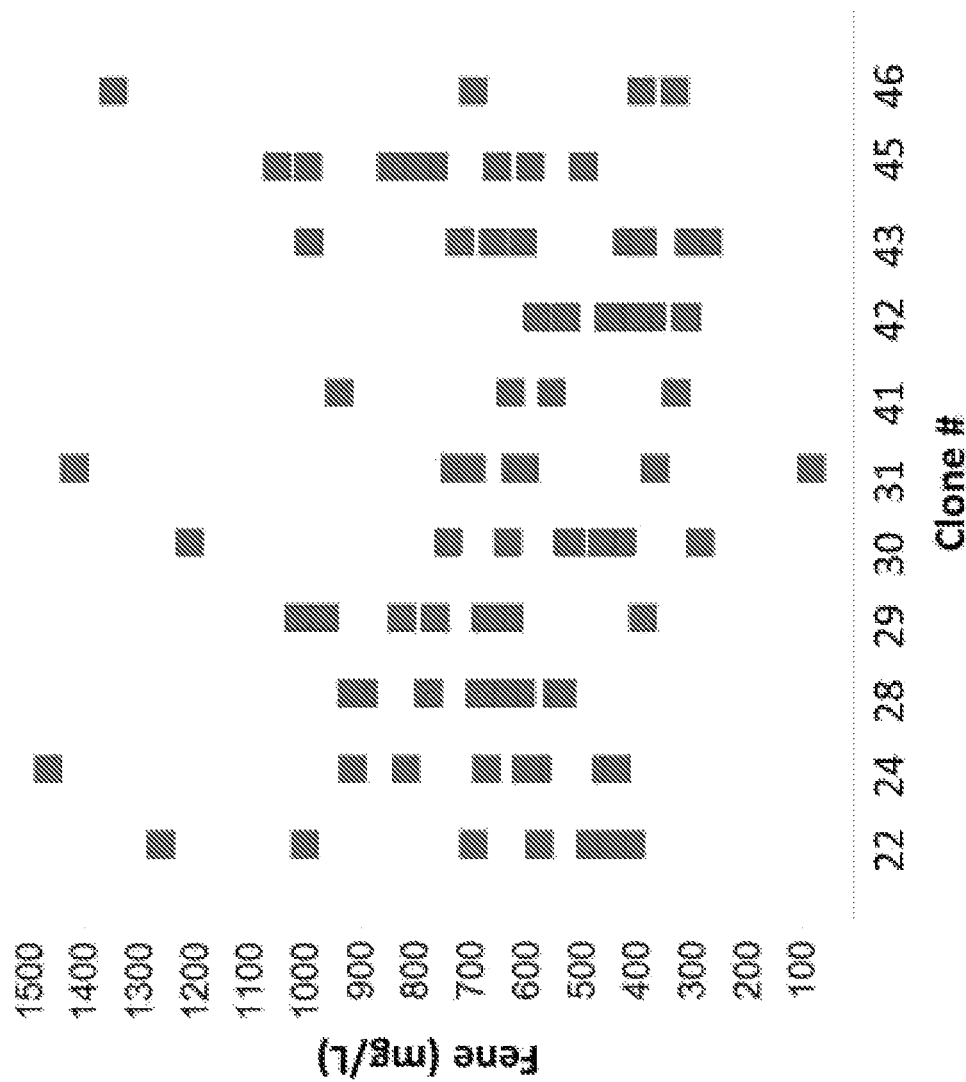

FIG. 21 provides the results of an experiment to confirm famesene production in a batch sucrose plate model assay for the 11 clones identified by cPCR as having fully integrated the famesene pathway. Each cPCR positive clone produced famesene in amounts ranging from ~0.1 to 1.5 g/L famesene.

Figure 22:
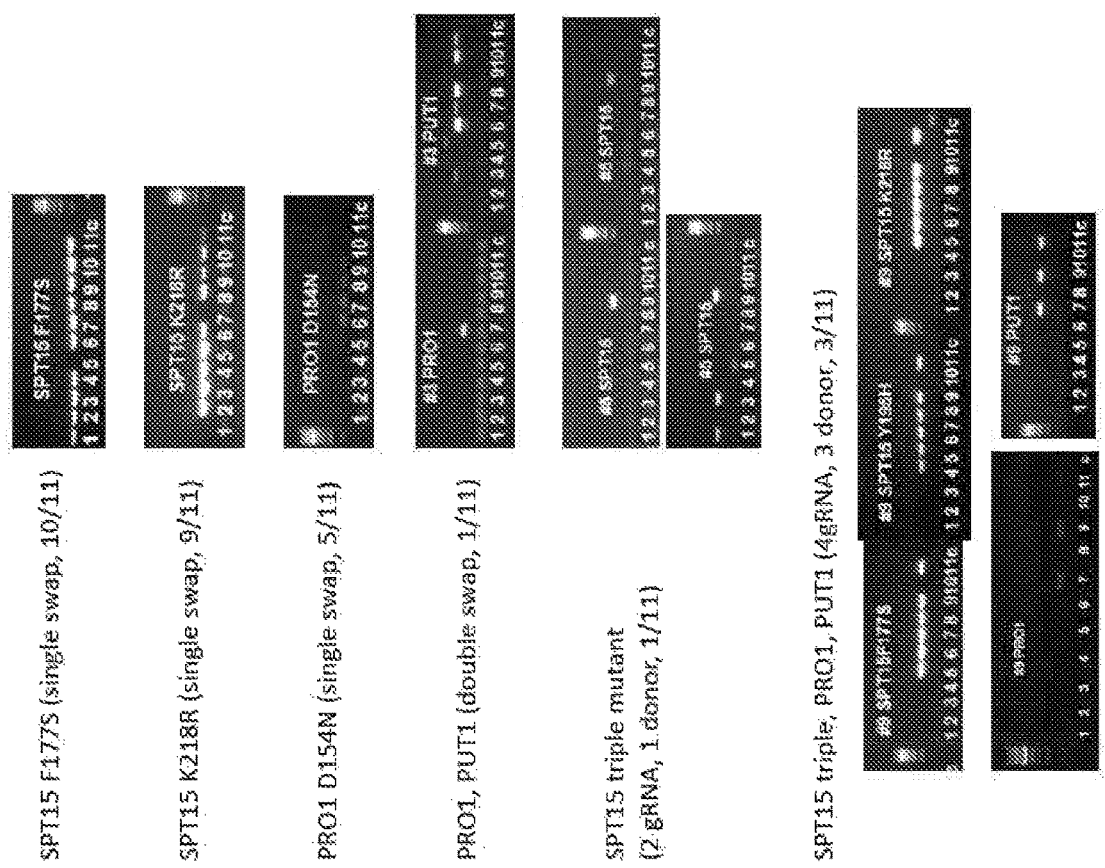

FIG. 22 provides the results of allele swap cPCRs which demonstrate high rates of single and multiplexed allele swaps.

FIGS. 23 (A)-(F) provide results of experiments that demonstrate that multiplexed allele swaps produced using CRISPR display synergistic phenotypes. (A) Truncation of ACE2 results in incomplete cell division and clumping. (B) Secretory and cell cycle mutants do not grow at 37° C. (C) Cell cycle mutants arrest in G1 at non-permissive temperature. (D) SEC3-GFP is localized correctly to the bud at permissive temperature (23° C.), but mislocalized at elevated temperature in secretory mutants. (E) Two alleles individually increase heat tolerance, and together produce an even more heat tolerant strain. (F) Several mutations impart ethanol resistance, but all alleles together synergize for even further increased ethanol tolerance. All five changes were made simultaneously using CRISPR.

Figure 24:
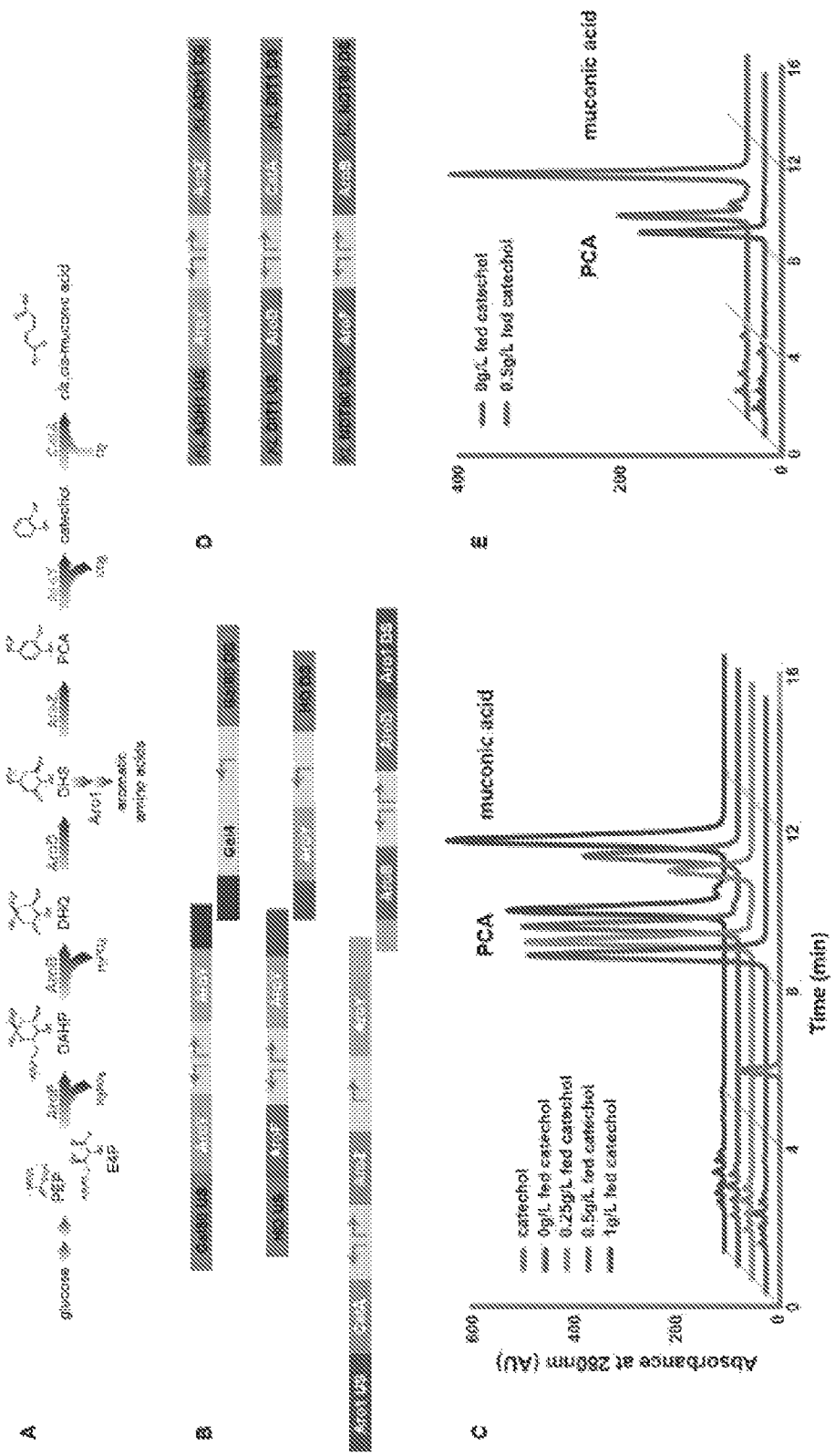

FIG. 24 provides results demonstrating integration of the entire muconic acid biosynthesis pathway into a naive yeast strain in a single transformation. (A) Schematic of the muconic biosynthesis pathway. (B) The muconic acid pathway was introduced into three separate loci via six pieces of donor DNA totaling 28 kb. Each piece recombined into the genome through a region of homology upstream (US) or downstream (DS) of the targeted locus (ends) as well as with another piece of donor DNA with overlapping homology (center). (C) One-step integration of the pathway permitted fast diagnosis of the pathway bottleneck: AroY. Strains with the integrated pathway produce ~3 g/L PCA (second line from bottom). When fed catechol (first line from bottom), these strains fully convert all available catechol to muconic acid (third, fourth, and fifth lines from bottom). (D) The muconic acid pathway was also introduced into three separate loci in *K. lactis* in a single step (10 kb). (E) *K. lactis* strains with the integrated pathway produce ~1 g/L PCA (first line from bottom), exhibiting the same pathway bottleneck as *S. cerevisiae*. When fed catechol, these strains also fully convert all available catechol to muconic acid (second line from bottom).

Figure 25:
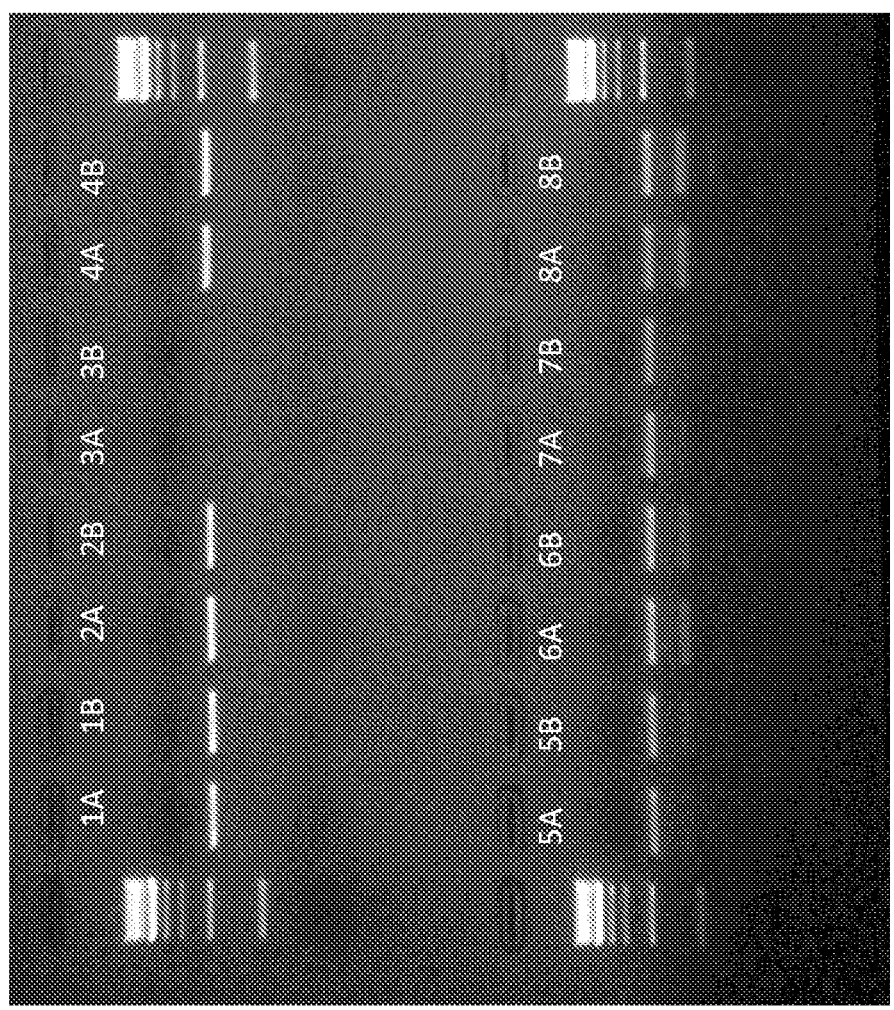

FIG. 25 provides results of an RFLP assay on amplicons of a targeted genomic locus in 293T cells following transfection with CRISPR reagents and donor DNA. Cells were transfected as follows: (2) Closed "no gRNA" plasmid+linear donor; (3) Open "no gRNA" plasmid; (4) Open "no gRNA" plasmid+CD4 gap fragment; (6) Closed gRNA plasmid+linear donor; (8) Open gRNA plasmid+full gap+linear donor.

5. DETAILED DESCRIPTION OF THE EMBODIMENTS

5.1 Definitions

As used herein, the terms "cleaves," "cleavage" and/or "cleaving" with respect to a nuclease, e.g. a homing endonuclease, zinc-finger nuclease, TAL-effector nuclease, or RNA-Guided DNA endonuclease (e.g., CRISPR/Cas9) refer to the act of creating a break in a particular nucleic acid. The break can leave a blunt end or sticky end (i.e., 5' or 3' overhang), as understood by those of skill in the art. The terms also encompass single strand DNA breaks ("nicks") and double strand DNA breaks.

As used herein, the term "engineered host cell" refers to a host cell that is generated by genetically modifying a parent cell using genetic engineering techniques (i.e., recombinant technology). The engineered host cell may comprise additions, deletions, and/or modifications of nucleotide sequences to the genome of the parent cell.

As used herein, the term "heterologous" refers to what is not normally found in nature. The term "heterologous nucleotide sequence" refers to a nucleotide sequence not normally found in a given cell in nature. As such, a heterologous nucleotide sequence may be: (a) foreign to its host cell (i.e., is "exogenous" to the cell); (b) naturally found in the host cell (i.e., "endogenous") but present at an unnatural quantity in the cell (i.e., greater or lesser quantity than naturally found in the host cell); or (c) be naturally found in the host cell but positioned outside of its natural locus.

As used herein, the term "homology" refers to the identity between two or more nucleic acid sequences, or two or more amino acid sequences. Sequence identity can be measured in terms of percentage identity (or similarity or homology); the higher the percentage, the more near to identical the sequences are to each other. Homologs or orthologs of nucleic acid or amino acid sequences possess a relatively high degree of sequence identity when aligned using standard methods. Methods of alignment of sequences for comparison are well known in the art. Various programs and alignment algorithms are described in: Smith & Waterman, *Adv. Appl. Math.* 2:482, 1981; Needleman & Wunsch, *J.*

Mol. Biol. 48:443, 1970; Pearson & Lipman, *Proc. Natl. Acad. Sci. USA* 85:2444, 1988; Higgins & Sharp, *Gene*, 73:237-44, 1988; Higgins & Sharp, *CABIOS* 5:151-3, 1989; Corpet et al., *Nuc. Acids Res.* 16:10881-90, 1988; Huang et al. *Computer Appls. Biosc.* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations. The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

As used herein, the term "markerless" refers to integration of a donor DNA into a target site within a host cell genome without accompanying integration of a selectable marker. In some embodiments, the term also refers to the recovery of such a host cell without utilizing a selection scheme that relies on integration of selectable marker into the host cell genome. For example, in certain embodiments, a selection marker that is episomal or extrachromasomal may be utilized to select for cells comprising a plasmid encoding a nuclease capable of cleaving a genomic target site. Such use would be considered "markerless" so long as the selectable marker is not integrated into the host cell genome.

As used herein, the term "operably linked" refers to a functional linkage between nucleic acid sequences such that the sequences encode a desired function. For example, a coding sequence for a gene of interest, e.g., a selectable marker, is in operable linkage with its promoter and/or regulatory sequences when the linked promoter and/or regulatory region functionally controls expression of the coding sequence. It also refers to the linkage between coding sequences such that they may be controlled by the same linked promoter and/or regulatory region; such linkage between coding sequences may also be referred to as being linked in frame or in the same coding frame. "Operably linked" also refers to a linkage of functional but non-coding sequences, such as an autonomous propagation sequence or origin of replication. Such sequences are in operable linkage when they are able to perform their normal function, e.g., enabling the replication, propagation, and/or segregation of a vector bearing the sequence in host cell.

As used herein, the term "selecting a host cell expressing a selectable marker" also encompasses enriching for host cells expressing a selectable marker from a population of transformed cells.

As used herein, the term "selectable marker" refers to a gene which functions as guidance for selecting a host cell comprising a marker vector as described herein. The selectable markers may include, but are not limited to: fluorescent markers, luminescent markers and drug selectable markers, and the like. The fluorescent markers may include, but are not limited to, genes encoding fluorescence proteins such as green fluorescent protein (GFP), cyan fluorescent protein (CFP), yellow fluorescent protein (YFP), red fluorescent protein (dsRFP) and the like. The luminescent markers may include, but are not limited to, genes encoding luminescent proteins such as luciferases. Drug selectable markers suitable for use with the methods and compositions provided herein include, but are not limited to, resistance genes to antibiotics, such as ampicillin, streptomycin, gentamicin, kanamycin, hygromycin, tetracycline, chloramphenicol, and neomycin. In some embodiments, the selection may be positive selection; that is, the cells expressing the marker are isolated from a population, e.g. to create an enriched population of cells comprising the selectable marker. In other instances, the selection may be negative selection; that is, the population is isolated away from the cells, e.g. to create an enriched population of cells that do not comprise the selectable marker. Separation may be by any convenient separation technique appropriate for the selectable marker used. For example, if a fluorescent marker has been utilized, cells may be separated by fluorescence activated cell sorting, whereas if a cell surface marker has been inserted, cells may be separated from the heterogeneous population by affinity separation techniques, e.g. magnetic separation, affinity chromatography, "panning" with an affinity reagent attached to a solid matrix, or other convenient technique.

As used herein, the term "simultaneous," when used with respect to multiple integration, encompasses a period of time beginning at the point at which a host cell is co-transformed with a nuclease, e.g. a plasmid encoding a nuclease, and more than one donor DNA to be integrated into the host cell genome, and ending at the point at which the transformed host cell, or clonal populations thereof, is screened for successful integration of the donor DNAs at their respective target loci. In some embodiments, the period of time encompassed by "simultaneous" is at least the amount of time required for the nuclease to bind and cleave its target sequence within the host cell's chromosome(s). In some embodiments, the period of time encompassed by "simultaneous" is at least 6, 12, 24, 36, 48, 60, 72, 96 or more than 96 hours, beginning at the point at which the a host cell is co-transformed with a nuclease, e.g. a plasmid encoding a nuclease, and more than one donor DNA.

5.2 Methods of Integrating Exogenous Nucleic Acids

Provided herein are methods of integrating one or more exogenous nucleic acids into one or more selected target sites of a host cell genome. In certain embodiments, the methods comprise contacting the host cell with one or more integration polynucleotides, i.e., donor DNAs, comprising an exogenous nucleic acid to be integrated into the genomic target site; one or more nucleases capable of causing a double-strand break near or within the genomic target site; and a linear nucleic acid capable of homologous recombination with itself or with one or more additional linear nucleic acids contacted with the host cell, whereupon said homologous recombination of the linear nucleic acid in the host cell results in formation of a circular extrachromosomal nucleic acid comprising a coding sequence for a selectable marker. In some embodiments, the contacted host cell is then grown under selective conditions. Without being bound by theory of operation, it is believed that forcing the host cell to circularize the expression vector via HR, in order to be selected in accordance with the methods described herein, increases the likelihood that the selected cell has also successfully performed the one or more intended HR-mediated genomic integrations of exogenous DNA.

In a particular aspect, provided herein is a method for markerless integration of an exogenous nucleic acid into a target site of a host cell genome, the method comprising:
(a) contacting a host cell with:
(i) an exogenous nucleic acid (ES) comprising a first homology region (HR1) and a second homology region (HR2), wherein (HR1) and (HR2) are capable of initiating host cell mediated homologous recombination at said target site (TS);
(ii) a nuclease (N) capable of cleaving at (TS), whereupon said cleaving results in homologous recombination of (ES) at (TS); and (iii) a linear nucleic acid capable of homologous recombination with itself or with one or more additional linear nucleic acids contacted with the host cell, whereupon said homologous recombination results in formation of a circular extrachromosomal nucleic acid comprising a coding sequence for a selectable marker; and (b) selecting a host cell that expresses the selectable marker.

In some embodiments, the method comprises recovering a host cell having (ES) integrated at (TS), wherein said recovering does not require integration of a selectable marker.

FIG. 1 provides an exemplary embodiment of genomic integration of an exogenous nucleic acid using a site-specific nuclease and a pre-recombination composition capable of assembling in vivo via host cell mediated HR to form a circular marker expression vector. A donor polynucleotide is introduced to a host cell, wherein the polynucleotide comprises a nucleic acid of interest (D) flanked by a first homology region (HR1) and a second homology region (HR2). HR1 and HR2 share homology with 5' and 3' regions, respectively, of a genomic target site (TS). A site-specific nuclease (N) is also introduced to the host cell, wherein the nuclease is capable of recognizing and cleaving a unique sequence within the target site. Also introduced to the cell is a pre-recombination composition, which in this example comprises two linear pre-recombination molecules each comprising two homology regions capable of homologously recombining with each other. In this example, the homology regions are positioned at the 5' and 3' termini of each pre-recombination molecule. One homology region of each pre-recombination molecule comprises a partial coding sequence for a selectable marker (GF and FP, respectively), such that upon HR between the two homology regions, a complete and operable coding sequence of the selectable marker (GFP) is reconstituted on a circularized marker expression vector. In general, such a circularization is selected for by culturing the cells under conditions that select for expression of the selectable marker, for example, by supplementing the culture medium with a selective agent (e.g., an antibiotic) where the selectable marker is a drug resistance marker, or sorting for cells which express a marker detectable by colorimetric or fluorescent detection methods. Concomitantly, in cells that are competent for HR, induction of a double-stranded break within the target site by the site-specific nuclease facilitates the HR-mediated integration of the donor nucleic acid of interest at the cleaved target site. By making it a requirement that the host cell circularize the expression vector via HR in order to be selected, the recovery of cells that have also performed HR-mediated integration of the exogenous donor DNA is also increased. This increased frequency of recovery obviates the need to co-integrate a selectable marker in order to select transformants having undergone a recombination event. By eliminating the need for selectable markers, for example, during construction of an engineered microbe, the time needed to engineer a host cell genome is greatly reduced. In addition, engineering strategies are no longer limited by the need to recycle selectable markers due to there being a limited cache of markers available for a given host organism.

In some embodiments, markerless recovery of a transformed cell comprising a successfully integrated exogenous nucleic acid occurs within a frequency of about one every 1000, 900, 800, 700, 600, 500, 400, 300, 200 or 100 contacted host cells, or clonal populations thereof, screened.

In particular embodiments, markerless recovery of a transformed cell comprising a successfully integrated exogenous nucleic acid occurs within a frequency of about one every 90, 80, 70, 60, 50, 40, 30, 20, or 10 contacted host cells, or clonal populations thereof, screened. In more particular embodiments, markerless recovery of a transformed cell comprising a successfully integrated exogenous nucleic acid occurs within a frequency of about one every 9, 8, 7, 6, 5, 4, 3, or 2 contacted host cells, or clonal populations thereof, screened.

A variety of methods are available to identify those cells having an altered genome at or near the target site without the use of a selectable marker. In some embodiments, such methods seek to detect any change in the target site, and include but are not limited to PCR methods, sequencing methods, nuclease digestion, e.g., restriction mapping, Southern blots, and any combination thereof. Phenotypic readouts, for example, a predicted gain or loss of function, can also be used as a proxy for effecting the intended genomic modification(s).

In another aspect, provided herein is a method for integrating a plurality of exogenous nucleic acids into a host cell genome, the method comprising:

(a) contacting a host cell with:

(i) a plurality of exogenous nucleic acids, wherein each exogenous nucleic acid $(ES)_x$ comprises a first homology region $(HR1)_x$ and a second homology region $(HR2)_x$, wherein $(HR1)_x$ and $(HR2)_x$ are capable of initiating host cell mediated homologous recombination of $(ES)_x$ at a target site $(TS)_x$ of said host cell genome;

(ii) for each said target site $(TS)_x$, a nuclease (N), capable of cleaving at $(TS)_x$, whereupon said cleaving results in homologous recombination of $(ES)_x$ at $(TS)_x$; and (iii) a linear nucleic acid capable of homologous recombination with itself or with one or more additional linear nucleic acids contacted with the host cell, whereupon said homologous recombination results in formation of a circular extrachromosomal nucleic acid comprising a coding sequence for a selectable marker; and (b) selecting a host cell that expresses the selectable marker.

In some embodiments, the method further comprises recovering a host cell wherein each selected exogenous nucleic acid $(ES)_x$ has integrated at each selected target sequence $(TS)_x$, wherein x is any integer from 1 to n wherein n is at least 2.

FIG. 2 provides an exemplary embodiment of simultaneous genomic integration of a plurality of exogenous nucleic acids using a plurality of site-specific nucleases. In this example, three different donor polynucleotides are introduced to a host cell, wherein each polynucleotide comprises an exogenous nucleic acid $(ES)_x$ comprising a nucleic acid of interest $(D)_x$, wherein x=1, 2 or 3. Each $(D)_x$ is flanked by a first homology region $(HR1)_x$ and a second homology region $(HR2)_x$. $(HR1)_x$ and $(HR2)_x$ share homology with 5' and 3' regions, respectively, of a selected target site $(TS)_x$, of three total unique target sites in the genome. One or more site-specific nucleases $(N)_x$ (for example, one or more (e.g. "x" number of) endonucleases having a unique recognition site; or an RNA-guided endonuclease together with one or more (e.g. "x" number of) guide RNAs) are also introduced to the host cell, wherein each nuclease $(N)_x$ is capable of recognizing and cleaving a unique sequence within its corresponding target site, $(TS)_x$. Also introduced to the cell is a pre-recombination composition, which in this example comprises two linear pre-recombination molecules each comprising two homology regions capable of homologously recombining with each other. In this example, the homology regions are positioned at the 5' and 3' termini of each pre-recombination molecule. One homology region of each pre-recombination molecule comprises a partial coding sequence for a selectable marker (GF and FP, respectively), such that upon HR between the two homology regions, a complete and operable coding sequence of the selectable marker (GFP) is reconstituted on a circularized marker expression vector. Such a circularization is selected for by culturing the cells under conditions that select for expression of the selectable marker. Concomitantly, in cells that are competent for HR, cleavage of a target site (TS)$_x$ by its corresponding site-specific nuclease (N)$_x$ facilitates integration of the corresponding nucleic acid interest (D)$_x$ at (TS)$_x$ by the host cell's endogenous homologous recombination machinery. By making it a requirement that the host cell circularize the expression vector via HR in order to be selected, the recovery of cells that have also performed HR-mediated integration of the exogenous donor DNAs is also increased.

In particular embodiments, each exogenous nucleic acid (ES)$_x$, optionally comprising a nucleic acid of interest (D)$_x$, is integrated into its respective genomic target site (TS)$_x$ simultaneously, i.e., with a single transformation of the host cell with the plurality of integration polynucleotides and plurality of nucleases. In some embodiments, the methods are useful to simultaneously integrate any plurality of exogenous nucleic acids (ES)$_x$, that is, where x is any integer from 1 to n wherein n is at least 2, in accordance with the variables recited for the above described method. In some embodiments, the method of simultaneous integration provided herein is useful to simultaneously integrate up to 10 exogenous nucleic acids (ES)$_x$ into 10 selected target sites (TS)$_x$, that is, where x is any integer from 1 to n wherein n=2, 3, 4, 5, 6, 7, 8, 9, or 10. In some embodiments, the method of simultaneous integration provided herein is useful to simultaneously integrate up to 20 exogenous nucleic acids (ES)$_x$ into 20 selected target sites (TS)$_x$, that is, where x is any integer from 1 to n wherein n=2, 3, 4, 5, 6, 7, 8, 9, 10, 11, 12, 13, 14, 15, 16, 17, 18, 19 or 20. In some embodiments, n=2. In some embodiments, n=3. In some embodiments, n=4. In some embodiments, n=5. In some embodiments, n=6. In some embodiments, n=7. In some embodiments, n=8. In some embodiments, n=9. In some embodiments, n=10. In some embodiments, n=11. In some embodiments, n=12. In some embodiments, n=13. In some embodiments, n=14. In some embodiments, n=15. In some embodiments, n=16. In some embodiments, n=17. In some embodiments, n=18. In some embodiments, n=19. In some embodiments, n=20. In some embodiments, the method of simultaneous integration provided herein is useful to simultaneously integrate more than 20 exogenous nucleic acids.

As with integration of a single exogenous nucleic acid at a single target site, the recovery of a host cell that has successfully integrated each exogenous nucleic acid at its respective target site occurs at a substantially higher frequency as compared to not contacting the host cell with one or more linear pre-recombination molecules described herein, and selecting for expression of the selectable marker. In some embodiments, this increased frequency of integration obviates the requirement for co-integration of one or more selectable markers for the identification of the plurality of recombination events. In some embodiments, markerless recovery of a transformed cell comprising a plurality of successfully integrated exogenous nucleic acid occurs within a frequency of about one every 1000, 900, 800, 700, 600, 500, 400, 300, 200 or 100 contacted host cells, or clonal populations thereof, screened. In particular embodiments, markerless recovery occurs within a frequency of about one every 90, 80, 70, 60, 50, 40, 30, 20, or 10 contacted host cells, or clonal populations thereof, screened. In more particular embodiments, markerless recovery occurs within a frequency of about one every 9, 8, 7, 6, 5, 4, 3, or 2 contacted host cells, or clonal populations thereof, screened.

5.2.1 HR-Mediated In Vivo Assembly of Circular Marker Expression Vectors

The methods provided herein comprise host cell mediated assembly of a circular expression vector via gap repair. Gap repair is a fast and efficient method for assembling recombinant DNA molecules in vivo. The technique has been described to be effective for assembling and/or repairing plasmids in a number of organisms, including bacteria (*Escherichia coli*; see, e.g., Datta et al., *Gene* 379:109-115 (2006)), yeast (*Saccharomyces cerevisiae*; see e.g., Bessa et al., *Yeast* 29:419-423 (2012)), insects (*Drosophila melanogaster*; see, e.g., Carreira-Rosario et al., *J Vis Exp* 77:e50346 (2013)) and mammalian cells (human cells; see e.g., Adar et al., *Nucleic Acids Research* 37(17):5737-5748 (2009)). Gap repair can produce a circular DNA molecule by homologous recombination between two homologous regions of a single linear DNA, or between two or more separate linear DNA fragments. Typically, the assembled circularized DNA acts as a vector carrying replicative sequences and a selective marker. See, e.g., Orr-Weaver et al., *Methods Enzymol* 101:228-245 (1983). The technique, outlined in FIG. 4, typically starts with co-transformation of a linear "gapped" vector and a linear DNA fragment (insert) (Orr-Weaver et al., 1983). In cells competent for homologous recombination, recombination occurs between two pairs of flanking stretches of homologous sequences between vector and insert, resulting in a larger circular vector wherein the gap has been repaired. A simple way to provide flanking homology of the insert is by polymerase chain reaction (PCR) where tailed primers provide the homology regions.

In one aspect of the methods and compositions provided herein, the host cell is contacted with a single contiguous linear (gapped) nucleic acid that serves as a pre-recombination vector intermediate. As used herein, the phrase "single nucleic acid" includes the embodiment of multiple copies of the same nucleic acid molecule. In some embodiments, the pre-recombination vector is self-circularizing, and comprises two sequence-specific recombination regions capable of homologous recombination with each other, such that introduction into a recombination-competent host cell results in formation of a circular expression vector. In some embodiments, the recombination regions are positioned at or near the termini of the linear pre-recombination vector (e.g, one recombination region is positioned at each termini of the linear vector, with additional sequences intervening the two regions), internal to the termini (e.g., each recombination region is flanked on both ends by additional sequences), or a combination thereof (e.g., one recombination is at one termini of the linear vector and the other is internal thereto and flanked on both sides by additional sequences). In some embodiments, the first and second recombination regions can comprise any nucleotide sequence of sufficient length and share any sequence identity that allows for homologous recombination with each other. In some embodiments, "sufficient sequence identity" refers to sequences with at least 70%, at least 75%, at least 80%, at least 85%, at least 90%, at least 95%, at least 99%, or 100%, identity between recombination regions, over a length of, for example, at least 15 base pairs, at least 20 base pairs, at least 50 base pairs, at least 100 base pairs, at least 250 base pairs, at least 500 base pairs, or more than 500 base pairs. The extent of sequence identity may be determined using any computer program and associated parameters, including those described herein, such as BLAST 2.2.2 or FASTA version 3.0t78, with the default parameters. For a discussion of effective lengths of homology between recombination regions, see Hasty et al., *Mol Cell Biol* 11:5586-91 (1991).

In some embodiments, the first and second recombination regions share at least 25% nucleotide sequence identity. In some embodiments, the first and second recombination regions share at least 30% nucleotide sequence identity. In some embodiments, the first and second recombination regions share at least 35% nucleotide sequence identity. In some embodiments, the first and second recombination regions share at least 40% nucleotide sequence identity. In some embodiments, the first and second recombination regions share at least 45% nucleotide sequence identity. In some embodiments, the first and second recombination regions share at least 50% nucleotide sequence identity. In some embodiments, the first and second recombination regions share at least 60% nucleotide sequence identity. In some embodiments, the first and second recombination regions share at least 65% nucleotide sequence identity. In some embodiments, the first and second recombination regions share at least 70% nucleotide sequence identity. In some embodiments, the first and second recombination regions share at least 75% nucleotide sequence identity. In some embodiments, the first and second recombination regions share at least 80% nucleotide sequence identity. In some embodiments, the first and second recombination regions share at least 85% nucleotide sequence identity. In some embodiments, the first and second recombination regions share at least 90% nucleotide sequence identity. In some embodiments, the first and second recombination regions share at least 95% nucleotide sequence identity. In some embodiments, the first and second recombination regions share at least 99% nucleotide sequence identity. In some embodiments, the first and second recombination regions share 100% nucleotide sequence identity.

In certain embodiments, each of the first and second recombination regions consists of about 50 to 5,000 nucleotides. In certain embodiments, each of the first and second recombination regions comprises about 50 to 5,000 nucleotides. In certain embodiments, each of the first and second recombination regions consists of about 100 to 2,500 nucleotides. In certain embodiments, each of the first and second recombination regions consists of about 100 to 1,000 nucleotides. In certain embodiments, each of first and second recombination regions consists of about 250 to 750 nucleotides. In certain embodiments, each of the first and second recombination regions consists of about 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900 or 5,000 nucleotides. In some embodiments, each of the first and second recombination regions consists of about 500 nucleotides. In some embodiments, each of first and second recombination regions comprises at least 18 nucleotide base pairs. In some embodiments, each of first and second recombination regions consists of 15 to 500 nucleotide base pairs. In some embodiments, each of first and second recombination regions consists of 15 to 500, 15 to 495, 15 to 490, 15 to 485, 15 to 480, 15 to 475, 15 to 470, 15 to 465, 15 to 460, 15 to 455, 15 to 450, 15 to 445, 15 to 440, 15 to 435, 15 to 430, 15 to 425, 15 to 420, 15 to 415, 15 to 410, 15 to 405, 15 to 400, 15 to 395, 15 to 390, 15 to 385, 15 to 380, 15 to 375, 15 to 370, 15 to 365, 15 to 360, 15 to 355, 15 to 350, 15 to 345, 15 to 340, 15 to 335, 15 to 330, 15 to 325, 15 to 320, 15 to 315, 15 to 310, 15 to 305, 15 to 300, 15 to 295, 15 to 290, 15 to 285, 15 to 280, 15 to 275, 15 to 270, 15 to 265, 15 to 260, 15 to 255, 15 to 250, 15 to 245, 15 to 240, 15 to 235, 15 to 230, 15 to 225, 15 to 220, 15 to 215, 15 to 210, 15 to 205, 15 to 200, 15 to 195, 15 to 190, 15 to 185, 15 to 180, 15 to 175, 15 to 170, 15 to 165, 15 to 160, 15 to 155, 15 to 150, 15 to 145, 15 to 140, 15 to 135, 15 to 130, 15 to 125, 15 to 120, 15 to 115, 15 to 110, 15 to 105, 15 to 100, 15 to 95, 15 to 90, 15 to 85, 15 to 80, 15 to 75, 15 to 70, 15 to 65, 15 to 60, 15 to 55, 15 to 50, 15 to 45, 15 to 40, 15 to 35, 15 to 30, 15 to 25, or 15 to 20 nucleotide base pairs. In some embodiments, each of first and second recombination regions consists of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199 or 200 nucleotide base pairs.

In preferable embodiments of the methods and compositions provided herein, each homology region of a homology region pair comprises nucleotide sequences of sufficient length and sequence identity that allows for homologous recombination with each other, but not with other regions of the pre-recombination molecule(s) participating in the assembly, nor with any genomic regions of the host cell.

While in some embodiments, the circularized expression vector is formed from a single pre-recombination molecule that is self-circularizing, in other embodiments, the circularized expression vector is formed by the HR-mediated assembly of two or more linear pre-recombination molecules. For example, a circularized vector may be assembled from two linear pre-recombination molecules, wherein the first molecule is a gapped vector and the second molecule is an insert comprising two separate homologous regions capable of recombining with two homology regions on the gapped vector. For each of the gapped linear vector and the linear insert, the recombination regions can be positioned at or near the termini of the linear pre-recombination vector (e.g, one recombination region is positioned at each termini, with additional sequences intervening the two regions), internal to the termini (e.g., each recombination region is flanked on both ends by additional sequences), or a combination thereof (e.g., one recombination is at one termini and the other is internal thereto and flanked on both sides by additional sequences). In still other embodiments, the insert which repairs the gapped vector can itself be assembled from at least two linear nucleic acids comprising homologous regions to each other. For example, the circularized vector may be formed from three distinct linear pre-recombination fragments, wherein the first linear molecule comprises homology regions $A_1$ and $B_1$, the second linear molecule comprises $B_2$ and $C_2$, and the third linear molecule comprises $C_3$ and $A_3$, such that recombination between homologous regions of each fragment (i.e., $A_1$ with $A_3$, $B_1$ with $B_2$, and $C_2$ with $C_3$) in an HR-competent host cell results in formation of a circularized expression vector comprising regions A→B→C.

In still other embodiments, the circularized vector is assembled in a HR-competent host cell from at least 4, 5, 6, 7, 8, 9 or 10 distinct linear pre-recombination fragments in a similar fashion. Without being bound by theory of operation, it is believed that requiring the circularized expression vector to be assembled from more than two linear pre-recombination molecules selects for host cells that are particularly adept at homologous recombination. Thus, assembly of the circular expression vector from multiple pre-recombination molecules may be preferred when higher order integration events are desired, e.g., multiplex genomic integration (for example, of 2 or more donor exogenous DNAs), or when performing genomic integration into a cell type known or suspected to have very low rates of HR. In one example, for a multiplex (i.e., simultaneous) integration of three exogenous donor nucleic acids into three respective genomic target sites of a host cell, the host cell is "forced" to assemble at least three linear pre-recombination fragments to form the circular expression vector. Only cells that can successfully recombine the three fragments to form the circular vector that expresses a selectable marker can survive the selection, i.e. be selected for, and these cells will to be more likely to have successfully integrated each of the three exogenous donor nucleic acids into their respective genomic target sites. In some embodiments, when multiplex integration of at least 2, 3, 4, 5, 6, 7, 8, 9, 10 or greater than 10 exogenous donor nucleic acids into at least 2, 3, 4, 5, 6, 7, 8, 9, 10 or greater than 10 respective genomic target sites is desired, the host cell is forced to assemble, i.e., recombine at least 2, 3, 4, 5, 6, 7, 8, 9, 10 or greater than 10 pre-recombination fragments to form the circular expression vector, from which a selectable marker is expressed in the host cell. In some embodiments, the in vivo assembly of at least 2, 3, 4, 5, 6, 7, 8, 9, 10 or greater than 10 pre-recombination fragments forms a circular expression vector comprising coding sequences for more than one selectable marker (e.g. two, three, or more than three different selectable markers).

In preferred embodiments, the circularized expression vector, once assembled, comprises a coding sequence for a selectable marker, and suitable regulatory sequences such as a promoter and/or a terminator that enables expression of the marker in the host cell. Selectable markers include those which both enable selection of host cells containing a selectable marker, while other embodiments enable selecting cells which do not contain the selectable maker, which find use in embodiments wherein elimination of the circularized expression vector after selection is desired (as discussed below). In some embodiments, prior to assembly of the circular expression vector, the linear pre-recombination molecule, or at least one of the pre-recombination fragments of a multi-fragment assembly, comprises an intact coding sequence for the selectable marker, in operable linkage to its regulatory sequences, separate and apart from the homology regions involved in the HR-mediated assembly. Thus, assembly of the circular expression vector does not alter the coding sequence of the selectable marker nor any of its regulatory sequences needed for expression. In some such embodiments, the circularization event merely enables the propagation of, and sustained expression from, the coding sequence of the marker, whereas non-circularized linear vector cannot be propagated and/or maintained in the host cell. In preferred embodiments, host cells which do not comprise a circularized expression vector do not survive the selection step and/or are not selected for, in the methods described herein. Without being bound by theory of operation, it is believed that by requiring the host cell to circularize the expression vector via HR, in order to be selected in accordance with the methods described herein, increases the likelihood that the selected cell has also successfully performed the one or more intended HR-mediated genomic integrations of exogenous DNA.

In other embodiments, the sequence encoding the selectable marker, and/or its regulatory sequences required for expression, is not intact, i.e., is not in operable linkage, on any single pre-recombination molecule. In some such embodiments, only when the expression vector is circularized is the marker coding sequence, along with its regulatory elements, brought into operable linkage. Thus, the sequence encoding the marker, and or its necessary regulatory sequences may be divided into any number of overlapping homologous sequences distributed among any number fragments participating in the assembly, so long as HR between the component pre-recombination fragments results in reconstitution of the coding sequence of the selectable marker in operable linkage with its regulatory sequences. These embodiments are particularly useful to avoid selecting host cells in which formation of a circularized expression vector results from joining of the pre-recombination fragments via non-HR mechanisms, for example, non-homologous end-joining or single strand annealing; such cells surviving the selection would represent false positives. The frequency of these unwanted events can be lowered by removing the 5'-phosphate groups on the pre-recombination fragment(s) using phosphatase, which is the standard method used for in vitro ligation. Vector relegation may also be avoided by treatment of the pre-recombination fragment(s) with Taq DNA polymerase and dATP; this has been reported to be particularly effective at preventing vector re-circularization in vivo, facilitating the screening for true recombinant clones. See Bessa et al., *Yeast* 29:419-423 (2012). In addition, false positives caused by erroneous introduction of pre-circularized DNA may be avoided by prepping the pre-recombination fragment(s) by PCR rather than linearizing a circular vector by endonuclease digestion then isolating the fragment, which may carry over non-digested circular template. Nevertheless, without being bound by theory of operation, it is believed that requiring the host cell to reconstitute the marker coding sequence via HR, e.g., from at least two partial sequences, in order to survive the selection process, increases the likelihood that a cell selected in accordance with the methods described herein has also successfully performed the one or more intended HR-mediated genomic integrations of exogenous DNA.

In some embodiments of the methods provided herein, the circularized expression vector, once assembled, further comprises a coding sequence for a site-specific nuclease described herein, and suitable regulatory sequences such as a promoter and/or a terminator that enables expression of the nuclease in the host cell. In some embodiments, the nuclease is selected from the group consisting of CRISPR/Cas-associated RNA-guided endonuclease, a meganuclease, a zinc finger nuclease, a TAL-effector DNA binding domain-nuclease fusion protein (TALEN), a transposase, and a site-specific recombinase. In some embodiments, the nuclease is a CRISPR-associated RNA-guided endonuclease. In some such embodiments, the circular expression vector further comprises a sequence or sequences that encode obligate guide sequences for a RNA-guided endonuclease, for example, a crRNA activity and a tracrRNA activity, which enables site-specific recognition and cleavage of the genomic target DNA by the RNA-guided DNA endonuclease. In some embodiments, the crRNA activity and the tracrRNA activity are expressed from the circular expression vector as a single contiguous RNA molecule, i.e., a chimeric guide RNA (gRNA) molecule. In some embodiments, the circular expression vector comprises one or more sequences encoding a guide sequence(s) (e.g., a gRNA) for an RNA-guided endonuclease, without also comprising the coding sequence for the nuclease. In some such embodiments, one or more sequences encoding the RNA-guided nuclease may be supplied on a separate vector, integrated into the genome, or the nuclease may be introduced to the cell as a protein, e.g., expressed and purified in vitro.

In any of the aforementioned embodiments in which nuclease coding sequences, and/or additional sequences required for expression and operability of the nuclease in the cell is included in the circularized expression vector, these sequences may be intact (i.e., in operable linkage) in any of the one or more pre-recombination linear fragment(s) participating in the assembly reaction, or alternatively, divided into any number of overlapping homologous sequences distributed among any number fragments participating in the assembly, so long as HR between the component pre-recombination fragments results in reconstitution of the coding sequence of the nuclease in operable linkage with its regulatory sequences. Advantageously, coupling the coding sequence of the nuclease (and/or sequences encoding guide RNA sequences where the nuclease is an RNA-guided nuclease) to the circularized expression vector ensures that expression of these sequences is maintained at a level and duration sufficient to assist in the HR-mediated integration event. In accordance with the methods described herein, the efficiency of gene targeting can be improved when combined with a targeted genomic double-stranded break (DSB) introduced near the intended site of integration. See e.g., Jasin, M., *Trends Genet* 12(6):224-228 (1996); and Urnov et al., *Nature* 435(7042):646-651 (2005). Moreover, coupling the coding sequence of the nuclease and/or associated guide sequence(s) to the circularized expression vector eliminates the need for introducing multiple vectors to the host cell in order to effect expression of these sequences. Additionally, such coupling allows for simultaneous elimination of the nuclease and the marked plasmid following selection of a host cell having performed the desired integrations. Thus, needlessly prolonged expression of the nuclease is avoided, and consequently, any toxicity associated therewith (see e.g., Cho et al., *Genome Res*, "Analysis of off-target effects of CRISPR/Cas-derived RNA-guided endonucleases and nickases," (2013); Sander et al., "In silico abstraction of zinc finger nuclease cleavage profiles reveals an expanded landscape of off-target sites," *Nucleic Acids Research* 41(19): e181 (2013)).

In some embodiments of the methods provided herein, the circularized expression vector, once assembled, further comprises one or more exogenous donor nucleic acids, described in Section 5.2.2 below. In some such embodiments, the exogenous donor nucleic acids may be released from the circularized expression vector by flanking the exogenous donor nucleic acids with recognition sequences for a nuclease also introduced into the host cell, for example a nuclease also encoded by the circularized expression vector.

As will be clear to those in the art, the circularized expression vector will preferably contain an autonomous propagation sequence which enables the expression vector to be replicated, propagated, and segregated during multiple rounds of host cell division. The autonomous propagation sequence can be either prokaryotic or eukaryotic, and includes an origin of replication. Replication origins are unique polynucleotides that comprise multiple short repeated sequences that are recognized by multimeric origin-binding proteins and that play a key role in assembling DNA replication enzymes at the origin site. Suitable origins of replication for use in the entry and assembly vectors provided herein include but are not limited to *E. coli* oriC, colE1 plasmid origin, 2μ and ARS (both useful in yeast systems), sfl, SV40 EBV oriP (useful in mammalian systems), or those found in pSC101. Particular embodiments of an expression vector include both prokaryotic and eukaryotic autonomous propagation sequences. This sequence may be intact (i.e., in operable linkage) in any of the one or more pre-recombination linear fragment(s) participating in the assembly reaction, or alternatively, divided into any number of overlapping homologous sequences distributed among any number fragments participating in the assembly, so long as HR between the component pre-recombination fragments results in reconstitution of the autonomous propagation sequence. In particular embodiments, the autonomous propagation sequence is not intact, i.e., is not in operable linkage, on any single pre-recombination molecule. In some such embodiments, only when the expression vector is circularized by recombination of the pre-recombination molecule(s) is the autonomous propagation sequence brought into operable linkage. These embodiments are particularly useful to avoid selecting host cells in which formation of a circularized expression vector results from non-HR joining of the pre-recombination fragments comprising an intact autonomous propagation sequence, for example, by non-homologous end-joining or single strand annealing; such cells surviving the selection would represent false positives.

As will also be clear to those of skill in the art, the in vivo recombination between one or more linear pre-recombination DNA fragments described above, which results in formation of a circular expression vector in the host cell, can also be achieved with circular pre-recombination nucleic acids comprising the appropriate (e.g., same) homology regions as a starting point. For any of the pre-recombination compositions described herein, the compositions can be transformed directly into a host cell as linear nucleic acid molecules, or alternatively, parental circular molecules comprising the pre-recombination molecules can be introduced into the host cell and cleaved in vivo by one or more nucleases to liberate the pre-recombination molecules. In some embodiments, the one or more linear pre-recombination molecules participating in the marker vector assembly can be liberated from a parental circular plasmid via in vivo cleavage in the host cell by the one or more nucleases targeting the one or more genomic target sites for cleavage.

In another aspect, provided herein are methods of making pre-recombination expression vector intermediates useful in the practice of the integration methods provided herein. In some embodiments, a base vector comprising an autonomous propagation sequence, a first primer binding sequence, and a second primer binding sequence is amplified using at least a first primer and a second primer. The first primer typically comprises of 5' portion having a first sequence-specific recombination sequence and a 3' portion having a priming portion substantially complementary (i.e., having sufficient complementarity to enable amplification of the desired nucleic acids but not other, undesired molecules) to the first primer binding sequence of the base vector. Similarly, the second primer comprises a 5' portion having a second sequence-specific recombination sequence and a 3' portion having a priming portion substantially complimentary to the second primer binding sequence of the base vector. Amplification of the base vector (which can be either linear or circular prior to initiation of the amplification process) results in the production of a linear expression vector intermediate having a first terminus comprising a first sequence-specific recombination region and a second terminus comprising a second sequence-specific recombination region. In certain embodiments, the base vector is a plasmid, particularly a plasmid such as are known in the art and which are based on various bacterial- or yeast-derived extra-chromosomal elements. In certain other embodiments, the base vector further comprises one or more selectable markers, transcription initiation sequences, and/or transcription termination sequences. As those in the art will appreciate, elements intended to regulate expression of genes carried in the target nucleic acid should be positioned in the expression vector so as to be functionally or operably associated with the gene(s) to be expressed, once the circular expression vector is assembled in vivo. The particular positioning of such elements depends upon those elements employed, the host cell, the gene(s) to be expressed, and other factors, including the number of desired integrations in the host cell, as described above. As a result, the final design of a particular expression vector made in accordance with the instant teachings is a matter of choice and depends upon the specific application.

Yet other aspects concern expression vector intermediates made in accordance with the foregoing methods, and host cells containing the same. Still another aspect relates to methods of making multiple distinct expression vector intermediates useful in the practice of the present integration methods. In such methods, a base vector is amplified to generate two or more expression vector intermediates each having unique sequence-specific recombination regions which allow for homologous recombination with different insert nucleic acids. Such amplification reactions are preferably carried in separate reaction mixtures to produce distinct expression vector intermediates. In particularly preferred embodiments of such a high throughput approach, the requisite manipulations are performed in an automated fashion wherein one or more steps are performed by a computer-controlled device.

In some embodiments, any vector may be used to construct a pre-recombination molecule as provided herein. In particular, vectors known in the art and those commercially available (and variants or derivatives thereof) may be engineered to include recombination regions as described above. Such vectors may be obtained from, for example, Vector Laboratories Inc., InVitrogen, Promega, Novagen, NEB, Clontech, Boehringer Mannheim, Pharmacia, EpiCenter, OriGenes Technologies Inc., Stratagene, Perkin Elmer, Pharmingen, Life Technologies, Inc., and Research Genetics. General classes of vectors of particular interest include prokaryotic and/or eukaryotic cloning vectors, expression vectors, fusion vectors, two-hybrid or reverse two-hybrid vectors, shuttle vectors for use in different hosts, mutagenesis vectors, transcription vectors, vectors for receiving large inserts, and the like. Other vectors of interest include viral origin vectors (M13 vectors, bacterial phage X vectors, adenovirus vectors, adeno-associated virus vectors (AAV) and retrovirus vectors), high, low and adjustable copy number vectors, vectors that have compatible replicons for use in combination in a single host (PACYC184 and pBR322) and eukaryotic episomal replication vectors (pCDM8). In other embodiments, a pre-recombination molecule may be obtained by standard procedures known in the art from cloned DNA (e.g., a DNA "library"), by chemical synthesis, by cDNA cloning, or by the cloning of genomic DNA, or fragments thereof, purified from the desired cell, or by PCR amplification and cloning. See, for example, Sambrook et al., Molecular Cloning, *A Laboratory Manual*, 3d. ed., Cold Spring Harbor Laboratory Press, Cold Spring Harbor, N.Y. (2001); Glover, D. M. (ed.), *DNA Cloning: A Practical Approach*, 2d. ed., MRL Press, Ltd., Oxford, U.K. (1995).

5.2.1.1 Selectable Markers

In preferred embodiments, the circularized expression vector, once assembled, comprises a coding sequence for a selectable marker, and suitable regulatory sequences such as a promoter and/or a terminator that enables expression of the marker in the host cell. Useful selectable markers include those which function in both positive and negative selection systems.

In some embodiments, selection of the desired cells is based on selecting for drug resistance encoded by the selectable marker (FIG. 3B). Positive selection systems are those that promote the growth of transformed cells. They may be divided into conditional-positive or non-conditional-positive selection systems. A conditional-positive selection system consists of a gene coding for a protein, usually an enzyme, that confers resistance to a specific substrate that is toxic to untransformed cells or that encourages growth and/or differentiation of the transformed cells. In conditional-positive selection systems the substrate may act in one of several ways. It may be an antibiotic, an herbicide, a drug or metabolite analogue, or a carbon supply precursor. In each case, the gene codes for an enzyme with specificity to a substrate to encourage the selective growth and proliferation of the transformed cells. The substrate may be toxic or non-toxic to the untransformed cells. The nptII gene, which confers kanamycin resistance by inhibiting protein synthesis, is a classic example of a system that is toxic to untransformed cells. The manA gene, which codes for phosphomannose isomerase, is an example of a conditional-positive selection system where the selection substrate is not toxic. In this system, the substrate mannose is unable to act as a carbon source for untransformed cells but it will promote the growth of cells transformed with manA. Non-conditional-positive selection systems do not require external substrates yet promote the selective growth and differentiation of transformed cells. An example in plants is the ipt gene that enhances shoot development by modifying the plant hormone levels endogenously.

Negative selection systems result in the death of transformed cells. These are dominant selectable marker systems that may be described as conditional and non-conditional selection systems. When the selection system is not substrate dependent, it is a non-conditional-negative selection system. An example is the expression of a toxic protein, such as a ribonuclease to ablate specific cell types. When the action of the toxic gene requires a substrate to express toxicity, the system is a conditional negative selection system. These include the bacterial codA gene, which codes for cytosine deaminase, the bacterial cytochrome P450 mono-oxygenase gene, the bacterial haloalkane dehalogenase gene, or the *Arabidopsis* alcohol dehydrogenase gene. Each of these converts non-toxic agents to toxic agents resulting in the death of the transformed cells. The coda gene has also been shown to be an effective dominant negative selection marker for chloroplast transformation. The *Agrobacterium* aux2 and tms2 genes are interesting in that they can also be used in positive selection systems. Combinations of positive-negative selection systems are particularly useful for the integration methods provided herein, as positive selection can be utilized to enrich for cells that have successfully recombined the circular expression vector (and presumptively, have performed one or more intended HR-mediated genomic integrations), and negative selection can be used to eliminate ("cure") the expression vector from the same population once the desired genomic integrations have been confirmed.

A wide variety of selectable markers are known in the art (see, for example, Kaufinan, *Meth. Enzymol.*, 185:487 (1990); Kaufman, *Meth. Enzymol.*, 185:537 (1990); Srivastava and Schlessinger, *Gene,* 103:53 (1991); Romanos et al., in *DNA Cloning* 2: Expression Systems, $2^{nd}$ Edition, pages 123-167 (IRL Press 1995); Markie, *Methods Mol. Biol.,* 54:359 (1996); Pfeifer et al., *Gene,* 188:183 (1997); Tucker and Burke, *Gene,* 199:25 (1997); Hashida-Okado et al., *FEBS Letters,* 425:117 (1998)). In some embodiments, the selectable marker is a drug resistant marker. A drug resistant marker enables cells to detoxify an exogenous drug that would otherwise kill the cell. Illustrative examples of drug resistant markers include but are not limited to those which confer resistance to antibiotics such as ampicillin, tetracycline, kanamycin, bleomycin, streptomycin, hygromycin, neomycin, Zeocin™, and the like. Other selectable markers include a bleomycin-resistance gene, a metallothionein gene, a hygromycin B-phosphotransferase gene, the AUR1 gene, an adenosine deaminase gene, an aminoglycoside phosphotransferase gene, a dihydrofolate reductase gene, a thymidine kinase gene, a xanthine-guanine phosphoribosyltransferase gene, and the like.

pBR and pUC-derived plasmids contain as a selectable marker the bacterial drug resistance marker $AMP^r$ or BLA gene (See, Sutcliffe, J. G., et al., *Proc. Natl. Acad. Sci. U.S.A.* 75:3737 (1978)). The BLA gene encodes the enzyme Tem-1, which functions as a beta-lactamase and is responsible for bacterial resistance to beta-lactam antibiotics, such as narrow-spectrum cephalosporins, cephamycins, and carbapenems (ertapenem), cefamandole, and cefoperazone, and all the anti-gram-negative-bacterium penicillins except temocillin.

Other useful selectable markers include but are not limited to: NAT1, PAT, AUR1-C, PDR4, SMR1, CAT, mouse dhfr, HPH, DSDA, $KAN^R$, and SHBLE genes. The NAT1 gene of *S. noursei* encodes nourseothricin N-acetyltransferase and confers resistance to nourseothricin. The PAT gene from *S. viridochromogenes* Tu94 encodes phosphinothricin N-acetyltransferase and confers resistance to bialophos. The AUR1-C gene from *S. cerevisiae* confers resistance to Auerobasidin A (AbA), an antifuncal antibiotic produced by *Auerobasidium pullulans* that is toxic to budding yeast *S. cerevisiae*. The PDR4 gene confers resistance to cerulenin. The SMR1 gene confers resistance to sulfometuron methyl. The CAT coding sequence from Tn9 transposon confers resistance to chloramphenicol. The mouse dhfr gene confers resistance to methotrexate. The HPH gene of *Klebsiella pneumonia* encodes hygromycin B phosphotransferase and confers resistance to Hygromycin B. The DSDA gene of *E. coli* encodes D-serine deaminase and allows yeast to grow on plates with D-serine as the sole nitrogen source. The $KAN^R$ gene of the Tn903 transposon encodes aminoglycoside phosphotransferase and confers resistance to G418. The SH BLE gene from *Streptoallotei-chus hindustanus* encodes a Zeocin binding protein and confers resistance to Zeocin (bleomycin).

In other embodiments, the selectable marker is an auxotrophic marker. An auxotrophic marker allows cells to synthesize an essential component (usually an amino acid) while grown in media that lacks that essential component. Selectable auxotrophic gene sequences include, for example, hisD, which allows growth in histidine free media in the presence of histidinol. In some embodiments, the selectable marker rescues a nutritional auxotrophy in the host strain. In such embodiments, the host strain comprises a functional disruption in one or more genes of the amino acid biosynthetic pathways of the host that cause an auxotrophic phenotype, such as, for example, HIS3, LEU2, LYS1, MET15, and TRP1, or a functional disruption in one or more genes of the nucleotide biosynthetic pathways of the host that cause an auxotrophic phenotype, such as, for example, ADE2 and URA3. In particular embodiments, the host cell comprises a functional disruption in the URA3 gene. The functional disruption in the host cell that causes an auxotrophic phenotype can be a point mutation, a partial or complete gene deletion, or an addition or substitution of nucleotides. Functional disruptions within the amino acid or nucleotide biosynthetic pathways cause the host strains to become auxotrophic mutants which, in contrast to the prototrophic wild-type cells, are incapable of optimum growth in media without supplementation with one or more nutrients. The functionally disrupted biosynthesis genes in the host strain can then serve as auxotrophic gene markers which can later be rescued, for example, upon introducing one or more plasmids comprising a functional copy of the disrupted biosynthesis gene.

In yeast, utilization of the URA3, TRP1, and LYS2 genes as selectable markers has a marked advantage because both positive and negative selections are possible. Positive selection is carried out by auxotrophic complementation of the URA3, TRP1, and LYS2 mutations whereas negative selection is based on the specific inhibitors 5-fluoro-orotic acid (FOA), 5-fluoroanthranilic acid, and a-aminoadipic acid (aAA), respectively, that prevent growth of the prototrophic strains but allow growth of the URA3, TRP1, and LYS2 mutants, respectively. The URA3 gene encodes orotidine-5'phosphate decarboxylase, an enzyme that is required for the biosynthesis of uracil. Ura3-(or ura5-) cells can be selected on media containing FOA, which kills all URA3+ cells but not ura3-cells because FOA appears to be converted to the toxic compound 5-fluorouracil by the action of decarboxylase. The negative selection on FOA media is highly discriminating, and usually less than $10^{-2}$ FOA-resistant colonies are Ura+. The FOA selection procedure can be used to produce ura3 markers in haploid strains by mutation, and, more importantly, for selecting those cells that do not have the URA3-containing plasmids. The TRP1 gene encodes a phosphoribosylanthranilate isomerase that catalyzes the third step in tryptophan biosynthesis. Counterselection using 5-fluoroanthranilic acid involves antimetabolism by the strains that lack enzymes required for the conversion of anthranilic acid to tryptophan and thus are resistant to 5-fluroanthranilic acid. The LYS2 gene encodes an aminoadipate reductase, an enzyme that is required for the biosynthesis of lysine. Lys2- and lys5-mutants, but not normal strains, grow on a medium lacking the normal nitrogen source but containing lysine and aAA. Apparently, lys2 and lys5 mutations cause the accumulation of a toxic intermediate of lysine biosynthesis that is formed by high levels of aAA, but these mutants still can use aAA as a nitrogen source. Similar with the FOA selection procedure, LYS2-containing plasmids can be conveniently expelled from lys2 hosts. In other embodiments, the selectable marker is a marker other than one which rescues an auxotophic mutation.

For any of the methods and compositions described herein, reporter genes, such as the lac Z reporter gene for facilitating blue/white selection of transformed colonies, or fluorescent proteins such as green, red and yellow fluorescent proteins, can be used as selectable marker genes to facilitate selection of HR-competent host cells that are able to successfully assemble the circular expression vector from one or more pre-recombination fragments (see FIG. 3A). In these embodiments, rather than growing the transformed cells in media containing selective compound, e.g., antibiotic, the cells are grown under conditions sufficient to allow expression of the reporter, and selection can be performed via visual, colorimetric or fluorescent detection of the reporter. Drug-free and selective pressure-free cell maintenance of the host cells can provide a number of advantages. For example, selective drugs and other selective pressure factors are often mutagenic or otherwise interfere with the physiology of the cells, leading to skewed results in cell-based assays. For example, selective drugs may decrease susceptibility to apoptosis (Robinson et al., Biochemistry, 36(37):11169-11178 (1997)), increase DNA repair and drug metabolism (Deffie et al., Cancer Res. 48(13):3595-3602 (1988)), increase cellular pH (Thiebaut et al., J Histochem Cytochem. 38(5):685-690 (1990); Roepe et al., Biochemistry. 32(41):11042-11056 (1993); Simon et al., Proc Natl Acad Sci USA. 91(3):1128-1132 (1994)), decrease lysosomal and endosomal pH (Schindler et al., Biochemistry. 35(9):2811-2817 (1996); Altan et al., J Exp Med. 187(10): 1583-1598 (1998)), decrease plasma membrane potential (Roepe et al., Biochemistry. 32(41):11042-11056 (1993)), increase plasma membrane conductance to chloride (Gill et al., Cell. 71(1):23-32 (1992)) and ATP (Abraham et al., Proc Natl Acad Sci USA. 90(1):312-316 (1993)), and increase rates of vesicle transport (Altan et al., Proc Natl Acad Sci USA. 96(8):4432-4437 (1999)). Thus, the methods provided herein can be practiced with drug-free selection that allows for screening that is free from the artifacts caused by selective pressure.

A flow cytometric cell sorter can be used to isolate cells positive for expression of fluorescent markers or proteins (e.g., antibodies) coupled to fluorophores and having affinity for the marker protein. In some embodiments, multiple rounds of sorting may be carried out. In one embodiment, the flow cytometric cell sorter is a FACS machine. Other fluorescence plate readers, including those that are compatible with high-throughput screening can also be used. MACS (magnetic cell sorting) can also be used, for example, to select for host cells with proteins coupled to magnetic beads and having affinity for the marker protein. This is especially useful where the selectable marker encodes, for example, a membrane protein, transmembrane protein, membrane anchored protein, cell surface antigen or cell surface receptor (e.g., cytokine receptor, immunoglobulin receptor family member, ligand-gated ion channel, protein kinase receptor, G-protein coupled receptor (GPCR), nuclear hormone receptor and other receptors; CD14 (monocytes), CD56 (natural killer cells), CD335 (NKp46, natural killer cells), CD4 (T helper cells), CD8 (cytotoxic T cells), CD1c (BDCA-1, blood dendritic cell subset), CD303 (BDCA-2), CD304 (BDCA-4, blood dendritic cell subset), NKp80 (natural killer cells, gamma/delta T cells, effector/memory T cells), "6B11" (Va24/Vb11; invariant natural killer T cells), CD137 (activated T cells), CD25 (regulatory T cells) or depleted for CD138 (plasma cells), CD4, CD8, CD19, CD25, CD45RA, CD45RO). Thus, in some embodiments, the selectable marker comprises a protein displayed on the host cell surface, which can be readily detected with an antibody, for example, coupled to a fluorphore or to a colorimetric or other visual readout.

5.2.1.2 Cell Culture

In some embodiments of the methods described herein, host cells transformed with one or more pre-recombination fragments are cultured for a period of time sufficient for expression of the selectable marker from the circularized expression vector.

In some embodiments where the selectable marker is a drug resistance marker, the culturing is carried out for a period of time sufficient to produce an amount of the marker protein that can support the survival of cells expressing the marker in selectable media. In preferable embodiments, these conditions also select against the survival of cells not expressing the selectable marker. Selective pressure can be applied to cells using a variety of compounds or treatments that would be known to one of skill in the art. Without being limited by theory, selective pressure can be applied by exposing host cells to conditions that are suboptimal for or deleterious to growth, progression of the cell cycle or viability, such that cells that are tolerant or resistant to these conditions are selected for compared to cells that are not tolerant or resistant to these conditions. Conditions that can be used to exert or apply selective pressure include but are not limited to antibiotics, drugs, mutagens, compounds that slow or halt cell growth or the synthesis of biological building blocks, compounds that disrupt RNA, DNA or protein synthesis, deprivation or limitation of nutrients, amino acids, carbohydrates or compounds required for cell growth and viability from cell growth or culture media, treatments such as growth or maintenance of cells under conditions that are suboptimal for cell growth, for instance at suboptimal temperatures, atmospheric conditions (e.g., % carbon dioxide, oxygen or nitrogen or humidity) or in deprived media conditions. The level of selective pressure that is used can be determined by one of skill in the art. This can be done, for example, by performing a kill curve experiment, where control cells and cells that comprise resistance markers or genes are tested with increasing levels, doses, concentrations or treatments of the selective pressure and the ranges that selected against the negative cells only or preferentially over a desired range of time (e.g., from 1 to 24 hours, 1 to 3 days, 3 to 5 days, 4 to 7 days, 5 to 14 days, 1 to 3 weeks, 2 to 6 weeks). The exact levels, concentrations, doses, or treatments of selective pressure that can be used depends on the cells that are used, the desired properties themselves, the markers, factors or genes that confer resistance or tolerance to the selective pressure as well as the levels of the desired properties that are desired in the cells that are selected and one of skill in the art would readily appreciate how to determine appropriate ranges based on these considerations.

The culturing may be performed in a suitable culture medium in a suitable container, including but not limited to a cell culture plate, a flask, or a fermentor. In some embodiments, the culture medium is an aqueous medium comprising assimilable carbon, nitrogen and phosphate sources. Such a medium can also include appropriate salts, minerals, metals and other nutrients. In some embodiments, in addition to the selection agent, the suitable medium is supplemented with one or more additional agents, such as, for example, an inducer (e.g., when one or more nucleotide sequences encoding a gene product are under the control of an inducible promoter), a repressor (e.g., when one or more nucleotide sequences encoding a gene product are under the control of a repressible promoter). Materials and methods for the maintenance and growth of cell cultures are well known to those skilled in the art of microbiology or fermentation science (see, for example, Bailey et al., *Biochemical Engineering Fundamentals*, second edition, McGraw Hill, New York, 1986). Consideration must be given to appropriate culture medium, pH, temperature, and requirements for aerobic, microaerobic, or anaerobic conditions, depending on the specific requirements of the host cell, the fermentation, and the process. In some embodiments, the culturing is carried out for a period of time sufficient for the transformed population to undergo a plurality of doublings until a desired cell density is reached. In some embodiments, the culturing is carried out for a period of time sufficient for the host cell population to reach a cell density ($OD_{600}$) of between 0.01 and 400 in the fermentation vessel or container in which the culturing is being carried out. In some embodiments, the culturing is carried out until an $OD_{600}$ of at least 0.01 is reached. In some embodiments, the culturing is carried out until an $OD_{600}$ of at least 0.1 is reached. In some embodiments, the culturing is carried out until an $OD_{600}$ of at least 1.0 is reached. In some embodiments, the culturing is carried out until an $OD_{600}$ of at least 10 is reached. In some embodiments, the culturing is carried out until an $OD_{600}$ of at least 100 is reached. In some embodiments, the culturing is carried out until an $OD_{600}$ of between 0.01 and 100 is reached. In some embodiments, the culturing is carried out until an $OD_{600}$ of between 0.1 and 10 is reached. In some embodiments, the culturing is carried out until an $OD_{600}$ of between 1 and 100 is reached. In other embodiments, the culturing is carried for a period of at least 12, 24, 36, 48, 60, 72, 84, 96 or more than 96 hours. In some embodiments, the culturing is carried out for a period of between 3 and 20 days. In some embodiments, the culturing is carried out for a period of 1, 2, 3, 4, 5, 6, 7, 8, 9, 10, 11, 12, 13, 14, 15, 16, 17, 18, 19, 20 or more than 20 days.

In some embodiments of the methods described herein, the methods further comprise the step of eliminating the circularized expression vector, i.e., plasmid, from the host cell, for example, once a selected host cell has been identified as comprising the desired genomic integration(s). Plasmid-based systems generally require selective pressure on the plasmids to maintain the foreign DNA in the cell. For example, most plasmids in yeast are relatively unstable, as a yeast cell typically loses 10% of plasmids contained in the cell after each mitotic division. Thus, in some embodiments, elimination of a plasmid encoding the selective marker from a selected cell can be achieved by allowing the selected cells to undergo sufficient mitotic divisions such that the plasmid is effectively diluted from the population. Alternatively, plasmid-free cells can be selected by selecting for the absence of the plasmid, e.g., by selecting against a counter-selectable marker (such as, for example, URA3) or by plating identical colonies on both selective media and non-selective media and then selecting a colony that does not grow on the selective media but does grow on the non-selective media.

5.2.2. Exogenous Donor Nucleic Acids

Advantageously, an integration polynucleotide, i.e., donor DNA, facilitates integration of one or more exogenous nucleic acid constructs into a selected target site of a host cell genome. In preferred embodiments, an integration polynucleotide comprises an exogenous nucleic acid $(ES)_x$ comprising a first homology region $(HR1)_x$ and a second homology region $(HR2)_x$, and optionally a nucleic acid of interest positioned between $(HR1)_x$ and $(HR2)_x$. In some embodiments, the integration polynucleotide is a linear DNA molecule. In other embodiments, the integration polynucleotide is a circular DNA molecule. In some embodiments, the integration polynucleotide is a single-stranded DNA molecule, i.e., an oligonucleotide. In other embodiments, the integration polynucleotide is a double-stranded DNA molecule.

The integration polynucleotide can be generated by any technique apparent to one skilled in the art. In certain embodiments, the integration polynucleotide is generated using polymerase chain reaction (PCR) and molecular cloning techniques well known in the art. See, e.g., *PCR Technology: Principles and Applications for DNA Amplification*, ed. H A Erlich, Stockton Press, New York, N.Y. (1989); Sambrook et al., 2001, *Molecular Cloning—A Laboratory Manual*, 3$^{rd}$ edition, Cold Spring Harbor Laboratory, Cold Spring Harbor, N.Y.; *PCR Technology: Principles and Applications for DNA Amplification*, ed. H A Erlich, Stockton Press, New York, N.Y. (1989); U.S. Pat. No. 8,110,360.

5.2.2.1 Genomic Integration Sequences

In preferred embodiments, an integration polynucleotide comprises an exogenous nucleic acid $(ES)_x$ comprising a first homology region $(HR1)_x$ and a second homology region $(HR2)_x$, wherein $(HR1)_x$ and $(HR2)_x$ are capable of initiating host cell mediated homologous recombination at a selected target site $(TS)_x$ within the host cell genome. To integrate an exogenous nucleic acid into the genome by homologous recombination, the integration polynucleotide preferably comprises $(HR1)_x$ at one terminus and $(HR2)_x$ at the other terminus. In some embodiments, $(HR1)_x$ is homologous to a 5' region of the selected genomic target site $(TS)_x$, and $(HR2)_x$ is homologous to a 3' region of the selected target site $(TS)_x$. In some embodiments, $(HR1)_x$ is about 70%, 75%, 80%, 85%, 90%, 95% or 100% homologous to a 5' region of the selected genomic target site $(TS)_x$. In some embodiments, $(HR2)_x$ is about 70%, 75%, 80%, 85%, 90%, 95% or 100% homologous to a 3' region of the selected target site $(TS)_x$.

In certain embodiments, $(HR1)_x$ is positioned 5' to a nucleic acid of interest $(D)_x$. In some embodiments, $(HR1)_x$ is positioned immediately adjacent to the 5' end of $(D)_x$. In some embodiments, $(HR1)_x$ is positioned upstream to the 5' of $(D)_x$. In certain embodiments, $(HR2)_x$ is positioned 3' to a nucleic acid of interest $(D)_x$. In some embodiments, $(HR2)_x$ is positioned immediately adjacent to the 3' end of $(D)_x$. In some embodiments, $(HR2)_x$ is positioned downstream to the 3' of $(D)_x$.

Properties that may affect the integration of an integration polynucleotide at a particular genomic locus include but are not limited to: the lengths of the genomic integration sequences, the overall length of the excisable nucleic acid construct, and the nucleotide sequence or location of the genomic integration locus. For instance, effective heteroduplex formation between one strand of a genomic integration sequence and one strand of a particular locus in a host cell genome may depend on the length of the genomic integration sequence. An effective range for the length of a genomic integration sequence is 50 to 5,000 nucleotides. For a discussion of effective lengths of homology between genomic integration sequences and genomic loci. See, Hasty et al., *Mol Cell Biol* 11:5586-91 (1991).

In some embodiments, $(HR1)_x$ and $(HR2)_x$ can comprise any nucleotide sequence of sufficient length and sequence identity that allows for genomic integration of the exogenous nucleic acid $(ES)_x$ at any yeast genomic locus. In certain embodiments, each of $(HR1)_x$ and $(HR2)_x$ independently consists of about 50 to 5,000 nucleotides. In certain embodiments, each of $(HR1)_x$ and $(HR2)_x$ independently consists of about 100 to 2,500 nucleotides. In certain embodiments, each of $(HR1)_x$ and $(HR2)_x$ independently consists of about 100 to 1,000 nucleotides. In certain embodiments, each of $(HR1)_x$ and $(HR2)_x$ independently consists of about 250 to 750 nucleotides. In certain embodiments, each of $(HR1)_x$ and $(HR2)_x$ independently consists of about 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900 or 5,000 nucleotides. In some embodiments, each of $(HR1)_x$ and $(HR2)_x$ independently consists of about 500 nucleotides.

5.2.2.2 Nucleic Acids of Interest

In some embodiments, the integration polynucleotide further comprises a nucleic acid of interest $(D)_x$. The nucleic acid of interest can be any DNA segment deemed useful by one of skill in the art. For example, the DNA segment may comprise a gene of interest that can be "knocked in" to a host genome. In other embodiments, the DNA segment functions as a "knockout" construct that is capable of specifically disrupting a target gene upon integration of the construct into the target site of the host cell genome, thereby rendering the disrupted gene non-functional. Useful examples of a nucleic acid of interest $(D)_x$ include but are not limited to: a protein-coding sequence, reporter gene, fluorescent marker coding sequence, promoter, enhancer, terminator, transcriptional activator, transcriptional repressor, transcriptional activator binding site, transcriptional repressor binding site, intron, exon, poly-A tail, multiple cloning site, nuclear localization signal, mRNA stabilization signal, integration loci, epitope tag coding sequence, degradation signal, or any other naturally occurring or synthetic DNA molecule. In some embodiments, $(D)_x$ can be of natural origin. Alternatively, $(D)_x$ can be completely of synthetic origin, produced in vitro. Furthermore, $(D)_x$ can comprise any combination of isolated naturally occurring DNA molecules, or any combination of an isolated naturally occurring DNA molecule and a synthetic DNA molecule. For example, $(D)_x$ may comprise a heterologous promoter operably linked to a protein coding sequence, a protein coding sequence linked to a poly-A tail, a protein coding sequence linked in-frame with a epitope tag coding sequence, and the like. The nucleic acid of interest $(D)_x$ may be obtained by standard procedures known in the art from cloned DNA (e.g., a DNA "library"), by chemical synthesis, by cDNA cloning, or by the cloning of genomic DNA, or fragments thereof, purified from the desired cell, or by PCR amplification and cloning. See, for example, Sambrook et al., *Molecular Cloning, A Laboratory Manual*, 3d. ed., Cold Spring Harbor Laboratory Press, Cold Spring Harbor, N.Y. (2001); Glover, D. M. (ed.), *DNA Cloning: A Practical Approach*, 2d. ed., MRL Press, Ltd., Oxford, U.K. (1995).

In particular embodiments, the nucleic acid of interest $(D)_x$ does not comprise nucleic acid encoding a selectable marker. In these embodiments, the high efficiency of integration provided by the methods described herein allows for the screening and identification of integration events without the requirement for growth of transformed cells on selection media. However, in other embodiments where growth on selective media is nonetheless desired, the nucleic acid of interest $(D)_x$ can comprise a selectable marker that may be used to select for the integration of the exogenous nucleic acid into a host genome.

The nucleic acid of interest $(D)_x$ can be of any size, including sizes ranging from about 300 nucleotides to up to about 1 million nucleotide base pairs. Such nucleic acids of interest may include one or more genes and/or their associated regulatory regions. These nucleic acids of interest can be derived from any source, for example, from genomic sources or from cDNA libraries, including tissue-specific, normalized, and subtractive cDNA libraries. Genomic sources include the genomes (or fragments thereof) of various organisms, including pathogenic organisms such as viruses (e.g, HIV and hepatitis viruses) and cellular pathogens. Moreover, nucleic acids of interest can be obtained from any organism, including any plant or any animal, be they eukaryotic or prokaryotic. In certain embodiments, a nucleic acid of interest encodes a gene which is a disease-associated gene, i.e., the presence, absence, expression, lack of expression, altered level of expression, or existence of an altered form of which correlates with or causes a disease.

In some embodiments, the nucleic acid of interest encodes a point mutation of a targeted allele of a host cell, which can be utilized for the introduction of a missense SNP (i.e. an "allele swap") to the targeted allele. In some such embodiments, the selection of nuclease (e.g., CRISPR/Cas9 and gRNA) target sites for an allele swap is considerably more constrained than for deletion or integration into an ORF. In preferred embodiments, the nuclease cleavage site should be unique in the genome, and should be as close to the targeted nucleotide as possible, such that recombination will incorporate the mutant sequence, rather than just the flanking sequence of the donor DNA. This is because recombination to repair the cut site does not require incorporation of the desired SNP, and the likelihood of its inclusion is expected to decrease with distance from the cut site. Additionally, for optimal efficiency, the donor DNA should be designed such that it is not also a target for the nuclease (e.g., CRISPR/Cas9 and gRNA). Thus, to make the donor DNA immune to cutting, and simultaneously improve the chances that recombination events include the desired SNP, a heterology block approach can be utilized whereby silent mutations are made in the codons between the target site and the point mutation, reducing the potential for recombination events that would omit the desired SNP. Donor DNAs can be designed with flanking homology surrounding a central "heterology block". The heterology block introduces silent mutations to the sequence surrounding the nuclease target site, and serves several purposes. First, it removes bases critical for nuclease (e.g., CRISPR-Cas9) recognition, such that the donor DNA will not be cut. Additionally, integration of the heterology block provides a novel primer binding site to identify candidate clones by PCR. FIG. 15 provides a schematic for CRISPR/Cas9-mediated introduction of a point mutation in the context of a "heterology block." A targeted amino acid is boxed, and an adjacent cleavage site is annotated with cleavage site and PAM sequence (Top panel). A donor DNA containing the desired point mutation in the context of a heterology block of silent codon changes and flanking homology can be generated synthetically by annealing and extending 60-mer oligos (Middle panel) or with larger cloned constructs. Integration of the donor DNA yields the desired point mutation (Lower panel).

5.2.3. Nucleases

In some embodiments of the methods described herein, a host cell genome is contacted with one or more nucleases capable of cleaving, i.e., causing a break at a designated region within a selected target site. In some embodiments, the break is a single-stranded break, that is, one but not both DNA strands of the target site are cleaved (i.e., "nicked"). In some embodiments, the break is a double-stranded break. In some embodiments, a break inducing agent is any agent that recognizes and/or binds to a specific polynucleotide recognition sequence to produce a break at or near the recognition sequence. Examples of break inducing agents include, but are not limited to, endonucleases, site-specific recombinases, transposases, topoisomerases, and zinc finger nucleases, and include modified derivatives, variants, and fragments thereof.

In some embodiments, each of the one or more nucleases is capable of causing a break at a designated region within a selected target site $(TS)_x$. In some embodiments, the nuclease is capable of causing a break at a region positioned between the 5' and 3' regions of $(TS)_x$ with which $(HR1)_x$ and $(HR2)_x$ share homology, respectively. In other embodiments, the nuclease is capable of causing a break at a region positioned upstream or downstream of the 5' and 3' regions of $(TS)_x$.

A recognition sequence is any polynucleotide sequence that is specifically recognized and/or bound by a break inducing agent. The length of the recognition site sequence can vary, and includes, for example, sequences that are at least 10, 12, 14, 16, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 or more nucleotides in length.

In some embodiments, the recognition sequence is palindromic, that is, the sequence on one strand reads the same in the opposite direction on the complementary strand. In some embodiments, the nick/cleavage site is within the recognition sequence. In other embodiments, the nick/cleavage site is outside of the recognition sequence. In some embodiments, cleavage produces blunt end termini. In other embodiments, cleavage produces single-stranded overhangs, i.e., "sticky ends," which can be either 5' overhangs, or 3' overhangs.

In some embodiments, the recognition sequence within the selected target site can be endogenous or exogenous to the host cell genome. When the recognition site is an endogenous sequence, it may be a recognition sequence recognized by a naturally-occurring, or native break inducing agent. Alternatively, an endogenous recognition site could be recognized and/or bound by a modified or engineered break inducing agent designed or selected to specifically recognize the endogenous recognition sequence to produce a break. In some embodiments, the modified break inducing agent is derived from a native, naturally-occurring break inducing agent. In other embodiments, the modified break inducing agent is artificially created or synthesized. Methods for selecting such modified or engineered break inducing agents are known in the art. For example, amino acid sequence variants of the protein(s) can be prepared by mutations in the DNA. Methods for mutagenesis and nucleotide sequence alterations include, for example, Kunkel, (1985) *Proc Natl Acad Sci USA* 82:488-92; Kunkel, et al., (1987) *Meth Enzymol* 154:367-82; U.S. Pat. No. 4,873, 192; Walker and Gaastra, eds. (1983) *Techniques in Molecular Biology* (MacMillan Publishing Company, New York) and the references cited therein. Guidance regarding amino acid substitutions not likely to affect biological activity of the protein is found, for example, in the model of Dayhoff, et al., (1978) *Atlas of Protein Sequence and Structure* (Natl Biomed Res Found, Washington, D.C.). Conservative substitutions, such as exchanging one amino acid with another having similar properties, may be preferable. Conservative deletions, insertions, and amino acid substitutions are not expected to produce radical changes in the characteristics of the protein, and the effect of any substitution, deletion, insertion, or combination thereof can be evaluated by routine screening assays. Assays for double strand break inducing activity are known and generally measure the overall activity and specificity of the agent on DNA substrates containing recognition sites.

5.2.3.1 Clustered Regulatory Interspaced Short Palindromic Repeats (CRISPR)

In some embodiments of the methods provided herein, the nuclease is a CRISPR/Cas-derived RNA-guided endonuclease. CRISPR is a genome editing tool based on the type II prokaryotic CRISPR (clustered regularly interspersed short palindromic repeats) adaptive immune system. CRISPR systems in eubacteria and archaea use small RNAs and CRISPR-associated (Cas) endonucleases to target and cleave invading foreign DNAs. See, e.g., Bhaya et al., Annu Rev Genet 45:273-297 (2011); Terns et al., Curr Opin Microbiol 14(3):321-327 (2011); and Wiedenheft et al., Nature 482 (7385):331-338. In bacteria, CRISPR loci are composed of a series of repeats separated by segments of exogenous DNA (of ~30 bp in length) called spacers. The repeat-spacer array is transcribed as a long precursor and processed within repeat sequences to generate small crRNAs that specify the target sequences (also known as protospacers) cleaved by the CRISPR nuclease. CRISPR spacers are then used to recognize and silence exogenous genetic elements at the RNA or DNA level. Essential for cleavage is a sequence motif immediately downstream on the 3' end of the target region, known as the protospacer-adjacent motif (PAM). The PAM is present in the target DNA, but not the crRNA that targets it.

One of the simplest CRISPR systems is the type II CRISPR system from *Streptococcus pyognes*. The CRISPR-associated Cas9 endonuclease and two small RNAs, a target-complimentary CRISPR RNA (crRNA); and a transacting crRNA (tracrRNA), are sufficient for RNA-guided cleavage of foreign DNAs. The Cas9 protein, a hallmark protein of the type II CRISPR-Cas system, is a large monomeric DNA nuclease containing two nuclease domains homologous to RuvC and HNH nucleases. Cas9 is guided to a DNA target sequence adjacent to the PAM (protospacer adjacent motif) sequence motif by a crRNA:tracrRNA complex. Mature crRNA base-pairs to tracrRNA to form a two-RNA structure that directs Cas9 to the target DNA. At sites complementary to the crRNA-guide sequence, the Cas9 HNH nuclease domain cleaves the complementary strand, whereas the Cas9 RuvC-like domain cleaves the noncomplementary strand, resulting in a double strand break in the target DNA. See, e.g., Deltcheva et al., Nature 47(7340):602-607 (2011).

Recent studies show that a single guide RNA (gRNA) chimera that mimics the crRNA:tracrRNA complex can be utilized with Cas9 as a genome editing tool to guide Cas9 to introduce site specific DNA double-stranded breaks in vitro. Specificity of the cleavage within the target genome is determined by the spacer-like moiety of a chimeric guide RNA molecule (gRNA), which mimics the native crRNA: tracrRNA complex. Thus, the minimum number of components in a functional CRISPR/Cas system is two: Cas9 and sgRNA. The sgRNA guide sequence located at its 5' end confers DNA target specificity. Therefore, by modifying the guide sequence, it is possible to create sgRNAs with different target specificities. The canonical length of the guide sequence is 20 bp. Consequently, a DNA target is also 20 bp followed by a PAM sequence that follows the consensus NGG. Use of this modified CRISPR system has been demonstrated in vitro (see, e.g., Jinek et al., Science 337 (6096):816-821 (2012)), in mammalian cell lines (see, e.g., Mali et al., *Science* 339(6121):823-826 (2013), Jinek et al., *Elife* 2:e00417 (2013); Cong et al., *Science* 339(6121):819-823 (2013); and Cho et al., *Nat Biotechnol* 31(3):230-232

(2013)), in bacteria (see, e.g., Jiang et al., *Nat Biotechnol* 31(3):233-239 (2013); and Gasiunas et al., Proc Natl Acad Sci USA 109(39):E2579-E2586. (2012)), yeast (see, e.g., DiCarlo et al, *Nucleic Acid Res* 41(7):4336-4343 (2013)), zebrafish (see, e.g., Hwang et al., Nat Biotechnol 31(3):227-229 (2013); and Chang et al., Cell Res 23(4):465-472 (2013)), mice (see, e.g, Wang et al., *Cell* 153(4):910-918 (2013), and plants (see e.g., Belhaj et al., Plant Methods 9:39 (2013)).

The Cas9 nuclease may be modified by: (1) codon optimization for increased expression within a heterologous host; (2) fusion to a nuclear localization signal (NLS) for proper compartmentalization; and (3) site directed mutagenesis of either the HNH or RuvC domain to convert the nuclease into a strand-specific nickase. Site-directed mutagenesis of Cas9 in either the RuvC- or HNH-motif showed strand cleavage specificity, thereby providing two strand-specific nickases, in addition to the wild-type endonuclease and enabling targeted single-strand breaks of DNA. See, e.g., Jinek et al., Science 337(6096):816-821 (2012), and Gasiunas et al., Proc Natl Acad Sci USA 109(39):E2579-E2586. (2012). As has been reported for zinc finger nucleases and TALENs, modifying the nuclease to function as a nickase that breaks only one strand reduces toxicity from off-target cutting, and may also lower rates of break repair via non-HR mechanisms, e.g., NHEJ. See, e.g., Jinek et al., Science 337(6096):816-821 (2012).

Any CRISPR/Cas system known in the art finds use as a nuclease in the methods and compositions provided herein. The highly diverse CRISPR-Cas systems are categorized into three major types, which are further subdivided into ten subtypes, based on core element content and sequences (see, e.g., Makarova et al., *Nat Rev Microbiol* 9:467-77 (2011)). The structural organization and function of nucleoprotein complexes involved in crRNA-mediated silencing of foreign nucleic acids differ between distinct CRISPR/Cas types (see Wiedenheft et al., *Nature* 482:331-338 (2012)). In the Type 1-E system, as exemplified by *Escherichia coli*, crRNAs are incorporated into a multisubunit effector complex called Cascade (CRISPR-associated complex for antiviral defence) (Brouns et al., *Science* 321: 960-4 (2008)), which binds to the target DNA and triggers degradation by the signature Cas3 protein (Sinkunas et al., *EMBO J* 30:1335^2 (2011); Beloglazova et al., *EMBO J* 30:616-27 (2011)). In Type III CRISPR/Cas systems of *Sulfolobus solfataricus* and *Pyrococcus furiosus*, Cas RAMP module (Cmr) and crRNA complex recognize and cleave synthetic RNA in vitro (Hale et al., *Mol Cell* 45:292-302 (2012); Zhang et al., *Mol Cell,* 45:303-13 (2012)), while the CRISPR/Cas system of *Staphylococcus epidermidis* targets DNA in vivo (Marraffini & Sontheimer, *Science*. 322:1843-5 (2008)). RNP complexes involved in DNA silencing by Type II CRISPR/Cas systems, more specifically in the CRISPR3/Cas system of *Streptococcus thermophilus* DGCC7710 (Horvath & Barrangou, *Science* 327:167-70 (2010)), consists of four cas genes: cas9, cas1, cas2, and csn2, that are located upstream of 12 repeat-spacer units. Cas9 (formerly named cas5 or csnl) is the signature gene for Type II systems (Makarova et al., *Nat Rev Microbiol* 9:467-77 (2011)).

CRISPR systems that find use in the methods and compositions provided herein also include those described in International Publication Numbers WO 2013/142578 A1 and WO 2013/098244 A1, the contents of which are hereby incorporated in their entireties.

5.2.3.2 Transcription Activator-like Effector Nucleases (TALENs)

In some embodiments of the methods provided herein, one or more of the nucleases is a TAL-effector DNA binding domain-nuclease fusion protein (TALEN). TAL effectors of plant pathogenic bacteria in the genus *Xanthomonas* play important roles in disease, or trigger defense, by binding host DNA and activating effector-specific host genes. see, e.g., Gu et al. (2005) *Nature* 435:1122-5; Yang et al., (2006) *Proc. Natl. Acad. Sci. USA* 103:10503-8; Kay et al., (2007) *Science* 318:648-51; Sugio et al., (2007) *Proc. Natl. Acad. Sci. USA* 104:10720-5; Romer et al., (2007) *Science* 318: 645-8; Boch et al., (2009) *Science* 326(5959):1509-12; and Moscou and Bogdanove, (2009) 326(5959):1501. A TAL effector comprises a DNA binding domain that interacts with DNA in a sequence-specific manner through one or more tandem repeat domains. The repeated sequence typically comprises 34 amino acids, and the repeats are typically 91-100% homologous with each other. Polymorphism of the repeats is usually located at positions 12 and 13, and there appears to be a one-to-one correspondence between the identity of repeat variable-diresidues at positions 12 and 13 with the identity of the contiguous nucleotides in the TAL-effector's target sequence.

The TAL-effector DNA binding domain may be engineered to bind to a desired target sequence, and fused to a nuclease domain, e.g., from a type II restriction endonuclease, typically a nonspecific cleavage domain from a type II restriction endonuclease such as FokI (see e.g., Kim et al. (1996) *Proc. Natl. Acad. Sci. USA* 93:1156-1160). Other useful endonucleases may include, for example, HhaI, HindIII, Nod, BbvCI, EcoRI, BglI, and AlwI. Thus, in preferred embodiments, the TALEN comprises a TAL effector domain comprising a plurality of TAL effector repeat sequences that, in combination, bind to a specific nucleotide sequence in the target DNA sequence, such that the TALEN cleaves the target DNA within or adjacent to the specific nucleotide sequence. TALENS useful for the methods provided herein include those described in WO10/079430 and U.S. Patent Application Publication No. 2011/0145940.

In some embodiments, the TAL effector domain that binds to a specific nucleotide sequence within the target DNA can comprise 10 or more DNA binding repeats, and preferably 15 or more DNA binding repeats. In some embodiments, each DNA binding repeat comprises a repeat variable-diresidue (RVD) that determines recognition of a base pair in the target DNA sequence, wherein each DNA binding repeat is responsible for recognizing one base pair in the target DNA sequence, and wherein the RVD comprises one or more of: HD for recognizing C; NG for recognizing T; NI for recognizing A; NN for recognizing G or A; NS for recognizing A or C or G or T; N* for recognizing C or T, where * represents a gap in the second position of the RVD; HG for recognizing T; H* for recognizing T, where * represents a gap in the second position of the RVD; IG for recognizing T; NK for recognizing G; HA for recognizing C; ND for recognizing C; HI for recognizing C; HN for recognizing G; NA for recognizing G; SN for recognizing G or A; and YG for recognizing T.

In some embodiments of the methods provided herein, one or more of the nucleases is a site-specific recombinase. A site-specific recombinase, also referred to as a recombinase, is a polypeptide that catalyzes conservative site-specific recombination between its compatible recombination sites, and includes native polypeptides as well as derivatives, variants and/or fragments that retain activity, and native polynucleotides, derivatives, variants, and/or fragments that encode a recombinase that retains activity. For reviews of site-specific recombinases and their recognition sites, see, Sauer (1994) *Curr Op Biotechnol* 5:521-7; and Sadowski, (1993) *FASEB* 7:760-7. In some embodiments, the recombinase is a serine recombinase or a tyrosine recombinase. In some embodiments, the recombinase is from the Integrase or Resolvase families. In some embodiments, the recombinase is an integrase selected from the group consisting of FLP, Cre, lambda integrase, and R. For other members of the Integrase family, see for example, Esposito, et al., (1997) *Nucleic Acids Res* 25:3605-14 and Abremski, et al., (1992) *Protein Eng* 5:87-91. Methods for modifying the kinetics, cofactor interaction and requirements, expression, optimal conditions, and/or recognition site specificity, and screening for activity of recombinases and variants are known, see for example Miller, et al., (1980) *Cell* 20:721-9; Lange-Gustafson and Nash, (1984) *J Biol Chem* 259:12724-32; Christ, et al., (1998) *J Mol Biol* 288:825-36; Lorbach, et al., (2000) *J Mol Biol* 296:1175-81; Vergunst, et al., (2000) *Science* 290:979-82; Dorgai, et al., (1995) *J Mol Biol* 252:178-88; Dorgai, et al., (1998) *J Mol Biol* 277:1059-70; Yagu, et al., (1995) *J Mol Biol* 252:163-7; Sclimente, et al., (2001) *Nucleic Acids Res* 29:5044-51; Santoro and Schultze, (2002) *Proc Natl Acad Sci USA* 99:4185-90; Buchholz and Stewart, (2001) *Nat Biotechnol* 19:1047-52; Voziyanov, et al., (2002) *Nucleic Acids Res* 30:1656-63; Voziyanov, et al., (2003) *J Mol Biol* 326:65-76; Klippel, et al., (1988) *EMBO J* 7:3983-9; Arnold, et al., (1999) *EMBO J* 18:1407-14; WO03/08045; WO99/25840; and WO99/25841. The recognition sites range from about 30 nucleotide minimal sites to a few hundred nucleotides. Any recognition site for a recombinase can be used, including naturally occurring sites, and variants. Variant recognition sites are known, see for example Hoess, et al., (1986) *Nucleic Acids Res* 14:2287-300; Albert, et al., (1995) *Plant J* 7:649-59; Thomson, et al., (2003) *Genesis* 36:162-7; Huang, et al., (1991) *Nucleic Acids Res* 19:443-8; Siebler and Bode, (1997) *Biochemistry* 36:1740-7; Schlake and Bode, (1994) *Biochemistry* 33:12746-51; Thygarajan, et al., (2001)*Mol Cell Biol* 21:3926-34; Umlauf and Cox, (1988) *EMBO J* 7:1845-52; Lee and Saito, (1998) *Gene* 216:55-65; WO01/23545; WO99/25821; WO99/25851; WO01/11058; WO01/07572 and U.S. Pat. No. 5,888,732.

In some embodiments of the methods provided herein, one or more of the nucleases is a transposase. Transposases are polypeptides that mediate transposition of a transposon from one location in the genome to another. Transposases typically induce double strand breaks to excise the transposon, recognize subterminal repeats, and bring together the ends of the excised transposon, in some systems other proteins are also required to bring together the ends during transposition. Examples of transposons and transposases include, but are not limited to, the Ac/Ds, Dt/rdt, Mu-M1/Mn, and Spm(En)/dSpm elements from maize, the Tam elements from snapdragon, the Mu transposon from bacteriophage, bacterial transposons (Tn) and insertion sequences (IS), Ty elements of yeast (retrotransposon), Ta1 elements from *Arabidopsis* (retrotransposon), the P element transposon from *Drosophila* (Gloor, et al., (1991) *Science* 253: 1110-1117), the Copia, Mariner and Minos elements from *Drosophila*, the Hermes elements from the housefly, the PiggyBack elements from *Trichplusia ni*, Tc1 elements from *C. elegans*, and IAP elements from mice (retrotransposon).

5.2.3.3 Zinc Finger Nucleases (ZFNs)

In some embodiments of the methods provided herein, one or more of the nucleases is a zinc-finger nuclease (ZFN). ZFNs are engineered break inducing agents comprised of a zinc finger DNA binding domain and a break inducing agent domain. Engineered ZFNs consist of two zinc finger arrays (ZFAs), each of which is fused to a single subunit of a nonspecific endonuclease, such as the nuclease domain from the FokI enzyme, which becomes active upon dimerization. Typically, a single ZFA consists of 3 or 4 zinc finger domains, each of which is designed to recognize a specific nucleotide triplet (GGC, GAT, etc.). Thus, ZFNs composed of two "3-finger" ZFAs are capable of recognizing an 18 base pair target site; an 18 base pair recognition sequence is generally unique, even within large genomes such as those of humans and plants. By directing the co-localization and dimerization of two FokI nuclease monomers, ZFNs generate a functional site-specific endonuclease that creates a break in DNA at the targeted locus.

Useful zinc-finger nucleases include those that are known and those that are engineered to have specificity for one or more target sites (TS) described herein. Zinc finger domains are amenable for designing polypeptides which specifically bind a selected polynucleotide recognition sequence, for example, within the target site of the host cell genome. ZFNs consist of an engineered DNA-binding zinc finger domain linked to a nonspecific endonuclease domain, for example nuclease domain from a Type IIs endonuclease such as HO or FokI. Alternatively, engineered zinc finger DNA binding domains can be fused to other break inducing agents or derivatives thereof that retain DNA nicking/cleaving activity. For example, this type of fusion can be used to direct the break inducing agent to a different target site, to alter the location of the nick or cleavage site, to direct the inducing agent to a shorter target site, or to direct the inducing agent to a longer target site. In some examples a zinc finger DNA binding domain is fused to a site-specific recombinase, transposase, or a derivative thereof that retains DNA nicking and/or cleaving activity. Additional functionalities can be fused to the zinc-finger binding domain, including transcriptional activator domains, transcription repressor domains, and methylases. In some embodiments, dimerization of nuclease domain is required for cleavage activity.

Each zinc finger recognizes three consecutive base pairs in the target DNA. For example, a 3 finger domain recognized a sequence of 9 contiguous nucleotides, with a dimerization requirement of the nuclease, two sets of zinc finger triplets are used to bind a 18 nucleotide recognition sequence. Useful designer zinc finger modules include those that recognize various GNN and ANN triplets (Dreier, et al., (2001) *J Biol Chem* 276:29466-78; Dreier, et al., (2000) *J Mol Biol* 303:489-502; Liu, et al., (2002) *J Biol Chem* 277:3850-6), as well as those that recognize various CNN or TNN triplets (Dreier, et al., (2005) *J Biol Chem* 280:35588-97; Jamieson, et al., (2003) *Nature Rev Drug Discov* 2:361-8). See also, Durai, et al., (2005) *Nucleic Acids Res* 33:5978-90; Segal, (2002) *Methods* 26:76-83; Porteus and Carroll, (2005) *Nat Biotechnol* 23:967-73; Pabo, et al., (2001) *Ann Rev Biochem* 70:313-40; Wolfe, et al., (2000) *Ann Rev Biophys Biomol Struct* 29:183-212; Segal and Barbas, (2001) *Curr Opin Biotechnol* 12:632-7; Segal, et al., (2003) *Biochemistry* 42:2137-48; Beerli and Barbas, (2002) *Nat Biotechnol* 20:135-41; Carroll, et al., (2006) *Nature Protocols* 1:1329; Ordiz, et al., (2002) *Proc Natl Acad Sci USA* 99:13290-5; Guan, et al., (2002) *Proc Natl Acad Sci USA* 99:13296-301; WO2002099084; WO00/42219; WO02/42459; WO2003062455; US20030059767; US Patent Application Publication Number 2003/0108880; U.S. Pat. Nos. 6,140,466, 6,511,808 and 6,453,242. Useful zinc-finger nucleases also include those described in WO03/080809;

WO05/014791; WO05/084190; WO08/021207; WO09/042186; WO09/054985; and WO10/065123.

5.2.3.4 Endonucleases

In some embodiments of the methods provided herein, one or more of the nucleases is an endonuclease. Endonucleases are enzymes that cleave the phosphodiester bond within a polynucleotide chain, and include restriction endonucleases that cleave DNA as specific sites without damaging the bases. Restriction endonucleases include Type I, Type II, Type III, and Type IV endonucleases, which further include subtypes. Restriction endonucleases are further described and classified, for example in the REBASE database (webpage at rebase.neb.com; Roberts, et al., (2003) *Nucleic Acids Res* 31:418-20), Roberts, et al., (2003) *Nucleic Acids Res* 31:1805-12, and Belfort, et al., (2002) in *Mobile DNA II*, pp. 761-783, Eds. Craigie, et al., ASM Press, Washington, D.C.

As used herein, endonucleases also include homing endonucleases, which like restriction endonucleases, bind and cut at a specific recognition sequence. However the recognition sites for homing endonucleases are typically longer, for example, about 18 bp or more. Homing endonucleases, also known as meganucleases, have been classified into the following families based on conserved sequence motifs: an LAGLIDADG (SEQ ID NO: 1) homing endonuclease, an HNH homing endonuclease, a His-Cys box homing endonuclease, a GIY-YIG (SEQ ID NO:2) homing endonuclease, and a cyanobacterial homing endonuclease. See, e.g., Stoddard, *Quarterly Review of Biophysics* 38(1): 49-95 (2006). These families differ greatly in their conserved nuclease active-site core motifs and catalytic mechanisms, biological and genomic distributions, and wider relationship to non-homing nuclease systems. See, for example, Guhan and Muniyappa (2003) *Crit Rev Biochem Mol Biol* 38:199-248; Lucas, et al., (2001) *Nucleic Acids Res* 29:960-9; Jurica and Stoddard, (1999) *Cell Mol Life Sci* 55:1304-26; Stoddard, (2006) *Q Rev Biophys* 38:49-95; and Moure, et al., (2002) *Nat Struct Biol* 9:764. Examples of useful specific homing endonucleases from these families include, but are not limited to: I-CreI (see, Rochaix et al., *Nucleic Acids Res.* 13: 975-984 (1985), I-MsoI (see, Lucas et al., *Nucleic Acids Res.* 29: 960-969 (2001), I-SceI (see, Foury et al., *FEBS Lett.* 440: 325-331 (1998), I-SceIV (see, Moran et al., *Nucleic Acids Res.* 20: 4069-4076 (1992), H-DreI (see, Chevalier et al., *Mol. Cell* 10: 895-905 (2002), I-HmuI (see, Goodrich-Blair et al., *Cell* 63: 417-424 (1990); Goodrich-Blair et al., *Cell* 84: 211-221 (1996), I-PpoI (see, Muscarella et al., *Mol. Cell. Biol.* 10: 3386-3396 (1990), I-DirI (see, Johansen et al., *Cell* 76: 725-734 (1994); Johansen, *Nucleic Acids Res.* 21: 4405 (1993), I-NjaI (see, Elde et al., *Eur. J. Biochem.* 259: 281-288 (1999); De Jonckheere et al., *J. Eukaryot. Microbiol.* 41: 457-463 (1994), I-NanI (see, Elde et al., *S. Eur. J. Biochem.* 259: 281-288 (1999); De Jonckheere et al., *J. Eukaryot. Microbiol.* 41: 457-463 (1994)), I-NitI (see, De Jonckheere et al., *J. Eukaryot. Microbiol.* 41: 457-463 (1994); Elde et al., *Eur. J. Biochem.* 259: 281-288 (1999), I-TevI (see, Chu et al., *Cell* 45: 157-166 (1986), I-TevII (see, Tomaschewski et al., *Nucleic Acids Res.* 15: 3632-3633 (1987), I-TevIII (see, Eddy et al., *Genes Dev.* 5: 1032-1041 (1991), F-TevI (see, Fujisawa et al., *Nucleic Acids Res.* 13: 7473-7481 (1985), F-TevII (see, Kadyrov et al., *Dokl. Biochem.* 339: 145-147 (1994); Kaliman, *Nucleic Acids Res.* 18: 4277 (1990), F-CphI (see, Zeng et al., *Curr. Biol.* 19: 218-222 (2009), PI-MgaI (see, Saves et al., *Nucleic Acids Res.* 29:4310-4318 (2001), I-CsmI (see, Colleaux et al., *Mol. Gen. Genet.* 223:288-296 (1990), I-CeuI (see, Turmel et al., *J. Mol. Biol.* 218: 293-311 (1991) and PI-SceI (see, Hirata et al., *J. Biol. Chem.* 265: 6726-6733 (1990).

In some embodiments of the methods described herein, a naturally occurring variant, and/or engineered derivative of a homing endonuclease is used. Methods for modifying the kinetics, cofactor interactions, expression, optimal conditions, and/or recognition site specificity, and screening for activity are known. See, for example, Epinat, et al., (2003) *Nucleic Acids Res* 31:2952-62; Chevalier, et al., (2002) *Mol Cell* 10:895-905; Gimble, et al., (2003) *Mol Biol* 334:993-1008; Seligman, et al., (2002) *Nucleic Acids Res* 30:3870-9; Sussman, et al., (2004) *J Mol Biol* 342:31-41; Rosen, et al., (2006) *Nucleic Acids Res* 34:4791-800; Chames, et al., (2005) *Nucleic Acids Res* 33:e178; Smith, et al., (2006) *Nucleic Acids Res* 34:e149; Gruen, et al., (2002) *Nucleic Acids Res* 30:e29; Chen and Zhao, (2005) *Nucleic Acids Res* 33:e154; WO2005105989; WO2003078619; WO2006097854; WO2006097853; WO2006097784; and WO2004031346. Useful homing endonucleases also include those described in WO04/067736; WO04/067753; WO06/097784; WO06/097853; WO06/097854; WO07/034262; WO07/049095; WO07/049156; WO07/057781; WO07/060495; WO08/152524; WO09/001159; WO09/095742; WO09/095793; WO10/001189; WO10/015899; and WO10/046786.

Any homing endonuclease can be used as a double-strand break inducing agent including, but not limited to: H-DreI, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, Pi-PspI, F-SceI, F-SceII, F-SuvI, F-CphI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp68031, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, I-ZbiIP, PI-MgaI, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, or PI-TliII, or any variant or derivative thereof.

In some embodiments, the endonuclease binds a native or endogenous recognition sequence. In other embodiments, the endonuclease is a modified endonuclease that binds a non-native or exogenous recognition sequence and does not bind a native or endogenous recognition sequence.

5.2.3.5 Genomic Target Sites

In the methods provided herein, a nuclease is introduced to the host cell that is capable of causing a double-strand break near or within a genomic target site, which greatly increases the frequency of homologous recombination at or near the cleavage site. In preferred embodiments, the recognition sequence for the nuclease is present in the host cell genome only at the target site, thereby minimizing any off-target genomic binding and cleavage by the nuclease.

In some embodiments, the genomic target site is endogenous to the host cell, such as a native locus. In some embodiments, the native genomic target site is selected according to the type of nuclease to be utilized in the methods of integration provided herein.

If the nuclease to be utilized is a CRISPR/Cas-derived RNA-guided endonuclease, optimal target sites may be selected in accordance with the requirements for target recognition of the particular CRISPR-Cas endonuclease being used. For example Cas9 target recognition occurs upon detection of complementarity between a "protospacer" sequence in the target DNA and the remaining spacer sequence in the crRNA. Cas9 cuts the DNA only if a correct protospacer-adjacent motif (PAM) is also present at the 3' end. Different Type II systems have differing PAM requirements. The *S. pyogenes* system requires an NGG sequence, where N can be any nucleotide. *S. thermophilus* Type II systems require NGGNG and NNAGAAW, respectively, while different *S. mutans* systems tolerate NGG or NAAR. Bioinformatic analyses have generated extensive databases of CRISPR loci in a variety of bacteria that may serve to identify new PAMs and expand the set of CRISPR-targetable sequences. See, e.g., Rho et al., *PLoS Genet.* 8, e1002441 (2012); and D. T. Pride et al., *Genome Res.* 21, 126 (2011). In *S. thermophilus*, Cas9 generates a blunt-ended double-stranded break 3 bp upstream of the protospacer, a process mediated by two catalytic domains in the Cas9 protein: an HNH domain that cleaves the complementary strand of the DNA and a RuvC-like domain that cleaves the non-complementary strand.

If the nuclease to be utilized is a zinc finger nuclease, optimal target sites may be selected using a number of publicly available online resources. See, e.g., Reyon et al., *BMC Genomics* 12:83 (2011), which is hereby incorporated by reference in its entirety. For example, Oligomerized Pool Engineering (OPEN) is a highly robust and publicly available protocol for engineering zinc finger arrays with high specificity and in vivo functionality, and has been successfully used to generate ZFNs that function efficiently in plants, zebrafish, and human somatic and pluripotent stem cells. OPEN is a selection-based method in which a preconstructed randomized pool of candidate ZFAs is screened to identify those with high affinity and specificity for a desired target sequence. ZFNGenome is a GBrowse-based tool for identifying and visualizing potential target sites for OPEN-generated ZFNs. ZFNGenome provides a compendium of potential ZFN target sites in sequenced and annotated genomes of model organisms. ZFNGenome currently includes a total of more than 11.6 million potential ZFN target sites, mapped within the fully sequenced genomes of seven model organisms; *S. cerevisiae, C. reinhardtii, A. thaliana, D. melanogaster, D. rerio, C. elegans*, and *H. sapiens*. Additional model organisms, including three plant species; *Glycine max* (soybean), *Oryza sativa* (rice), *Zea mays* (maize), and three animal species *Tribolium castaneum* (red flour beetle), *Mus musculus* (mouse), *Rattus norvegicus* (brown rat) will be added in the near future. ZFNGenome provides information about each potential ZFN target site, including its chromosomal location and position relative to transcription initiation site(s). Users can query ZFNGenome using several different criteria (e.g., gene ID, transcript ID, target site sequence).

If the nuclease to be utilized is a TAL-effector nuclease, in some embodiments, optimal target sites may be selected in accordance with the methods described by Sanjana et al., *Nature Protocols*, 7:171-192 (2012), which is hereby incorporated by reference in its entirety. In brief, TALENs function as dimers, and a pair of TALENs, referred to as the left and right TALENs, target sequences on opposite strands of DNA. TALENs are engineered as a fusion of the TALE DNA-binding domain and a monomeric FokI catalytic domain. To facilitate FokI dimerization, the left and right TALEN target sites are chosen with a spacing of approximately 14-20 bases. Therefore, for a pair of TALENs, each targeting 20-bp sequences, an optimal target site should have the form 5'-TN$^{19}$N$^{14-20}$N$^{19}$A-3', where the left TALEN targets 5'-TN$^{19}$-3' and the right TALEN targets the antisense strand of 5'-N$^{19}$A-3' (N=A, G, T or C).

In other embodiments of the methods provided herein, the genomic target site is exogenous to the host cell. For example, one or more genomic target sites can be engineered into the host cell genome using traditional methods, e.g., gene targeting, prior to performing the methods of integration described herein. In some embodiments, multiple copies of the same target sequence are engineered into the host cell genome at different loci, thereby facilitating simultaneous multiple integration events with the use of only a single nuclease that specifically recognizes the target sequence. In other embodiments, a plurality of different target sequences is engineered into the host cell genome at different loci. In some embodiments, the engineered target site comprises a target sequence that is not otherwise represented in the native genome of the host cell. For example, homing endonucleases target large recognition sites (12-40 bp) that are usually embedded in introns or inteins, and as such, their recognition sites are extremely rare, with none or only a few of these sites present in a mammalian-sized genome. Thus, in some embodiments, the exogenous genomic target site is a recognition sequence for a homing endonuclease. In some embodiments, the homing nuclease is selected from the group consisting of: H-DreI, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, Pi-PspI, F-SceI, F-SceII, F-SuvI, F-CphI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp68031, I-SthPhiJP, I-SthPhiST3P, I-SthPhiSTe3bP, I-TdeIP, I-TevI, I-TevII, I-TevIII, I-UarAP, I-UarHGPAIP, I-UarHGPA13P, I-VinIP, I-ZbiIP, PI-MgaI, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, or PI-TliII, or any variant or derivative thereof. In particular embodiments, the exogenous genomic target site is the recognition sequence for I-SceI, VDE (PI-SceI), F-CphI, PI-MgaI or PI-MtuII, each of which are provided below.

TABLE 1

Recognition and cleavage sites for select homing endonucleases.

| Nuclease | Recognition sequence |
|---|---|
| I-SceI | TAGGGATAACAGGGTAAT (SEQ ID NO: 121) |
| VDE (PI-SceI) | TATGTCGGGTGCGGAGAAAGAGGTAATGAAA (SEQ ID NO: 122) |
| F-CphI | GATGCACGAGCGCAACGCTCACAA (SEQ ID NO: 123) |
| PI-MgaI | GCGTAGCTGCCCAGTATGAGTCAG (SEQ ID NO: 124) |
| PI-MtuII | ACGTGCACTACGTAGAGGGTCGCACCGCACCGATCTACAA (SEQ ID NO: 125) |

5.2.3.6 Delivery

In some embodiments, the one or more nucleases useful for the methods described herein are provided, e.g., delivered into the host cell as a purified protein. In other embodiments, the one or more nucleases are provided via polynucleotide(s) comprising a nucleic acid encoding the nuclease. In other embodiments, the one or more nucleases are introduced into the host cell as purified RNA which can be directly translated in the host cell nucleus.

In certain embodiments, an integration polynucleotide, a polynucleotide encoding a nuclease, or a purified nuclease protein as described above, or any combination thereof, may be introduced into a host cell using any conventional technique to introduce exogenous protein and/or nucleic acids into a cell known in the art. Such methods include, but are not limited to, direct uptake of the molecule by a cell from solution, or facilitated uptake through lipofection using, e.g., liposomes or immunoliposomes; particle-mediated transfection; etc. See, e.g., U.S. Pat. No. 5,272,065; Goeddel et al., eds, 1990, *Methods in Enzymology*, vol. 185, Academic Press, Inc., CA; Krieger, 1990, *Gene Transfer and Expression—A Laboratory Manual*, Stockton Press, NY; Sambrook et al., 1989, *Molecular Cloning—A Laboratory Manual*, Cold Spring Harbor Laboratory, NY; and Ausubel et al., eds., Current Edition, *Current Protocols in Molecular Biology*, Greene Publishing Associates and Wiley Interscience, NY. Particular methods for transforming cells are well known in the art. See Hinnen et al., *Proc. Natl. Acad. Sci. USA* 75:1292-3 (1978); Cregg et al., *Mol. Cell. Biol.* 5:3376-3385 (1985). Exemplary techniques include but are not limited to, spheroplasting, electroporation, PEG 1000 mediated transformation, and lithium acetate or lithium chloride mediated transformation.

In some embodiments, biolistics are utilized to introduce an integration polynucleotide, a polynucleotide encoding a nuclease, a purified nuclease protein, or any combination thereof into the host cell, in particular, host cells that are otherwise difficult to transform/transfect using conventional techniques, such as plants. Biolistics work by binding the transformation reaction to microscopic gold particles, and then propelling the particles using compressed gas at the target cells.

In some embodiments, the polynucleotide comprising nucleic acid encoding the nuclease is an expression vector that allows for the expression of a nuclease within a host cell. Suitable expression vectors include but are not limited to those known for use in expressing genes in *Escherichia coli*, yeast, or mammalian cells. Examples of *Escherichia coli* expression vectors include but are not limited to pSCM525, pDIC73, pSCM351, and pSCM353. Examples of yeast expression vectors include but are not limited to pPEX7 and pPEX408. Other examples of suitable expression vectors include the yeast-*Escherichia coli* pRS series of shuttle vectors comprising CEN.ARS sequences and yeast selectable markers; and 2 µplasmids. In some embodiments, a polynucleotide encoding a nuclease can be modified to substitute codons having a higher frequency of usage in the host cell, as compared to the naturally occurring polynucleotide sequence. For example the polynucleotide encoding the nuclease can be modified to substitute codons having a higher frequency of usage in *S. cerevisiae*, as compared to the naturally occurring polynucleotide sequence.

In some embodiments where the nuclease functions as a heterodimer requiring the separate expression of each monomer, as is the case for zinc finger nucleases and TAL-effector nucleases, each monomer of the heterodimer may be expressed from the same expression plasmid, or from different plasmids. In embodiments where multiple nucleases are introduced to the cell to effect double-strand breaks at different target sites, the nucleases may be encoded on a single plasmid or on separate plasmids.

In certain embodiments, the nuclease expression vector further comprises a selectable marker that allows for selection of host cells comprising the expression vector. Such selection can be helpful to retain the vector in the host cell for a period of time necessary for expression of sufficient amounts of nuclease to occur, for example, for a period of 12, 24, 36, 48, 60, 72, 84, 96, or more than 96 hours, after which the host cells may be grown under conditions under which the expression vector is no longer retained. In certain embodiments, the selectable marker is selected from the group consisting of: URA3, hygromycin B phosphotransferase, aminoglycoside phosphotransferase, zeocin resistance, and phosphinothricin N-acetyltransferase. In some embodiments, the nuclease expression vector vector may comprise a counter-selectable marker that allows for selection of host cells that do not contain the expression vector subsequent to integration of the one or more donor nucleic acid molecules. The nuclease expression vector used may also be a transient vector that has no selection marker, or is one that is not selected for. In particular embodiments, the progeny of a host cell comprising a transient nuclease expression vector loses the vector over time.

In certain embodiments, the expression vector further comprises a transcription termination sequence and a promoter operatively linked to the nucleotide sequence encoding the nuclease. In some embodiments, the promoter is a constitutive promoter. In some embodiments, the promoter is an inducible promoter. Illustrative examples of promoters suitable for use in yeast cells include, but are not limited to the promoter of the TEF1 gene of *K. lactis*, the promoter of the PGK1 gene of *Saccharomyces cerevisiae*, the promoter of the TDH3 gene of *Saccharomyces cerevisiae*, repressible promoters, e.g., the promoter of the CTR3 gene of *Saccharomyces cerevisiae*, and inducible promoters, e.g., galactose inducible promoters of *Saccharomyces cerevisiae* (e.g., promoters of the GAL1, GAL7, and GAL10 genes).

In some embodiments, an additional nucleotide sequence comprising a nuclear localization sequence (NLS) is linked to the 5' of the nucleotide sequence encoding the nuclease. The NLS can facilitate nuclear localization of larger nucleases (>25 kD). In some embodiments, the nuclear localization sequence is an SV40 nuclear localization sequence. In some embodiments, the nuclear localization sequence is a yeast nuclear localization sequence.

A nuclease expression vector can be made by any technique apparent to one skilled in the art. In certain embodiments, the vector is made using polymerase chain reaction (PCR) and molecular cloning techniques well known in the art. See, e.g., *PCR Technology: Principles and Applications for DNA Amplification*, ed. H A Erlich, Stockton Press, New York, N.Y. (1989); Sambrook et al., 2001, *Molecular Cloning—A Laboratory Manual*, 3$^{rd}$ edition, Cold Spring Harbor Laboratory, Cold Spring Harbor, N.Y.

5.3 Host Cells

In another aspect, provided herein is a modified host cell generated by any of the methods of genomically integrating one or more exogenous nucleic acids described herein. Suitable host cells include any cell in which integration of a nucleic acid or "donor DNA" of interest into a chromosomal or episomal locus is desired. In some embodiments, the cell is a cell of an organism having the ability to perform homologous recombination. Although several of the illustrative embodiments are demonstrated in yeast (*S. cerevisiae*), it is believed that the methods of genomic modification provided herein can be practiced on all biological organisms having a functional recombination system, even where the recombination system is not as proficient as in yeast. Other cells or cell types that have a functional homologous recombination systems include bacteria such as *Bacillus subtilis* and *E. coli* (which is RecE RecT recombination proficient; Muyrers et al., *EMIBO rep.* 1: 239-243, 2000); protozoa (e.g., *Plasmodium, Toxoplasma*); other yeast (e.g., *Schizosaccharomyces pombe*); filamentous fungi (e.g., *Ashbya gossypii*); plants, for instance the moss *Physcomitrella patens* (Schaefer and Zryd, *Plant J.* 11: 1195-1206, 1997); and animal cells, such as mammalian cells and chicken DT40 cells (Dieken et al., *Nat. Genet.* 12:174-182, 1996).

In some embodiments, the host cell is a prokaryotic cell. In some embodiments, the host cell is a eukaryotic cell. In some embodiments, the host cell is selected from the group consisting of a fungal cell, a bacterial cell, a plant cell, an insect cell, an avian cell, a fish cell and a mammalian cell. In some embodiments, the mammalian cell selected from the group consisting a rodent cell, a primate cell and a human cell. In some embodiments, the cell is a fungal cell (for instance, a yeast cell), a bacteria cell, a plant cell, or an animal cell (for instance, a chicken cell). In some embodiments, the host cell is a Chinese hamster ovary (CHO) cell, a COS-7 cell, a mouse fibroblast cell, a mouse embryonic carcinoma cell, or a mouse embryonic stem cell. In some embodiments, the host cell is an insect cell. In some embodiments, the host cell is a S2 cell, a Schneider cell, a S12 cell, a 5B1-4 cell, a Tn5 cell, or a Sf9 cell. In some embodiments, the host cell is a unicellular eukaryotic organism cell.

In particular embodiments, the host cell is a yeast cell. Useful yeast host cells include yeast cells that have been deposited with microorganism depositories (e.g. IFO, ATCC, etc.) and belong to the genera *Aciculoconidium, Ambrosiozyma, Arthroascus, Arxiozyma, Ashbya, Babjevia, Bensingtonia, Botryoascus, Botryozyma, Brettanomyces, Bullera, Bulleromyces, Candida, Citeromyces, Clavispora, Cryptococcus, Cystofilobasidium, Debaryomyces, Dekkara, Dipodascopsis, Dipodascus, Eeniella, Endomycopsella, Eremascus, Eremothecium, Erythrobasidium, Fellomyces, Filobasidium, Galactomyces, Geotrichum, Guilliermondella, Hanseniaspora, Hansenula, Hasegawaea, Holtermannia, Hormoascus, Hyphopichia, Issatchenkia, Kloeckera, Kloeckeraspora, Kluyveromyces, Kondoa, Kuraishia, Kurtzmanomyces, Leucosporidium, Lipomyces, Lodderomyces, Malassezia, Metschnikowia, Mrakia, Myxozyma, Nadsonia, Nakazawaea, Nematospora, Ogataea, Oosporidium, Pachysolen, Phachytichospora, Phaffia, Pichia, Rhodosporidium, Rhodotorula, Saccharomyces, Saccharomycodes, Saccharomycopsis, Saitoella, Sakaguchia, Saturnospora, Schizoblastosporion, Schizosaccharomyces, Schwanniomyces, Sporidiobolus, Sporobolomyces, Sporopachydermia, Stephanoascus, Sterigmatomyces, Sterigmatosporidium, Symbiotaphrina, Sympodiomyces, Sympodiomycopsis, Torulaspora, Trichosporiella, Trichosporon, Trigonopsis, Tsuchiyaea, Udeniomyces, Waltomyces, Wickerhamia, Wickerhamiella, Williopsis, Yamadazyma, Yarrowia, Zygoascus, Zygosaccharomyces, Zygowilliopsis,* and *Zygozyma,* among others.

In some embodiments, the yeast host cell is a *Saccharomyces cerevisiae* cell, a *Pichia pastoris* cell, a *Schizosaccharomyces pombe* cell, a *Dekkera bruxellensis* cell, a *Kluyveromyces lactis* cell, a *Arxula adeninivorans* cell, or a *Hansenula polymorpha* (now known as *Pichia angusta*) cell. In a particular embodiment, the yeast host cell is a *Saccharomyces cerevisiae* cell. In some embodiments, the yeast host cell is a *Saccharomyces fragilis* cell or a *Kluyveromyces lactis* (previously called *Saccharomyces lactis*) cell. In some embodiments, the yeast host cell is a cell belonging to the genus *Candida*, such as *Candida lipolytica, Candida guilliermondii, Candida krusei, Candida pseudotropicalis,* or *Candida utilis*. In another particular embodiment, the yeast host cell is a *Kluveromyces marxianus* cell.

In particular embodiments, the yeast host cell is a *Saccharomyces cerevisiae* cell selected from the group consisting of a Baker's yeast cell, a CBS 7959 cell, a CBS 7960 cell, a CBS 7961 cell, a CBS 7962 cell, a CBS 7963 cell, a CBS 7964 cell, a IZ-1904 cell, a TA cell, a BG-1 cell, a CR-1 cell, a SA-1 cell, a M-26 cell, a Y-904 cell, a PE-2 cell, a PE-5 cell, a VR-1 cell, a BR-1 cell, a BR-2 cell, a ME-2 cell, a VR-2 cell, a MA-3 cell, a MA-4 cell, a CAT-1 cell, a CB-1 cell, a NR-1 cell, a BT-1 cell, and a AL-1 cell. In some embodiments, the host cell is a *Saccharomyces cerevisiae* cell selected from the group consisting of a PE-2 cell, a CAT-1 cell, a VR-1 cell, a BG-1 cell, a CR-1 cell, and a SA-1 cell. In a particular embodiment, the *Saccharomyces cerevisiae* host cell is a PE-2 cell. In another particular embodiment, the *Saccharomyces cerevisiae* host cell is a CAT-1 cell. In another particular embodiment, the *Saccharomyces cerevisiae* host cell is a BG-1 cell.

In some embodiments, the yeast host cell is a cell that is suitable for industrial fermentation, e.g., bioethanol fermentation. In particular embodiments, the cell is conditioned to subsist under high solvent concentration, high temperature, expanded substrate utilization, nutrient limitation, osmotic stress due, acidity, sulfite and bacterial contamination, or combinations thereof, which are recognized stress conditions of the industrial fermentation environment.

5.4 Applications 5.4.1. Gene and Cell Therapy

The methods and compositions described herein provide advantages in therapeutic applications which seek to correct genetic defects e.g., ex vivo in a cell population derived from a subject. For example, Schwank et al. (*Cell Stem Cell* 13:653-658 (2013)) recently reported utilization of the CRISPR/Cas9 genome editing system to correct the CFTR locus by homologous recombination in cultured intestinal stem cells of human CF patients. The corrected allele was expressed and fully functional as measured in clonally expanded organoids, and thus this report provides proof of concept for gene correction by homologous recombination in primary adult stem cells derived from patients with a single-gene hereditary defect. However, correction of the CFTR locus in the cultured stem cells required genomic integration of a puromycin resistance cassette along with the donor DNA, followed by selection in puromycin. It has been reported that integration of the neomycin resistance gene into human cell genomes, followed by extended culturing times in G418, causes changes to the cell's characteristics, while expression of enhanced green fluorescent protein (EGFP) and other fluorescent proteins has been reported to cause immunogenicity and toxicity. See, e.g., Barese et al., *Human Gene Therapy* 22:659-668 (2011); Morris et al., *Blood* 103:492-499 (2004); and Hanazono et al., *Human Gene Therapy* 8:1313-1319 (1997). Thus, the methods and compositions provided herein can be utilized to perform gene correction by homologous recombination in primary adult stem cells without the need for integration of a selectable marker.

In another report of HR-mediated correction of a genetic disease, Wu et al. (*Cell Stem Cell* 13:659-662 (2013)) demonstrated that mice with a dominant mutation in the Crygc gene that causes cataracts could be rescued by coinjection into zygotes of Cas9 mRNA and a single-guide RNA (sgRNA) targeting the mutant allele. Correction occurred via homology-directed repair (HDR) based on an exogenously supplied oligonucleotide or the endogenous WT allele, and the resulting mice were fertile and able to transmit the corrected allele to their progeny. However, the rate of HDR-mediated repair was much lower than the incidence of repair or non-repair by NHEJ (see Wu et al. at Table 1). Thus, the methods and compositions provided herein can be utilized to improve the efficiency of gene correction by providing a useful selection mechanism that selects for HR-mediated gene modifications.

5.4.2. Methods for Metabolic Pathway Engineering

The methods and compositions described herein provide particular advantages for constructing recombinant organisms comprising optimized biosynthetic pathways, for example, towards the conversion of biomass into biofuels, pharmaceuticals or biomaterials. Functional non-native biological pathways have been successfully constructed in microbial hosts for the production of precursors to the antimalarial drug artemisinin (see, e.g., Martin et al., *Nat Biotechnol* 21:796-802 (2003); fatty acid derives fuels and chemicals (e.g., fatty esters, fatty alcohols and waxes; see, e.g., Steen et al., *Nature* 463:559-562 (2010); methyl halide-derived fuels and chemicals (see, e.g., Bayer et al., *J Am Chem Soc* 131:6508-6515 (2009); polyketide synthases that make cholesterol lowering drugs (see, e.g., Ma et al., *Science* 326:589-592 (2009); and polyketides (see, e.g., Kodumal, *Proc Natl Acad Sci USA* 101:15573-15578 (2004).

Traditionally, metabolic engineering, and in particular, the construction of biosynthetic pathways, has proceeded in a one-at-a-time serial fashion whereby pathway components have been introduced, i.e., integrated into the host cell genome at a single loci at a time. The methods of integration provided herein can be utilized to reduce the time typically required to engineer a host cell, for example, a microbial cell, to comprise one or more heterologous nucleotide sequences encoding enzymes of a new metabolic pathway, i.e., a metabolic pathway that produces a metabolite that is not endogenously produced by the host cell. In other particular embodiments, the methods of integration provided herein can be used to efficiently engineer a host cell to comprise one or more heterologous nucleotide sequences encoding enzymes of a metabolic pathway that is endogenous to the host cell, i.e., a metabolic pathway that produces a metabolite that is endogenously produced by the host cell. In one example, a design strategy may seek to replace three native genes of a host cell with a complementary exogenous pathway. Modifying these three endogenous loci using the current state of the art requires three separate transformations. By contrast, the methods of simultaneous multiple integration provided herein enables all three integrations to be performed in a single transformation, thus reducing the rounds of engineering needed by three-fold. Moreover, the methods enable the porting of DNA assemblies, comprising optimized pathway components integrated at multiple sites in one host cell chassis, to analogous sites in a second host cell chassis. By reducing the number of rounds needed to engineer a desired genotype, the pace of construction of metabolic pathways is substantially increased.

5.4.2.1 Isoprenoid Pathway Engineering

In some embodiments, the methods provided herein can be utilized to simultaneously introduce or replace one or more components of a biosynthetic pathway to modify the product profile of an engineered host cell. In some embodiments, the biosynthetic pathway is the isoprenoid pathway.

Terpenes are a large class of hydrocarbons that are produced in many organisms. When terpenes are chemically modified (e.g., via oxidation or rearrangement of the carbon skeleton) the resulting compounds are generally referred to as terpenoids, which are also known as isoprenoids. Isoprenoids play many important biological roles, for example, as quinones in electron transport chains, as components of membranes, in subcellular targeting and regulation via protein prenylation, as photosynthetic pigments including carotenoids, chlorophyll, as hormones and cofactors, and as plant defense compounds with various monoterpenes, sesquiterpenes, and diterpenes. They are industrially useful as antibiotics, hormones, anticancer drugs, insecticides, and chemicals.

Terpenes are derived by linking units of isoprene ($C_5H_8$), and are classified by the number of isoprene units present. Hemiterpenes consist of a single isoprene unit. Isoprene itself is considered the only hemiterpene. Monoterpenes are made of two isoprene units, and have the molecular formula $C_{10}H_{16}$. Examples of monoterpenes are geraniol, limonene, and terpineol. Sesquiterpenes are composed of three isoprene units, and have the molecular formula $C_{15}H_{24}$. Examples of sesquiterpenes are farnesenes and farnesol. Diterpenes are made of four isoprene units, and have the molecular formula $C_{20}H_{32}$. Examples of diterpenes are cafestol, kahweol, cembrene, and taxadiene. Sesterterpenes are made of five isoprene units, and have the molecular formula $C_{25}H_{40}$. An example of a sesterterpenes is geranylfarnesol. Triterpenes consist of six isoprene units, and have the molecular formula $C_{30}H_{48}$. Tetraterpenes contain eight isoprene units, and have the molecular formula $C_{40}H_{64}$. Biologically important tetraterpenes include the acyclic lycopene, the monocyclic gamma-carotene, and the bicyclic alpha- and beta-carotenes. Polyterpenes consist of long chains of many isoprene units. Natural rubber consists of polyisoprene in which the double bonds are cis.

Terpenes are biosynthesized through condensations of isopentenyl pyrophosphate (isopentenyl diphosphate or IPP) and its isomer dimethylallyl pyrophosphate (dimethylallyl diphosphate or DMAPP). Two pathways are known to generate IPP and DMAPP, namely the mevalonate-dependent (MEV) pathway of eukaryotes (FIG. 3), and the mevalonate-independent or deoxyxylulose-5-phosphate (DXP) pathway of prokaryotes. Plants use both the MEV pathway and the DXP pathway. IPP and DMAPP in turn are condensed to polyprenyl diphosphates (e.g., geranyl disphosphate or GPP, farnesyl diphosphate or FPP, and geranylgeranyl diphosphate or GGPP) through the action of prenyl disphosphate synthases (e.g., GPP synthase, FPP synthase, and GGPP synthase, respectively). The polyprenyl diphosphate intermediates are converted to more complex isoprenoid structures by terpene synthases.

Terpene synthases are organized into large gene families that form multiple products. Examples of terpene synthases include monoterpene synthases, which convert GPP into monoterpenes; diterpene synthases, which convert GGPP into diterpenes; and sesquiterpene synthases, which convert FPP into sesquiterpenes. An example of a sesquiterpene synthase is farnesene synthase, which converts FPP to farnesene. Terpene synthases are important in the regulation of pathway flux to an isoprenoid because they operate at metabolic branch points and dictate the type of isoprenoid produced by the cell. Moreover, the terpene synthases hold the key to high yield production of such terpenes. As such, one strategy to improve pathway flux in hosts engineered for heterologous isoprenoid production is to introduce multiple copies of nucleic acids encoding terpene synthases. For example, in engineered microbes comprising the MEV pathway where the production of sesquiterpenes such as farnesene is desired, a sesquiterpene synthase, e.g., a farnesene synthase is utilized as the terminal enzyme of the pathway, and multiple copies of farnesene synthase genes may be introduced into the host cell towards the generation of a strain optimized for farnesene production.

Because the biosynthesis of any isoprenoid relies on the same pathway components upstream of the prenyl diphosphate synthase and terpene synthase, these pathway components, once engineered into a host "platform" strain, can be utilized towards the production of any sesquiterpene, and the identity of the sesquiterpene can be dictated by the particular sesquiterpene synthase introduced into the host cell. Moreover, where production of terpenes having different isoprene units is desired, for example a monoterpene instead of a sesquiterpene, both the prenyl diphosphate synthase and the terpene synthase can be replaced to produce the different terpene while still utilizing the upstream components of the pathway.

Accordingly, the methods and compositions provided herein can be utilized to efficiently modify a host cell comprising an isoprenoid producing pathway, e.g., the MEV pathway to produce a desired isoprenoid. In some embodiments, the host cell comprises the MEV pathway, and the methods of simultaneous multiple integration provided herein can be utilized to simultaneously introduce multiple copies of a prenyl diphosphate synthase and/or a terpene synthase to define the terpene product profile of the host cell. In some embodiments, the prenyl diphosphate synthase is GPP synthase and the terpene synthase is a monoterpene synthase. In some embodiments, the prenyl diphosphate synthase is FPP synthase and the terpene synthase is a sesquiterpene synthase. In some embodiments, the prenyl diphosphate synthase is GGPP synthase and the terpene synthase is a diterpene synthase. In other embodiments, the host cell comprises the MEV pathway and a prenyl diphosphate synthase and/or a terpene synthase for the production of a first type of terpene, for example, farnesene, and the methods of simultaneous multiple integration provided herein can be utilized to simultaneously replace one or more copies of the prenyl diphosphate synthase and/or a terpene synthase to produce a second type of terpene, for example, amorphadiene. These embodiments are exemplified in Examples 3 and 4 below. The methods provided herein can be similarly utilized towards the construction and/or modification of any biosynthetic pathway which utilizes multiple copies of pathway components, and are particularly useful for engineering host cells whose product profile can be readily modified with the addition or exchange of multiple copies of a single pathway component.

6. EXAMPLES 6.1 Example 1: A Comparison of Multiple Modes of gRNA Delivery for Simultaneous Deletion, Via Integration of Deletion Constructs, of 3 Genes Using CRISPR This Example provides results which demonstrate the use of CRISPR for simultaneous deletion of the RHR2, HO and ADH5 ORFs (with integration of a short linker sequence) in S. cerevisiae. In brief, chimeric gRNAs were generated targeting unique sequences contained in the ORF of RHR2, HO and ADH5, and were transformed in various configurations into host cells expressing the Cas9 protein from the type II bacterial CRISPR system of Streptococcus pyogenes. Transformed colonies were screened by colony PCR (cPCR) for the replacement of one, two or three ORFs with a short linker sequence.

6.1.1. Constitutive Expression of Cas9p

A wild-type Saccharomyces cerevisiae strain, (CEN.PK2, Mat a, ura3-, TRP1+, leu2-, MAL2-8C, SUC2) was used as a host for the constitutive expression of Cas9p from Streptococcus pyogenes. Genomic integration of a construct containing a yeast codon optimized coding sequence for Cas9 under the control of the medium strength FBA1 promoter (SEQ ID NO:3) was targeted to the GRE3 locus.

6.1.2. Selection of CRISPR Target Sites in RHR2, HO and ADH5 ORFs

Candidate CRISPR targets inside the targeted ORFs were identified based on the presence of a PAM sequence $N_{(19)}$ NGG. The NGG sequence is referred to as a PAM sequence and the 8 base pairs of DNA preceding the PAM sequence are especially important for enforcing specificity (Fu et al., Nat Biotechnol 31(9):822-826 (2013); Ran et al., Nat Protoc 8(11):2281-2308 (2013)). Candidate sites were then ranked based on uniqueness of the target sequence in the genome, and the site with the lowest similarity to other sites in the genome was chosen to minimize the risk of off target cutting. Target sites are shown in Table 2.

TABLE 2

| CRISPR Target sites | |
|---|---|
| ORF | Target Sequence (NGG omitted) |
| RHR2 | ACCTCTGGTACCCGTGACA (SEQ ID NO: 4) |
| HO | CCGGCTTGATCGACTCAGA (SEQ ID NO: 5) |
| ADH5 | GGGTCATTGGTATCGATGG (SEQ ID NO: 6) |

6.1.3. gRNA Delivery Modes

Cas9p is targeted to cut sites by association with a generic structural RNA and a specific targeting RNA. The now standard "chimeric" configuration was adopted in this work, in which the targeting and structural RNAs are fused to create a single guide RNA, or gRNA (Ran, Hsu et al. 2013). Expression of the gRNA construct(s) was driven by the SNR52 polymerase III promoter, with a SUP4 terminator (DiCarlo, Norville et al. 2013). Sequences for gRNA constructs targeting the RHR2, HO and ADH5 loci, respectively, are provided herein as SEQ ID NOs: 7, 8 and 9. Several modes of gRNA delivery were used, as described in section 5.2.1 above and depicted in FIG. 7. Expression of the gRNA cassette from a pRS4XX-series 2μ vectors (Sikorski and Hieter 1989) was achieved either by: 1) standard cloning methods to generate finished circular plasmids (FIGS. 7.1 and 7.2) prior to transformation into a Cas9-expressing yeast strain, or 2) by assembling the gRNA cassette into a circularized plasmid by gap repair in vivo, by transforming the cassette directly into a Cas9-expressing yeast strain, along with a linearized vector backbone (Orr-Weaver, Szostak et al. 1983) (FIG. 7.4). Regions of homology (~500 bp) between the termini of the gRNA cassette and the linear vector backbone (SEQ ID NO: 10) facilitate assembly of a circular gRNA plasmid in vivo. Alternatively, 3) the gRNA was expressed directly from the linear cassette, co-transformed with a closed plasmid bearing a NatA (Nourseothricin acetyltransferase from Streptomyces noursei) selectable marker (SEQ ID NO: 11) to select for transformed cells (FIG. 7.3). Finally, in a variation of the third method, 4) the linear cassette was co-transformed with vector linearized by PCR inside of the NatA marker (SEQ ID NO: 12) such that a central coding sequence for the NatA marker is missing; a complementary overlapping NatA ORF fragment (SEQ ID NO: 13) that can recombine via gap repair to re-create the closed plasmid bearing a complete NatA expression cassette was also co-transformed (FIG. 9B; discussed in Example 2 below).

To create circular gRNA plasmids (delivery mode 1), annealed oligonucleotides containing the CRISPR seed sequence and 20 bp of upstream/downstream homology to the cassette were gap-repaired into a linearized backbone in E. coli (Mandecki 1986), correct clones were identified, and the finished plasmid transformed into a host strain. To prepare full length linear gRNA cassettes with ~500 bp flanking homology to the linearized vector (delivery modes 2, 3 and 4), a PCR assembly method was employed. Using a generic gRNA cassette as template, half cassettes were amplified using primers to create a central overlap of 22 base pairs comprising the unique CRISPR seed sequence. The two half cassettes were then assembled in a second PCR reaction to generate a full length gRNA expression cassette. 10 µl of unpurified PCR assembly (typically 20-60 ng/µl concentration as determined by comparison to DNA marker ladder) and 150 ng of linearized 2µ vector were used per transformation.

6.1.4. Generation of Linear Donor DNA

Linear donor DNAs comprise 500 bp upstream and downstream homology regions targeting each ORF, flanking a central linker (CGCTCGTCCAACGCCGGCGGACCT), and were generated by the methods of polynucleotide assembly described in U.S. Pat. No. 8,221,982. Donor DNA sequences for integration into the RHR2, HO and ADH5 locus, respectively, are provided herein as SEQ ID NOs: 14, 15 and 16.

6.1.5. Simultaneous Deletion of ORF and Integration of a Short Linker Sequence Using CRISPR Donor DNA (~1 µg) and the appropriate gRNA reagents were co-transformed into each Cas9 expressing strain using optimized LiAc methods (Gietz and Woods 2002) with the addition of a 30 minute incubation of cells at 30 degrees C. prior to heat shock at 42 degrees C. Cells were recovered overnight in non-selective YPD (Yeast extract peptone dextrose) media before plating to selective, antibiotic-containing media (nourseothricin, 100 µg/ml) to maintain the gRNA or marker plasmid. Marker-less integrations were scored as positive if colony PCR (cPCR) using primers binding upstream of the 5' integration flank and to the integrated linker sequence (Table 3) produced the correct amplicon, a result indicative of a targeted integration event.

TABLE 3

Primer sequences for cPCR verification of linker integration at RHR2, HO and ADH5 loci

| Primer Name | Description | Sequence | SEQ ID NO |
|---|---|---|---|
| RHR2-US-F | RHR2 locus US FOR | gggtgcgaagtaccacc acgtttctttttcatctct | SEQ ID NO: 17 |
| HO-US-F | HO locus US FOR | acgtgtgtgtctcatggaaatt gatgcagttgaagaca | SEQ ID NO: 18 |
| ADH5-US-F | ADH5 locus US FOR | ggcgttatatccaaacattt cagacagaagatt | SEQ ID NO: 19 |
| R5 | Linker REV | AGGTCCGCCGGCGTT GGACGAGCG | SEQ ID NO: 20 |

6.1.6. Results and Discussion

Gap Repair Delivery Modes: Four modes of gRNA delivery were assessed for efficiency of simultaneous deletion of the RHR2, HO and AHD5 open reading frames, with integration of a short linker sequence. Colony PCR results for assessing triple integration are shown in FIG. 8 and rates are summarized in Table 4.

TABLE 4

Rates of triple integrations with varying delivery of gRNA constructs

| Description | Triple rate |
|---|---|
| Triple selection, plasmid gRNAs | 0.91 |
| Single selection, plasmid gRNAs | 0 |
| marker plasmid, linear gRNAs | 0 |
| gap repair linear gRNAs | 0.64 |

In the first mode of gRNA delivery, each of three gRNAs (targeting RHR2, HO and ADH5, respectively) was supplied on a plasmid bearing unique markers (NatA, URA3 cassette and HIS3 cassette; see FIG. 7.1), and cells were transformed with all three plasmids and triply selected for the expression of each marker. Very high efficiencies (91%) of triple deletion (via integration) were observed (FIG. 8, panel 1). These high frequencies likely result from sustained expression of all three gRNAs by triple selection for the plasmids bearing their cassettes. By contrast, the second mode, where the gRNAs were supplied on three plasmids bearing the same marker (NatA; see FIG. 7.2), failed to generate any triple deletions (FIG. 8, panel 2). Instead, single deletions dominated, which is consistent with the selection requirement to maintain only one of the three plasmids. In the third mode, the gRNAs were supplied as linear cassettes, with a NatA marked plasmid included to select for transformed cells (see FIG. 7.3). No triple deletions were observed, and very low rates of any deletion event were observed (FIG. 8, panel 3). This mode of delivery is expected to result in transient expression of the gRNA constructs, and this seems to be inferior to sustained expression. The fourth delivery mode that was explored requires gap repair of the three gRNA cassettes into a linearized vector bearing the NatA marker (see FIG. 7.4). We observed 64% of colonies were triply deleted (FIG. 8, panel 4). This is a surprising result as this mode of delivery does not enforce sustained expression of all three gRNAs as the first mode does. Indeed, results from the second mode indicate clearly that co-transformation of three like-marked gRNA plasmids is ineffective, and the results from the third mode indicate that transient expression of gRNAs from linear cassettes is also non-functional. Thus, there is an unexpected advantageous benefit towards CRISPR/Cas-9 mediated genomic integration events associated with gap repair as a mode of delivery for gRNA cassettes.

6.2 Example 2: Selection of HR Competent Cells Via Gap Repair

This example demonstrates the benefit of gap repair, independent of the benefit of selecting for gRNA expression, for improving the efficiency of a nuclease-mediated integration event.

One mechanism by which gap repair might improve the recovery of clones engineered by CRISPR (or any site-specific nuclease) is by enforcing an additional selection for cells that are proficient for homologous recombination (HR). HR proficiency can vary widely in an asynchronous cell population (see e.g., Branzei and Foiani, *Nat Rev Mol Cell*

Bio 9(4):297-308 (2008)), and selection for cells that can accomplish gap repair of a plasmid bearing a selectable marker may select a population that is particularly HR proficient. This could explain the surprising success of the fourth mode of gRNA delivery (FIGS. 7.4 and 8.4), discussed in Example 1. To uncouple the effects of gap repair as a selection mechanism from that of sustained expression of at least one of the gRNAs, we assessed rates of single deletion of the RHR2, HO and ADH5 locus, respectively, by co-transformation of the appropriate donor DNA and linear gRNA cassette (described in Example 1, above) and one of two marker vectors. The first marker vector was closed, i.e. no gap repair is required for the expression of a NatA marker in transformed cells (FIG. 9A). The second marker was linearized such that a central portion of the NatA marker was missing, but could be complemented by gap repair of an overlapping fragment to produce a closed, functional marker vector bearing a complete NatA expression cassette (FIG. 9B). In both cases, expression of the gRNA is transient only. Over three independent experiments, we noted improvements up to 8-fold (~3-5-fold range average) in the rate of single locus deletion (integration) when the marker plasmid required gap repair (FIG. 9, with rates summarized in FIGS. 10-12).

These results support the hypothesis that gap repair can act as an additional selection for cells proficient in HR, and thus most capable of successful nuclease-assisted engineering, and in particular, targeted integrations of donor DNA. We note that *S. cerevisiae* are especially adept at HR, and in cells that favor NHEJ and other imperfect repair methods (e.g. mammalian cells), we propose that gap repair may be particularly effective at increasing the recovery of cells bearing one or more targeted integrations.

6.3 Example 3: Enhanced Selection of HR-Competent Cells Via Multi-Piece Gap Repair This example demonstrates that by increasing the complexity of gap repair of a marker vector by further fragmenting the vector, it is possible to further increase the efficiency of nuclease-assisted engineering.

ORF was comprised on one of the two backbone fragments while the promoter driving NatA expression (*K. lactis* Tef1 promoter) was comprised on the other, and thus, NatA expression is possible only upon HR-mediated assembly of the fragments. Sequences of donor DNA targeting each of the Gal80, HO and ADH5 locus, respectively; gRNA constructs targeting each locus; and marker plasmid fragments for two-piece and three-piece in vivo assembly are provided herein as SEQ ID NOs:21 to 29.

Target sites for the Gal80, HO and ADH5 locus, respectively, are shown in Table 5.

TABLE 5

CRISPR Target sites

| ORF | Target Sequence (NGG omitted) | SEQ ID NO |
|---|---|---|
| Gal80 | TAAGGCTGCTGCTGAACGT | SEQ ID NO: 30 |
| HO | CCGGCTTGATCGACTCAGA | SEQ ID NO: 31 |
| ADH5 | GGGTCATTGGTATCGATGG | SEQ ID NO: 32 |

Cells were transformed and cultured as described in Example 1, and colonies appearing on selection were assayed for integration of the deletion construct at each locus by cPCR using an upstream forward primer that binds outside of the deletion construct, and a reverse primer that binds to a short linker sequence integrated in place of each open reading frame. 11 colonies were assayed for each delivery mode, as well as a parent colony THAT serves as a negative control ("N").

TABLE 6

Primer sequences for cPCR verification of linker integration at Gal80, HO and ADH5 loci

| Primer Name | Description | Sequence | SEQ ID NO |
|---|---|---|---|
| Gal80-US-F | Gal80 locus US FOR | CAAACGGCCGCCTCTGCCATGGC AAAGAATGCTTTCCA | SEQ ID NO: 33 |
| HO-US-F | HO locus US FOR | ACGTGTGTGTCTCATGGAAATTG ATGCAGTTGAAGACA | SEQ ID NO: 34 |
| ADH5-US-F | ADH5 locus US FOR | GGCGTTATATCCAAACATTTCAG ACAGAAGATT | SEQ ID NO: 35 |
| R_ | Linker REV | AGGTCCGCCGGCGTTGGACGAGCG | SEQ ID NO: 36 |

Cas9-expressing haploid yeast cells (*S. cerevisiae*) were transformed with donor DNAs for simultaneous, markerless deletion of Gal80, HO and ADH5 open reading frames, gRNA constructs targeting each locus, and linearized vector backbone, as described in Example 1, with the addition of a transformation whereby the vector backbone was fragmented into two pieces, with each piece comprising overlapping homologous regions to each other (47 bp) as well as to the gRNA cassette (~500 bp). This allowed for a 3-piece in vivo assembly via gap repair of a circular NatA marker plasmid incorporating the gRNA cassette. The NatA marker As shown in FIG. 13, the rate of simultaneous triple integration at all three loci was substantially higher when three HR events were required to assemble the marker vector, compared to when only two HR events were required. In particular, with a 2-piece in vivo assembly of the marker vector, 6/11 colonies had an integration at the Gal80 locus, 10/11 had an integration at the HO locus, 7/11 colonies had an integration at the ADH5 locus, and 5/11 colonies (45.4%) had an integration at all three loci. By comparison, with a 3-piece in vivo assembly of the marker vector, 9/11 colonies had an integration at the Gal80 locus, 10/11 had an integration at the HO locus, 10/11 colonies had an integration at the ADH5 locus, and 9/11 colonies (81.8%) had an integration at all three loci. Thus, requiring a 3-piece gap repair of the marker vector instead of a 2-piece gap repair improved the rate of triple integration by nearly two-fold.

To determine if this improvement in multiplex integration rate could also be seen in diploid strains of S. cerevisiae, Cas9-expressing cells of the diploid yeast strain CAT-1 were similarly transformed with donor DNAs for simultaneous, pan-allelic, marker-less deletion of Gal80, HO and ADH5 open reading frames, gRNA constructs targeting each locus, and selective DNA fragmented into either 2 or 3 overlapping pieces. Colonies were assayed by cPCR using an upstream forward primer outside of the deletion construct, and a reverse primer binding to a short linker sequence integrated in place of each open reading frame (Table 6).

As shown in FIG. 14, the rate of simultaneous triple integration at all three loci of the diploid strain was also substantially higher when three HR events were required to assemble the marker vector. In particular, with a 2-piece in vivo assembly of the marker vector, 3/24 colonies had an integration at the Gal80 locus, 7/24 had an integration at the HO locus, 2/24 had an integration at the ADH5 locus, and 1/24 colonies (4.2%) had an integration at all three loci. By comparison, with a 3-piece in vivo assembly of the marker vector, 3/8 colonies had an integration at the Gal80 locus, 5/8 had an integration at the HO locus, 3/8 colonies had an integration at the ADH5 locus, and 3/8 colonies (37.5%) had an integration at all three loci. Thus, requiring a 3-piece gap repair of the marker vector instead of a 2-piece gap repair improved the rate of triple integration in the diploid strain by nearly ten-fold. The number of colonies recovered from the experiment was also roughly ten-fold fewer when 3 events were required (data not shown), suggesting that requiring higher order assembly of the marker vector selects for only the most HR competent cells of the population.

6.4 Example 4: Introduction of Single and Multiplex Point Mutations Using CRISPR in Combination with Gap Repair This example demonstrates the application of the optimized protocol as described in Example 1 (mode 4: in vivo HR-mediated incorporation of gRNA cassette(s) into a marker vector backbone) for introducing precise point mutations or corrections to point mutations.

Currently, introduction of a point mutation at a single locus is a tedious process. The Delitto Perfetto method allows marker-less introduction of point mutations, but requires integration of a marked cassette containing an inducible meganuclease in close proximity to the targeted site (Storici et al., Proc Natl Acad Sci USA 100(25):14994-9 (2003)). Alternatively, a complex integration cassette bearing a URA3 marker can be designed and integrated at the target site, such that subsequent loop out of the URA3 by 5-FOA counter selection reconstitutes the genetic locus with the point mutation included. Both of these methods are problematic for essential genes, require at least two rounds of genetic engineering, and are not amenable to multiplexing.

There are several considerations for the introduction of a point mutation (i.e., a missense SNP) by CRISPR. First, in addition to being unique in the genome, the site targeted for cutting should be as close as possible to the site of the desired SNP (FIG. 15). This is because recombination to repair the cut site does not require incorporation of the desired SNP, and the likelihood of its inclusion is expected to decrease with distance from the cut site. Secondly, for optimal efficiency, the donor DNA should be designed such that it is not also a target for CRISPR. Indeed, this issue was cited by DiCarlo et al. to explain the low rates of SNP integration by CRISPR observed in their experiments (DiCarlo et al., Nucleic Acids Res., 7, 4336-4343 (2013))). To escape cutting, the desired SNP would need to disrupt the CRISPR target site in the donor DNA, an impossible requirement to satisfy at most loci. To make the donor DNA immune to cutting, and simultaneously improve the chances that recombination events include the desired SNP, a heterology block approach was adopted whereby silent mutations were made in the codons between the target site and the point mutation, reducing the potential for recombination events that would omit the desired SNP (FIG. 15). Additionally, integration of the heterology block provides a novel primer binding site to identify candidate clones by PCR.

As a proof of principle, mutant alleles of yeast cells (S. cerevisiae) that had undergone mutagenesis were targeted for replacement with corresponding wild type alleles using the above-described approach. The mutagenized strain was made to constitutively express Cas9 under the control of the medium strength FBA1 promoter as described in Example 1. The Cas9p-expressing strain was then transformed with donor DNAs (one at a time, for single integration events) targeting each of the TRS31, CUES, ECM38, PGD1, SMC6, NTO1 and DGA1 open reading frames, and gRNA constructs targeting each locus, each comprising overlapping homologous with a linear NatA marker plasmid backbone, allowing for in vivo assembly of a circular plasmid via gap repair. Cells were transformed and cultured as described in Example 1, then assessed for introduction of a point mutation (reversion allele) at each of the 7 loci. Candidate colonies and parent negative control (c) were assayed by colony PCR against the heterology block and flanking sequence, and selected positive colonies were confirmed by sequencing a larger PCR product spanning the integration locus.

TABLE 7

Primer sequences for cPCR verification of allele swaps

| Primer Name | Description | Sequence | SEQ ID NO |
|---|---|---|---|
| TRS31-US-F | TRS31 locus US FOR | GTGCATTTGGCTCGAGTTGCTG | SEQ ID NO: 37 |
| TRS31-DS-R | TRS31 locus DS REV | GGGAAGTTATCTACTATCATATA TTCATTGTCACG | SEQ ID NO: 38 |
| TRS31-het-R | Heterology block primer | GAAAAGTAGAGATTCAGAATAG ATCCTTGAC | SEQ ID NO: 39 |

TABLE 7-continued

Primer sequences for cPCR verification of allele swaps

| Primer Name | Description | Sequence | SEQ ID NO |
|---|---|---|---|
| CUE5-US-F | CUE5 locus US FOR | GGAAGGTATCAAGGATTCTTCTCTCC | SEQ ID NO: 40 |
| CUE5-DS-R | CUE5 locus DS REV | GAGGTGGCACATCTTCATCATCTTC | SEQ ID NO: 41 |
| CUE5-het-R | Heterology block primer | CCAATAACTCATCCTGCTCCAATTGT | SEQ ID NO: 42 |
| ECM38-US-F | ECM38 locus US FOR | CAGACGCTGCAGTAACACAAGC | SEQ ID NO: 43 |
| ECM38-DS-R | ECM38 locus DS REV | CTGAAGTGGGCAGTTCCATGC | SEQ ID NO: 44 |
| ECM38-het-R | Heterology block primer | CAGTGATCTGGATCGTAGAAGGGC | SEQ ID NO: 45 |
| PGD1-US-F | PGD-1 locus US FOR | CCAAGAGCATGCCACGGTTG | SEQ ID NO: 46 |
| PGD1-DS-R | PGD-1 locus DS REV | GAGTTCCCATAGTACTACCGC | SEQ ID NO: 47 |
| PGD1-het-R | Heterology block primer | GCAGACCTTATCTCTTGTCTCG | SEQ ID NO: 48 |
| SMC6-US-F | SMC6 locus US FOR | GAGCTACTTTCACTGACTGCGC | SEQ ID NO: 49 |
| SMC6-DS-R | SMC6 locus DS REV | GCGCTTCAATAGTAGTACCATCAGATG | SEQ ID NO: 50 |
| SMC6-het-R | Heterology block primer | GCCGTTCTCTGATCTCAAAGAGAAT | SEQ ID NO: 51 |
| NTO1-US-F | NTO1 locus US FOR | CTCAGTATGACATGGATGAACAGGATG | SEQ ID NO: 52 |
| NTO1-DS-R | NTO1 locus DS REV | GGTACCTCCTGTAAGCTCCCTTTTC | SEQ ID NO: 53 |
| NTO1-het-R | Heterology block primer | GACTGAGACGTTCTGGACTCCTTC | SEQ ID NO: 54 |
| DGA1-US-F | DGA1 locus US FOR | CTTAACCAAGCACGACAGTGGTC | SEQ ID NO: 55 |
| DGA1-DS-R | DGA1 locus DS REV | GATTCCCTAGCGCCACCAAC | SEQ ID NO: 56 |
| DGA1-het-R | Heterology block primer | CCTCTCCGGTGGCTGGTGATCTG | SEQ ID NO: 57 |
| ADH2-US-F | ADH2 locus US FOR | CGAGACTGATCTCCTCTGCCGGAAC | SEQ ID NO: 58 |
| ADH2-DS-R | ADH2 locus DS REV | GAATACTTCACCACCGAGCGAG | SEQ ID NO: 59 |
| ADH2-het-R | Heterology block primer | GCATGTAAGTCTGTATGACATACTCCTG | SEQ ID NO: 60 |
| SIN4-US-F | SIN4 locus US FOR | CAAACGTCCTAAATGACCCATCGTTG | SEQ ID NO: 61 |
| SIN4-DS-R | SIN4 locus DS REV | CAACTTCGGGTTTTGTTGTTGGTTAG | SEQ ID NO: 62 |
| SIN4-het-R | Heterology block primer | CAATGGCAATTTACCGTAGTTGAAACCG | SEQ ID NO: 63 |
| CYS4-US-F | CYS4 locus US FOR | CTCCAGAATCACATATTGGTGTTGC | SEQ ID NO: 64 |

TABLE 7-continued

Primer sequences for cPCR verification of allele swaps

| Primer Name | Description | Sequence | SEQ ID NO |
|---|---|---|---|
| CYS4-DS-R | CYS4 locus DS REV | CCATCTTAGTAACGATATGGATTGGTTTC | SEQ ID NO: 65 |
| CYS4-het-R | Heterology block primer | CTGATGGAGTCAGGAAAGATGGC | SEQ ID NO: 66 |

Sequences of donor DNA targeting each of the TRS31, CUES, ECM38, PGD1, SMC6, NTO1, DGA1, ADH2, SIN4 and CYS4 locus, respectively; the target sequence of each locus, and gRNA constructs targeting each locus are provided herein as SEQ ID NOs:67-96.

As shown in FIG. 16, a high rate of heterology block integration was observed at each locus (ranging from 36.4% to 90.9%), and subsequent sequencing of PCR fragments spanning the desired mutations revealed a majority of clones contained the desired allele.

To determine the feasibility of multiplex introduction of point mutations, three loci (ECM38, PGD1 and ADH2) were targeted simultaneously for heterology block integration (allele swapping) using the optimized delivery mode for multiple gRNAs. As shown in FIG. 17, high rates of triple heterology block integration were observed by PCR assay (90.9 to 100%). To determine if even higher order multiplex integrations were feasible, five loci (ADH2, PGD1, ECM38, SIN4 and CYS4) were simultaneously targeted in a similar fashion. As shown in FIG. 18, simultaneous quintuple heterology block integration was confirmed by cPCR assay in 2/11 colonies (18.2%).

As a second proof of principle, eleven different mutant alleles were introduced into naïve S. cerevisiae strains and the resulting strains were tested for phenotypes conferred by these SNPs. Among the alleles examined was one allele relevant to industrial fermentation, conferring faster sedimentation (ACE2 S372*) (Oud, Guadalupe-Medina et al., Proc Natl Acad Sci USA 110(45): E4223-4231, 2013), a series of temperature sensitive alleles in genes essential for cell division and the secretory pathway (SEC1 G443E, SEC6 L633P, MYO2 E511K, CDC28 R283Q) (Lorincz and Reed, Mol Cell Biol 6(11): 4099-4103, 1986; Roumanie, Wu et al. J Cell Biol 170(4): 583-594, 2005) and another pair related to improved high temperature growth (NCS2 H71L and END3 S258N) (Sinha, David et al., Genetics 180(3): 1661-1670, 2008; Yang, Foulquie-Moreno et al., PLoS Genet 9(8): e1003693, 2013). In addition, a series of five alleles associated with resistance to elevated ethanol concentrations were tested (SPT15 F177S, SPT15 Y195H, SPT15 K218R, PRO1 D154N and PUT1 deletion) (Takagi, Takaoka et al., Appl Environ Microbiol 71(12): 8656-8662, 2005; Alper, Moxley et al., Science 314(5805): 1565-1568, 2006).

High rates of heterology block integration (>90%) were observed for the introduction of most individual alleles (FIG. 22), and subsequent sequencing of PCR fragments spanning the desired mutations confirmed these changes. The temperature sensitive mutants were assayed at permissive and restrictive temperatures to confirm their intended phenotypes. Incomplete separation of cells during division caused by truncation of ACE2 was confirmed by bright-field microscopy, with dramatic clumping of cells (FIG. 23 A). Temperature-sensitive alleles of CDC28, MYO2 and SEC1 failed to grow at 37° C. as expected (FIG. 23 B), and the CDC28 allele strain arrested in the G1 phase of growth (FIG. 23 C). To demonstrate secretory defects at the restrictive temperature in the SEC1 and SEC6 mutants, the exocyst complex component SEC3 was carboxy-terminally GFP-tagged at its endogenous locus (also using CRISPR) to function as a reporter of secretory activity. SEC3 is normally localized to the bud in wild-type cells but its localization is clearly disrupted in both secretory mutants (FIG. 23 D).

In many cases, a phenotype results from the synergy of multiple alleles, but engineering such strains is even more time consuming, and is often not attempted. The optimized multiplex method was applied to this problem. Naïve CENPK2 bears one allele for high temperature growth (MKT1 D30G) (Yang, Foulquie-Moreno et al. 2013), and two additional mutations were introduced in NCS2 and END3. When grown overnight at a range of temperatures, neither of the individual alleles had an effect. However, strains containing both additional alleles integrated in a single step survived temperatures up to 42.7° C. (FIG. 23 E).

Figure 23A:
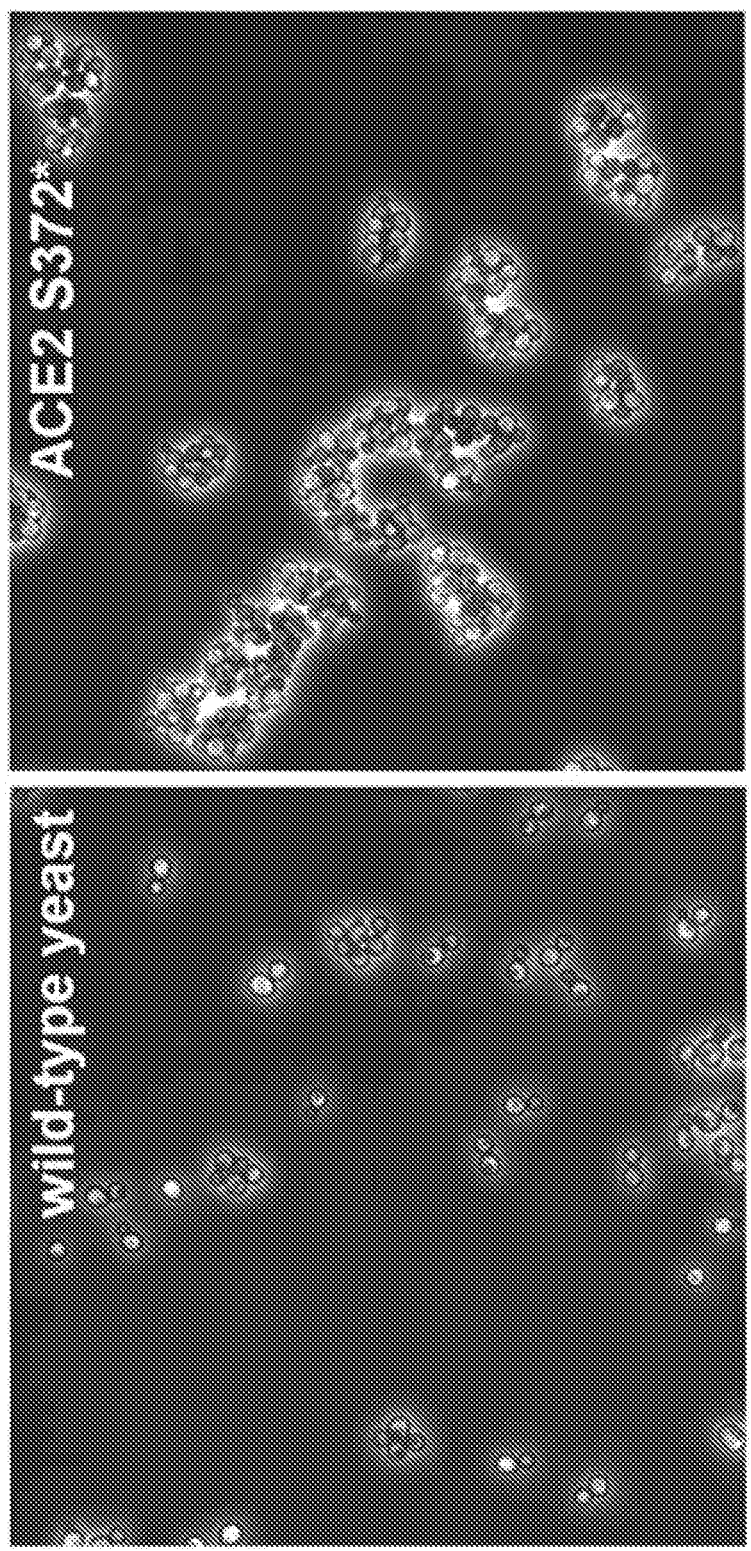
Figure 23B:
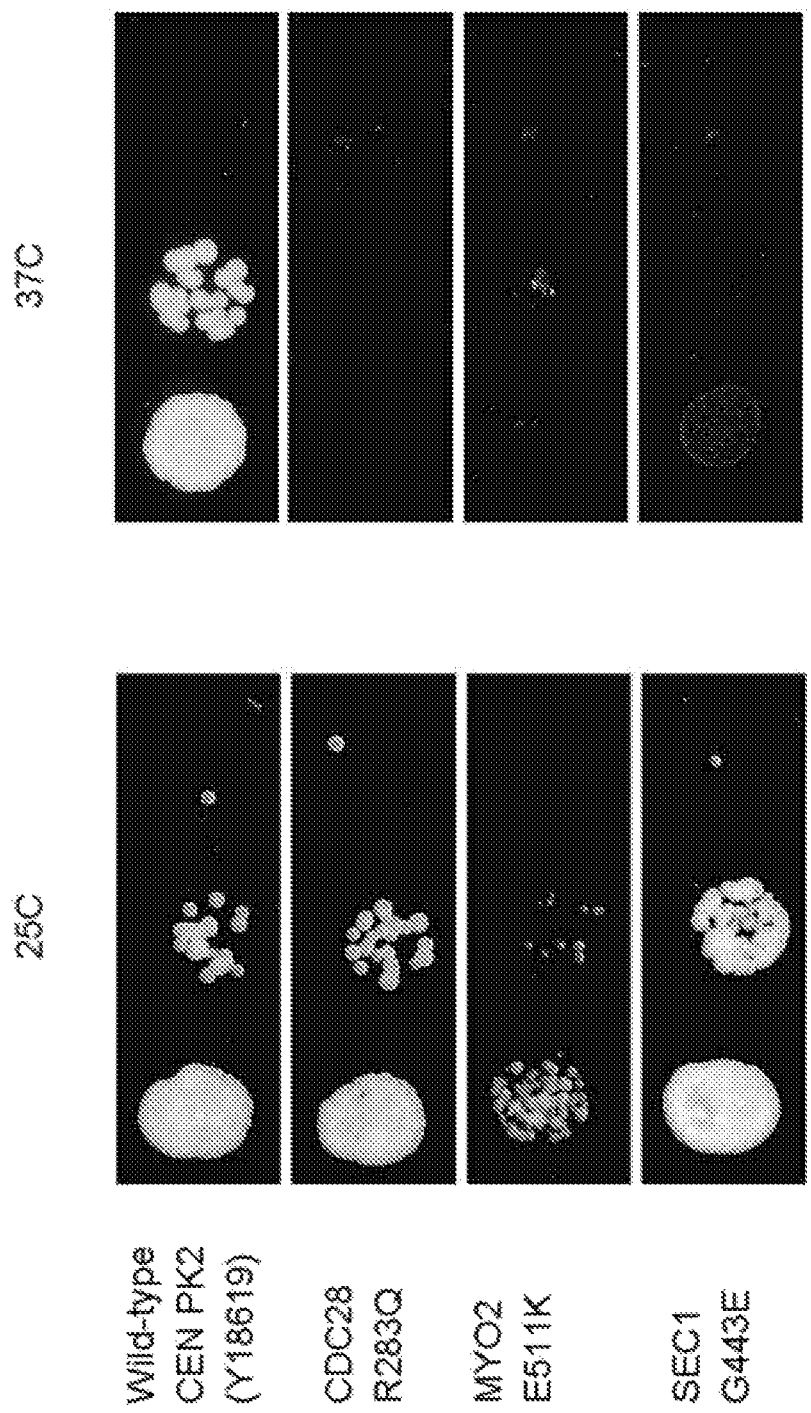
Figure 23C:
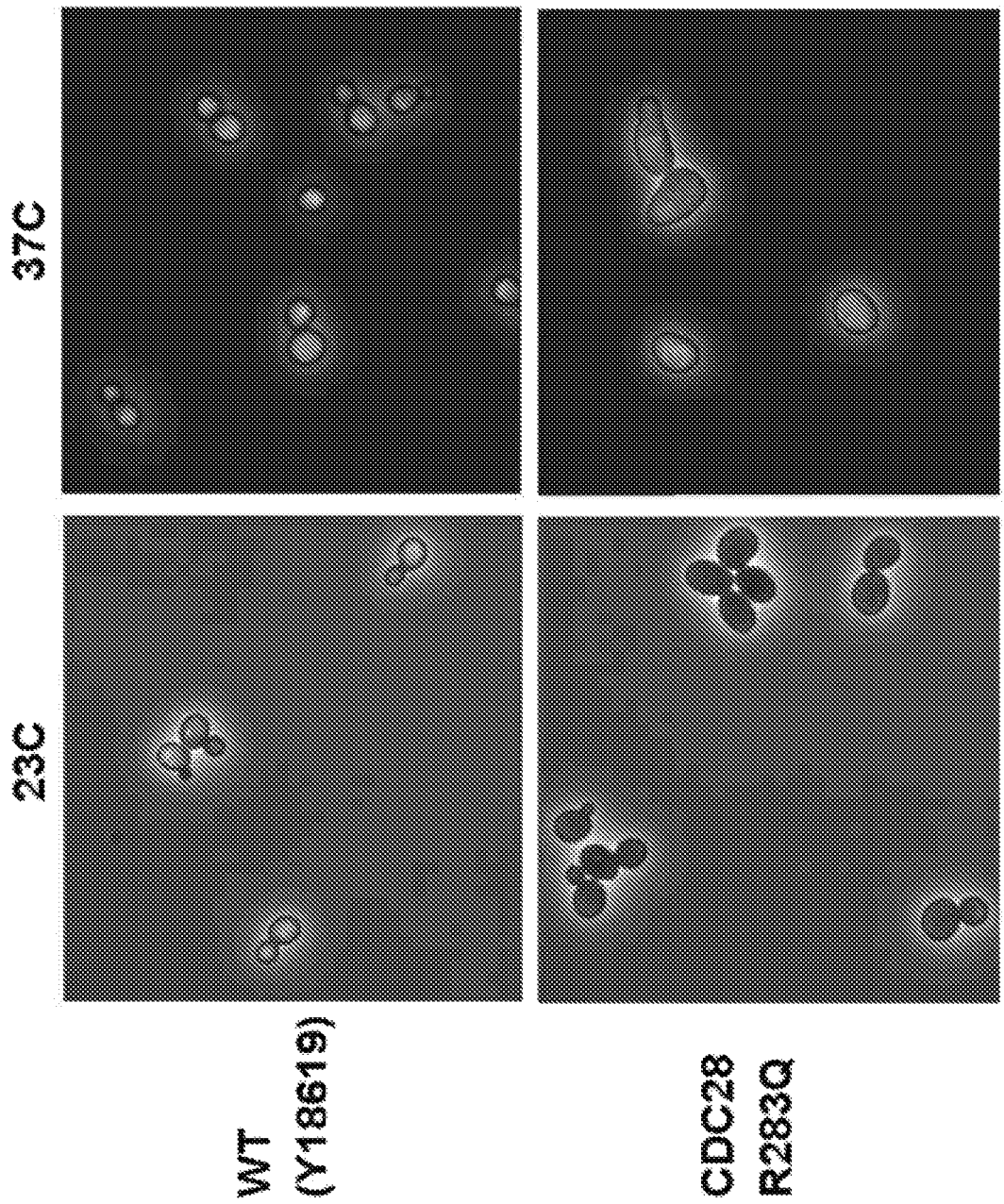
Figure 23D:
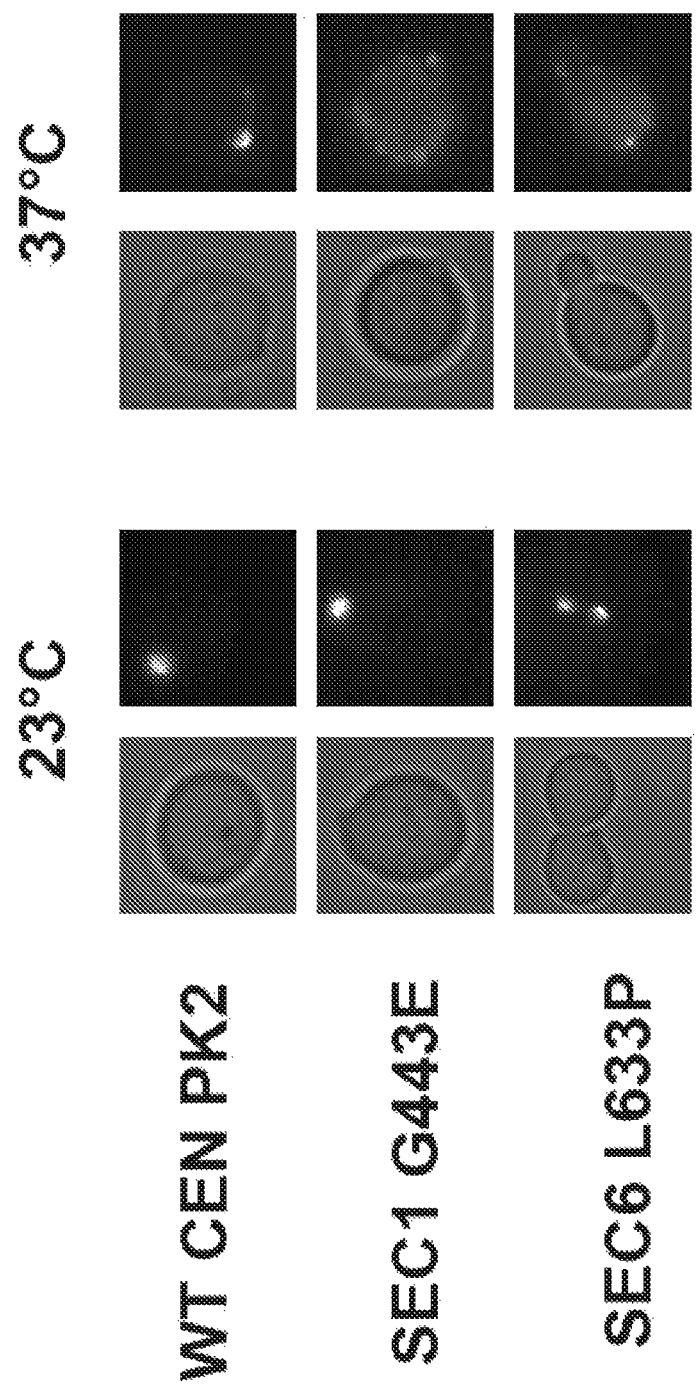
Figure 23E:
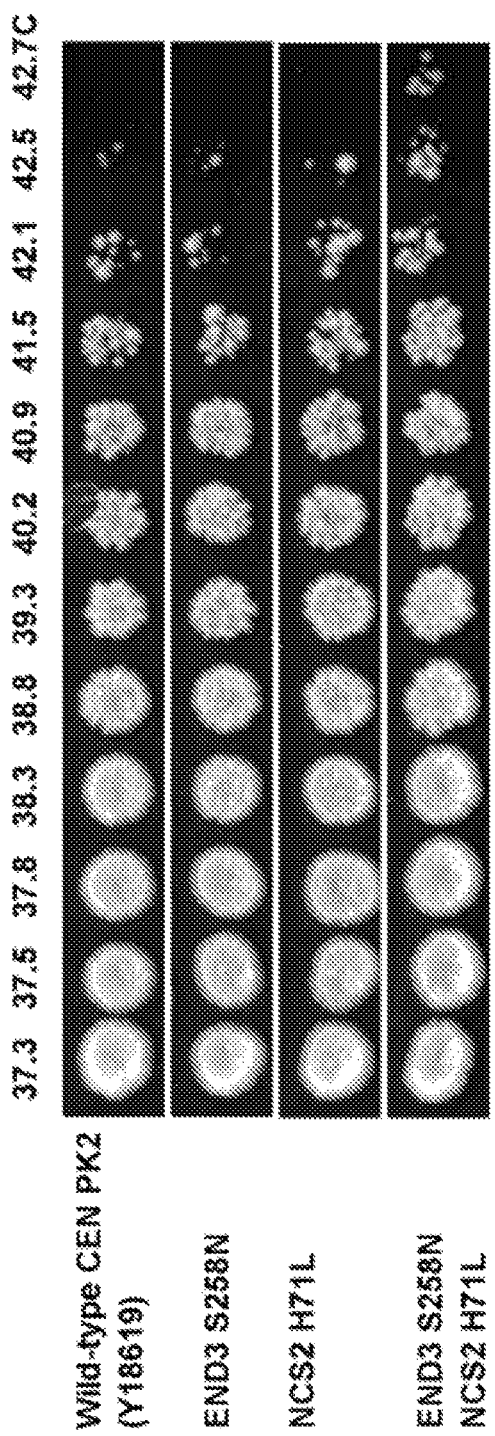
Figure 23F:
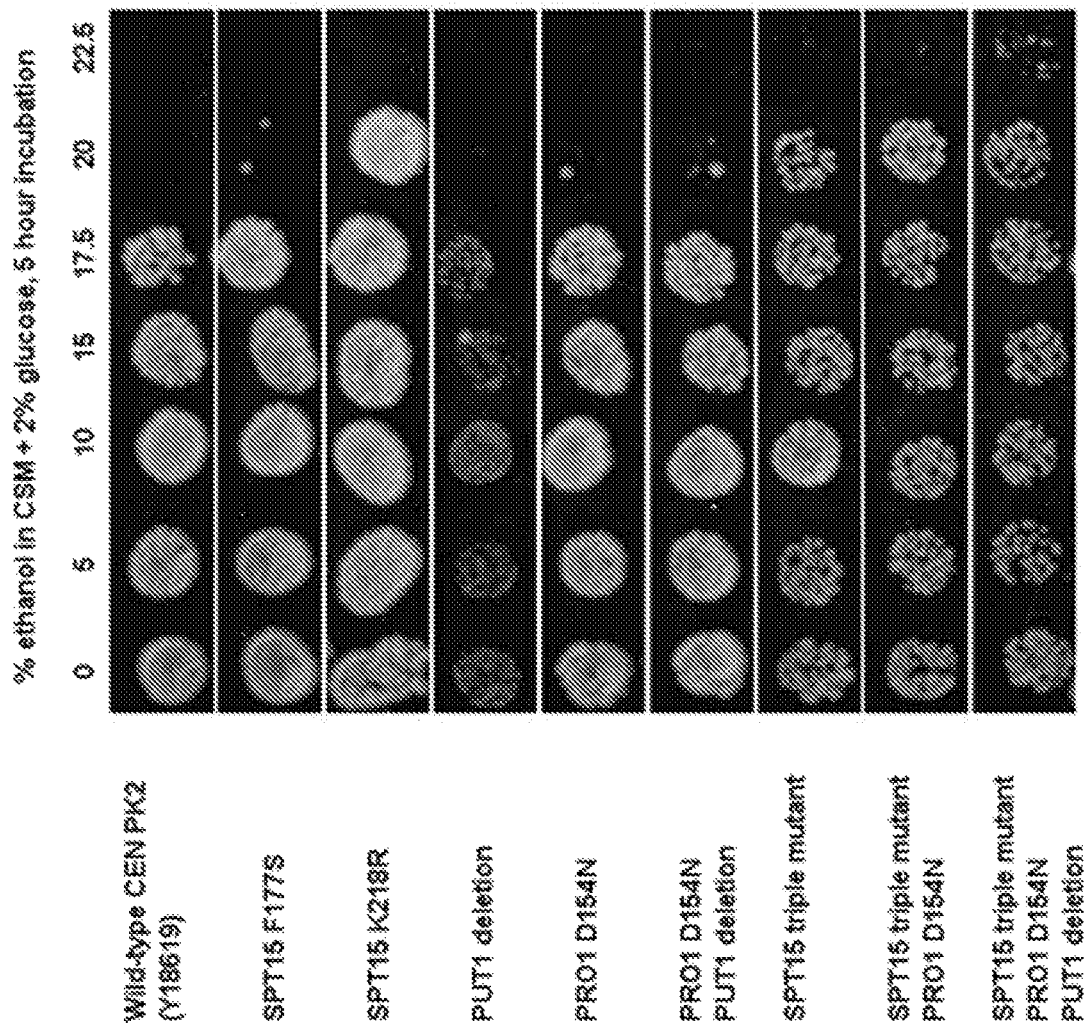

Ethanol resistance alleles also conferred a synergistic effect. Wild-type CENPK2 tolerated up to 17.5% ethanol in this experiment (FIG. 23F). Mutations in SPT15 increased resistance up to 20% ethanol (FIG. 23F). To examine the interaction of these alleles, five targeted changes over three loci were simultaneously introduced into a naïve strain (three mutations in SPT15, PRO1 D154N and the deletion of PUT1). The three mutations in SPT15 were introduced on a single donor DNA by using two gRNAs to excise ~150 bp of the gene containing the three alleles. 27% of the resulting clones contained all five modifications as assessed by colony PCR and confirmed by sequencing (FIG. 22). The resulting strain had the highest ethanol tolerance, up to 22.5% ethanol (FIG. 23F). As these results demonstrate, multiplexed CRISPR allows rapid evaluation of hypotheses about combinations of causal alleles.

These results demonstrate that precise point mutations or reversions can be achieved at a high efficiency and at high multiplexity using the optimized methods and compositions for CRISPR-mediated genomic integration provided herein.

6.5 Example 5: Bi-Allelic Engineering of Diploid Cells

This example demonstrates application of the optimized protocol as described in Example 1 (mode 4: in vivo HR-mediated incorporation of gRNA cassette(s) into a marker vector backbone) for simultaneous bi-allelic integration in diploid yeast strains.

Diploid industrial SC strains are highly heterozygous, with many unmapped but advantageous traits for fermentation. However, these strains are difficult to engineer by standard methods, requiring two sequential integration steps and distinct markers to delete a gene or to introduce bi-allelic engineering. Thus, the efficacy of CRISPR-mediated bi-allelic deletion of the GAL80 locus in the CAT-1 and PE-2 diploid industrial strains of S. cerevisiae was tested using the optimized protocol of Example 1. Donor and gRNA sequences targeting the Gal80 locus are described in Example 3.

As shown in FIG. 19, cPCR of Cas9-expressing strains transformed with donor DNA and a linear gRNA cassette targeting the Gal80 locus and having homologous ends to a co-transformed linear NatA marker vector backbone revealed bi-allelic donor integration rates of 100% in CAT-1 diploid cells (FIG. 19B) and 90% in PE-2 diploid cells (FIG. 19C). These rates are comparable to the rate at which the same deletion in a haploid CENPK2 strain was obtained (100%; FIG. 19A). These results demonstrate the efficacy of the optimized methods and compositions for CRISPR-mediated genomic integration provided herein for engineering diploid host cells.

6.6 Example 6: Multiplex Integration of a Complete Biosynthetic Pathway

This example demonstrates application of the optimized protocol as described in Example 1 (mode 4: in vivo HR-mediated incorporation of gRNA cassette(s) into a marker vector backbone) for simultaneous integration into a naïve yeast strain of an entire biosynthetic pathway.

Typically, engineering metabolic pathways, even in tractable hosts such as *S. cerevisiae*, is time consuming. This timetable would be greatly improved if integrations of genetic cassettes could be conducted in parallel, and without requiring any integration of drug selectable markers. Therefore, the optimized protocol for CRISPR-mediated integration was applied towards the simultaneous integration of 12 gene cassettes totaling approximately 30 kb of DNA, encoding a functional pathway for production of farnesene (see U.S. Pat. No. 8,415,136), into *S. cerevisiae*. Gene cassettes were designed and cloned using methods of polynucleotide assembly described in U.S. Pat. Nos. 8,221,982 and 8,332,160. The pathway was divided into three donor constructs for integration of 12 genes: ERG10, encoding acetyl-CoA thiolase; ERG13, encoding HMG-CoA synthase; tHMG1 (2 copies), encoding HMG-CoA reductase; ERG12, encoding mevalonate kinase; ERG8, encoding phosphomevalonate kinase; ERG19, encoding mevalonate pyrophosphate decarboxylase; IDI1, encoding isopentenyl pyrophosphate isomerase; farnesene synthase (2 copies) from *Artemisia annua*; ERG20, encoding farnesyl pyrophosphate synthetase; and the transcriptional regulator GAL4. The three constructs were targeted for integration into the Gal80, HO, and BUD9 loci in a naïve CENPK2 *S. cerevisiae*, wherein Cas9 under the control of the medium strength FBA1 promoter (SEQ ID NO:3) was targeted to the GRE3 locus. Simultaneous, marker-less integration of all three constructs was attempted using the optimized gap repair method described in Example 1, and clones were assayed by cPCR primer pairs that bind the 5' flank of the integration target locus and an internal linker sequence within each donor construct.

As shown in FIG. 20, out of 47 clones screened, 11 clones (23.4%) were positive for integration of the 30 kb constituting the entire farnesene pathway (clones 22, 24, 29-32, 41-43, 45 and 46). The 48th clone is a parent negative control. All triple positive candidates were subsequently assayed by cPCR at the 3' flank of each target locus as well and confirmed to be positive for integration at both flanks. Subsequently, the 11 cPCR positive clones were tested for farnesene production in a batch sucrose plate model assay. As shown in FIG. 21, all 11 clones produced farnesene in amounts ranging from 0.1 to near 1.5 g/L amounts. Taken together, these results demonstrate the efficacy of the optimized methods and compositions for CRISPR-mediated genomic integration provided herein for rapid, multiplex, metabolic engineering. The optimized protocol for multiplex engineering can be applied to drastically shorten the timeline for engineering of complex pathways. For example, the simultaneous introduction of three point mutations in an *S. cerevisiae* strain would require approximately 6 weeks of work (1 week to introduce each allele, 1 week to recycle each marker, 3 cycles total), versus 1 week when using the optimized methods provided herein. The timeline for introduction of a rudimentary farnesene pathway demonstrated here is likewise compressed 6-fold, as the amount of time saved scales with the number of loci targeted in parallel.

As an additional proof of concept, multiplex integration of 11 gene cassettes containing 24 kb of DNA distributed over three loci, encoding a novel route to muconic acid was attempted in haploid CENPK2 (FIG. 24). Muconic acid is a precursor molecule with great potential for the production of bioplastics including nylon-6,6, polyurethane, and polyethylene terephthalate (PET). Currently, muconic acid is obtained from petroleum derived feedstocks via organic synthesis, but a renewable source is desirable. Biosynthesis of muconic acid is achieved by overexpression of the aromatic amino acid (shikimate) biosynthetic pathway. Previously, high level production of muconic acid (36.8 g/L, fed batch fermentation) was achieved in *E. coli* (Niu, Draths et al., *Biotechnol Prog* 18(2): 201-211, 2002). However, lower pH fermentation with *S. cerevisiae* would facilitate downstream processing and industrialization of the process. In a proof of principle effort, titers up to 141 mg/L have been observed in shake flask experiments in an engineered *S. cerevisiae* strain (Curran, Leavitt et al., *Metab Eng* 15: 55-66, 2013). In contrast to this initial attempt in *S. cerevisiae*, this experiment utilized the *E. coli* shikimate pathway genes AROF, AROB and AROD rather than the native ARO1 gene. The engineered pathway is shown in FIG. 24A.

For integration, the pathway was divided into three split constructs (with internal overlap for reconstitution by homologous recombination in vivo) targeting the GAL80, HO, and ARO1 loci in CENPK (FIG. 24B). HO was chosen as a neutral locus, while GAL80 was selected to remove glucose repression of the galactose operon, and the ARO1 locus was deleted to force flux through the engineered pathway. ARO1 deletion also makes the strains auxotrophic for aromatic amino acids, creating a simple switch mechanism between the biomass production phase (in rich media) and the production phase (in minimal media). Simultaneous, marker-less integration of all three constructs was attempted using the optimized gap repair method, and clones were assayed by PCR, revealing a 4.2% rate of triple integration (n=48). It is notable that integration of these three constructs requires nine recombination events (two flanking and one internal event per locus). While the observed rate is lower than seen for multiplex deletions, introduction of a complete biosynthetic pathway is expected to confer a fitness defect, and this may limit recovery of properly integrated strains.

Production of muconic acid and intermediates were tested in a 96 well shake-plate assay, with analysis by HPLC. The one-step integrated strains showed high titers of PCA (~3 g/L), indicating a bottleneck at AroY, which converts PCA to catechol (FIG. 24A). To confirm functionality of the downstream pathway, up to 1 g/L catechol was supplied directly to the production media wells, and quantitative conversion of catechol to cis-trans muconic acid was observed in the engineered, but not parent strain, unambiguously identifying a single defect in the pathway design at AroY.

To test the efficacy of the optimized gap repair method in a second industrially relevant yeast, an attempt was made to integrate a more compact version of the muconic acid pathway comprising six genes in *K. lactis*. The pathway was divided into three integration constructs targeting the DIT1, ADH1, and NDT80 loci. A naïve *K. lactis* strain (ATCC 8585) was prepared by integrating Cas9 at the GAL80 locus, and deleting YKU80 to minimize the effects of non-homologous end joining (Kooistra, Hooykaas et al., Yeast 21(9): 781-792, 2004; Wesolowski-Louvel, FEMS Yeast Res 11(6): 509-513, 2011). Marker-less integration of all three constructs was accomplished in one step using the same gap-repair method, but with a plasmid backbone containing the pKD1 stability element (Chen, Wesolowski-Louvel et al., J Basic Microbiol 28(4): 211-220, 1988). Triple integrations occurred at a rate of 2.1%, as assayed by PCR (n=48). In analogy to the CENPK results, high titers of PCA (1 g/L) were observed, but no muconic acid production (FIG. 24E). Catechol feeding experiments confirmed the same defect in AROY function. It is notable that ARO1 was not deleted in this *K. lactis* strain, and this discrepancy may explain the lower titers of PCA that were observed. Nonetheless, these results demonstrate the ability to prototype muconic acid production in two industrially relevant yeast strains and identify a limiting enzyme in less than a month, a workflow that facilitates rapid design iterations and allowed sampling of two potential hosts.

6.7 Example 7: Improved Integration in Mammalian Cells

This example demonstrates application of the optimized protocol as described in Example 1 (mode 4: in vivo HR-mediated incorporation of gRNA cassette(s) into a marker vector backbone) to achieve improved integration rates in a mammalian host cell.

To test whether the gap repair delivery method for gRNAs described above for *S. cerevisiae* might also improve integration rates in mammalian cells, a series of reagents were generated for transfection experiments in HEK-293T cells. In broad overview, cells were co-transfected with a linearized plasmid backbone containing a Cas9 expression cassette fused via 2A-linker to the 5' portion of the CD4 epitope tag, with a fragment containing a gRNA cassette targeting the AAVS1 locus, and with a donor DNA fragment for repair of the locus by homologous recombination, comprising upstream and downstream homology flanking an EcoRI site for later diagnostic purposes (gap repair condition). This transfection was compared to a control reaction with a Cas9-2A-CD4 expression cassette and gRNA cassette contained in a closed plasmid (positive control). In addition, a plasmid containing no gRNA was used as a negative control to assess whether homologous integration of the donor DNA occurred at a measurable rate in the absence of CRISPR-Cas9. Following transfection, CD4+ cells (transfected cells) were isolated using antibody-coupled magnetic beads, and cells were eluted and used in genomic DNA preparations. PCR of a region encompassing the integration site was performed, and PCR products were digested using EcoRI to determine the fraction of cells that had integrated the donor DNA at the target site.

Materials and Methods

Expression of the Cas9 Nuclease and Associated gRNA.

The LifeTech/GeneArt CRISPR Nuclease with CD4 enrichment kit (A21175) was used. Following manufacturer's instructions, a double-stranded oligonucleotide (prepared by annealing oligos CUT1216 and CUT1217) encoding a sequence inside the AAVS1 region (AAVS1, T2 gRNA from Mali et al) was ligated into the provided linearized vector to create pAM3473 (SEQ ID NO:98). The plasmid was maxi-prepped (Qiagen).

Generation of a Version of pAM3473 Suitable for Testing Gap Repair.

The pAM3473 plasmid was digested with Bst1107I and NheI to remove the entire gRNA cassette a portion of the CD4 ORF. The backbone was CIP (alkaline phosphatase) treated and gel purified. A multiple cloning site (MCS) double stranded oligo containing unique ClaI and XmaI sites and with compatible overhangs to the linear vector was prepared by annealing CUT1214 (SEQ ID NO:103) and CUT1215 (SEQ ID NO:104) oligos. The double-stranded oligo was ligated into the purified backbone to create pAM3472 (SEQ ID NO:97). The plasmid was maxi-prepped (Qiagen). Prior to use, the plasmid was linearized by digestion with ClaI and NheI, and purified/concentrated by ethanol precipitation.

Generation of a Control Plasmid Containing CD4 Epitope Only (and No gRNA).

pAM3473 (SEQ ID NO:98) was digested with Bst11071 and PacI, and the backbone was CIP treated and gel purified. A double-stranded oligo designed to re-circularize the gRNA cassette-less backbone was prepared by annealing CUT1254 (SEQ ID NO: 113) and CUT1255 (SEQ ID NO: 114) oligos and ligated into the vector backbone to create pAM15068 (SEQ ID NO: 102; formerly known as "A2").

Preparation of Fragments for Gap Repair of the AAVS1 gRNA Cassette into Linearized pAM3472.

The primers CUT 1220 (SEQ ID NO:107) and CUT1221 (SEQ ID NO: 108) were used to amplify a 2850 bp fragment from pAM3473. The product was sub-cloned by gap repair (*E. coli*) into the RYSE09 acceptor vector, and the construct was verified by sequencing to make pAM3515 (SEQ ID NO: 100). Prior to transfection, linear fragment was prepared by Phusion PCR amplification using flanking RYSE0 (SEQ ID NO: 117) and RYSE19 (SEQ ID NO: 118) primers, and the PCR product was purified using Ampure beads (Axygen). Prior to transfection, linear fragment was prepared by Phusion PCR amplification using flanking RYSE0 and RYSE19 primers, and the PCR product was purified using Ampure beads (Axygen).

Preparation of Fragments for Gap Repair of the CD4-Only Control Fragment into Linearized pAM3472.

Primers CUT1220 (SEQ ID NO: 107) and CUT1252 (SEQ ID NO: 111) were used in a Phusion PCR reaction to amplify an upstream fragment containing the 3' end of the CD4 ORF using pAM3473 as template, and primers CUT1253 (SEQ ID NO:112) and CUT1221 (SEQ ID NO: 108) were used to amplify a downstream fragment containing flanking homology downstream of the gRNA cassette. These two fragments were gel purified and used in a second fusion PCR reaction, with primers RYSE0 and RYSE19 used for amplification of the ~2 kb product. The product was sub-cloned by gap repair (*E. coli*) into the RYSE09 acceptor vector, and the construct was verified by sequencing to make pAM3516 (SEQ ID NO: 101). Prior to transfection, linear fragment was prepared from this template by Phusion PCR PCR amplification using flanking RYSE0 and RYSE19 primers, and the PCR product was purified using Ampure beads (Axygen).

Preparation of Donor DNA for Introduction of an EcoRI Site at the AAVS1 Target Locus.

Primers CUT1226 (SEQ ID NO:119) and CUT1223 (SEQ ID NO: 120) were used to amplify a ~570 bp upstream fragment containing a synthetic EcoRI site at its 3' end from human genomic DNA (derived from HEK-293 cells) using Phusion polymerase. Primers CUT1224 (SEQ ID NO:109) and CUT1227 (SEQ ID NO:110) were used to amplify a ~540 bp downstream fragment containing the EcoRI site at its 5' end from the same human genomic template. The fragments were assembled by fusion PCR using Phusion polymerase with the flanking RYSE0 and RYSE19 primers, and the ~1100 bp fragment was sub-cloned into linearized RYSE09 vector by gap repair (*E. coli*). The construct was verified by sequencing to make pAM3514 (SEQ ID NO:99). Prior to transfection, linear fragment was prepared from this template by Phusion PCR amplification using flanking RYSE0 and RYSE19 primers, and the PCR product was purified using Ampure beads (Axygen).

Transfection Experiments.

70% confluent adherent 293T cells were transfected with DNA using Lipofectamine 3000 according to manufacturer's instructions (with a 1.5 fold DNA to LF3000 ratio). Table 8 provides the DNA constructs and amount of DNA used for each transfection (performed in duplicate).

Results

To test whether imposing a requirement for gap repair might increase rates of homologous integration, we compared rates of EcoRI site donor DNA insertion in HEK-293T cells transfected with several different combinations of plasmid and linear DNA (Table 8 and FIG. 25). To assess whether the EcoRI donor DNA might integrate at the AAVS1 locus at some measurable level in the absence of targeted cutting by CRISPR-Cas9, cells were transfected with plasmid pAM15068, which contains the Cas9-2A-CD4 ORF, but no gRNA cassette, and linear donor DNA (pAM3514 PCR product). Transfected cells were purified using the dynabeads, genomic template was prepared, and digestion of the PCR product spanning the integration site yielded no digestion products, indicating that the rate of EcoRI site integration is not measurable in the absence of CRISPR-Cas9 (FIG. 25, transfection 2). To confirm that the linearized pAM3472 plasmid lacking a complete CD4 ORF could not confer a CD4+ phenotype on its own, transfections were conducted with just this linear fragment. No PCR product was obtained from template prepared from these purified cells, indicating that there was insufficient association of the transfected cells with the dynabeads to act as template for a PCR reaction (FIG. 25, transfection 3). To confirm that gap repair could reconstitute the CD4 ORF, the linearized pAM3472 plasmid was co-transfected with the CD4 gap repair fragment (pAM3516 PCR product), and template from cells purified from these transfections yielded a 920 bp band but no digestion products, as no gRNA was present. (FIG. 25, transfection 4). Next, transfections including the AAVS1 gRNA were examined. To establish a baseline for functionality of the CRISPR-Cas9 system with the AAVS1 gRNA, we co-transfected a closed plasmid containing an expression cassette for Cas9, CD4 and the gRNA (pAM3473) and the linear donor DNA construct (pAM3514 PCR product). EcoRI digestion of the PCR product showed

TABLE 8

| | Vectors | | Linear Fragments | | | | |
|---|---|---|---|---|---|---|---|
| Transfection | linear pAM3472 | closed pAM3473 | No gRNA "A2" | linear pAM3514 | full gap pAM3515 | CD4 gap pAM3516 | ug total DNA |
| 2 | | | 10 | 5 | | | 15 |
| 3 | 10 | | | | | | 10 |
| 4 | 10 | | | | | 5 | 15 |
| 6 | | 10 | | 5 | | | 15 |
| 8 | 10 | | | 5 | 5 | | 20 |

After 48 hrs, cells were harvested using TryplE reagent (LifeTech), and CD4+ cells were purified using the Dynabeads CD4 Positive Isolation Kit (LifeTech). Bound cells were eluted from beads per manufacturer's instructions, and genomic DNA was prepared using the Prepgem Tissue Kit (Zygem) according to manufacturer's instructions.

RFLP Assay for Integration of EcoRI Site.

An RFLP assay was performed on PCR fragments (920 bp) amplified using Phusion Polymerase with a primer set (CUT1297 (SEQ ID NO: 116) and CUT1294 (SEQ ID NO: 115)) encompassing the EcoRI integration site with an "outside" primer, such that only donor DNA in the context of the intended genomic integration would yield a product. Fragments were purified using Ampure beads (Axygen) and digested with EcoRI. PCR products with an EcoRI site integrated by homologous recombination yielded 348 bp and 572 bp fragments. The fraction of template with integrated EcoRI site was calculated by densitometry (Image J) using the formula: digest band density (348 bp+572 bp densities)/Total density (348 bp+572 bp+920 bp densities).

dropout products of 572 and 348 bp, indicative of digestion of a fraction of the total PCR product (FIG. 25, transfection 6). Quantification of the band densities using Image J software revealed that 22.5% of the total template contained an EcoRI site. To assess whether gap repair might improve this rate, we substituted the linearized pAM3472 vector and the gap repair fragment containing the missing portion of CD4 and the gRNA cassette (pAM3515 PCR product) for the closed vector (FIG. 25, transfection 8). Repeating the densitometry process, we observed that 47.5% of total template contained an EcoRI site. This represents a 2.1% fold improvement over the rate observed for the closed plasmid (transfection 6), thus confirming in mammalian cells the efficacy of the improved gap repair method for genomic integration.

All publications, patents and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed:

1. A composition comprising:
   (a) a site-specific nuclease, or a nucleic acid comprising a coding sequence for a site-specific nuclease; and
   (b) a first linear nucleic acid and one or more additional linear nucleic acid, wherein the first and second linear nucleic acids are capable of homologously recombining with each other in a host cell, whereupon said homologous recombination results in formation of a circular nucleic acid comprising a coding sequence for a selectable marker.

2. The composition of claim 1, wherein each linear nucleic acid comprises a partial, interrupted and/or non-contiguous coding sequence for the selectable marker, wherein the selectable marker cannot be expressed from each linear nucleic acid in a host cell, whereupon said formation of the circular nucleic acid results in formation of a complete coding sequence of the selectable marker, wherein the selectable marker can be expressed from the circular nucleic acid in a host cell.

3. The composition of claim 1, wherein the circular nucleic acid further comprises a coding sequence for a site-specific nuclease.

4. The composition of claim 1, wherein the site-specific nuclease is an RNA-guided DNA endonuclease.

5. The composition of claim 4, wherein the RNA-guided DNA endonuclease is a Cas9 endonuclease.

6. The composition of claim 5, wherein the circular nucleic acid further comprises a deoxyribonucleic acid that encodes a ribonucleic acid comprising a crRNA activity and a deoxyribonucleic acid that encodes a ribonucleic acid comprising a tracrRNA activity.

7. The composition of claim 4, further comprising:
   i. a ribonucleic acid comprising a crRNA activity and a ribonucleic acid comprising a tracrRNA activity; or
   ii. a deoxyribonucleic acid that encodes a ribonucleic acid comprising a crRNA activity and a deoxyribonucleic acid that encodes a ribonucleic acid comprising a tracrRNA activity.

8. The composition of claim 7, wherein the deoxyribonucleic acid that encodes the crRNA activity and the tracrRNA activity encodes said activities on a single contiguous RNA molecule.

9. The composition of claim 1, wherein the site-specific nuclease is selected from the group consisting of an endonuclease, a zinc finger nuclease, a TAL-effector DNA binding domain-nuclease fusion protein (TALEN), a transposase, and a site-specific recombinase.

10. The composition of claim 9, wherein the zinc finger nuclease is a fusion protein comprising the cleavage domain of a TypeIIS restriction endonuclease fused to an engineered zinc finger binding domain.

11. The composition of claim 10, wherein the TypeIIS restriction endonuclease is selected from the group consisting of HO endonuclease and Fok I endonuclease.

12. The composition of claim 10, wherein the zinc finger binding domain comprises 3, 5 or 6 zinc fingers.

13. The composition of claim 9, wherein the endonuclease is a homing endonuclease selected from the group consisting of: an LAGLIDADG (SEQ ID NO: 1) homing endonuclease, an HNH homing endonuclease, a His-Cys box homing endonuclease, a GIY-YIG homing endonuclease, and a cyanobacterial homing endonuclease.

14. The composition of claim 9, wherein the endonuclease is selected from the group consisting of: H-DreI, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, Pi-PspI, F-SceI, F-SceII, F-SuvI, F-CphI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomIP, I-SpomIIP, I-SquIP, I-Ssp68031, I-SthPhiJP, I-SthPhiST3P, I-SthPhiSTe3bP, I-TdeIP, I-TevI, I-TevII, I-TevIII, i-UarAP, i-UarHGPAIP, I-UarHGPA13P, I-VinIP, I-ZbiIP, PI-MgaI, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, or PI-TliII.

15. The composition of claim 9, wherein the endonuclease is modified to specifically bind an endogenous genomic sequence, wherein the modified endonuclease no longer binds to its wild type endonuclease recognition sequence.

16. The composition of claim 15, wherein the modified endonuclease is derived from a homing endonuclease selected from the group consisting of: an LAGLIDADG (SEQ ID NO: 1) homing endonuclease, an HNH homing endonuclease, a His-Cys box homing endonuclease, a GIY-YIG homing endonuclease, and a cyanobacterial homing endonuclease.

17. The composition of claim 15, wherein the modified endonuclease is derived from an endonuclease selected from the group consisting of: H-DreI, I-SceI, I-SceII, I-SceIII, I-SceIV, I-SceV, I-SceVI, I-SceVII, I-CeuI, I-CeuAIIP, I-CreI, I-CrepsbIP, I-CrepsbIIP, I-CrepsbIIIP, I-CrepsbIVP, I-TliI, I-PpoI, Pi-PspI, F-SceI, F-SceII, F-SuvI, F-CphI, F-TevI, F-TevII, I-AmaI, I-AniI, I-ChuI, I-CmoeI, I-CpaI, I-CpaII, I-CsmI, I-CvuI, I-CvuAIP, I-DdiI, I-DdiII, I-DirI, I-DmoI, I-HmuI, I-HmuII, I-HsNIP, I-LlaI, I-MsoI, I-NaaI, I-NanI, I-NclIP, I-NgrIP, I-NitI, I-NjaI, I-Nsp236IP, I-PakI, I-PboIP, I-PcuIP, I-PcuAI, I-PcuVI, I-PgrIP, I-PobIP, I-PorI, I-PorIIP, I-PbpIP, I-SpBetaIP, I-ScaI, I-SexIP, I-SneIP, I-SpomI, I-SpomCP, I-SpomCP, I-SpomIP, I-SpomIIP, I-SquIP, I-Ssp68031, I-SthPhiJP, I-SthPhiST3P, I-SthPhiSTe3bP, I-TdeIP, I-TdeIP, I-TevI, I-TevII, I-TevIII, i-UarAP, i-UarHGPAIP, I-UarHGPA13P, I-VinIP, I-ZbiIP, PI-MgaI, PI-MtuI, PI-MtuHIP PI-MtuHIIP, PI-PfuI, PI-PfuII, PI-PkoI, PI-PkoII, PI-Rma43812IP, PI-SpBetaIP, PI-SceI, PI-TfuI, PI-TfuII, PI-ThyI, PI-TliI, or PI-TliII.

\* \* \* \* \*

```
                        SEQUENCE LISTING

<160> NUMBER OF SEQ ID NOS: 125

<210> SEQ ID NO 1
<211> LENGTH: 9
<212> TYPE: PRT
<213> ORGANISM: Artificial Sequence
<220> FEATURE:
<223> OTHER INFORMATION: Synthetic: Homing endonuclease conserved
      sequence motif

<400> SEQUENCE: 1

Leu Ala Gly Leu Ile Asp Ala Asp Gly
1               5

<210> SEQ ID NO 2
<211> LENGTH: 6
<212> TYPE: PRT
<213> ORGANISM: Artificial Sequence
<220> FEATURE:
<223> OTHER INFORMATION: Synthetic: Homing endonuclease conserved
      sequence motif

<400> SEQUENCE: 2

Gly Ile Tyr Tyr Ile Gly
1               5

<210> SEQ ID NO 3
<211> LENGTH: 7804
<212> TYPE: DNA
<213> ORGANISM: Artificial Sequence
<220> FEATURE:
<223> OTHER INFORMATION: Synthetic: Cas9 Genomic Expression Construct

<400> SEQUENCE: 3
gacggcacgg ccacgcgttt aaaccgccga ccagagattt tgcattccag tattcatcaa      60
tgatgaattc gtagacgcag atactgtaaa tgccgtgttc atcaagaaat gggcgcatta     120
ctacaagaag ttttgatatt ttttgtaact gtaatttcac tcatgcacaa gaaaaaaaaa     180
actggattaa aagggagccc aaggaaaact cctcagcata tatttagaag tctcctcagc     240
atatagttgt ttgttttctt tacacattca ctgtttaata aaacttttat aatatttcat     300
tatcggaact ctagattcta tacttgtttc ccaattgttg ctggtagtaa acgtatacgt     360
cataaaaggg aaaagccaca tgcggaagaa ttttatggaa aaaaaaaaaa cctcgaagtt     420
actacttcta gggggcctat caagtaaatt actcctggta cactgaagta tataagggat     480
atagaagcaa atagttgtca gtgcaatcct tcaagacgct cgtccaacgc cggcggacct     540
cgaatcctta catcacaccc aatcccccac aagtgatccc ccacacacca tagcttcaaa     600
atgtttctac tcctttttta ctcttccaga ttttctcgga ctccgcgcat cgccgtacca     660
cttcaaaaca cccaagcaca gcatactaaa tttcccctct ttcttcctct agggtgtcgt     720
taattacccg tactaaaggt ttggaaaaga aaaagagac cgcctcgttt cttttttcttc    780 gtcgaaaaag gcaataaaaa tttttatcac gtttcttttt cttgaaaatt ttttttttg     840 atttttttct ctttcgatga cctcccattg atatttaagt taataaacgg tcttcaattt     900
ctcaagtttc agtttcattt ttcttgttct attcaaactt tttttacttc ttgctcatta     960
gaaagaaagc atagcaaacc tcccgcgacc tccaaaatcg aactaccttc acaatggata    1020
```

```
agaaatactc tatcggtttg atattggta ctaactccgt tggttgggcc gttatcactg    1080
atgaatacaa ggttccatct aagaagttca aagttttggg taacactgat agacactcta    1140
tcaagaagaa cttgattggt gctttgttat ttgactctgg tgaaaccgct gaggctaccc    1200
gtttaaaaag aactgctaga cgtagataca cccgtcgtaa aaacagaatc tgttatttgc    1260
aagagatctt ctccaacgaa atggctaagg ttgacgactc ttttttccat agattagaag    1320
aatctttctt agttgaagaa gataagaagc acgaacgtca tccaatcttc ggtaacattg    1380
tcgacgaagt tgcttaccat gaaaagtacc caactatcta tcacttgaga agaaattgg     1440 ttgattctac tgacaaagcc gacttgagat tgatctactt ggctttagct catatgatca    1500
aattccgtgg tcatttttta attgaaggtg atttgaaccc agacaactct gacgttgata    1560
aattgttcat ccaattggtt caaacctata accaattgtt tgaagaaaac ccaattaacg    1620
cttctggtgt tgatgctaag gctatcttgt ctgctagatt gtctaaatct agaagattgg    1680
aaaacttaat tgctcaattg ccaggtgaaa aaaaaaacgg tttgttcggt aatttgattg    1740
ctttatcctt gggtttgacc ccaaatttca gtccaacttt tgatttggct gaagatgcca    1800
agttgcaatt gtctaaggat acttacgatg atgatttaga taacttattg gctcaaattg    1860
gtgatcaata cgctgatttg ttttttagctg ccaagaattt gtccgacgcc attttgttgt    1920
ctgacatctt gagagtcaac actgaaatta ccaaggcccc tttgtctgct tctatgatta    1980
agagatatga cgaacaccac caagacttga ccttgttgaa ggctttggtt agacaacaat    2040
tacctgaaaa gtataaggaa atttttttcg accaatctaa gaacggttac gctggttaca    2100
ttgacggtgg tgcctctcaa gaagaattct acaaattcat caaaccaatc ttggaaagga    2160
tggacggtac tgaagaattg ttagttaaat tgaacagaga agacttgttg agaaaacaaa    2220
gaaccttgga caacggttcc attcctcacc aaatccactt gggtgagtta cacgctattt    2280
tgagaagaca agaagatttc tacccattct aaaggacaa ccgtgaaaag attgaaaaga    2340
ttttgacctt cagaattcca tactacgtcg gtcctttggc tcgtggtaac tccagattcg    2400
cctggatgac tagaaagtcc gaagaaacta ttactccatg gaacttcgaa gaagtcgttg    2460
acaagggtgc ttctgctcaa tcctttatcg aaagaatgac caacttcgac aaaaacttgc    2520
caaacgaaaa agtcttgcca agcactctt tgttgtatga atactttact gtttataatg    2580
aattgactaa agttaagtac gttactgaag gtatgagaaa accagctttt ttatctggtg    2640
aacaaaaaaa agctatcgtc gatttgttgt tcaaaactaa ccgtaaagtt accgtcaagc    2700
aattgaagga agattacttc aagaagattg aatgttttga ctccgtcgaa atctccggtg    2760
ttgaagacag attcaatgct tctttgggta cttaccacga cttgttgaaa attatcaagg    2820
acaaggattt cttagataac gaagaaaacg aagacatttt ggaagatatt gtcttgactt    2880
tgactttgtt cgaagataga gaaatgattg aagaaagatt gaagacttat gctcatttgt    2940
tcgacgataa ggtcatgaag caattaaaga gaagacgtta cactggttgg ggtagattgt    3000
ctagaaaatt gattaacggt atccgtgata acaatctgg taagaccatc ttggattcct    3060
taaagtctga tggttttgcc aacagaaact tcatgcaatt gatccacgac gactctttga    3120
ctttcaagga ggacattcaa aaggctcaag tttctggtca agtgactct ttgcatgaac    3180 acattgccaa cttggctggt tctccagcta ttaagaaggg tatcttgcaa actgttaagg    3240
ttgttgatga attagttaag gtcatgggta gacacaagcc agaaaacatc gtcatcgaaa    3300
tggctagaga aaaccaaact actcaaaagg gtcaaaagat tctagagaa agaatgaaga    3360 gaattgagga aggtattaag gaattaggtt cccaaatttt gaaggaacat ccagtcgaaa    3420
```

-continued

```
acactcaatt gcaaaacgaa aaattgtact tgtactactt acaaaacggt agagatatgt    3480
atgtcgacca agagttggac atcaacagat tgtccgacta cgatgttgat cacatcgttc    3540
cacaatcctt cttaaaggac gactctatcg acaacaaggt cttaaccaga tccgacaaaa    3600
acagaggtaa gtctgacaac gttccatccg aagaagttgt taaaaagatg aagaactact    3660
ggagacaatt gttgaacgcc aaattgatca ctcaaagaaa gttcgataat ttgaccaagg    3720
ctgaaagagg tggtttgtct gaattggata aggctggttt tattaaaaga caattggttg    3780
agactagaca aatcaccaag catgtcgctc aaattttaga ttccagaatg aacactaaat    3840
acgacgaaaa cgataagtta attagagaag ttaaggttat taccttgaag tctaagttgg    3900
tttctgattt cagaaaggac ttccaatttt acaaggtcag agaaattaac aactaccatc    3960
acgctcatga tgcttacttg aacgccgttg ttggtaccgc tttgattaaa aagtacccaa    4020
agttggaatc cgaatttgtc tacggtgact acaaggtcta cgatgtcaga aaaatgatcg    4080
ctaagtccga acaagagatt ggtaaggcta ctgccaagta cttcttttac tctaacatca    4140 tgaactttt caagactgaa atcactttag ctaacggtga aattcgtaag agaccattga    4200
ttgaaaccaa cggtgagact ggtgaaatcg tttgggataa gggtcgtgat ttcgctactg    4260
ttagaaaggt cttatctatg ccacaagtta acatcgtcaa gaaaaccgaa gttcaaactg    4320
gtggtttttc taaggaatct atcttgccaa aagaaactc tgataaattg attgctagaa    4380
agaaggattg ggacccaaag aagtacggtg gtttcgattc cccaaccgtc gcttactccg    4440
tcttggttgt cgctaaagtt gaaaagggta gtccaagaa attgaagtct gttaaggaat    4500
tgttgggtat cactatcatg gaaagatctt ccttcgaaaa gaacccaatc gatttttag    4560 aggccaaggg ttataaggaa gttaaaaagg acttaattat taagttgcca aagtactctt    4620
tgttcgaatt agaaaacggt agaaaagaa tgttggcctc tgctggtgag ttgcaaaaag    4680
gtaacgaatt ggccttgcca tctaagtatg ttaactttt gtacttggcc tctcattacg    4740
agaagttgaa gggttcccca gaagataacg aacaaaagca attgttcgtc gaacaacaca    4800
aacattactt ggatgaaatt atcgaacaaa tctccgagtt ttccaaacgt gttatcttgg    4860
ctgacgccaa tttggataag gttttgtctg cttataataa gcatagagat aagccaatta    4920
gagaacaagc cgagaacatc attcacttgt tcactttgac taatttaggt gctccagctg    4980
ccttcaaata tttcgacacc accattgata gaaagagata cacctccact aaggaagtct    5040
tggatgccac cttgattcac caatctatca ctggtttgta cgaaactaga atcgatttgt    5100
ctcaattagg tggtgattcc cgtgccgacc caaagaagaa gagaaaggtc taaacaggcc    5160
cctttccctt tgtcgatatc atgtaattag ttatgtcacg cttacattca cgccctcccc    5220
ccacatccgc tctaaccgaa aaggaaggag ttagacaacc tgaagtctag gtccctattt    5280
atttttttat agttatgtta gtattaagaa cgttatttat atttcaaatt tttctttttt    5340
ttctgtacaa acgcgtgtac gcatgtaaca ttatactgaa aaccttgctt gagaaggttt    5400 tgggcatcccc gcgtgcttgg ccggccgttt aatcagcgcc cagagactag cactgaatga    5460
tcaacgggta gttcacacga tgcacgagcg caacgctcac aatgacagtc tggacatcaa    5520
tagtcacact acagaaggtg atctctcaac ttcagcagac catagcgtgt aataaatgca    5580
taattatttt tctctaaaaa aaactcagct gaaatttat ataagtacta cattttatat    5640
acatattaca tactgaacaa taagcgcgtt tgacatttta attttcgaag accgcgaatc    5700
cttacatcac acccagtccc ccaatagttc ccccacacac catgcttcaa aaacgcactg    5760
tactcctttt tactcttccg gattttctcg gactctccgc atcgccgcac gagccaagcc    5820
```

| | |
|---|---|
| acacccacac acctcatacc atgtttcccc tctttgactc tttcgtgcgg ctccattacc | 5880 |
| cgcatgaaac tgtataaaag taacaaaaga ctatttcgtt tcttttcctt tgtcggaaaa | 5940 |
| ggcaaaaaaa aaaattttta tcacatttct ttttcttgaa aattttttt gggatttttt | 6000 |
| ctctttcgat gacctcccat tgatatttaa gttaataaaa ggtctcccgt tttccaagtt | 6060 |
| ttaatttgtt cctcttgttt agtcattctt cttctcagca ttggtcaatt agaaagagag | 6120 |
| catagcaaac tgatctaagt tttaattacc atatgaaaaa gcctgaactc accgcgacgt | 6180 |
| ctgtcgagaa gtttctgatc gaaaagttcg acagcgtctc cgacctgatg cagctctcgg | 6240 |
| agggcgaaga atctcgtgct ttcagcttcg atgtaggagg cgtggatat gtcctgcggg | 6300 |
| taaatagctg cgccgatggt ttctacaaag atcgttatgt ttatcggcac tttgcatcgg | 6360 |
| ccgcgctccc gattccggaa gtgcttgaca ttggggaatt cagcgagagc ctgacctatt | 6420 |
| gcatctcccg ccgtgcacag ggtgtcacgt tgcaagacct gcctgaaacc gaactgcccg | 6480 |
| ctgttctgca gccggtcgcg gaggccatgg atgcgatcgc tgcggccgat cttagccaga | 6540 |
| cgagcgggtt cggcccattc ggaccgcaag gaatcggtca atacactaca tggcgtgatt | 6600 |
| tcatatgcgc gattgctgat ccccatgtgt atcactggca aactgtgatg gacgacaccg | 6660 |
| tcagtgcgtc cgtcgcgcag gctctcgatg agctgatgct ttgggccgag gactgccccg | 6720 |
| aagtccggca cctcgtgcac gcggatttcg gctccaacaa tgtcctgacg gacaatggcc | 6780 |
| gcataacagc ggtcattgac tggagcgagg cgatgttcgg ggattcccaa tacgaggtcg | 6840 |
| ccaacatctt cttctggagg ccgtggttgg cttgtatgga gcagcagacg cgctacttcg | 6900 |
| agcggaggca tccggagctt gcaggatcgc cgcggctccg ggcgtatatg ctccgcattg | 6960 |
| gtcttgacca actctatcag agcttggttg acggcaattt cgatgatgca gcttgggcgc | 7020 |
| agggtcgatg cgacgcaatc gtccgatccg gagccgggac tgtcgggcgt acacaaatcg | 7080 |
| cccgcagaag cgcggccgtc tggaccgatg gctgtgtaga agtactcgcc gatagtggaa | 7140 |
| accgacgccc cagcactcgt ccgagggcaa aggaataggg aaattgataa gacttttcta | 7200 |
| gttgcatatc ttttatattt aaatcttatc tattagttaa ttttttgtaa tttatcctta | 7260 |
| tatagtctgg ttattctaaa atatcatttc agtatctaaa atagttcttt ttttttttga | 7320 |
| gttagatttt tatgggggag agttgaagtg ttgaattttc ccactttgct tcgggattgt | 7380 |
| gggtcattct gtcgataact gatatcacat catcaataga acctcttaga tgcacgagcg | 7440 |
| caacgctcac aattaatcag cgcccagaga ctagcactga atgatcaacg ggtagttcac | 7500 |
| acaggtccgc cggcgttgga cgagcgtcca gccagtaaaa tccatactca acgacgatat | 7560 |
| gaacaaattt ccctcattcc gatgctgtat atgtgtataa attttttacat gctcttctgt | 7620 |
| ttagacacag aacagcttta aataaaatgt tggatatact ttttctgcct gtggtgtcat | 7680 |
| ccacgctttt aattcatctc ttgtatggtt gacaatttgg ctattttta acagaaccca | 7740 |
| acggtaattg aaattaaaag ggaaacgagt gggggcggcg gtttaaacgc gtggccgtgc | 7800 |
| cgtc | 7804 |

<210> SEQ ID NO 4
<211> LENGTH: 19
<212> TYPE: DNA
<213> ORGANISM: Artificial Sequence
<220> FEATURE:
<223> OTHER INFORMATION: Synthetic: RHR2 genomic target Sequence

<400> SEQUENCE: 4

| | |
|---|---|
| acctctggta cccgtgaca | 19 |

```
<210> SEQ ID NO 5
<211> LENGTH: 19
<212> TYPE: DNA
<213> ORGANISM: Artificial Sequence
<220> FEATURE:
<223> OTHER INFORMATION: Synthetic: HO genomic target Sequence

<400> SEQUENCE: 5
ccggcttgat cgactcaga                                                  19

<210> SEQ ID NO 6
<211> LENGTH: 19
<212> TYPE: DNA
<213> ORGANISM: Artificial Sequence
<220> FEATURE:
<223> OTHER INFORMATION: Synthetic: ADH5 genomic target sequence

<400> SEQUENCE: 6
gggtcattgg tatcgatgg                                                  19

<210> SEQ ID NO 7
<211> LENGTH: 1026
<212> TYPE: DNA
<213> ORGANISM: Artificial Sequence
<220> FEATURE:
<223> OTHER INFORMATION: Synthetic: gRNA construct targeting RHR2 locus

<400> SEQUENCE: 7
ccttataaat caaaagaata gaccgagata gggttgagtg ttgttccagt ttggaacaag      60
agtccactat taaagaacgt ggactccaac gtcaaagggc gaaaaaccgt ctatcagggc     120
gatggcccac tacgtgaacc atcaccctaa tcaagttttt tggggtcgag gtgccgtaaa     180
gcactaaatc ggaaccctaa agggagcccc cgatttagag cttgacgggg aaagcctctt     240
tgaaaagata atgtatgatt atgctttcac tcatatttat acagaaactt gatgttttct     300
ttcgagtata tacaaggtga ttacatgtac gtttgaagta caactctaga ttttgtagtg     360
ccctcttggg ctagcggtaa aggtgcgcat ttttcacac cctacaatgt tctgttcaaa     420
agattttggt caaacgctgt agaagtgaaa gttggtgcgc atgtttcggc gttcgaaact     480
tctccgcagt gaaagataaa tgatcgccgc caatgatgtc aagcagtttt agagctagaa     540
atagcaagtt aaaataaggc tagtccgtta tcaacttgaa aaagtggcac cgagtcggtg     600 gtgcttttt tgtttttat gtctcagctt ttgttccctt tagtgagggt taattgcgcg     660
cttggcgtaa tcatggtcat agctgttttc tgtgtgaaat tgttatccgc tcacaattcc     720
acacaacata ggagccggaa gcataaagtg taaagcctgg ggtgcctaat gagtgaggta     780
actcacatta attgcgttgc gctcactgcc cgctttccag tcgggaaacc tgtcgtgcca     840
gctgcattaa tgaatcggcc aacgcgcggg gagaggcggt ttgcgtattg ggcgctcttc     900
cgcttcctcg ctcactgact cgctgcgctc ggtcgttcgg ctgcggcgag cggtatcagc     960
tcactcaaag gcggtaatac ggttatccac agaatcaggg gataacgcag gaagaacat    1020 gtgagc                                                               1026

<210> SEQ ID NO 8
<211> LENGTH: 1080
<212> TYPE: DNA
<213> ORGANISM: Artificial Sequence
<220> FEATURE:
<223> OTHER INFORMATION: Synthetic: gRNA construct targeting HO locus
```

<400> SEQUENCE: 8

```
gacggcacgg ccacgcgttt aaaccgcctt ataaatcaaa agaatagacc gagatagggt      60
tgagtgttgt tccagtttgg aacaagagtc cactattaaa gaacgtggac tccaacgtca     120
aagggcgaaa aaccgtctat cagggcgatg gcccactacg tgaaccatca ccctaatcaa     180
gttttttggg gtcgaggtgc cgtaaagcac taaatcggaa ccctaaaggg agcccccgat     240
ttagagcttg acggggaaag cctctttgaa aagataatgt atgattatgc tttcactcat     300
atttatacag aaacttgatg ttttctttcg agtatataca aggtgattac atgtacgttt     360
gaagtacaac tctagatttt gtagtgccct cttgggctag cggtaaaggt gcgcattttt     420
tcacacccta caatgttctg ttcaaaagat tttggtcaaa cgctgtagaa gtgaaagttg     480
gtgcgcatgt ttcggcgttc gaaacttctc cgcagtgaaa gataaatgat cgccggcttg     540
atcgactcag agttttagag ctagaaatag caagttaaaa taaggctagt ccgttatcaa     600
cttgaaaaag tggcaccgag tcggtggtgc ttttttgtt ttttatgtct cagcttttgt     660
tccctttagt gagggttaat tgcgcgcttg gcgtaatcat ggtcatagct gtttcctgtg     720
tgaaattgtt atccgctcac aattccacac aacataggag ccggaagcat aaagtgtaaa     780
gcctggggtg cctaatgagt gaggtaactc acattaattg cgttgcgctc actgcccgct     840
ttccagtcgg gaaacctgtc gtgccagctg cattaatgaa tcggccaacg cgcggggaga     900
ggcggtttgc gtattgggcg ctcttccgct tcctcgctca ctgactcgct gcgctcggtc     960
gttcggctgc ggcgagcggt atcagctcac tcaaaggcgg taatacggtt atccacagaa    1020
tcaggggata acgcaggaaa gaacatgtga gccggtgttt aaaccccagc gcctggcggg    1080
```

<210> SEQ ID NO 9
<211> LENGTH: 1080
<212> TYPE: DNA
<213> ORGANISM: Artificial Sequence
<220> FEATURE:
<223> OTHER INFORMATION: Synthetic: gRNA construct targeting ADH5 locus

<400> SEQUENCE: 9

```
gacggcacgg ccacgcgttt aaaccgcctt ataaatcaaa agaatagacc gagatagggt      60
tgagtgttgt tccagtttgg aacaagagtc cactattaaa gaacgtggac tccaacgtca     120
aagggcgaaa aaccgtctat cagggcgatg gcccactacg tgaaccatca ccctaatcaa     180
gttttttggg gtcgaggtgc cgtaaagcac taaatcggaa ccctaaaggg agcccccgat     240
ttagagcttg acggggaaag cctctttgaa aagataatgt atgattatgc tttcactcat     300
atttatacag aaacttgatg ttttctttcg agtatataca aggtgattac atgtacgttt     360
gaagtacaac tctagatttt gtagtgccct cttgggctag cggtaaaggt gcgcattttt     420
tcacacccta caatgttctg ttcaaaagat tttggtcaaa cgctgtagaa gtgaaagttg     480
gtgcgcatgt ttcggcgttc gaaacttctc cgcagtgaaa gataaatgat cggggtcatt     540
ggtatcgatg ggttttagag ctagaaatag caagttaaaa taaggctagt ccgttatcaa     600
cttgaaaaag tggcaccgag tcggtggtgc ttttttgtt ttttatgtct cagcttttgt     660
tccctttagt gagggttaat tgcgcgcttg gcgtaatcat ggtcatagct gtttcctgtg     720
tgaaattgtt atccgctcac aattccacac aacataggag ccggaagcat aaagtgtaaa     780
gcctggggtg cctaatgagt gaggtaactc acattaattg cgttgcgctc actgcccgct     840
ttccagtcgg gaaacctgtc gtgccagctg cattaatgaa tcggccaacg cgcggggaga     900
ggcggtttgc gtattgggcg ctcttccgct tcctcgctca ctgactcgct gcgctcggtc     960
```

```
gttcggctgc ggcgagcggt atcagctcac tcaaaggcgg taatacggtt atccacagaa    1020 tcagggga ta acgcaggaaa gaacatgtga gccggtgttt aaaccccagc gcctggcggg    1080
```

<210> SEQ ID NO 10
<211> LENGTH: 5994
<212> TYPE: DNA
<213> ORGANISM: Artificial Sequence
<220> FEATURE:
<223> OTHER INFORMATION: Synthetic: pRS4XX vector backbone

<400> SEQUENCE: 10

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
aaatacacat catcgtccta caagttcatc aaagtgttgg acagacaact ataccagcat     240
ggatctcttg tatcggttct tttctcccgc tctctcgcaa taacaatgaa cactgggtca     300
atcatagcct acacaggtga acagagtagc gtttatacag ggtttatacg gtgattccta     360
cggcaaaaat ttttcatttc taaaaaaaaa agaaaaattt tttctttcca acgctagaag     420
gaaaagaaaa atctaattaa attgatttgg tgattttctg agagttccct ttttcatata     480
tcgaattttg aatataaaag gagatcgaaa aattttttct attcaatctg ttttctggtt     540
ttatttgata gttttttgt gtattattat tatggattag tactggttta tatgggtttt     600
tctgtataac ttctttttat tttagtttgt ttaatcttat tttgagttac attatagttc     660
cctaactgca agagaagtaa cattaaaaat gaccactctt gacgacacgg cttaccggta     720
ccgcaccagt gtcccggggg acgccgaggc catcgaggca ctggatgggt ccttcaccac     780
cgacaccgtc ttccgcgtca ccgccaccgg ggacggcttc accctgcggg aggtgccggt     840
ggacccgccc ctgaccaagg tgttccccga cgacgaatcg gacgcgaat cggacgccgg     900 ggaggacggc gacccggact cccggacgtt cgtcgcgtac ggggacgacg cgacctggc     960 gggcttcgtg gtcgtctcgt actccggctg gaaccgccgg ctgaccgtcg aggacatcga    1020
ggtcgccccg gagcaccggg ggcacggggt cgggcgcgcg ttgatggggc tcgcgacgga    1080
gttcgcccgc gagcggggcg ccgggcacct ctggctggag gtcaccaacg tcaacgcacc    1140
ggcgatccac gcgtaccggc ggatgggggtt caccctctgc ggcctggaca ccgccctgta    1200
cgacggcacc gcctcggacg gcgagcaggc gctctacatg agcatgccct gccctgagt     1260 ttaacttgat actactagat ttttctctt cattataaa attttggtt ataattgaag    1320 ctttagaagt atgaaaaaat ccttttttt cattctttgc aaccaaaata agaagcttct    1380
tttattcatt gaaatgatga atataaacct aacaaaagaa aaagactcga atatcaaaca    1440
ttaaaaaaaa ataaagagg ttatctgttt tcccatttag ttggagtttg cattttctaa    1500
tagatagaac tctcaattaa tgtggattta gtttctctgt tcgttttttt ttgttttgtt    1560
ctcactgtat ttacatttct atttagtatt tagttattca tataatctta acttgcggtg    1620
tgaaataccg cacagatgcg taaggagaaa ataccgcatc aggaaattgt aagcgttaat    1680
attttgttaa aattcgcgtt aaattttgt taaatcagct cattttttaa ccaataggcc    1740
gaaatcggca aaatccctta taaatcaaaa gaatagaccg atagggtt gagtgttgtt    1800 ccagtttgga acaagagtcc actattaaag aacgtggact ccaacgtcaa agggcgaaaa    1860
accgtctatc agggcgatgg cccactacgt gaaccatcac cctaatcaag ttttttgggg    1920
tcgaggtgcc gtaaagcact aaatcggaac cctaaaggga gcccccgatt tagagcttga    1980
```

```
cggggaaagc ctctttgaaa agataatgta tgattatgct ttcactcata tttatacaga    2040
aacttgatgt tttcttttcga gtatatacaa ggtgattaca tgtacgtttg aagtacaact   2100
ctagattttg tagtgccctc ttgggctagc ggtaaaggtg cgcattttt cacaccctac     2160 aatgttctgt tcaaaagatt ttggtcaaac gctgtagaag tgaaagttgg tgcgcatgtt    2220
tcggcgttcg aaacttctcc gcagtgaaag ataaatgatc gatacgttct ctatggagga    2280
gttttagagc tagaaatagc aagttaaaat aaggctagtc cgttatcaac ttgaaaaagt    2340
ggcaccgagt cggtggtgct ttttttgttt tttatgtctc agcttttgtt ccctttagtg    2400
agggttaatt gcgcgcttgg cgtaatcatg gtcatagctg tttcctgtgt gaaattgtta    2460
tccgctcaca attccacaca acataggagc cggaagcata aagtgtaaag cctggggtgc    2520
ctaatgagtg aggtaactca cattaattgc gttgcgctca ctgcccgctt tccagtcggg    2580
aaacctgtcg tgccagctgc attaatgaat cggccaacgc gcggggagag gcggtttgcg    2640
tattgggcgc tcttccgctt cctcgctcac tgactcgctg cgctcggtcg ttcggctgcg    2700
gcgagcggta tcagctcact caaaggcggt aatacggtta tccacagaat caggggataa    2760
cgcaggaaag aacatgtgag caaaaggcca gcaaaaggcc aggaaccgta aaaaggccgc    2820
gttgctggcg ttttccata ggctccgccc cctgacgag catcacaaaa atcgacgctc      2880
aagtcagagg tggcgaaacc cgacaggact ataaagatac caggcgtttc ccctggaag    2940 ctccctcgtg cgctctcctg ttccgaccct gccgcttacc ggatacctgt ccgccttct    3000 cccttcggga agcgtggcgc tttctcatag ctcacgctgt aggtatctca gttcggtgta   3060
ggtcgttcgc tccaagctgg gctgtgtgca cgaacccccc gttcagcccg accgctgcgc   3120
cttatccggt aactatcgtc ttgagtccaa cccggtaaga cacgacttat cgccactggc   3180
agcagccact ggtaacagga ttagcagagc gaggtatgta ggcggtgcta cagagttctt   3240
gaagtggtgg cctaactacg gctacactag aaggacagta tttggtatct gcgctctgct   3300
gaagccagtt accttcggaa aaagagttgg tagctcttga tccggcaaac aaaccaccgc   3360
tggtagcggt ggtttttttg tttgcaagca gcagattacg cgcagaaaaa aaggatctca   3420
agaagatcct ttgatctttt ctacgggtc tgacgctcag tggaacgaaa actcacgtta    3480
agggattttg gtcatgagat tatcaaaaag gatcttcacc tagatccttt taaattaaaa   3540
atgaagtttt aaatcaatct aaagtatata tgagtaaact tggtctgaca gttaccaatg   3600
cttaatcagt gaggcaccta tctcagcgat ctgtctattt cgttcatcca tagttgcctg   3660
actccccgtc gtgtagataa ctacgatacg ggagggctta ccatctggcc ccagtgctgc   3720
aatgataccg cgagacccac gctcaccggc tccagattta tcagcaataa accagccagc   3780
cggaagggcc gagcgcagaa gtggtcctgc aactttatcc gcctccatcc agtctattaa   3840
ttgttgccgg gaagctagag taagtagttc gccagttaat agtttgcgca acgttgttgc   3900
cattgctaca gcatcgtgg tgtcacgctc gtcgtttggt atggcttcat tcagctccgg    3960
ttcccaacga tcaaggcgag ttacatgatc ccccatgttg tgcaaaaaag cggttagctc    4020
cttcggtcct ccgatcgttg tcagaagtaa gttggccgca gtgttatcac tcatggttat    4080
ggcagcactg cataattctc ttactgtcat gccatccgta agatgctttt ctgtgactgg    4140
tgagtactca accaagtcat tctgagaata gtgtatgcgg cgaccgagtt gctcttgccc    4200
ggcgtcaata cggataata ccgcgccaca tagcagaact ttaaaagtgc tcatcattgg     4260
aaaacgttct cggggcgaa aactctcaag gatcttaccg ctgttgagat ccagttcgat    4320
gtaacccact cgtgcaccca actgatcttc agcatctttt actttcacca gcgtttctgg    4380
```

```
gtgagcaaaa acaggaaggc aaaatgccgc aaaaaaggga ataagggcga cacggaaatg      4440
ttgaatactc atactcttcc tttttcaata ttattgaagc atttatcagg gttattgtct      4500
catgagcgga tacatatttg aatgtattta gaaaaataaa caaatagggg ttccgcgcac      4560
atttccccga aaagtgccac ctgaacgaag catctgtgct tcattttgta gaacaaaaat      4620
gcaacgcgag agcgctaatt tttcaaacaa agaatctgag ctgcatttttt acagaacaga      4680 aatgcaacgc gaaagcgcta ttttaccaac gaagaatctg tgcttcattt ttgtaaaaca      4740
aaaatgcaac gcgagagcgc taatttttca acaaagaat  ctgagctgca tttttacaga      4800
acagaaatgc aacgcgagag cgctatttta ccaacaaaga atctatactt cttttttgtt      4860
ctacaaaaat gcatcccgag agcgctatttt ttctaacaaa gcatcttaga ttactttttt      4920
tctcctttgt gcgctctata atgcagtctc ttgataactt tttgcactgt aggtccgtta      4980
aggttagaag aaggctactt tggtgtctat tttctcttcc ataaaaaaag cctgactcca      5040
cttcccgcgt ttactgatta ctagcgaagc tgcgggtgca ttttttcaag ataaaggcat      5100
ccccgattat attctatacc gatgtggatt gcgcatactt tgtgaacaga aagtgatagc      5160
gttgatgatt cttcattggt cagaaaatta tgaacggttt cttctatttt gtctctatat      5220
actacgtata ggaaatgttt acattttcgt attgttttcg attcactcta tgaatagttc      5280
ttactacaat tttttttgtct aaagagtaat actagagata aacataaaaa atgtagaggt      5340
cgagtttaga tgcaagttca aggagcgaaa ggtggatggg taggttatat agggatatag      5400
cacagagata tatagcaaag agatactttt gagcaatgtt tgtggaagcg gtattcgcaa      5460 tatttttagta gctcgttaca gtccggtgcg ttttggtttt tttgaaagtg cgtcttcaga      5520
gcgcttttgg ttttcaaaag cgctctgaag ttcctatact ttctagagaa taggaacttc      5580
ggaataggaa cttcaaagcg tttccgaaaa cgagcgcttc cgaaaatgca acgcgagctg      5640
cgcacataca gctcactgtt cacgtcgcac ctatatctgc gtgttgcctg tatatatata      5700
tacatgagaa gaacggcata gtgcgtgttt atgcttaaat gcgtacttat atgcgtctat      5760
ttatgtagga tgaaaggtag tctagtacct cctgtgatat tatcccattc catgcggggt      5820
atcgtatgct tccttcagca ctacccttta gctgttctat atgctgccac tcctcaattg      5880
gattagtctc atccttcaat gctatcattt cctttgatat tggatcatat taagaaacca      5940
ttattatcat gacattaacc tataaaaata ggcgtatcac gaggccctt cgtc             5994
```

<210> SEQ ID NO 11
<211> LENGTH: 6039
<212> TYPE: DNA
<213> ORGANISM: Artificial Sequence
<220> FEATURE:
<223> OTHER INFORMATION: Synthetic: pAM1114 - closed plasmid bearing a
      NatA (Nourseothricin acetyltransferase from Streptomyces noursei)
      selectable marker

<400> SEQUENCE: 11

```
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcgggctgg cttaactatg cggcatcaga gcagattgta ctgagagtgc       180
aaatacacat catcgtccta caagttcatc aaagtgttgg acagacaact ataccagcat      240
ggatctcttg tatcggttct tttctcccgc tctctcgcaa taacaatgaa cactgggtca      300
atcatagcct acacaggtga acagagtagc gtttatacag ggtttatacg gtgattccta      360
cggcaaaaat ttttcatttc taaaaaaaaa agaaaaatt tttctttcca acgctagaag       420
```

```
gaaaagaaaa atctaattaa attgatttgg tgattttctg agagttccct tttcatata     480 tcgaattttg aatataaaag gagatcgaaa aaattttct attcaatctg ttttctggtt     540
ttatttgata gttttttttgt gtattattat tatggattag tactggttta tatgggtttt   600
tctgtataac ttcttttttat tttagtttgt ttaatcttat tttgagttac attatagttc   660
cctaactgca agagaagtaa cattaaaaat gaccactctt gacgacacgg cttaccggta    720
ccgcaccagt gtcccggggg acgccgaggc catcgaggca ctggatgggt ccttcaccac    780
cgacaccgtc ttccgcgtca ccgccaccgg ggacggcttc accctgcggg aggtgccggt    840
ggacccgccc ctgaccaagg tgttccccga cgacgaatcg gacgcgaat cggacgccgg     900 ggaggacggc gacccggact cccggacgtt cgtcgcgtac ggggacgacg gcgacctggc    960
gggcttcgtg gtcgtctcgt actccggctg gaaccgccgg ctgaccgtcg aggacatcga    1020
ggtcgccccg gagcaccggg ggcacggggt cgggcgcgcg ttgatggggc tcgcgacgga    1080
gttcgcccgc gagcggggcg ccgggcacct ctggctggag gtcaccaacg tcaacgcacc    1140
ggcgatccac gcgtaccggc ggatgggggtt caccctctgc ggcctggaca ccgccctgta   1200
cgacggcacc gcctcggacg gcgagcaggc gctctacatg agcatgccct gcccctgagt    1260
ttaacttgat actactagat ttttttctctt catttataaa atttttggtt ataattgaag   1320
ctttagaagt atgaaaaaat ccttttttt cattctttgc aaccaaaata agaagcttct     1380
tttattcatt gaaatgatga atataaacct aacaaaagaa aaagactcga atatcaaaca    1440
ttaaaaaaaa ataaaagagg ttatctgttt tcccatttag ttggagtttg cattttctaa    1500
tagatagaac tctcaattaa tgtggattta gtttctctgt tcgtttttttt ttgttttgtt   1560 ctcactgtat ttacatttct atttagtatt tagttattca tataatctta acttgcggtg    1620
tgaaataccg cacagatgcg taaggagaaa ataccgcatc aggaaattgt aagcgttaat    1680
attttgttaa aattcgcgtt aaattttgt taaatcagct cattttttaa ccaataggcc     1740
gaaatcggca aaatccctta taaatcaaaa gaatagaccg atagggtt gagtgttgtt      1800 ccagtttgga acaagagtcc actattaaag aacgtggact ccaacgtcaa agggcgaaaa    1860
accgtctatc agggcgatgg cccactacgt gaaccatcac cctaatcaag ttttttgggg    1920
tcgaggtgcc gtaaagcact aaatcggaac cctaaaggga gccccccgatt tagagcttga   1980 cggggaaagc cggcgaacgt ggcgagaaag gaagggaaga aagcgaaagg agcgggcgct    2040
agggcgctgg caagtgtagc ggtcacgctg cgcgtaacca ccacacccgc cgcgcttaat    2100
gcgccgctac agggcgcgtc gcgccattcg ccattcaggc tgcgcaactg ttgggaaggg    2160
cgatcggtgc gggcctcttc gctattacgc cagctggcga aaggggggatg tgctgcaagg   2220 cgattaagtt gggtaacgcc agggttttcc cagtcacgac gttgtaaaac gacggccagt    2280
gagcgcgcgt aatacgactc actatagggc gaattgggta ccgggccccc cctcgaggtc    2340
gacggtatcg ataagcttga tatcgaattc ctgcagcccg ggggatccac tagttctaga    2400
gcggccgcca ccgcggtgga gctccagctt ttgttccctt tagtgagggt taattgcgcg    2460
cttggcgtaa tcatggtcat agctgtttcc tgtgtgaaat tgttatccgc tcacaattcc    2520
acacaacata ggagccggaa gcataaagtg taaagcctgg ggtgcctaat gagtgaggta    2580
actcacatta attgcgttgc gctcactgcc cgctttccag tcgggaaacc tgtcgtgcca    2640
gctgcattaa tgaatcggcc aacgcgcggg gagaggcggt ttgcgtattg ggcgctcttc    2700
cgcttcctcg ctcactgact cgctgcgctc ggtcgttcgg ctgcggcgag cggtatcagc    2760
tcactcaaag gcggtaatac ggttatccac agaatcaggg gataacgcag gaaagaacat    2820
```

```
gtgagcaaaa ggccagcaaa aggccaggaa ccgtaaaaag gccgcgttgc tggcgttttt    2880
ccataggctc cgccccctg acgagcatca caaaaatcga cgctcaagtc agaggtggcg    2940
aaacccgaca ggactataaa gataccaggc gtttccccct ggaagctccc tcgtgcgctc    3000
tcctgttccg accctgccgc ttaccggata cctgtccgcc tttctccctt cgggaagcgt    3060
ggcgctttct catagctcac gctgtaggta tctcagttcg gtgtaggtcg ttcgctccaa    3120
gctgggctgt gtgcacgaac cccccgttca gcccgaccgc tgcgccttat ccggtaacta    3180
tcgtcttgag tccaacccgg taagacacga cttatcgcca ctggcagcag ccactggtaa    3240
caggattagc agagcgaggt atgtaggcgg tgctacagag ttcttgaagt ggtggcctaa    3300
ctacggctac actagaagga cagtatttgg tatctgcgct ctgctgaagc cagttacctt    3360
cggaaaaaga gttggtagct cttgatccgg caaacaaacc accgctggta gcggtggttt    3420
ttttgtttgc aagcagcaga ttacgcgcag aaaaaaagga tctcaagaag atcctttgat    3480
cttttctacg gggtctgacg ctcagtggaa cgaaaactca cgttaaggga ttttggtcat    3540
gagattatca aaaaggatct tcacctagat ccttttaaat taaaaatgaa gttttaaatc    3600
aatctaaagt atatatgagt aaacttggtc tgacagttac caatgcttaa tcagtgaggc    3660
acctatctca gcgatctgtc tatttcgttc atccatagtt gcctgactcc ccgtcgtgta    3720
gataactacg atacgggagg gcttaccatc tggccccagt gctgcaatga taccgcgaga    3780
cccacgctca ccggctccag atttatcagc aataaaccag ccagccggaa gggccgagcg    3840
cagaagtggt cctgcaactt tatccgcctc catccagtct attaattgtt gccgggaagc    3900
tagagtaagt agttcgccag ttaatagttt gcgcaacgtt gttgccattg ctacaggcat    3960
cgtggtgtca cgctcgtcgt ttggtatggc ttcattcagc tccggttccc aacgatcaag    4020
gcgagttaca tgatccccca tgttgtgcaa aaaagcggtt agctccttcg gtcctccgat    4080
cgttgtcaga agtaagttgg ccgcagtgtt atcactcatg gttatggcag cactgcataa    4140
ttctcttact gtcatgccat ccgtaagatg cttttctgtg actggtgagt actcaaccaa    4200
gtcattctga gaatagtgta tgcggcgacc gagttgctct tgcccggcgt caatacggga    4260
taataccgcg ccacatagca gaactttaaa agtgctcatc attggaaaac gttcttcggg    4320
gcgaaaactc tcaaggatct taccgctgtt gagatccagt tcgatgtaac ccactcgtgc    4380
acccaactga tcttcagcat cttttacttt caccagcgtt tctgggtgag caaaaacagg    4440
aaggcaaaat gccgcaaaaa agggaataag ggcgacacgg aaatgttgaa tactcatact    4500
cttccttttt caatattatt gaagcattta tcagggttat tgtctcatga gcggatacat    4560
atttgaatgt atttagaaaa ataaacaaat aggggttccg cgcacatttc cccgaaaagt    4620
gccacctgaa cgaagcatct gtgcttcatt ttgtagaaca aaaatgcaac gcgagagcgc    4680
taattttca aacaaagaat ctgagctgca ttttacaga acagaaatgc aacgcgaaag    4740
cgctatttta ccaacgaaga atctgtgctt cattttgta aaacaaaaat gcaacgcgag    4800
agcgctaatt tttcaaacaa agaatctgag ctgcattttt acagaacaga aatgcaacgc    4860
gagagcgcta ttttaccaac aaagaatcta tacttctttt ttgttctaca aaaatgcatc    4920
ccgagagcgc tatttttcta caaagcatc ttagattact tttttctcc tttgtgcgct    4980
ctataatgca gtctcttgat aacttttgc actgtaggtc cgttaaggtt agaagaaggc    5040
tactttggtg tctattttct cttccataaa aaaagcctga ctccacttcc cgcgtttact    5100
gattactagc gaagctgcgg gtgcattttt tcaagataaa ggcatccccg attatattct    5160
ataccgatgt ggattgcgca tactttgtga acagaaagtg atagcgttga tgattcttca    5220
```

```
ttggtcagaa aattatgaac ggtttcttct attttgtctc tatatactac gtataggaaa    5280
tgtttacatt ttcgtattgt tttcgattca ctctatgaat agttcttact acaattttt     5340 tgtctaaaga gtaatactag agataaacat aaaaaatgta gaggtcgagt ttagatgcaa    5400
gttcaaggag cgaaaggtgg atgggtaggt tatataggga tatagcacag agatatatag    5460
caaagagata cttttgagca atgtttgtgg aagcggtatt cgcaatattt tagtagctcg    5520
ttacagtccg gtgcgttttt ggttttttga aagtgcgtct tcagagcgct tttggttttc    5580
aaaagcgctc tgaagttcct atactttcta gagaatagga acttcggaat aggaacttca    5640
aagcgtttcc gaaaacgagc gcttccgaaa atgcaacgcg agctgcgcac atacagctca    5700
ctgttcacgt cgcacctata tctgcgtgtt gcctgtatat atatatacat gagaagaacg    5760
gcatagtgcg tgtttatgct taaatgcgta cttatatgcg tctatttatg taggatgaaa    5820
ggtagtctag tacctcctgt gatattatcc cattccatgc ggggtatcgt atgcttcctt    5880
cagcactacc ctttagctgt tctatatgct gccactcctc aattggatta gtctcatcct    5940
tcaatgctat catttccttt gatattggat catactaaga aaccattatt atcatgacat    6000
taacctataa aaataggcgt atcacgaggc cctttcgtc                           6039
```

<210> SEQ ID NO 12
<211> LENGTH: 5662
<212> TYPE: DNA
<213> ORGANISM: Artificial Sequence
<220> FEATURE:
<223> OTHER INFORMATION: Synthetic: pAM1114 vector linearized using
    DRPE308/309 (the linear cassette was co-transformed with vector
    linearized by PCR inside of the NatA marker)

<400> SEQUENCE: 12

```
atggggttca ccctctgcgg cctggacacc gccctgtacg acggcaccgc ctcggacggc     60
gagcaggcgc tctacatgag catgccctgc ccctgagttt aacttgatac tactagattt    120
tttctcttca tttataaaat tttggttat aattgaagct ttagaagtat gaaaaatcc      180 ttttttttca ttctttgcaa ccaaaataag aagcttcttt tattcattga aatgatgaat    240
ataaacctaa caaagaaaa agactcgaat atcaaacatt aaaaaaaaat aaagagtt       300 atctgttttc ccatttagtt ggagtttgca ttttctaata gatagaactc tcaattaatg    360
tggatttagt ttctctgttc gttttttttt gttttgttct cactgtattt acatttctat    420
ttagtattta gttattcata taatcttaac ttgcggtgtg aaataccgca cagatgcgta    480
aggagaaaat accgcatcag gaaattgtaa gcgttaatat tttgttaaaa ttcgcgttaa    540
atttttgtta aatcagctca tttttaacc aataggccga atcggcaaa atcccttata     600 aatcaaaaga atagaccgag atagggttga gtgttgttcc agtttggaac aagagtccac    660
tattaaagaa cgtggactcc aacgtcaaag ggcgaaaaac cgtctatcag ggcgatggcc    720
cactacgtga accatcaccc taatcaagtt ttttggggtc gaggtgccgt aaagcactaa    780
atcggaaccc taagggagc ccccgattta gagcttgacg gggaaagccg gcgaacgtgg    840
cgagaaagga agggaagaaa gcgaaaggag cgggcgctag ggcgctggca agtgtagcgg    900
tcacgctgcg cgtaaccacc acacccgccg cgcttaatgc gccgctacag ggcgcgtcgc    960
gccattcgcc attcaggctg cgcaactgtt gggaagggcg atcggtgcgg gcctcttcgc   1020
tattacgcca gctggcgaaa gggggatgtg ctgcaaggcg attaagttgg gtaacgccag   1080
ggttttccca gtcacgacgt tgtaaaacga cggccagtga gcgcgcgtaa tacgactcac   1140
tatagggcga attgggtacc gggcccccc tcgaggtcga cggtatcgat aagcttgata   1200
```

```
tcgaattcct gcagcccggg ggatccacta gttctagagc ggccgccacc gcggtggagc    1260
tccagctttt gttcccttta gtgagggtta attgcgcgct tggcgtaatc atggtcatag    1320
ctgtttcctg tgtgaaattg ttatccgctc acaattccac acaacatagg agccggaagc    1380
ataaagtgta aagcctgggg tgcctaatga gtgaggtaac tcacattaat tgcgttgcgc    1440
tcactgcccg ctttccagtc gggaaacctg tcgtgccagc tgcattaatg aatcggccaa    1500
cgcgcgggga gaggcggttt gcgtattggg cgctcttccg cttcctcgct cactgactcg    1560
ctgcgctcgg tcgttcggct gcggcgagcg gtatcagctc actcaaaggc ggtaatacgg    1620
ttatccacag aatcagggga taacgcagga agaacatgt gagcaaaagg ccagcaaaag    1680
gccaggaacc gtaaaaaggc cgcgttgctg cgttttttcc ataggctccg ccccctgac    1740 gagcatcaca aaaatcgacg ctcaagtcag aggtggcgaa acccgacagg actataaaga    1800
taccaggcgt ttccccctgg aagctccctc gtgcgctctc ctgttccgac cctgccgctt    1860
accggatacc tgtccgcctt tctcccttcg ggaagcgtgg cgctttctca tagctcacgc    1920
tgtaggtatc tcagttcggt gtaggtcgtt cgctccaagc tgggctgtgt gcacgaaccc    1980
cccgttcagc ccgaccgctg cgccttatcc ggtaactatc gtcttgagtc caacccggta    2040
agacacgact tatcgccact ggcagcagcc actggtaaca ggattagcag agcgaggtat    2100
gtaggcggtg ctacagagtt cttgaagtgg tggcctaact acggctacac tagaaggaca    2160
gtatttggta tctgcgctct gctgaagcca gttaccttcg gaaaaagagt tggtagctct    2220
tgatccggca aacaaaccac cgctggtagc ggtggttttt tgtttgcaa gcagcagatt    2280 acgcgcagaa aaaaggatc tcaagaagat cctttgatct tttctacggg gtctgacgct    2340
cagtggaacg aaaactcacg ttaagggatt ttggtcatga gattatcaaa aaggatcttc    2400
acctagatcc ttttaaatta aaaatgaagt tttaaatcaa tctaaagtat atatgagtaa    2460
acttggtctg acagttacca atgcttaatc agtgaggcac ctatctcagc gatctgtcta    2520
tttcgttcat ccatagttgc ctgactcccc gtcgtgtaga taactacgat acgggagggc    2580
ttaccatctg gccccagtgc tgcaatgata ccgcgagacc cacgctcacc ggctccagat    2640
ttatcagcaa taaaccagcc agccggaagg gccgagcgca gaagtggtcc tgcaacttta    2700
tccgcctcca tccagtctat taattgttgc cgggaagcta gagtaagtag ttcgccagtt    2760
aatagtttgc gcaacgttgt tgccattgct acaggcatcg tggtgtcacg ctcgtcgttt    2820
ggtatggctt cattcagctc cggttcccaa cgatcaaggc gagttacatg atccccatg    2880 ttgtgcaaaa aagcggttag ctccttcggt cctccgatcg ttgtcagaag taagttggcc    2940
gcagtgttat cactcatggt tatggcagca ctgcataatt ctcttactgt catgccatcc    3000
gtaagatgct tttctgtgac tggtgagtac tcaaccaagt cattctgaga atagtgtatg    3060
cggcgaccga gttgctcttg cccggcgtca atacgggata ataccgcgcc acatagcaga    3120
actttaaaag tgctcatcat tggaaaacgt tcttcggggc gaaaactctc aaggatctta    3180
ccgctgttga gatccagttc gatgtaaccc actcgtgcac ccaactgatc ttcagcatct    3240
tttactttca ccagcgtttc tgggtgagca aaaacaggaa ggcaaaatgc cgcaaaaaag    3300
ggaataaggg cgacacggaa atgttgaata ctcatactct tcctttttca atattattga    3360
agcatttatc agggttattg tctcatgagc ggatacatat ttgaatgtat ttagaaaaat    3420
aaacaaatag gggttccgcg cacatttccc cgaaaagtgc cacctgaacg aagcatctgt    3480
gcttcatttt gtagaacaaa aatgcaacgc gagagcgcta ttttcaaa caagaatctc    3540 gagctgcatt tttacagaac agaaatgcaa cgcgaaagcg ctattttacc aacgaagaat    3600
```

```
ctgtgcttca ttttttgtaaa acaaaaatgc aacgcgagag cgctaattt tcaaacaaag      3660 aatctgagct gcatttttac agaacagaaa tgcaacgcga gagcgctatt ttaccaacaa      3720
agaatctata cttcttttt gttctacaaa aatgcatccc gagagcgcta ttttttctaac     3780 aaagcatctt agattacttt ttttctcctt tgtgcgctct ataatgcagt ctcttgataa      3840 cttttttgcac tgtaggtccg ttaaggttag aagaaggcta ctttggtgtc tattttctct    3900
tccataaaaa aagcctgact ccacttcccg cgtttactga ttactagcga agctgcgggt     3960 gcatttttc aagataaagg catccccgat tatattctat accgatgtgg attgcgcata      4020
ctttgtgaac agaaagtgat agcgttgatg attcttcatt ggtcagaaaa ttatgaacgg     4080
tttcttctat tttgtctcta tatactacgt ataggaaatg tttacatttt cgtattgttt    4140
tcgattcact ctatgaatag ttcttactac aattttttg tctaaagagt aatactagag      4200
ataaacataa aaaatgtaga ggtcgagttt agatgcaagt tcaaggagcg aaaggtggat     4260
gggtaggtta tatagggata tagcacagag atatatagca aagagatact tttgagcaat    4320
gtttgtggaa gcggtattcg caatattta gtagctcgtt acagtccggt gcgttttgg      4380 tttttgaaa gtgcgtcttc agagcgcttt tggttttcaa aagcgctctg aagttcctat     4440
actttctaga aataggaac ttcggaatag aacttcaaa gcgtttccga aaacgagcgc       4500
ttccgaaaat gcaacgcgag ctgcgcacat acagctcact gttcacgtcg cacctatatc    4560
tgcgtgttgc ctgtatatat atatacatga aagaacggc atagtgcgtg tttatgctta     4620
aatgcgtact tatatgcgtc tatttatgta ggatgaaagg tagtctagta cctcctgtga    4680
tattatccca ttccatgcgg ggtatcgtat gcttccttca gcactaccct ttagctgttc    4740
tatatgctgc cactcctcaa ttggattagt ctcatccttc aatgctatca tttcctttga    4800
tattggatca tactaagaaa ccattattat catgacatta acctataaaa ataggcgtat    4860
cacgaggccc tttcgtctcg cgcgtttcgg tgatgacggt gaaaacctct gacacatgca    4920
gctcccggag acggtcacag cttgtctgta agcggatgcc gggagcagac aagcccgtca    4980
gggcgcgtca gcgggtgttg gcgggtgtcg gggctggctt aactatgcgg catcagagca    5040
gattgtactg agagtgcaaa tacacatcat cgtcctacaa gttcatcaaa gtgttggaca    5100
gacaactata ccagcatgga tctcttgtat cggttctttt ctcccgctct ctcgcaataa    5160
caatgaacac tgggtcaatc atagcctaca caggtgaaca gagtagcgtt tatacagggt    5220
ttatacggtg attcctacgg caaaaatttt tcatttctaa aaaaaaaag aaaaattttt     5280 cttttccaacg ctagaaggaa aagaaaaatc taattaaatt gatttggtga ttttctgaga    5340
gttccctttt tcatatatcg aattttgaat ataaaaggag atcgaaaaaa ttttttctatt   5400 caatctgttt tctggtttta tttgatagtt tttttgtgta ttattattat ggattagtac    5460
tggtttatat gggttttct gtataacttc ttttatttt agtttgttta atcttatttt      5520
gagttacatt atagttccct aactgcaaga gaagtaacat taaaaatgac cactcttgac    5580
gacacggctt accggtaccg caccagtgtc ccgggggacg ccgaggccat cgaggcactg    5640
gatgggtcct tcaccaccga ca                                              5662
```

<210> SEQ ID NO 13
<211> LENGTH: 651
<212> TYPE: DNA
<213> ORGANISM: Artificial Sequence
<220> FEATURE:
<223> OTHER INFORMATION: Synthetic: DRPE310/311 PCR fragment from pAM1114 (a complementary overlapping NatA ORF fragment)

<400> SEQUENCE: 13

```
cttattttga gttacattat agttccctaa ctgcaagaga agtaacatta aaaatgacca      60
ctcttgacga cacggcttac cggtaccgca ccagtgtccc gggggacgcc gaggccatcg     120
aggcactgga tgggtccttc accaccgaca ccgtcttccg cgtcaccgcc accggggacg     180
gcttcaccct gcgggaggtg ccggtggacc cgcccctgac caaggtgttc cccgacgacg     240
aatcggacga cgaatcggac gccggggagg acggcgaccc ggactcccgg acgttcgtcg     300
cgtacgggga cgacggcgac ctggcgggct tcgtggtcgt ctcgtactcc ggctggaacc     360
gccggctgac cgtcgaggac atcgaggtcg ccccggagca ccgggggcac ggggtcgggc     420
gcgcgttgat ggggctcgcg acggagttcg cccgcgagcg gggcgccggg cacctctggc     480
tggaggtcac caacgtcaac gcaccggcga tccacgcgta ccggcggatg gggttcaccc     540
tctgcggcct ggacaccgcc ctgtacgacg gcaccgcctc ggacggcgag caggcgctct     600
acatgagcat gccctgcccc tgagtttaac ttgatactac tagatttttt c             651
```

<210> SEQ ID NO 14
<211> LENGTH: 1024
<212> TYPE: DNA
<213> ORGANISM: Artificial Sequence
<220> FEATURE:
<223> OTHER INFORMATION: Synthetic: Donor DNA for integration at RHR2 locus

<400> SEQUENCE: 14

```
ggaaatccgt atcattttct cgcatacacg aacccgcgtg cgcctggtaa attgcaggat      60
tctcattgtc cggttttctt tatgggaata atcatcatca ccattatcac tgttactctt     120
gcgatcatca tcaataacat aattttttta acgctgtttg atgatggtat gtgcttttgt     180
tgttccttac tcaccttttc ctttgtgtct tttaattttg accattttga ccattttgac     240
ctttgatgat gtgtgagttc ctcttttctt ttttctttt cttttttcct tttttttct     300
tttcttactc tgttaatcac tttctttcct ttttcttcat attgtcgtct tgttcatttt     360
cgttcaattg ataatgtata taaatctttc ctaagtatct cttgattgcc attttttttct    420
ttccaagttt ccttgttatg aaacgtttca atgttttaaa atatatcaga acaacaaaag     480
caaatataca aaccatcgca cgctcgtcca acgccggcgg accttttttct tttatttttt     540
tgataaaact actacgctaa aaataaaata aaaatgtatg atttccctcc atttccgacc     600
aattgtataa ttttatatct gcatgactta ataatataat ataatactta taaaatacga     660
atagaaaaat ttaaaccgat gtaatgcatc cttttctttg ttgtcttcgg atgatctgcc     720
gtgacaggtg gttcgcgcaa atcaaactgg attagagaat taacacaga ataaaaaag      780
gaagattcaa tcttcgtttt tgttttatat cttactataa aagtgttttt ttttagtacg     840
acgagaagtt agagtaatta taaaggaat gcttatttaa atttatttct tagacttctt     900
ttcagacttc ttagcagcct cagtttgttc cttaacgacc ttcttaacaa tcttttgttc     960
ctcaatcaag aaagctctga cgattctttc cttgacacag ttggcacatc tggaaccacc    1020
gtaa                                                                 1024
```

<210> SEQ ID NO 15
<211> LENGTH: 1024
<212> TYPE: DNA
<213> ORGANISM: Artificial Sequence
<220> FEATURE:
<223> OTHER INFORMATION: Synthetic: Donor DNA for integration at HO locus

<400> SEQUENCE: 15

```
cgcaagtcct gtttctatgc ctttctctta gtaattcacg aaataaacct atggtttacg      60
aaatgatcca cgaaaatcat gttattattt acatcaacat atcgcgaaaa ttcatgtcat     120
gtccacatta acatcattgc agagcaacaa ttcattttca tagagaaatt tgctactatc    180
acccactagt actaccattg gtacctacta ctttgaattg tactaccgct gggcgttatt    240
aggtgtgaaa ccacgaaaag ttcaccataa cttcgaataa agtcgcggaa aaagtaaac     300
agctattgct actcaaatga ggtttgcaga agcttgttga agcatgatga agcgttctaa    360
acgcactatt catcattaaa tatttaaagc tcataaaatt gtattcaatt cctattctaa    420
atggctttta tttctattac aactattagc tctaaatcca tatcctcata agcagcaatc    480
aattctatct atactttaaa cgctcgtcca acgccggcgg acctaatgtg tatattagtt    540
taaaaagttg tatgtaataa aagtaaaatt taatattttg gatgaaaaaa accatttta     600
gactttttct taactagaat gctggagtag aaatacgcca tctcaagata caaaaagcgt    660
taccggcact gatttgtttc aaccagtata tagattatta ttgggtcttg atcaactttc    720
ctcagacata tcagtaacag ttatcaagct aaatatttac gcgaaagaaa acaaatatt    780
ttaattgtga tacttgtgaa tttattta ttaaggatac aaagttaaga gaaaacaaaa     840
tttatataca atataagtaa tattcatata tatgtgatga atgcagtctt aacgagaaga    900
catggccttg gtgacaactc tcttcaaacc aacttcagcc tttctcaatt catcagcaga    960
tgggtcttcg atttgcaaag cagccaaagc atcggacaaa gcagcttcaa tcttggactt   1020
ggaa                                                                1024
```

<210> SEQ ID NO 16
<211> LENGTH: 1024
<212> TYPE: DNA
<213> ORGANISM: Artificial Sequence
<220> FEATURE:
<223> OTHER INFORMATION: Synthetic: Donor DNA for integration at ADH5 locus

<400> SEQUENCE: 16

```
taattttaca agtagtgtct tcatgacgga ttcatagtct atccaagcgt ttgcccaaaa      60
ttttgcagta aatttaatgt tttctgtata ggataatggt gcgccattca agtcccgcga    120
aaaatgactg atgtctacag gacagggcg caatatatgt tctctgacat tgcaccttt     180
gaatatatca tgtgtttgtt ctgctatctg cttgtagaag ggtacgctaa cagagccggc    240
ggcattgtaa aaagttctcc tttcgcggaa ggatgagtca aaaagcatgt gacaatgaaa    300
taatcaaatt gtgacatctg ctgacgcggg atcgttcctt cgtattgtct agattgtaat    360
ctatataaca tactacgaat ataaaagagg gactacaaga tatttctagc gcaaactact    420
gctttactgt ctcacaatgt ctctgattgg aagataccta agaaaattat ttaactacat    480
atctacaaaa tcaaagcatc cgctcgtcca acgccggcgg accttctttt gtaacgaatt    540
tgatgaatat attttactt tttatataag ctattttgta gatattgact ttttacgatt    600
tatttgtaac aatgagaatt actccatttc tgaacttcag taaatagcga gtgattctgt    660
actttgcgag aaccggtgga catttggtat tttgccttac aagaacaacc tatacaaacg    720
tttcaatatc taattctttg taatccattg ttttacgaga catataatgt gatatataga    780
tgaactttac gtataaaatg atatatttaa aactagcaac tgcgtgcgta agacaaactg    840
aaataggcca tttacggaaa agaaatttaa taatgtcgac tggaaactga aaccaggagg    900
```

```
agtagaaatt ggttaaattg attagctaaa atttactcgt tgtggacaga gtttgagcca    960
agcggaatgt tttcaaggct ttctttgttt cgaagggcag ctctggctcc tgccectatg   1020 agaa                                                                1024
```

```
<210> SEQ ID NO 17
<211> LENGTH: 36
<212> TYPE: DNA
<213> ORGANISM: Artificial Sequence
<220> FEATURE:
<223> OTHER INFORMATION: Synthetic: RHR2 upstream primer

<400> SEQUENCE: 17
gggtgcgaag taccaccacg tttcttttc atctct                               36

<210> SEQ ID NO 18
<211> LENGTH: 38
<212> TYPE: DNA
<213> ORGANISM: Artificial Sequence
<220> FEATURE:
<223> OTHER INFORMATION: Synthetic: HO upstream primer

<400> SEQUENCE: 18
acgtgtgtgt ctcatggaaa ttgatgcagt tgaagaca                             38

<210> SEQ ID NO 19
<211> LENGTH: 33
<212> TYPE: DNA
<213> ORGANISM: Artificial Sequence
<220> FEATURE:
<223> OTHER INFORMATION: Synthetic: ADH5 upstream primer

<400> SEQUENCE: 19
ggcgttatat ccaaacattt cagacagaag att                                  33

<210> SEQ ID NO 20
<211> LENGTH: 24
<212> TYPE: DNA
<213> ORGANISM: Artificial Sequence
<220> FEATURE:
<223> OTHER INFORMATION: Synthetic: Primer for deletion linker

<400> SEQUENCE: 20
aggtccgccg gcgttggacg agcg                                            24

<210> SEQ ID NO 21
<211> LENGTH: 1078
<212> TYPE: DNA
<213> ORGANISM: Artificial Sequence
<220> FEATURE:
<223> OTHER INFORMATION: Synthetic: Donor DNA for integration at Gal80
      locus

<400> SEQUENCE: 21
gacggcacgg ccacgcgttt aaaccgccca gatggaatcc cttccataga gagaaggagc     60
aagcaactga cccaatattg actgccactg gacctgaaga catgcaacaa agtgcaagca    120
tagtggggcc ttcttccaat gctaatccgg tcactgccac tgctgctacg gaaaaccaac    180
ctaaaggtat taacttcttc actataagaa atcacacga gcgcccggac gatgtctctg     240
tttaaatggc gcaagttttc cgctttgtaa tatatattta tacccctttc ttctctcccc    300
tgcaatataa tagtttaatt ctaatattaa taatatccta tattttcttc atttaccggc    360
gcactctcgc ccgaacgacc tcaaaatgtc tgctacattc ataataacca aaagctcata    420
```

```
acttttttt     ttgaacctga     atatatatac     atcacatgtc     actgctggtc     cttgccgacc     480
agcgtataca    atctcgatag     ttggtttccc     gttctttcca     ctcccgtccg     ctcgtccaac     540
gccggcggac    ctaagcatct     tgccctgtgc     ttggccccca     gtgcagcgaa     cgttataaaa     600
acgaatactg    agtatatatc     tatgtaaaac     aaccatatca     tttcttgttc     tgaactttgt     660
ttacctaact    agttttaaat     ttccctttt      cgtgcatgcg     ggtgttctta     tttattagca     720
tactacattt    gaaatatcaa     atttccttag     tagaaaagtg     agagaaggtg     cactgacaca     780
aaaaataaaa    tgctacgtat     aactgtcaaa     actttgcagc     agcgggcatc     cttccatcat     840
agcttcaaac    atattagcgt     tcctgatctt     catacccgtg     ctcaaaatga     tcaaacaaac     900
tgttattgcc    aagaaataaa     cgcaaggctg     ccttcaaaaa     ctgatccatt     agatcctcat     960
atcaagcttc    ctcatagaac     gcccaattac     aataagcatg     ttttgctgtt     atcaccgggt     1020
gataggtttg    ctcaaccatg     gaaggtagca     cggtgtttaa     accccagcgc     ctggcggg       1078
```

<210> SEQ ID NO 22
<211> LENGTH: 1069
<212> TYPE: DNA
<213> ORGANISM: Artificial Sequence
<220> FEATURE:
<223> OTHER INFORMATION: Synthetic: Donor DNA for integration at HO
      locus

<400> SEQUENCE: 22

```
gacggcacgg    ccacgcgttt     aaaccgcccg     caagtcctgt     ttctatgcct     ttctcttagt     60
aattcacgaa    ataaacctat     ggtttacgaa     atgatccacg     aaaatcatgt     tattatttac     120
atcaacatat    cgcgaaaatt     catgtcatgt     ccacattaac     atcattgcag     agcaacaatt     180
cattttcata    gagaaatttg     ctactatcac     ccactagtac     taccattggt     acctactact     240
ttgaattgta    ctaccgctgg     gcgttattag     gtgtgaaacc     acgaaaagtt     caccataact     300
tcgaataaag    tcgcggaaaa     aagtaaacag     ctattgctac     tcaaatgagg     tttgcagaag     360
cttgttgaag    catgatgaag     cgttctaaac     gcactattca     tcattaaata     tttaaagctc     420
ataaaattgt    attcaattcc     tattctaaat     ggcttttatt     tctattacaa     ctattagctc     480
taaatccata    tcctcataag     cagcaatcaa     ttctcgctcg     tccaacgccg     gcggacctaa     540
tgtgtatatt    agtttaaaaa     gttgtatgta     ataaaagtaa     aatttaatat     tttggatgaa     600
aaaaaccatt    tttagactt      tcttaacta     gaatgctgga     gtagaaatac     gccatctcaa     660
gatacaaaaa    gcgttaccgg     cactgatttg     tttcaaccag     tatatagatt     attattgggt     720
cttgatcaac    tttcctcaga     catatcagta     acagttatca     agctaaatat     ttacgcgaaa     780 gaaaacaaa    tattttaatt     gtgatacttg     tgaattttat     tttattaagg     atacaaagtt     840
aagagaaaac    aaaatttata     tacaatataa     gtaatattca     tatatatgtg     atgaatgcag     900
tcttaacgag    aagacatggc     cttggtgaca     actctcttca     aaccaacttc     agcctttctc     960
aattcatcag    cagatgggtc     ttcgatttgc     aaagcagcca     aagcatcgga     caaagcagct     1020
tcaatcttgg    acttggaacc     tcggtgttta     accccagcg      cctggcggg                   1069
```

<210> SEQ ID NO 23
<211> LENGTH: 1053
<212> TYPE: DNA
<213> ORGANISM: Artificial Sequence
<220> FEATURE:
<223> OTHER INFORMATION: Synthetic: Donor DNA for integration at ADH5
      locus

<400> SEQUENCE: 23

```
gacggcacgg ccacgcgttt aaaccgccaa ttttacaagt agtgtcttca tgacggattc      60
atagtctatc caagcgtttg cccaaaattt tgcagtaaat ttaatgtttt ctgtatagga     120
taatggtgcg ccattcaagt cccgcgaaaa atgactgatg tctacaggac aggggcgcaa     180
tatatgttct ctgacattgc accttttgaa tatatcatgt gtttgttctg ctatctgctt     240
gtagaagggt acgctaacag agccggcggc attgtaaaaa gttctccttt cgcggaagga     300
tgagtcaaaa agcatgtgac aatgaaataa tcaaattgtg acatctgctg acgcgggatc     360
gttccttcgt attgtctaga ttgtaatcta tataacatac tacgaatata aagagggac      420
tacaagatat ttctagcgca aactactgct ttactgtctc acaatgtctc tgattggaag     480
atacctaaga aaattattta actacatatc tacaaaatca aagcatccgc tcgtccaacg     540
ccggcggacc ttcttttgta acgaatttga tgaatatatt tttactttttt atataagcta     600
ttttgtagat attgactttt tacgatttat ttgtaacaat gagaattact ccatttctga     660
acttcagtaa atagcgagtg attctgtact ttgcagaaac cggtggacat ttggtatttt     720
gccttacaag aacaacctat acaaacgttt caatatctaa ttctttgtaa tccattgttt     780
tacgagacat ataatgtgat atatagatga actttacgta taaatgata tatttaaaac     840
tagcaactgc gtgcgtaaga caaactgaaa taggccattt acggaaaaga aatttaataa     900
tgtcgactgg aaaactgaaac caggaggagt agaaattggt taaattgatt agctaaaatt     960
tactcgttgt ggacagagtt tgagccaagc ggaatgtttt caaggctttc tttgtttcga    1020
agggccggtg tttaaaccc agcgcctggc ggg                                   1053
```

<210> SEQ ID NO 24
<211> LENGTH: 1026
<212> TYPE: DNA
<213> ORGANISM: Artificial Sequence
<220> FEATURE:
<223> OTHER INFORMATION: Synthetic: gRNA construct targeting Gal80 locus

<400> SEQUENCE: 24

```
ccttataaat caaagaata gaccgagata gggttgagtg ttgttccagt ttggaacaag       60
agtccactat taaagaacgt ggactccaac gtcaagggc gaaaaaccgt ctatcagggc     120
gatggcccac tacgtgaacc atcaccctaa tcaagttttt tggggtcgag gtgccgtaaa    180
gcactaaatc ggaaccctaa agggagcccc cgatttagag cttgacgggg aaagcctctt    240
tgaaaagata atgtatgatt atgctttcac tcatatttat acagaaactt gatgtttttct    300
ttcgagtata tacaaggtga ttacatgtac gtttgaagta caactctaga ttttgtagtg    360
ccctcttggg ctagcggtaa aggtgcgcat ttttttcacac cctacaatgt tctgttcaaa    420
agatttggt caaacgctgt agaagtgaaa gttggtgcgc atgtttcggc gttcgaaact    480
tctccgcagt gaaagataaa tgatcgtaag gctgctgctg aacgtgtttt agagctagaa    540
atagcaagtt aaaataaggc tagtccgtta tcaacttgaa aaagtggcac cgagtcggtg    600
gtgctttttt tgtttttat gtctcagctt ttgttccctt tagtgagggt taattgcgcg    660
cttggcgtaa tcatggtcat agctgtttcc tgtgtgaaat tgttatccgc tcacaattcc    720
acacaacata ggagccggaa gcataaagtg taaagcctgg ggtgcctaat gagtgaggta    780
actcacatta attgcgttgc gctcactgcc cgctttccag tcgggaaacc tgtcgtgcca    840
gctgcattaa tgaatcggcc aacgcgcggg gagaggcggt ttgcgtattg ggcgctcttc    900
cgcttcctcg ctcactgact cgctgcgctc ggtcgttcgg ctgcggcgag cggtatcagc    960
```

```
tcactcaaag gcggtaatac ggttatccac agaatcaggg gataacgcag gaaagaacat    1020
gtgagc                                                                1026

<210> SEQ ID NO 25
<211> LENGTH: 1026
<212> TYPE: DNA
<213> ORGANISM: Artificial Sequence
<220> FEATURE:
<223> OTHER INFORMATION: Synthetic: gRNA construct targeting HO locus

<400> SEQUENCE: 25
ccttataaat caaaagaata gaccgagata gggttgagtg ttgttccagt ttggaacaag      60
agtccactat taaagaacgt ggactccaac gtcaaagggc gaaaaaccgt ctatcagggc    120
gatggcccac tacgtgaacc atcaccctaa tcaagttttt tggggtcgag gtgccgtaaa    180
gcactaaatc ggaaccctaa agggagcccc cgatttagag cttgacgggg aaagcctctt    240
tgaaaagata atgtatgatt atgctttcac tcatatttat acagaaactt gatgttttct    300
ttcgagtata tacaaggtga ttacatgtac gtttgaagta caactctaga ttttgtagtg    360
ccctcttggg ctagcggtaa aggtgcgcat tttttcacac cctacaatgt tctgttcaaa    420
agattttggt caaacgctgt agaagtgaaa gttggtgcgc atgtttcggc gttcgaaact    480
tctccgcagt gaaagataaa tgatcgccgg cttgatcgac tcagagtttt agagctagaa    540
atagcaagtt aaaataaggc tagtccgtta tcaacttgaa aaagtggcac cgagtcggtg    600
gtgctttttt tgttttttat gtctcagctt ttgttccctt tagtgagggt taattgcgcg    660
cttggcgtaa tcatggtcat agctgtttcc tgtgtgaaat tgttatccgc tcacaattcc    720
acacaacata ggagccggaa gcataaagtg taaagcctgg ggtgcctaat gagtgaggta    780
actcacatta attgcgttgc gctcactgcc cgctttccag tcgggaaacc tgtcgtgcca    840
gctgcattaa tgaatcggcc aacgcgcggg gagaggcggt ttgcgtattg ggcgctcttc    900
cgcttcctcg ctcactgact cgctgcgctc ggtcgttcgg ctgcggcgag cggtatcagc    960
tcactcaaag gcggtaatac ggttatccac agaatcaggg gataacgcag gaaagaacat    1020
gtgagc                                                                1026

<210> SEQ ID NO 26
<211> LENGTH: 1026
<212> TYPE: DNA
<213> ORGANISM: Artificial Sequence
<220> FEATURE:
<223> OTHER INFORMATION: Synthetic: gRNA construct targeting ADH5 locus

<400> SEQUENCE: 26
ccttataaat caaaagaata gaccgagata gggttgagtg ttgttccagt ttggaacaag      60
agtccactat taaagaacgt ggactccaac gtcaaagggc gaaaaaccgt ctatcagggc    120
gatggcccac tacgtgaacc atcaccctaa tcaagttttt tggggtcgag gtgccgtaaa    180
gcactaaatc ggaaccctaa agggagcccc cgatttagag cttgacgggg aaagcctctt    240
tgaaaagata atgtatgatt atgctttcac tcatatttat acagaaactt gatgttttct    300
ttcgagtata tacaaggtga ttacatgtac gtttgaagta caactctaga ttttgtagtg    360
ccctcttggg ctagcggtaa aggtgcgcat tttttcacac cctacaatgt tctgttcaaa    420
agattttggt caaacgctgt agaagtgaaa gttggtgcgc atgtttcggc gttcgaaact    480
tctccgcagt gaaagataaa tgatcggggt cattggtatc gatgggtttt agagctagaa    540
atagcaagtt aaaataaggc tagtccgtta tcaacttgaa aaagtggcac cgagtcggtg    600
```

```
gtgcttttttt tgttttttat gtctcagctt ttgttccctt tagtgagggt taattgcgcg    660
cttggcgtaa tcatggtcat agctgtttcc tgtgtgaaat tgttatccgc tcacaattcc    720
acacaacata ggagccggaa gcataaagtg taaagcctgg ggtgcctaat gagtgaggta    780
actcacatta attgcgttgc gctcactgcc cgctttccag tcgggaaacc tgtcgtgcca    840
gctgcattaa tgaatcggcc aacgcgcggg gagaggcggt ttgcgtattg ggcgctcttc    900
cgcttcctcg ctcactgact cgctgcgctc ggtcgttcgg ctgcggcgag cggtatcagc    960
tcactcaaag gcggtaatac ggttatccac agaatcaggg gataacgcag aaagaacat    1020 gtgagc                                                              1026
```

<210> SEQ ID NO 27
<211> LENGTH: 5975
<212> TYPE: DNA
<213> ORGANISM: Artificial Sequence
<220> FEATURE:
<223> OTHER INFORMATION: Synthetic: Vector backbone for 2-piece assembly

<400> SEQUENCE: 27

```
gttttagagc tagaaatagc aagttaaaat aaggctagtc cgttatcaac ttgaaaaagt     60
ggcaccgagt cggtggtgct ttttttgttt tttatgtctc agcttttgtt cccttttagtg   120 agggttaatt gcgcgcttgg cgtaatcatg gtcatagctg tttcctgtgt gaaattgtta   180
tccgctcaca attccacaca acataggagc cggaagcata agtgtaaag cctggggtgc    240 ctaatgagtg aggtaactca cattaattgc gttgcgctca ctgcccgctt tccagtcggg   300
aaacctgtcg tgccagctgc attaatgaat cggccaacgc gcggggagag gcggtttgcg   360
tattgggcgc tcttccgctt cctcgctcac tgactcgctg cgctcggtcg ttcggctgcg   420
gcgagcggta tcagctcact caaaggcggt aatacggtta ccacagaat caggggataa    480 cgcaggaaag aacatgtgag caaaaggcca gcaaaaggcc aggaaccgta aaaaggccgc   540
gttgctggcg ttttttccata ggctccgccc cctgacgag catcacaaaa atcgacgctc    600
aagtcagagg tggcgaaacc cgacaggact ataaagatac caggcgtttc ccctggaag    660 ctccctcgtg cgctctcctg ttccgaccct gccgcttacc ggatacctgt ccgcctttct    720
cccttcggga agcgtggcgc tttctcatag ctcacgctgt aggtatctca gttcggtgta    780
ggtcgttcgc tccaagctgg gctgtgtgca cgaaccccc gttcagcccg accgctgcgc    840
cttatccggt aactatcgtc ttgagtccaa cccggtaaga cacgacttat cgccactggc    900
agcagccact ggtaacagga ttagcagagc gaggtatgta ggcggtgcta cagagttctt    960
gaagtggtgg cctaactacg gctacactag aaggacagta tttggtatct gcgctctgct   1020
gaagccagtt accttcggaa aaagagttgg tagctcttga tccggcaaac aaaccaccgc   1080
tggtagcggt ggtttttttg tttgcaagca gcagattacg cgcagaaaaa aaggatctca   1140
agaagatcct ttgatctttt ctacggggtc tgacgctcag tggaacgaaa actcacgtta   1200
agggattttg gtcatgagat tatcaaaaag gatcttcacc tagatccttt taaattaaaa   1260
atgaagtttt aaatcaatct aaagtatata tgagtaaact tggtctgaca gttaccaatg   1320
cttaatcagt gaggcaccta tctcagcgat ctgtctattt cgttcatcca tagttgcctg   1380
actccccgtc gtgtagataa ctacgatacg ggagggctta ccatctggcc ccagtgctgc   1440
aatgataccg cgagacccac gctcaccggc tccagattta tcagcaataa accagccagc   1500
cggaagggcc gagcgcagaa gtggtcctgc aactttatcc gcctccatcc agtctattaa   1560
ttgttgccgg gaagctagag taagtagttc gccagttaat agtttgcgca acgttgttgc   1620
```

```
cattgctaca ggcatcgtgg tgtcacgctc gtcgtttggt atggcttcat tcagctccgg   1680
ttcccaacga tcaaggcgag ttacatgatc ccccatgttg tgcaaaaaag cggttagctc   1740
cttcggtcct ccgatcgttg tcagaagtaa gttggccgca gtgttatcac tcatggttat   1800
ggcagcactg cataattctc ttactgtcat gccatccgta agatgctttt ctgtgactgg   1860
tgagtactca accaagtcat tctgagaata gtgtatgcgg cgaccgagtt gctcttgccc   1920
ggcgtcaata cgggataata ccgcgccaca tagcagaact taaaagtgc tcatcattgg    1980 aaaacgttct tcggggcgaa aactctcaag gatcttaccg ctgttgagat ccagttcgat   2040
gtaacccact cgtgcaccca actgatcttc agcatctttt actttcacca gcgtttctgg   2100
gtgagcaaaa acaggaaggc aaaatgccgc aaaaaaggga ataagggcga cacggaaatg   2160
ttgaatactc atactcttcc ttttcaata ttattgaagc atttatcagg gttattgtct    2220
catgagcgga tacatatttg aatgtattta gaaaaataaa caaatagggg ttccgcgcac   2280
atttccccga aaagtgccac ctgaacgaag catctgtgct tcattttgta gaacaaaaat   2340
gcaacgcgag agcgctaatt tttcaaacaa agaatctgag ctgcattttt acagaacaga   2400
aatgcaacgc gaaagcgcta ttttaccaac gaagaatctg tgcttcattt ttgtaaaaca   2460
aaaatgcaac gcgagagcgc taattttttca aacaaagaat ctgagctgca ttttttacaga  2520 acagaaatgc aacgcgagag cgctatttta ccaacaaaga atctatactt ctttttttgtt  2580 ctacaaaaat gcatcccgag agcgctattt ttctaacaaa gcatcttaga ttactttttt    2640
tctcctttgt gcgctctata atgcagtctc ttgataactt tttgcactgt aggtccgtta   2700
aggttagaag aaggctactt tggtgtctat tttctcttcc ataaaaaaag cctgactcca   2760
cttcccgcgt ttactgatta ctagcgaagc tgcgggtgca ttttttcaag ataaaggcat   2820
ccccgattat attctatacc gatgtggatt gcgcatactt tgtgaacaga agtgatagc    2880 gttgatgatt cttcattggt cagaaaatta tgaacggttt cttctatttt gtctctatat   2940
actacgtata ggaaatgttt acattttcgt attgttttcg attcactcta tgaatagttc   3000
ttactacaat tttttttgtct aaagagtaat actagagata aacataaaaa atgtagaggt  3060
cgagtttaga tgcaagttca aggagcgaaa ggtggatggg taggttatat agggatatag   3120
cacagagata tatagcaaag agatactttt gagcaatgtt tgtggaagcg gtattcgcaa   3180
tattttagta gctcgttaca gtccggtgcg ttttttggttt tttgaaagtg cgtcttcaga   3240
gcgcttttgg ttttcaaaag cgctctgaag ttcctatact ttctagagaa taggaacttc   3300
ggaataggaa cttcaaagcg tttccgaaaa cgagcgcttc cgaaaatgca acgcgagctg   3360
cgcacataca gctcactgtt cacgtcgcac ctatatctgc gtgttgcctg tatatatata   3420
tacatgagaa gaacggcata gtgcgtgttt atgcttaaat gcgtacttat atgcgtctat   3480
ttatgtagga tgaaaggtag tctagtacct cctgtgatat tatcccattc catgcgggt    3540 atcgtatgct tccttcagca ctaccctta gctgttctat atgctgccac tcctcaattg    3600
gattagtctc atccttcaat gctatcattt cctttgatat tggatcatat taagaaacca   3660
ttattatcat gacattaacc tataaaaata ggcgtatcac gaggcccttt cgtctcgcgc   3720
gtttcggtga tgacggtgaa aacctctgac acatgcagct cccggagacg gtcacagctt   3780
gtctgtaagc ggatgccggg agcagacaag cccgtcaggg cgcgtcagcg ggtgttggcg   3840
ggtgtcgggg ctggcttaac tatgcggcat cagagcagat tgtactgaga gtgcaaatac   3900
acatcatcgt cctacaagtt catcaaagtg ttggacagac aactatacca gcatggatct   3960
cttgtatcgg ttcttttctc ccgctctctc gcaataacaa tgaacactgg gtcaatcata   4020
```

```
gcctacacag gtgaacagag tagcgtttat acagggttta tacggtgatt cctacggcaa    4080
aaatttttca tttctaaaaa aaaaagaaa aattttcttt tccaacgcta gaaggaaaag     4140
aaaaatctaa ttaaattgat ttggtgattt tctgagagtt cccttttca tatatcgaat     4200 tttgaatata aaggagatc gaaaaattt ttctattcaa tctgttttct ggttttattt      4260
gatagttttt ttgtgtatta ttattatgga ttagtactgg tttatatggg tttttctgta   4320
taacttcttt ttattttagt ttgtttaatc ttattttgag ttacattata gttccctaac   4380
tgcaagagaa gtaacattaa aaatgaccac tcttgacgac acggcttacc ggtaccgcac   4440
cagtgtcccg ggggacgccg aggccatcga ggcactggat gggtccttca ccaccgacac   4500
cgtcttccgc gtcaccgcca ccggggacgg cttcaccctg cgggaggtgc cggtggaccc   4560 gccccctgacc aaggtgttcc ccgacgacga atcggacgac gaatcggacg ccggggagga  4620
cggcgacccg gactcccgga cgttcgtcgc gtacgggac gacggcgacc tggcgggctt    4680
cgtggtcgtc tcgtactccg gctggaaccg ccggctgacc gtcgaggaca tcgaggtcgc   4740
cccggagcac cggggcacg gggtcgggcg cgcgttgatg gggctcgcga cggagttcgc    4800
ccgcgagcgg ggcgccgggc acctctggct ggaggtcacc aacgtcaacg caccggcgat   4860
ccacgcgtac cggcggatgg ggttcaccct ctgcggcctg gacaccgccc tgtacgacgg   4920
caccgcctcg gacggcgagc aggcgctcta catgagcatg ccctgcccct gagtttaact   4980
tgatactact agatttttc tcttcattta taaaattttt ggttataatt gaagctttag    5040
aagtatgaaa aaatccttt ttttcattct ttgcaaccaa aataagaagc ttcttttat     5100 cattgaaatg atgaatataa acctaacaaa agaaaaagac tcgaatatca acattaaaa    5160 aaaaataaaa gaggttatct gttttcccat ttagttggag tttgcatttt ctaatagata   5220
gaactctcaa ttaatgtgga tttagtttct ctgttcgttt tttttgttt tgttctcact    5280 gtatttacat ttctatttag tatttagtta ttcatataat cttaacttgc ggtgtgaaat   5340
accgcacaga tgcgtaagga gaaaataccg catcaggaaa ttgtaagcgt taatattttg   5400
ttaaaattcg cgttaaattt ttgttaaatc agctcatttt ttaaccaata ggccgaaatc   5460
ggcaaaatcc cttataaatc aaaagaatag accgagatag ggttgagtgt tgttccagtt   5520
tggaacaaga gtccactatt aaagaacgtg gactccaacg tcaaagggcg aaaaaccgtc   5580
tatcagggcg atggcccact acgtgaacca tcaccctaat caagttttt ggggtcgagg    5640 tgccgtaaag cactaaatcg gaaccctaaa gggagccccc gatttagagc ttgacgggga   5700
aagcctcttt gaaaagataa tgtatgatta tgctttcact catatttata cagaaacttg   5760
atgttttctt tcgagtatat acaaggtgat tacatgtacg tttgaagtac aactctagat   5820
tttgtagtgc cctcttgggc tagcggtaaa ggtgcgcatt ttttcacacc ctacaatgtt   5880
ctgttcaaaa gattttggtc aaacgctgta gaagtgaaag ttggtgcgca tgtttcggcg   5940
ttcgaaactt ctccgcagtg aaagataaat gatcg                               5975
```

<210> SEQ ID NO 28
<211> LENGTH: 1594
<212> TYPE: DNA
<213> ORGANISM: Artificial Sequence
<220> FEATURE:
<223> OTHER INFORMATION: Synthetic: Vector backbone fragment 1 for 3-piece assembly

<400> SEQUENCE: 28

```
gcaagagaag taacattaaa aatgaccact cttgacgaca cggcttaccg gtaccgcacc      60
agtgtcccgg gggacgccga ggccatcgag gcactggatg ggtccttcac caccgacacc     120
gtcttccgcg tcaccgccac cggggacggc ttcaccctgc gggaggtgcc ggtgacccg      180
cccctgacca aggtgttccc cgacgacgaa tcggacgacg aatcggacgc cggggaggac     240
ggcgacccgg actcccggac gttcgtcgcg tacgggacg acggcgacct ggcgggcttc      300
gtggtcgtct cgtactccgg ctggaaccgc cggctgaccg tcgaggacat cgaggtcgcc     360
ccggagcacc gggggcacgg ggtcgggcgc gcgttgatgg ggctcgcgac ggagttcgcc     420
cgcgagcggg gcgccgggca cctctggctg gaggtcacca acgtcaacgc accggcgatc     480
cacgcgtacc ggcggatggg gttcaccctc tgcggcctgg acaccgccct gtacgacggc     540
accgcctcgg acggcgagca ggcgctctac atgagcatgc cctgccctg agtttaactt      600
gatactacta gatttttct cttcatttat aaaattttg gttataattg aagctttaga       660
agtatgaaaa atccttttt tttcattctt tgcaaccaaa ataagaagct tcttttattc      720
attgaaatga tgaatataaa cctaacaaaa gaaaagact cgaatatcaa acattaaaaa      780
aaaataaaag aggttatctg ttttcccatt tagttggagt ttgcattttc taatagatag     840
aactctcaat taatgtggat ttagtttctc tgttcgtttt tttttgtttt gttctcactg     900
tatttacatt tctatttagt atttagttat tcatataatc ttaacttgcg gtgtgaaata    960
ccgcacagat gcgtaaggag aaaataccgc atcaggaaat tgtaagcgtt aatattttgt   1020
taaaattcgc gttaaatttt tgttaaatca gctcatttt taaccaatag gccgaaatcg    1080
gcaaaatccc ttataaatca aaagaataga ccgagatagg gttgagtgtt gttccagttt   1140
ggaacaagag tccactatta agaacgtgg actccaacgt caaagggcga aaaccgtct    1200
atcagggcga tggcccacta cgtgaaccat caccctaatc aagttttttg gggtcgaggt   1260
gccgtaaagc actaaatcgg aaccctaaag ggagccccg atttagagct tgacggggaa    1320
agcctctttg aaaagataat gtatgattat gctttcactc atatttatac agaaacttga   1380
tgttttcttt cgagtatata caaggtgatt acatgtacgt tgaagtaca actctagatt    1440
ttgtagtgcc ctcttgggct agcggtaaag gtgcgcattt tttcacaccc tacaatgttc   1500
tgttcaaaag attttggtca aacgctgtag aagtgaaagt tggtgcgcat gtttcggcgt    1560
tcgaaacttc tccgcagtga agataaatg atcg                                  1594
```

<210> SEQ ID NO 29
<211> LENGTH: 4428
<212> TYPE: DNA
<213> ORGANISM: Artificial Sequence
<220> FEATURE:
<223> OTHER INFORMATION: Synthetic: Vector backbone fragment 2 for 3-piece assembly

<400> SEQUENCE: 29

```
gttttagagc tagaaatagc aagttaaaat aaggctagtc cgttatcaac ttgaaaaagt      60
ggcaccgagt cggtggtgct ttttttgttt tttatgtctc agcttttgtt ccctttagtg     120
agggttaatt gcgcgcttgg cgtaatcatg gtcatagctg tttcctgtgt gaaattgtta    180
tccgctcaca attccacaca acataggagc cggaagcata aagtgtaaag cctggggtgc     240
ctaatgagtg aggtaactca cattaattgc gttgcgctca ctgcccgctt tccagtcggg    300
aaacctgtcg tgccagctgc attaatgaat cggccaacgc gcggggagag gcggtttgcg    360
```

```
tattgggcgc tcttccgctt cctcgctcac tgactcgctg cgctcggtcg ttcggctgcg    420
gcgagcggta tcagctcact caaaggcggt aatacggtta tccacagaat cagggggataa   480 cgcaggaaag aacatgtgag caaaaggcca gcaaaaggcc aggaaccgta aaaaggccgc    540
gttgctggcg ttttttccata ggctccgccc ccctgacgag catcacaaaa atcgacgctc   600
aagtcagagg tggcgaaacc cgacaggact ataaagatac caggcgtttc ccctggaag    660 ctccctcgtg cgctctcctg ttccgaccct gccgcttacc ggatacctgt ccgccttttct  720 cccttcggga agcgtggcgc tttctcatag ctcacgctgt aggtatctca gttcggtgta   780
ggtcgttcgc tccaagctgg gctgtgtgca cgaaccccc gttcagcccg accgctgcgc    840
cttatccggt aactatcgtc ttgagtccaa cccggtaaga cacgacttat cgccactggc   900
agcagccact ggtaacagga ttagcagagc gaggtatgta ggcggtgcta cagagttctt   960
gaagtggtgg cctaactacg gctacactag aaggacagta tttggtatct gcgctctgct   1020
gaagccagtt accttcggaa aaagagttgg tagctcttga tccggcaaac aaaccaccgc   1080
tggtagcggt ggtttttttg tttgcaagca gcagattacg cgcagaaaaa aaggatctca   1140
agaagatcct ttgatctttt ctacggggtc tgacgctcag tggaacgaaa actcacgtta   1200
agggattttg gtcatgagat tatcaaaaag gatcttcacc tagatccttt taaattaaaa   1260
atgaagtttt aaatcaatct aaagtatata tgagtaaact tggtctgaca gttaccaatg   1320
cttaatcagt gaggcaccta tctcagcgat ctgtctattt cgttcatcca tagttgcctg   1380
actccccgtc gtgtagataa ctacgatacg ggagggctta ccatctggcc ccagtgctgc   1440
aatgataccg cgagacccac gctcaccggc tccagattta tcagcaataa accagccagc   1500
cggaagggcc gagcgcagaa gtggtcctgc aactttatcc gcctccatcc agtctattaa   1560
ttgttgccgg gaagctagag taagtagttc gccagttaat agtttgcgca acgttgttgc   1620
cattgctaca ggcatcgtgg tgtcacgctc gtcgtttggt atggcttcat tcagctccgg   1680
ttcccaacga tcaaggcgag ttacatgatc ccccatgttg tgcaaaaaag cggttagctc   1740
cttcggtcct ccgatcgttg tcagaagtaa gttggccgca gtgttatcac tcatggttat   1800
ggcagcactg cataattctc ttactgtcat gccatccgta agatgctttt ctgtgactgg   1860
tgagtactca accaagtcat tctgagaata gtgtatgcgg cgaccgagtt gctcttgccc   1920
ggcgtcaata cgggataata ccgcgccaca tagcagaact ttaaaagtgc tcatcattgg   1980
aaaacgttct cggggcgaaa actctcaag gatcttaccg ctgttgagat ccagttcgat    2040
gtaacccact cgtgcaccca actgatcttc agcatctttt actttcacca gcgtttctgg   2100
gtgagcaaaa acaggaaggc aaaatgccgc aaaaaaggga taagggcga cacggaaatg    2160 ttgaatactc atactcttcc tttttcaata ttattgaagc atttatcagg gttattgtct   2220
catgagcgga tacatatttg aatgtattta gaaaaataaa caaatagggg ttccgcgcac   2280
atttccccga aaagtgccac ctgaacgaag catctgtgct tcattttgta gaacaaaaat   2340
gcaacgcgag agcgctaatt tttcaaacaa agaatctgag ctgcatttttt acagaacaga   2400 aatgcaacgc gaaagcgcta ttttaccaac gaagaatctg tgcttcattt ttgtaaaaca   2460
aaaatgcaac gcgagagcgc taattttttca aacaagaat ctgagctgca ttttacagaa   2520
acagaaatgc aacgcgagag cgctatttta ccaacaaaga atctatactt ctttttttgtt   2580 ctacaaaaat gcatcccgag agcgctattt ttctaacaaa gcatcttaga ttacttttttt   2640 tctcctttgt gcgctctata atgcagtctc ttgataactt tttgcactgt aggtccgtta   2700
aggttagaag aaggctactt tggtgtctat tttctcttcc ataaaaaaag cctgactcca   2760
```

```
cttcccgcgt ttactgatta ctagcgaagc tgcgggtgca ttttttcaag ataaaggcat    2820
ccccgattat attctatacc gatgtggatt gcgcatactt tgtgaacaga aagtgatagc    2880
gttgatgatt cttcattggt cagaaaatta tgaacggttt cttctatttt gtctctatat    2940
actacgtata ggaaatgttt acattttcgt attgttttcg attcactcta tgaatagttc    3000
ttactacaat ttttttgtct aaagagtaat actagagata aacataaaaa atgtagaggt    3060
cgagtttaga tgcaagttca aggagcgaaa ggtggatggg taggttatat agggatatag    3120
cacagagata tatagcaaag agatactttt gagcaatgtt tgtggaagcg gtattcgcaa    3180
tattttagta gctcgttaca gtccggtgcg ttttggttt tttgaaagtg cgtcttcaga     3240
gcgcttttgg ttttcaaaag cgctctgaag ttcctatact ttctagagaa taggaacttc    3300
ggaataggaa cttcaaagcg tttccgaaaa cgagcgcttc cgaaaatgca acgcgagctg    3360
cgcacataca gctcactgtt cacgtcgcac ctatatctgc gtgttgcctg tatatatata    3420
tacatgagaa gaacggcata gtgcgtgttt atgcttaaat gcgtacttat atgcgtctat    3480
ttatgtagga tgaaaggtag tctagtacct cctgtgatat tatcccattc catgcggggt    3540
atcgtatgct tccttcagca ctacccttta gctgttctat atgctgccac tcctcaattg    3600
gattagtctc atccttcaat gctatcattt cctttgatat tggatcatat taagaaacca    3660
ttattatcat gacattaacc tataaaaata ggcgtatcac gaggcccttt cgtctcgcgc    3720 gttttcggtga tgacggtgaa aacctctgac acatgcagct cccggagacg gtcacagctt   3780
gtctgtaagc ggatgccggg agcagacaag cccgtcaggg cgcgtcagcg ggtgttggcg    3840
ggtgtcgggg ctggcttaac tatgcggcat cagagcagat tgtactgaga gtgcaaatac    3900
acatcatcgt cctacaagtt catcaaagtg ttggacagac aactatacca gcatggatct    3960
cttgtatcgg ttcttttctc ccgctctctc gcaataacaa tgaacactgg gtcaatcata    4020
gcctacacag gtgaacagag tagcgtttat acagggttta tacggtgatt cctacggcaa    4080
aaatttttca tttctaaaaa aaaaagaaa aatttttctt tccaacgcta gaaggaaaag     4140
aaaaatctaa ttaaattgat ttggtgattt tctgagagtt ccctttttca tatatcgaat    4200
tttgaatata aaaggagatc gaaaaaattt ttctattcaa tctgtttct ggttttattt     4260 gatagttttt ttgtgtatta ttattatgga ttagtactgg tttatatggg ttttttctgta   4320 taacttcttt ttattttagt ttgttttaatc ttatttttgag ttacattata gttccctaac  4380
tgcaagagaa gtaacattaa aaatgaccac tcttgacgac acggctta                 4428
```

<210> SEQ ID NO 30
<211> LENGTH: 19
<212> TYPE: DNA
<213> ORGANISM: Artificial Sequence
<220> FEATURE:
<223> OTHER INFORMATION: Synthetic: Gal80 genomic target sequence

<400> SEQUENCE: 30
taaggctgct gctgaacgt                                                  19

<210> SEQ ID NO 31
<211> LENGTH: 19
<212> TYPE: DNA
<213> ORGANISM: Artificial Sequence
<220> FEATURE:
<223> OTHER INFORMATION: Synthetic: HO genomic target sequence

<400> SEQUENCE: 31
ccggcttgat cgactcaga                                                  19

```
<210> SEQ ID NO 32
<211> LENGTH: 19
<212> TYPE: DNA
<213> ORGANISM: Artificial Sequence
<220> FEATURE:
<223> OTHER INFORMATION: Synthetic: ADH5 genomic target sequence

<400> SEQUENCE: 32
gggtcattgg tatcgatgg                                              19

<210> SEQ ID NO 33
<211> LENGTH: 38
<212> TYPE: DNA
<213> ORGANISM: Artificial Sequence
<220> FEATURE:
<223> OTHER INFORMATION: Synthetic: Gal80 upstream primer

<400> SEQUENCE: 33
caaacggccg cctctgccat ggcaaagaat gctttcca                         38

<210> SEQ ID NO 34
<211> LENGTH: 38
<212> TYPE: DNA
<213> ORGANISM: Artificial Sequence
<220> FEATURE:
<223> OTHER INFORMATION: Synthetic: HO upstream primer

<400> SEQUENCE: 34
acgtgtgtgt ctcatggaaa ttgatgcagt tgaagaca                         38

<210> SEQ ID NO 35
<211> LENGTH: 33
<212> TYPE: DNA
<213> ORGANISM: Artificial Sequence
<220> FEATURE:
<223> OTHER INFORMATION: Synthetic: ADH5 upstream primer

<400> SEQUENCE: 35
ggcgttatat ccaaacattt cagacagaag att                              33

<210> SEQ ID NO 36
<211> LENGTH: 24
<212> TYPE: DNA
<213> ORGANISM: Artificial Sequence
<220> FEATURE:
<223> OTHER INFORMATION: Synthetic: Primer for deletion linker

<400> SEQUENCE: 36
aggtccgccg gcgttggacg agcg                                        24

<210> SEQ ID NO 37
<211> LENGTH: 22
<212> TYPE: DNA
<213> ORGANISM: Artificial Sequence
<220> FEATURE:
<223> OTHER INFORMATION: Synthetic: TRS31 upstream primer

<400> SEQUENCE: 37
gtgcatttgg ctcgagttgc tg                                          22

<210> SEQ ID NO 38
<211> LENGTH: 35
<212> TYPE: DNA
<213> ORGANISM: Artificial Sequence
<220> FEATURE:
<223> OTHER INFORMATION: Synthetic: TRS31 downstream primer
```

<400> SEQUENCE: 38
gggaagttat ctactatcat atattcattg tcacg                         35

<210> SEQ ID NO 39
<211> LENGTH: 31
<212> TYPE: DNA
<213> ORGANISM: Artificial Sequence
<220> FEATURE:
<223> OTHER INFORMATION: Synthetic: TRS31 heterology block primer

<400> SEQUENCE: 39
gaaaagtaga gattcagaat agatccttga c                             31

<210> SEQ ID NO 40
<211> LENGTH: 26
<212> TYPE: DNA
<213> ORGANISM: Artificial Sequence
<220> FEATURE:
<223> OTHER INFORMATION: Synthetic: CUE5 upstream primer

<400> SEQUENCE: 40
ggaaggtatc aaggattctt ctctcc                                   26

<210> SEQ ID NO 41
<211> LENGTH: 25
<212> TYPE: DNA
<213> ORGANISM: Artificial Sequence
<220> FEATURE:
<223> OTHER INFORMATION: Synthetic: CUE5 downstream primer

<400> SEQUENCE: 41
gaggtggcac atcttcatca tcttc                                    25

<210> SEQ ID NO 42
<211> LENGTH: 26
<212> TYPE: DNA
<213> ORGANISM: Artificial Sequence
<220> FEATURE:
<223> OTHER INFORMATION: Synthetic: CUE5 heterology block primer

<400> SEQUENCE: 42
ccaataactc atcctgctcc aattgt                                   26

<210> SEQ ID NO 43
<211> LENGTH: 22
<212> TYPE: DNA
<213> ORGANISM: Artificial Sequence
<220> FEATURE:
<223> OTHER INFORMATION: Synthetic: ECM38 upstream primer

<400> SEQUENCE: 43
cagacgctgc agtaacacaa gc                                       22

<210> SEQ ID NO 44
<211> LENGTH: 21
<212> TYPE: DNA
<213> ORGANISM: Artificial Sequence
<220> FEATURE:
<223> OTHER INFORMATION: Synthetic: ECM38 downstream primer

<400> SEQUENCE: 44
ctgaagtggg cagttccatg c                                        21

```
<210> SEQ ID NO 45
<211> LENGTH: 24
<212> TYPE: DNA
<213> ORGANISM: Artificial Sequence
<220> FEATURE:
<223> OTHER INFORMATION: Synthetic: ECM38 heterology block primer

<400> SEQUENCE: 45
cagtgatctg gatcgtagaa gggc                                          24

<210> SEQ ID NO 46
<211> LENGTH: 20
<212> TYPE: DNA
<213> ORGANISM: Artificial Sequence
<220> FEATURE:
<223> OTHER INFORMATION: Synthetic: PGD-1 upstream primer

<400> SEQUENCE: 46
ccaagagcat gccacggttg                                               20

<210> SEQ ID NO 47
<211> LENGTH: 21
<212> TYPE: DNA
<213> ORGANISM: Artificial Sequence
<220> FEATURE:
<223> OTHER INFORMATION: Synthetic: PGD-1  downstream primer

<400> SEQUENCE: 47
gagttcccat agtactaccg c                                             21

<210> SEQ ID NO 48
<211> LENGTH: 22
<212> TYPE: DNA
<213> ORGANISM: Artificial Sequence
<220> FEATURE:
<223> OTHER INFORMATION: Synthetic: PGD-1  heterology block primer

<400> SEQUENCE: 48
gcagacctta tctcttgtct cg                                            22

<210> SEQ ID NO 49
<211> LENGTH: 22
<212> TYPE: DNA
<213> ORGANISM: Artificial Sequence
<220> FEATURE:
<223> OTHER INFORMATION: Synthetic: SMC6 upstream primer

<400> SEQUENCE: 49
gagctacttt cactgactgc gc                                            22

<210> SEQ ID NO 50
<211> LENGTH: 27
<212> TYPE: DNA
<213> ORGANISM: Artificial Sequence
<220> FEATURE:
<223> OTHER INFORMATION: Synthetic: SMC6 downstream primer

<400> SEQUENCE: 50
gcgcttcaat agtagtacca tcagatg                                       27

<210> SEQ ID NO 51
<211> LENGTH: 25
<212> TYPE: DNA
<213> ORGANISM: Artificial Sequence
<220> FEATURE:
<223> OTHER INFORMATION: Synthetic: SMC6 heterology block primer
```

```
<400> SEQUENCE: 51
gccgttctct gatctcaaag agaat                                              25

<210> SEQ ID NO 52
<211> LENGTH: 27
<212> TYPE: DNA
<213> ORGANISM: Artificial Sequence
<220> FEATURE:
<223> OTHER INFORMATION: Synthetic: NTO1  upstream primer

<400> SEQUENCE: 52
ctcagtatga catggatgaa caggatg                                            27

<210> SEQ ID NO 53
<211> LENGTH: 25
<212> TYPE: DNA
<213> ORGANISM: Artificial Sequence
<220> FEATURE:
<223> OTHER INFORMATION: Synthetic: NTO1 downstream primer

<400> SEQUENCE: 53
ggtacctcct gtaagctccc ttttc                                              25

<210> SEQ ID NO 54
<211> LENGTH: 24
<212> TYPE: DNA
<213> ORGANISM: Artificial Sequence
<220> FEATURE:
<223> OTHER INFORMATION: Synthetic: NTO1 heterology block primer

<400> SEQUENCE: 54
gactgagacg ttctggactc cttc                                               24

<210> SEQ ID NO 55
<211> LENGTH: 23
<212> TYPE: DNA
<213> ORGANISM: Artificial Sequence
<220> FEATURE:
<223> OTHER INFORMATION: Synthetic: DGA1 upstream primer

<400> SEQUENCE: 55
cttaaccaag cacgacagtg gtc                                                23

<210> SEQ ID NO 56
<211> LENGTH: 20
<212> TYPE: DNA
<213> ORGANISM: Artificial Sequence
<220> FEATURE:
<223> OTHER INFORMATION: Synthetic: DGA1 downstream primer

<400> SEQUENCE: 56
gattccctag cgccaccaac                                                    20

<210> SEQ ID NO 57
<211> LENGTH: 23
<212> TYPE: DNA
<213> ORGANISM: Artificial Sequence
<220> FEATURE:
<223> OTHER INFORMATION: Synthetic: DGA1 heterology block primer

<400> SEQUENCE: 57
cctctccggt ggctggtgat ctg                                                23
```

```
<210> SEQ ID NO 58
<211> LENGTH: 25
<212> TYPE: DNA
<213> ORGANISM: Artificial Sequence
<220> FEATURE:
<223> OTHER INFORMATION: Synthetic: ADH2 upstream primer

<400> SEQUENCE: 58
cgagactgat ctcctctgcc ggaac                                    25

<210> SEQ ID NO 59
<211> LENGTH: 22
<212> TYPE: DNA
<213> ORGANISM: Artificial Sequence
<220> FEATURE:
<223> OTHER INFORMATION: Synthetic: ADH2 downstream primer

<400> SEQUENCE: 59
gaatacttca ccaccgagcg ag                                       22

<210> SEQ ID NO 60
<211> LENGTH: 28
<212> TYPE: DNA
<213> ORGANISM: Artificial Sequence
<220> FEATURE:
<223> OTHER INFORMATION: Synthetic: ADH2 heterology block primer

<400> SEQUENCE: 60
gcatgtaagt ctgtatgaca tactcctg                                 28

<210> SEQ ID NO 61
<211> LENGTH: 26
<212> TYPE: DNA
<213> ORGANISM: Artificial Sequence
<220> FEATURE:
<223> OTHER INFORMATION: Synthetic: SIN4 upstream primer

<400> SEQUENCE: 61
caaacgtcct aaatgaccca tcgttg                                   26

<210> SEQ ID NO 62
<211> LENGTH: 26
<212> TYPE: DNA
<213> ORGANISM: Artificial Sequence
<220> FEATURE:
<223> OTHER INFORMATION: Synthetic: SIN4 downstream primer

<400> SEQUENCE: 62
caacttcggg ttttgttgtt ggttag                                   26

<210> SEQ ID NO 63
<211> LENGTH: 28
<212> TYPE: DNA
<213> ORGANISM: Artificial Sequence
<220> FEATURE:
<223> OTHER INFORMATION: Synthetic: SIN4 heterology block primer

<400> SEQUENCE: 63
caatggcaat ttaccgtagt tgaaaccg                                 28

<210> SEQ ID NO 64
<211> LENGTH: 25
<212> TYPE: DNA
<213> ORGANISM: Artificial Sequence
<220> FEATURE:
<223> OTHER INFORMATION: Synthetic: CYS4 upstream primer
```

<400> SEQUENCE: 64
ctccagaatc acatattggt gttgc                                    25

<210> SEQ ID NO 65
<211> LENGTH: 29
<212> TYPE: DNA
<213> ORGANISM: Artificial Sequence
<220> FEATURE:
<223> OTHER INFORMATION: Synthetic: CYS4 downstream primer

<400> SEQUENCE: 65
ccatcttagt aacgatatgg attggtttc                                29

<210> SEQ ID NO 66
<211> LENGTH: 23
<212> TYPE: DNA
<213> ORGANISM: Artificial Sequence
<220> FEATURE:
<223> OTHER INFORMATION: Synthetic: CYS4 heterology block primer

<400> SEQUENCE: 66
ctgatggagt caggaaagat ggc                                      23

<210> SEQ ID NO 67
<211> LENGTH: 100
<212> TYPE: DNA
<213> ORGANISM: Artificial Sequence
<220> FEATURE:
<223> OTHER INFORMATION: Synthetic: TRS31 donor DNA

<400> SEQUENCE: 67
aagcaagcga taacaagcga agcttcaaca acatacattc cgtcaaggat ctattctgaa    60
tctctacttt tcaaaaggca agaagcgtct ttatcagcaa                        100

<210> SEQ ID NO 68
<211> LENGTH: 22
<212> TYPE: DNA
<213> ORGANISM: Artificial Sequence
<220> FEATURE:
<223> OTHER INFORMATION: Synthetic: TRS31 locus target sequence

<400> SEQUENCE: 68
gactttgagt atattctaga gg                                       22

<210> SEQ ID NO 69
<211> LENGTH: 1080
<212> TYPE: DNA
<213> ORGANISM: Artificial Sequence
<220> FEATURE:
<223> OTHER INFORMATION: Synthetic: TRS31 gRNA construct

<400> SEQUENCE: 69
gacggcacgg ccacgcgttt aaaccgcctt ataaatcaaa agaatagacc gagatagggt    60
tgagtgttgt tccagtttgg aacaagagtc cactattaaa gaacgtggac tccaacgtca   120
aagggcgaaa aaccgtctat cagggcgatg cccactacg tgaaccatca ccctaatcaa   180
gttttttggg gtcgaggtgc cgtaaagcac taaatcggaa ccctaaaggg agcccccgat   240
ttagagcttg acggggaaag cctctttgaa aagataatgt atgattatgc tttcactcat   300
atttatacag aaacttgatg ttttctttcg agtatataca aggtgattac atgtacgttt   360
gaagtacaac tctagatttt gtagtgccct cttgggctag cggtaaaggt gcgcattttt   420
tcacacccta caatgttctg ttcaaaagat tttggtcaaa cgctgtagaa gtgaaagttg   480

```
gtgcgcatgt tcggcgttc gaaacttctc cgcagtgaaa gataaatgat cggactttga    540
gtatattcta ggttttagag ctagaaatag caagttaaaa taaggctagt ccgttatcaa    600
cttgaaaaag tggcaccgag tcggtggtgc ttttttgtt tttatgtct cagcttttgt    660 tccctttagt gagggttaat tgcgcgcttg gcgtaatcat ggtcatagct gtttcctgtg    720
tgaaattgtt atccgctcac aattccacac aacataggag ccggaagcat aaagtgtaaa    780
gcctggggtg cctaatgagt gaggtaactc acattaattg cgttgcgctc actgcccgct    840
ttccagtcgg gaaacctgtc gtgccagctg cattaatgaa tcggccaacg cgcggggaga    900
ggcggtttgc gtattgggcg ctcttccgct tcctcgctca ctgactcgct gcgctcggtc    960
gttcggctgc ggcgagcggt atcagctcac tcaaaggcgg taatacggtt atccacagaa   1020
tcaggggata acgcaggaaa gaacatgtga gccggtgttt aaaccccagc gcctggcggg   1080

<210> SEQ ID NO 70
<211> LENGTH: 100
<212> TYPE: DNA
<213> ORGANISM: Artificial Sequence
<220> FEATURE:
<223> OTHER INFORMATION: Synthetic: CUE5 donor DNA

<400> SEQUENCE: 70
gtaagaaaga acccagaggc gccggcaaga agacgacaaa cacaattgga gcaggatgag     60
ttattggcaa ggcaattaga tgagcaattc aacagctcac                         100

<210> SEQ ID NO 71
<211> LENGTH: 22
<212> TYPE: DNA
<213> ORGANISM: Artificial Sequence
<220> FEATURE:
<223> OTHER INFORMATION: Synthetic: CUE5 locus target sequence

<400> SEQUENCE: 71
aagtttgtcg tcttcttgcc gg                                             22

<210> SEQ ID NO 72
<211> LENGTH: 1080
<212> TYPE: DNA
<213> ORGANISM: Artificial Sequence
<220> FEATURE:
<223> OTHER INFORMATION: Synthetic: CUE5 gRNA construct

<400> SEQUENCE: 72
gacggcacgg ccacgcgttt aaaccgcctt ataaatcaaa agaatagacc gagatagggt     60
tgagtgttgt tccagtttgg aacaagagtc cactattaaa gaacgtggac tccaacgtca    120
aagggcgaaa aaccgtctat cagggcgatg gcccactacg tgaaccatca ccctaatcaa    180
gttttttggg gtcgaggtgc cgtaaagcac taaatcggaa ccctaaaggg agcccccgat    240
ttagagcttg acggggaaag cctctttgaa aagataatgt atgattatgc tttcactcat    300
atttatacag aaacttgatg ttttctttcg agtatataca aggtgattac atgtacgttt    360
gaagtacaac tctagatttt gtagtgccct cttgggctag cggtaaaggt gcgcattttt    420
tcacacccta caatgttctg ttcaaaagat tttggtcaaa cgctgtagaa gtgaaagttg    480
gtgcgcatgt ttcggcgttc gaaacttctc cgcagtgaaa gataaatgat cgaagtttgt    540
cgtcttcttg cgttttagag ctagaaatag caagttaaaa taaggctagt ccgttatcaa    600
cttgaaaaag tggcaccgag tcggtggtgc ttttttgtt tttatgtct cagcttttgt    660 tccctttagt gagggttaat tgcgcgcttg gcgtaatcat ggtcatagct gtttcctgtg    720
```

```
tgaaattgtt atccgctcac aattccacac aacataggag ccggaagcat aaagtgtaaa    780
gcctggggtg cctaatgagt gaggtaactc acattaattg cgttgcgctc actgcccgct    840
ttccagtcgg gaaacctgtc gtgccagctg cattaatgaa tcggccaacg cgcggggaga    900
ggcggtttgc gtattgggcg ctcttccgct tcctcgctca ctgactcgct gcgctcggtc    960
gttcggctgc ggcgagcggt atcagctcac tcaaaggcgg taatacggtt atccacagaa   1020
tcaggggata acgcaggaaa gaacatgtga gccggtgttt aaaccccagc gcctggcggg   1080
```

<210> SEQ ID NO 73
<211> LENGTH: 100
<212> TYPE: DNA
<213> ORGANISM: Artificial Sequence
<220> FEATURE:
<223> OTHER INFORMATION: Synthetic: ECM38 donor DNA

<400> SEQUENCE: 73

```
tctaacatgc taatggaact ggctaaaaat ggttccgtgg cgcccttcta cgatccagat     60
cactggattg caaaatccat gattgatact gtcgcaaaat                          100
```

<210> SEQ ID NO 74
<211> LENGTH: 22
<212> TYPE: DNA
<213> ORGANISM: Artificial Sequence
<220> FEATURE:
<223> OTHER INFORMATION: Synthetic: ECM38 locus target sequence

<400> SEQUENCE: 74

```
tgatcgaggt cataaaatgg gg                                              22
```

<210> SEQ ID NO 75
<211> LENGTH: 1080
<212> TYPE: DNA
<213> ORGANISM: Artificial Sequence
<220> FEATURE:
<223> OTHER INFORMATION: Synthetic: ECM38 gRNA construct

<400> SEQUENCE: 75

```
gacggcacgg ccacgcgttt aaaccgcctt ataaatcaaa agaatagacc gagatagggt     60
tgagtgttgt tccagtttgg aacaagagtc cactattaaa gaacgtggac tccaacgtca    120
aagggcgaaa aaccgtctat cagggcgatg gcccactacg tgaaccatca ccctaatcaa    180
gttttttggg gtcgaggtgc cgtaaagcac taaatcggaa ccctaaaggg agcccccgat    240
ttagagcttg acggggaaag cctctttgaa aagataatgt atgattatgc tttcactcat    300
atttatacag aaacttgatg tttctttcg agtatataca aggtgattac atgtacgttt    360
gaagtacaac tctagatttt gtagtgccct cttgggctag cggtaaaggt gcgcattttt    420
tcacacccta caatgttctg ttcaaaagat tttggtcaaa cgctgtagaa gtgaaagttg    480
gtgcgcatgt ttcggcgttc gaaacttctc cgcagtgaaa gataaatgat cgtgatcgag    540
gtcataaaat ggttttagag ctagaaatag caagttaaaa taaggctagt ccgttatcaa    600
cttgaaaaag tggcaccgag tcggtggtgc ttttttttgtt ttttatgtct cagcttttgt    660 tcccttttagt gagggttaat tgcgcgcttg gcgtaatcat ggtcatagct gtttcctgtg    720
tgaaattgtt atccgctcac aattccacac aacataggag ccggaagcat aaagtgtaaa    780
gcctggggtg cctaatgagt gaggtaactc acattaattg cgttgcgctc actgcccgct    840
ttccagtcgg gaaacctgtc gtgccagctg cattaatgaa tcggccaacg cgcggggaga    900
```

```
ggcggtttgc gtattgggcg ctcttccgct tcctcgctca ctgactcgct gcgctcggtc    960
gttcggctgc ggcgagcggt atcagctcac tcaaaggcgg taatacggtt atccacagaa   1020 tcagggagata acgcaggaaa gaacatgtga gccggtgttt aaaccccagc gcctggcggg  1080
```

```
<210> SEQ ID NO 76
<211> LENGTH: 100
<212> TYPE: DNA
<213> ORGANISM: Artificial Sequence
<220> FEATURE:
<223> OTHER INFORMATION: Synthetic: PGD-1 donor DNA

<400> SEQUENCE: 76
ggcgtcaagc tagatgattt acaagtgata ttggctaaaa atgaaaacga gacaagagat     60
aaggtctgca agcagatcaa cgaagcacgc gatgaaattc                          100
```

```
<210> SEQ ID NO 77
<211> LENGTH: 22
<212> TYPE: DNA
<213> ORGANISM: Artificial Sequence
<220> FEATURE:
<223> OTHER INFORMATION: Synthetic: PGD-1 locus target sequence

<400> SEQUENCE: 77
aagaacgaga atgaaaccag gg                                              22
```

```
<210> SEQ ID NO 78
<211> LENGTH: 1080
<212> TYPE: DNA
<213> ORGANISM: Artificial Sequence
<220> FEATURE:
<223> OTHER INFORMATION: Synthetic: PGD-1 gRNA construct

<400> SEQUENCE: 78
gacggcacgg ccacgcgttt aaaccgcctt ataaatcaaa agaatagacc gagataggt      60 tgagtgttgt tccagtttgg aacaagagtc cactattaaa gaacgtggac tccaacgtca   120
aagggcgaaa aaccgtctat cagggcgatg gcccactacg tgaaccatca ccctaatcaa   180
gttttttggg gtcgaggtgc cgtaaagcac taaatcggaa ccctaaaggg agcccccgat   240
ttagagcttg acggggaaag cctctttgaa aagataatgt atgattatgc tttcactcat   300
atttatacag aaacttgatg ttttctttcg agtatataca aggtgattac atgtacgttt   360
gaagtacaac tctagatttt gtagtgccct cttgggctag cggtaaaggt gcgcattttt   420
tcacacccta caatgttctg ttcaaaagat tttggtcaaa cgctgtagaa gtgaagttg    480 gtgcgcatgt ttcggcgttc gaaacttctc cgcagtgaaa gataaatgat cgaagaacga   540
gaatgaaacc agttttagag ctagaaatag caagttaaaa taaggctagt ccgttatcaa   600
cttgaaaaag tggcaccgag tcggtggtgc ttttttttgtt ttttatgtct cagcttttgt   660 tcccttagt gagggttaat tgcgcgcttg gcgtaatcat ggtcatagct gtttcctgtg   720
tgaaattgtt atccgctcac aattccacac aacataggag ccggaagcat aaagtgtaaa   780
gcctggggtg cctaatgagt gagtaactc acattaattg cgttgcgctc actgcccgct   840
ttccagtcgg gaaacctgtc gtgccagctg cattaatgaa tcggccaacg cgcggggaga   900
ggcggtttgc gtattgggcg ctcttccgct tcctcgctca ctgactcgct gcgctcggtc   960
gttcggctgc ggcgagcggt atcagctcac tcaaaggcgg taatacggtt atccacagaa  1020 tcagggagata acgcaggaaa gaacatgtga gccggtgttt aaaccccagc gcctggcggg 1080
```

<210> SEQ ID NO 79
<211> LENGTH: 100
<212> TYPE: DNA
<213> ORGANISM: Artificial Sequence
<220> FEATURE:
<223> OTHER INFORMATION: Synthetic: SMC6 donor DNA

<400> SEQUENCE: 79

| cgaaattata gtagaaagga taattaagag agatgggccc gcttcattct ctttgagatc | 60 |
| agagaacggc aaggaaatta gcaataagaa aaaggatatt | 100 |

<210> SEQ ID NO 80
<211> LENGTH: 22
<212> TYPE: DNA
<213> ORGANISM: Artificial Sequence
<220> FEATURE:
<223> OTHER INFORMATION: Synthetic: SMC6 locus target sequence

<400> SEQUENCE: 80

| gcttctttta gattaaggtc gg | 22 |

<210> SEQ ID NO 81
<211> LENGTH: 1080
<212> TYPE: DNA
<213> ORGANISM: Artificial Sequence
<220> FEATURE:
<223> OTHER INFORMATION: Synthetic: SMC6 gRNA construct

<400> SEQUENCE: 81

| gacggcacgg ccacgcgttt aaaccgcctt ataaatcaaa agaatagacc gagatagggt | 60 |
| tgagtgttgt tccagtttgg aacaagagtc cactattaaa gaacgtggac tccaacgtca | 120 |
| aagggcgaaa aaccgtctat cagggcgatg gcccactacg tgaaccatca ccctaatcaa | 180 |
| gttttttggg gtcgaggtgc cgtaaagcac taaatcggaa ccctaaaggg agcccccgat | 240 |
| ttagagcttg acggggaaag cctctttgaa aagataatgt atgattatgc tttcactcat | 300 |
| atttatacag aaacttgatg ttttctttcg agtatataca aggtgattac atgtacgttt | 360 |
| gaagtacaac tctagatttt gtagtgccct cttgggctag cggtaaaggt gcgcattttt | 420 |
| tcacacccta caatgttctg ttcaaaagat tttggtcaaa cgctgtagaa gtgaaagttg | 480 |
| gtgcgcatgt ttcggcgttc gaaacttctc cgcagtgaaa gataaatgat cggcttcttt | 540 |
| tagattaagg tgttttagag ctagaaatag caagttaaaa taaggctagt ccgttatcaa | 600 |
| cttgaaaaag tggcaccgag tcggtggtgc ttttttttgtt ttttatgtct cagcttttgt | 660 |
| tcccttttagt gagggttaat tgcgcgcttg gcgtaatcat ggtcatagct gtttcctgtg | 720 |
| tgaaattgtt atccgctcac aattccacac aacataggag ccggaagcat aaagtgtaaa | 780 |
| gcctggggtg cctaatgagt gaggtaactc acattaattg cgttgcgctc actgcccgct | 840 |
| ttccagtcgg gaaacctgtc gtgccagctg cattaatgaa tcggccaacg cgcgggggaga | 900 |
| ggcggtttgc gtattgggcg ctcttccgct tcctcgctca ctgactcgct gcgctcggtc | 960 |
| gttcggctgc ggcgagcggt atcagctcac tcaaaggcgg taatacggtt atccacagaa | 1020 |
| tcagggggata acgcaggaaa gaacatgtga gccggtgttt aaaccccagc gcctggcggg | 1080 |

<210> SEQ ID NO 82
<211> LENGTH: 99
<212> TYPE: DNA
<213> ORGANISM: Artificial Sequence
<220> FEATURE:
<223> OTHER INFORMATION: Synthetic: NTO1 donor DNA

<400> SEQUENCE: 82

```
atacttttca aacttacatt atatggaacc tatagaagga gtccagaacg tctcagtctc    60
taggtggaaa cttaactgct acatctgtaa aagaagat                            99
```

<210> SEQ ID NO 83
<211> LENGTH: 22
<212> TYPE: DNA
<213> ORGANISM: Artificial Sequence
<220> FEATURE:
<223> OTHER INFORMATION: Synthetic: NT01 locus target sequence

<400> SEQUENCE: 83

```
aaatgttagc gtatcacgat gg                                             22
```

<210> SEQ ID NO 84
<211> LENGTH: 1080
<212> TYPE: DNA
<213> ORGANISM: Artificial Sequence
<220> FEATURE:
<223> OTHER INFORMATION: Synthetic: NT01 gRNA construct

<400> SEQUENCE: 84

```
gacggcacgg ccacgcgttt aaaccgcctt ataaatcaaa agaatagacc gagataggt     60
tgagtgttgt tccagtttgg aacaagagtc cactattaaa gaacgtggac tccaacgtca   120
aagggcgaaa aaccgtctat cagggcgatg gcccactacg tgaaccatca ccctaatcaa   180
gttttttggg gtcgaggtgc cgtaaagcac taaatcggaa ccctaaaggg agcccccgat   240
ttagagcttg acggggaaag cctctttgaa aagataatgt atgattatgc tttcactcat   300
atttatacag aaacttgatg ttttctttcg agtatataca aggtgattac atgtacgttt   360
gaagtacaac tctagatttt gtagtgccct cttgggctag cggtaaaggt gcgcattttt   420
tcacacccta caatgttctg ttcaaaagat tttggtcaaa cgctgtagaa gtgaaagttg   480
gtgcgcatgt ttcggcgttc gaaacttctc cgcagtgaaa gataaatgat cgaaatgtta   540
gcgtatcacg agttttagag ctagaaatag caagttaaaa taaggctagt ccgttatcaa   600
cttgaaaaag tggcaccgag tcggtggtgc tttttttgtt ttttatgtct cagcttttgt   660
tcccttagt gagggttaat tgcgcgcttg gcgtaatcat ggtcatagct gtttcctgtg   720
tgaaattgtt atccgctcac aattccacac aacataggag ccggaagcat aaagtgtaaa   780
gcctggggtg cctaatgagt gaggtaactc acattaattg cgttgcgctc actgcccgct   840
ttccagtcgg gaaacctgtc gtgccagctg cattaatgaa tcggccaacg cgcggggaga   900
ggcggtttgc gtattgggcg ctcttccgct tcctcgctca ctgactcgct gcgctcggtc   960
gttcggctgc ggcgagcggt atcagctcac tcaaaggcgg taatacggtt atccacagaa  1020
tcaggggata acgcaggaaa gaacatgtga gccggtgttt aaaccccagc gcctggcggg  1080
```

<210> SEQ ID NO 85
<211> LENGTH: 99
<212> TYPE: DNA
<213> ORGANISM: Artificial Sequence
<220> FEATURE:
<223> OTHER INFORMATION: Synthetic: DGA1 donor DNA

<400> SEQUENCE: 85

```
gggttcttgc tattccatat atgatttatt ttttttttga cagatcacca gccaccggag    60
aggttgtcaa tcgatactct cttcgatttc gttcattgc                           99
```

```
<210> SEQ ID NO 86
<211> LENGTH: 22
<212> TYPE: DNA
<213> ORGANISM: Artificial Sequence
<220> FEATURE:
<223> OTHER INFORMATION: Synthetic: DGA1 locus target sequence

<400> SEQUENCE: 86
tcgataggtc tcctgcaact gg                                              22

<210> SEQ ID NO 87
<211> LENGTH: 1080
<212> TYPE: DNA
<213> ORGANISM: Artificial Sequence
<220> FEATURE:
<223> OTHER INFORMATION: Synthetic: DGA1 gRNA construct

<400> SEQUENCE: 87
gacggcacgg ccacgcgttt aaaccgcctt ataaatcaaa agaatagacc gagataggt      60 tgagtgttgt tccagtttgg aacaagagtc cactattaaa gaacgtggac tccaacgtca    120
aagggcgaaa aaccgtctat cagggcgatg gcccactacg tgaaccatca ccctaatcaa    180
gttttttggg gtcgaggtgc cgtaaagcac taaatcggaa ccctaaaggg agccccgat    240 ttagagcttg acggggaaag cctctttgaa aagataatgt atgattatgc tttcactcat    300
atttatacag aaacttgatg ttttctttcg agtatataca aggtgattac atgtacgttt    360
gaagtacaac tctagatttt gtagtgccct cttgggctag cggtaaaggt gcgcattttt    420
tcacacccta caatgttctg ttcaaaagat tttggtcaaa cgctgtagaa gtgaaagttg    480
gtgcgcatgt ttcggcgttc gaaacttctc cgcagtgaaa gataaatgat cgtcgatagg    540
tctcctgcaa cgttttagag ctagaaatag caagttaaaa taaggctagt ccgttatcaa    600
cttgaaaaag tggcaccgag tcggtggtgc ttttttttgtt ttttatgtct cagcttttgt    660
tccctttagt gagggttaat tgcgcgcttg gcgtaatcat ggtcatagct gtttcctgtg    720
tgaaattgtt atccgctcac aattccacac aacataggag ccggaagcat aaagtgtaaa    780
gcctggggtg cctaatgagt gaggtaactc acattaattg cgttgcgctc actgcccgct    840
ttccagtcgg gaaacctgtc gtgccagctg cattaatgaa tcggccaacg cgcggggaga    900
ggcggtttgc gtattgggcg ctcttccgct tcctcgctca ctgactcgct gcgctcggtc    960
gttcggctgc ggcgagcggt atcagctcac tcaaaggcgg taatacggtt atccacagaa   1020
tcaggggata acgcaggaaa gaacatgtga gccggtgttt aaacccccagc gcctggcggg   1080

<210> SEQ ID NO 88
<211> LENGTH: 929
<212> TYPE: DNA
<213> ORGANISM: Artificial Sequence
<220> FEATURE:
<223> OTHER INFORMATION: Synthetic: ADH2 donor DNA

<400> SEQUENCE: 88
ccgggcatct ccaacttata agttggagaa ataagagaat ttcagattga gagaatgaaa     60
aaaaaaaaaa aaaaaaggc agaggagagc ataaaaatgg ggttcacttt ttggtaaagc    120
tatagcatgc ctatcacata taaatagagt gccagtagcg acttttttca cactcgaaat    180
actcttacta ctgctctctt gttgttttta tcacttcttg tttcttcttg gtaaatagaa    240
tatcaagcta caaaaagcat acaatcaact atcaactatt aactatatcg taatacacaa    300
tgtctattcc agaaactcaa aaagccatta tcttctacga atccaacggc aagttggagc    360
```

| | |
|---|---|
| ataaggatat cccagttcca aagccaaagc ccaacgaatt gttaatcaac gtcaaatatt | 420 |
| caggagtatg tcatacagac ttacatgcat ggcatggtga ctggccattg ccaactaagt | 480 |
| taccattagt tggtgggcac gaaggtgctg gggtcgttgt tgccatgggt gaaaacgtta | 540 |
| agggctggaa gatcggtgac tacgccggta ttaaatggtt gaacagttca tgtatggcct | 600 |
| gcgaatactg tgaattgggt aacgaatcca actgtcctca cgctgacttg tctggttaca | 660 |
| cccatgacgt ttcttttcca acatacgcta ctgctgacgc ggttcaagcc gctcacattc | 720 |
| ctcaaggtac tgacttggct gaagtcgccc ccatcttgtg tgctggtatc accgtataca | 780 |
| aggctttgaa gtctgccaac ttgagagcag gccactgggt ggccatttct ggtgctgctg | 840 |
| gtggtctagg ttctttggct gttcaatatg ctaaggcgat gggttacaga gtcttaggta | 900 |
| ttgatggtgg tccaggaaag gaagaattg | 929 |

<210> SEQ ID NO 89
<211> LENGTH: 22
<212> TYPE: DNA
<213> ORGANISM: Artificial Sequence
<220> FEATURE:
<223> OTHER INFORMATION: Synthetic: ADH2 locus target sequence

<400> SEQUENCE: 89

| | |
|---|---|
| taatcaacgt caaatacttt gg | 22 |

<210> SEQ ID NO 90
<211> LENGTH: 1080
<212> TYPE: DNA
<213> ORGANISM: Artificial Sequence
<220> FEATURE:
<223> OTHER INFORMATION: Synthetic: ADH2 gRNA construct

<400> SEQUENCE: 90

| | |
|---|---|
| gacggcacgg ccacgcgttt aaaccgcctt ataaatcaaa agaatagacc gagatagggt | 60 |
| tgagtgttgt tccagtttgg aacaagagtc cactattaaa gaacgtggac tccaacgtca | 120 |
| aagggcgaaa aaccgtctat cagggcgatg gcccactacg tgaaccatca ccctaatcaa | 180 |
| gttttttggg gtcgaggtgc cgtaaagcac taaatcggaa ccctaaaggg agcccccgat | 240 |
| ttagagcttg acggggaaag cctctttgaa aagataatgt atgattatgc tttcactcat | 300 |
| atttatacag aaacttgatg ttttctttcg agtatataca aggtgattac atgtacgttt | 360 |
| gaagtacaac tctagatttt gtagtgccct cttgggctag cggtaaaggt gcgcattttt | 420 |
| tcacacccta caatgttctg ttcaaaagat tttggtcaaa cgctgtagaa gtgaaagttg | 480 |
| gtgcgcatgt ttcggcgttc gaacttctc cgcagtgaaa gataaatgat cgtaatcaac | 540 |
| gtcaaatact tgttttagag ctagaaatag caagttaaaa taaggctagt ccgttatcaa | 600 |
| cttgaaaaag tggcaccgag tcggtggtgc tttttttgtt ttttatgtct cagcttttgt | 660 |
| tccctttagt gagggttaat tgcgcgcttg gcgtaatcat ggtcatagct gtttcctgtg | 720 |
| tgaaattgtt atccgctcac aattccacac aacataggag ccggaagcat aaagtgtaaa | 780 |
| gcctggggtg cctaatgagt gaggtaactc acattaattg cgttgcgctc actgcccgct | 840 |
| ttccagtcgg gaaacctgtc gtgccagctg cattaatgaa tcggccaacg cgcggggaga | 900 |
| ggcggtttgc gtattgggcg ctcttccgct tcctcgctca ctgactcgct gcgctcggtc | 960 |
| gttcggctgc ggcgagcggt atcagctcac tcaaaggcgg taatacggtt atccacagaa | 1020 |
| tcaggggata acgcaggaaa gaacatgtga gccggtgttt aaacccccagc gcctggcggg | 1080 |

```
<210> SEQ ID NO 91
<211> LENGTH: 979
<212> TYPE: DNA
<213> ORGANISM: Artificial Sequence
<220> FEATURE:
<223> OTHER INFORMATION: Synthetic: SIN4 donor DNA

<400> SEQUENCE: 91
gcactacttt agatccaacg gatgatgaag ggcatgtgtt gaagttagaa aacctgcatg      60
ttgtgtctaa atcatcaatt gagaaagatc cctccccaga aatttttagtt ttgtataatg    120 tttgcgatac atcaaaatca ttggtgaaaa gatatagact agctccaaca caactttcag    180
ctgagtattt ggtgatattg aaaccagatt taaatatcga tcgaaataat tctacgaatc    240
aaatattcca atcacgccgt tacaaccttc gtcgccacag tgatatcgtt ctcgacaaaa    300
aagtcacctt gataacttct gagatgttcg atggatttgt ttcatttac tttgaagatg     360 gtaccatcga atcctacaat caaaatgatt ggaagttgga gactgaacga cttataggtc    420
agagccaatt aggaaaattc aaaaatatta ttgcatcccc actaagcgcc ggtttcaact    480
acggtaaatt gccattgcca ccatcggttg agtggatgaa ggtttcacca tctatgtgtg    540
gggttatcgt taaacagtat aataaaaaat ggccacagtt ttatgctgct gttcaaaaaa    600
actacgcaga tcctgagaag gattctataa atgctacagc tttggcattt ggatacgtga    660
aaagtttaca taagcaaata tctgccgaag acttgaccat cgctgcgaag acgcacatac    720
tcagaatttc attcttggat agaaaaaggg ccaaagaatt tattacgact ttgttgaaaa    780
gcctatactc gttttcaac atttctcctg atgcgcctaa agagattatg gataaaataa    840
taacaagtag gccacttcaa aaaattatgc tattgcagct ggaacttggc agttgttttt    900
cgcaagaaaa tattgaagaa atggcgagag ttatactcta cttgaaaaat gttttgtttg    960
cgttcaatgg cgtggcgag                                                 979

<210> SEQ ID NO 92
<211> LENGTH: 22
<212> TYPE: DNA
<213> ORGANISM: Artificial Sequence
<220> FEATURE:
<223> OTHER INFORMATION: Synthetic: SIN4 locus target sequence

<400> SEQUENCE: 92
actcaaccga tggaggtaaa gg                                              22

<210> SEQ ID NO 93
<211> LENGTH: 1080
<212> TYPE: DNA
<213> ORGANISM: Artificial Sequence
<220> FEATURE:
<223> OTHER INFORMATION: Synthetic: SIN4 gRNA construct

<400> SEQUENCE: 93
gacggcacgg ccacgcgttt aaaccgcctt ataaatcaaa agaatagacc gagatagggt     60
tgagtgttgt tccagtttgg aacaagagtc cactattaaa gaacgtggac tccaacgtca    120
aagggcgaaa aaccgtctat cagggcgatg gcccactacg tgaaccatca ccctaatcaa    180
gttttttggg gtcgaggtgc cgtaaagcac taaatcggaa ccctaaaggg agcccccgat    240
ttagagcttg acggggaaag cctctttgaa aagataatgt atgattatgc tttcactcat    300
atttatacag aaacttgatg ttttctttcg agtatataca aggtgattac atgtacgttt    360
gaagtacaac tctagatttt gtagtgccct cttgggctag cggtaaaggt gcgcattttt    420
```

| | |
|---|---|
| tcacaccta caatgttctg ttcaaaagat tttggtcaaa cgctgtagaa gtgaaagttg | 480 |
| gtgcgcatgt ttcggcgttc gaaacttctc cgcagtgaaa gataaatgat cgactcaacc | 540 |
| gatggaggta agttttagag ctagaaatag caagttaaaa taaggctagt ccgttatcaa | 600 |
| cttgaaaaag tggcaccgag tcggtggtgc ttttttttgtt ttttatgtct cagcttttgt | 660 |
| tcccttttagt gagggttaat tgcgcgcttg gcgtaatcat ggtcatagct gtttcctgtg | 720 |
| tgaaattgtt atccgctcac aattccacac aacataggag ccggaagcat aaagtgtaaa | 780 |
| gcctggggtg cctaatgagt gaggtaactc acattaattg cgttgcgctc actgcccgct | 840 |
| ttccagtcgg gaaacctgtc gtgccagctg cattaatgaa tcggccaacg cgcggggaga | 900 |
| ggcggtttgc gtattgggcg ctcttccgct tcctcgctca ctgactcgct gcgctcggtc | 960 |
| gttcggctgc ggcgagcggt atcagctcac tcaaaggcgg taatacggtt atccacagaa | 1020 |
| tcagggata cgcaggaaa gaacatgtga gccggtgttt aaaccccagc gcctggcggg | 1080 |

<210> SEQ ID NO 94
<211> LENGTH: 1038
<212> TYPE: DNA
<213> ORGANISM: Artificial Sequence
<220> FEATURE:
<223> OTHER INFORMATION: Synthetic: CYS4 donor DNA

<400> SEQUENCE: 94

| | |
|---|---|
| gttggaaaaa gagattcctg gtgctgttat acttgaccaa tataacaata tgatgaaccc | 60 |
| agaagctcat tactttggta ctggtcgcga aatccaaaga cagctagaag acttgaattt | 120 |
| atttgataat ctacgcgctg ttgttgctgg tgctggtact ggtgggacta ttagcggtat | 180 |
| ttccaagtac ttgaaagaac agaatgataa gatccaaatc gttggtgctg acccattcgg | 240 |
| ttcaatttta gcccaacctg aaaacttgaa taagactgat atcactgact acaaagttga | 300 |
| gggtattggt tatgatttttg ttcctcaggt tttggacaga aaattaattg atgtttggta | 360 |
| taagacagac gacaagcctt ctttcaaata cgccagacaa ttgatttcta acgaaggtgt | 420 |
| cttggtgggt ggttcttccg gttctgcctt cactgcggtt gtgaaatact gtgaagacca | 480 |
| ccctgaactg actgaagatg atgtcatcgt cgccatcttt cctgactcca tcaggtcgta | 540 |
| cctaaccaaa ttcgtcgatg acgaatggtt gaaaaagaac aatttgtggg atgatgacgt | 600 |
| gttggcccgt tttgactctt caaagctgga ggcttcgacg acaaaatacg ctgatgtgtt | 660 |
| tggtaacgct actgtaaagg atcttcactt gaaaccggtt gtttccgtta aggaaaccgc | 720 |
| taaggtcact gatgttatca agatattaaa agacaatggc tttgaccaat tgcctgtgtt | 780 |
| gactgaagac ggcaagttgt ctggtttagt tactctctct gagcttctaa gaaaactatc | 840 |
| aatcaataat tcaaacaacg acaacactat aaagggtaaa tacttggact tcaagaaatt | 900 |
| aaacaatttc aatgatgttt cctcttacaa cgaaaataaa tccggtaaga agaagtttat | 960 |
| taaattcgat gaaaactcaa agctatctga cttgaatcgt ttctttgaaa aaaactcatc | 1020 |
| tgccgttatc actgatgg | 1038 |

<210> SEQ ID NO 95
<211> LENGTH: 22
<212> TYPE: DNA
<213> ORGANISM: Artificial Sequence
<220> FEATURE:
<223> OTHER INFORMATION: Synthetic: CYS4 locus target sequence

<400> SEQUENCE: 95

| | |
|---|---|
| ggtacgacct gatggaatct gg | 22 |

<210> SEQ ID NO 96
<211> LENGTH: 1080
<212> TYPE: DNA
<213> ORGANISM: Artificial Sequence
<220> FEATURE:
<223> OTHER INFORMATION: Synthetic: CYS4 gRNA construct

<400> SEQUENCE: 96

```
gacggcacgg ccacgcgttt aaaccgcctt ataaatcaaa agaatagacc gagatagggt    60
tgagtgttgt tccagtttgg aacaagagtc cactattaaa gaacgtggac tccaacgtca   120
aagggcgaaa aaccgtctat cagggcgatg gcccactacg tgaaccatca ccctaatcaa   180
gttttttggg gtcgaggtgc cgtaaagcac taaatcggaa ccctaaaggg agcccccgat   240
ttagagcttg acggggaaag cctctttgaa aagataatgt atgattatgc tttcactcat   300
atttatacag aaacttgatg ttttctttcg agtatataca aggtgattac atgtacgttt   360
gaagtacaac tctagatttt gtagtgccct cttgggctag cggtaaaggt gcgcattttt   420
tcacacccta caatgttctg ttcaaaagat tttggtcaaa cgctgtagaa gtgaaagttg   480
gtgcgcatgt ttcggcgttc gaaacttctc cgcagtgaaa gataaatgat cgggtacgac   540
ctgatgaat cgttttagag ctagaaatag caagttaaaa taaggctagt ccgttatcaa   600
cttgaaaaag tggcaccgag tcggtggtgc ttttttttgtt ttttatgtct cagcttttgt   660
tccctttagt gagggttaat tgcgcgcttg gcgtaatcat ggtcatagct gtttcctgtg   720
tgaaattgtt atccgctcac aattccacac aacataggag ccggaagcat aaagtgtaaa   780
gcctggggtg cctaatgagt gaggtaactc acattaattg cgttgcgctc actgcccgct   840
ttccagtcgg gaaacctgtc gtgccagctg cattaatgaa tcggccaacg cgcggggaga   900
ggcggtttgc gtattgggcg ctcttccgct tcctcgctca ctgactcgct gcgctcggtc   960
gttcggctgc ggcgagcggt atcagctcac tcaaaggcgg taatacggtt atccacagaa  1020
tcagggggata acgcaggaaa gaacatgtga gccggtgttt aaaccccagc gcctggcggg  1080
```

<210> SEQ ID NO 97
<211> LENGTH: 8045
<212> TYPE: DNA
<213> ORGANISM: Artificial Sequence
<220> FEATURE:
<223> OTHER INFORMATION: Synthetic: pAM3472

<400> SEQUENCE: 97

```
gttaggcgtt ttgcgctgct tcgcgatgta cgggccagat atacgcgttg acattgatta    60
ttgactagtt attaatagta atcaattacg ggtcattag ttcatagccc atatatggag   120
ttccgcgtta cataacttac ggtaaatggc ccgcctggct gaccgcccaa cgacccccgc   180
ccattgacgt caataatgac gtatgttccc atagtaacgc caatagggac tttccattga   240
cgtcaatggg tggagtattt acggtaaact gcccacttgg cagtacatca agtgtatcat   300
atgccaagta cgccccctat tgacgtcaat gacggtaaat ggcccgcctg gcattatgcc   360
cagtacatga ccttatggga ctttcctact tggcagtaca tctacgtatt agtcatcgct   420
attaccatgg tgatgcggtt ttggcagtac atcaatgggc gtggatagcg gtttgactca   480
cggggatttc caagtctcca ccccattgac gtcaatggga gtttgttttg gcaccaaaat   540
caacgggact ttccaaaatg tcgtaacaac tccgccccat tgacgcaaat gggcggtagg   600
cgtgtacggt gggaggtcta tataagcaga gctcgtttag tgaaccgtca gatcgcctgg   660
agacgccatc cacgctgttt tgacctccat agaagacacc gggaccgatc cagcctccgg   720
```

```
agcggccgcc accatgggca agcccatccc taacccCctg ttggggctgg acagcaccgc    780
tcccaaaaag aaaaggaagg tgggcattca cggcgtgcct gcggccgaca aaaagtacag    840
catcggcctt gatatcggca ccaatagcgt gggctgggcc gttatcacag acgaatacaa    900
ggtacccagc aagaagttca aggtgctggg aatacagac aggcactcta tcaagaaaaa    960
ccttatcggg gctctgctgt ttgactcagg cgagaccgcc gaggccacca ggttgaagag   1020
gaccgcaagg cgaaggtaca cccggaggaa gaacaggatc tgctatctgc aggagatctt   1080
cagcaacgag atggccaagg tggacgacag cttcttccac aggctggagg agagcttcct   1140
tgtcgaggag gataagaagc acgaacgaca ccccatcttc ggcaacatag tcgacgaggt   1200
cgcttatcac gagaagtacc ccaccatcta ccacctgcga aagaaattgg tggatagcac   1260
cgataaagcc gacttgcgac ttatctactt ggctctggcg cacatgatta agttcagggg   1320
ccacttcctg atcgagggcg accttaaccc cgacaacagt gacgtagaca aattgttcat   1380
ccagcttgta cagacctata accagctgtt cgaggaaaac cctattaacg ccagcggggt   1440
ggatgcgaag gccatactta gcgccaggct gagcaaaagc aggcgcttgg agaacctgat   1500
agcccagctg cccggtgaaa agaagaacgg cctcttcggt aatctgattg ccctgagcct   1560
gggcctgacc cccaacttca agagcaactt cgacctggca gaagatgcca agctgcagtt   1620
gagtaaggac acctatgacg acgacttgga caatctgctc gcccaaatcg gcgaccagta   1680
cgctgacctg ttcctcgccg ccaagaacct ttctgacgca atcctgctta gcgatatcct   1740
tagggtgaac acagagatca ccaaggcccc cctgagcgcc agcatgatca gaggtacga   1800 cgagcaccat caggacctga cccttctgaa ggccctggtg aggcagcaac tgcccgagaa   1860
gtacaaggag atcttttttcg accagagcaa gaacggctac gccggctaca tcgacggcgg   1920
agccagccaa gaggagttct acaagttcat caagcccatc ctggagaaga tggatggcac   1980
cgaggagctg ctggtgaagc tgaacaggga agatttgctc cggaagcaga ggacctttga   2040
caacggtagc atcccccacc agatccacct gggcgagctg cacgcaatac tgaggcgaca   2100
ggaggatttc taccccttcc tcaaggacaa tagggagaaa atcgaaaaga ttctgacctt   2160
caggatcccc tactacgtgg gccctcttgc caggggcaac agccgattcg cttggatgac   2220
aagaaagagc gaggagacca tcacccctg gaacttcgag gaagtggtgg acaaaggagc   2280
aagcgcgcag tcttttcatcg aacggatgac caatttcgac aaaaacctgc ctaacgagaa   2340
ggtgctgccc aagcacagcc tgctttacga gtacttcacc gtgtacaacg agctcaccaa   2400
ggtgaaatat gtgaccgagg gcatgcgaaa acccgctttc ctgagcggcg agcagaagaa   2460
ggccatcgtg gacctgctgt tcaagaccaa caggaaggtg accgtgaagc agctgaagga   2520
ggactacttc aagaagatcg agtgctttga tagcgtggaa ataagcggcg tggaggacag   2580
gttcaacgcc agcctgggca cctaccacga cttgttgaag ataatcaaag acaaggattt   2640
cctggataat gaggagaacg aggatatact cgaggacatc gtgctgactt tgacCctgtt   2700
tgaggaccga gagatgattg aagaaaggct caaaacctac gcccacctgt tcgacgacaa   2760
agtgatgaaa caactgaaga gacgaagata caccggctgg ggcagactgt ccaggaagct   2820
catcaacggc attagggaca gcagagcgg caagaccatc ctggatttcc tgaagtccga   2880
cggcttcgcc aaccgaaact tcatgcagct gattcacgat gacagcttga ccttcaagga   2940
ggacatccag aaggcccagg ttagcggcca gggcgactcc ctgcacgaac atattgcaaa   3000
cctggcaggc tcccctgcga tcaagaaggg catactgcag accgttaagg ttgtggacga   3060
attggtcaag gtcatgggca ggcacaagcc cgaaaacata gttatagaga tggccagaga   3120
```

```
gaaccagacc acccaaaagg gccagaagaa cagccgggag cgcatgaaaa ggatcgagga    3180
gggtatcaag gaactcggaa gccagatcct caaagagcac cccgtggaga atacccagct    3240
ccagaacgag aagctgtacc tgtactacct gcagaacggc agggacatgt acgttgacca    3300
ggagttggac atcaacaggc tttcagacta tgacgtggat cacatagtgc cccagagctt    3360
tcttaaagac gatagcatcg acaacaaggt cctgacccgc tccgacaaaa acaggggcaa    3420
aagcgacaac gtgccaagcg aagaggtggt taaaaagatg aagaactact ggaggcaact    3480
gctcaacgcg aaattgatca cccagagaaa gttcgataac ctgaccaagg ccgagagggg    3540
cggactctcc gaacttgaca aagcgggctt cataaagagg cagctggtcg agacccgaca    3600
gatcacgaag cacgtggccc aaatcctcga cagcagaatg aataccaagt acgatgagaa    3660
tgacaaactc atcagggaag tgaaagtgat taccctgaag agcaagttgg tgtccgactt    3720
tcgcaaagat ttccagttct acaaggtgag ggagatcaac aactaccacc atgcccacga    3780
cgcatacctg aacgccgtgg tcggcaccgc cctgattaag aagtatccaa agctggagtc    3840
cgaatttgtc tacggcgact acaaagttta cgatgtgagg aagatgatcg ctaagagcga    3900
acaggagatc ggcaaggcca ccgctaagta tttcttctac agcaacatca tgaacttttt    3960
caagaccgag atcacacttg ccaacggcga aatcaggaag aggccgctta tcgagaccaa    4020
cggtgagacc ggcgagatcg tgtgggacaa gggcagggac ttcgccaccg tgaggaaagt    4080
cctgagcatg ccccaggtga atattgtgaa aaaaactgag gtgcagacag gcggcttttag    4140 caaggaatcc atcctgccca gaggaacaga cgacaagctg atcgcccgga gaaggactg     4200 ggaccctaag aagtatggag gcttcgacag ccccaccgta gcctacagcg tgctggtggt    4260
cgcgaaggta gagaagggga agagcaagaa actgaagagc gtgaaggagc tgctcggcat    4320
aaccatcatg gagaggtcca gctttgagaa gaacccatt gacttttggg aagccaaggg    4380
ctacaaagag gtcaaaaagg acctgatcat caaactcccc aagtactccc tgtttgaatt    4440
ggagaacggc agaaagagga tgctggcgag cgctggggaa ctgcaaaagg caacgaact     4500 ggcgctgccc agcaagtacg tgaattttct gtacctggcg tcccactacg aaaagctgaa    4560
aggcagcccc gaggacaacg agcagaagca gctgttcgtg gagcagcaca gcattacct    4620 ggacgagata atcgagcaaa tcagcgagtt cagcaagagg gtgattctgg ccgacgcgaa    4680
cctggataag gtcctcagcg cctacaacaa gcaccgagac aaaacccatca gggagcaggc    4740 cgagaatatc atacacctgt tcaccctgac aaatctgggc gcacctgcgg cattcaaata    4800
cttcgatacc accatcgaca ggaaaaggta cactagcact aaggaggtgc tggatgccac    4860
cttgatccac cagtccatta ccggcctgta tgagaccagg atcgacctga gccagcttgg    4920
aggcgactct agggcggacc caaaaaagaa aaggaaggtg aattctcta gaggcagtgg    4980 agagggcaga ggaagtctgc taacatgcgg tgacgtcgag gagaatcctg gcccaatgaa    5040
ccggggagtc ccttttaggc acttgcttct ggtgctgcaa ctggcgctcc tcccagcagc    5100
cactcaggga aagaaagtgg tgctgggcaa aaaaggggat acagtggaac tgacctgtac    5160
agcttcccag aagaagagca tacaattcca ctggaaaaac tccaaccaga taaagattct    5220
gggaaatcag ggctccttct taactaaagg tccatccaag ctgaatgatc gcgctgactc    5280
aagaagaagc ctttgggacc aaggaaactt ccccctgatc atcaagaatc ttaagataga    5340
agactcagat acttacatct gtgaagtgga ggaccgaaag gaggaggtgc aattgctagt    5400
gttcggattg actgccaact ctgacaccca cctgcttcag gggcagagcc tgaccctgac    5460
cttggagagc ccccctggta gtagcccctc agtgcaatgt aggagtccaa ggggtaaaaa    5520
```

```
catacagggg gggaagaccc tctccgtgtc tcagctggag ctccaggata gtggcacctg   5580
gacatgcact gtcttgcaga accagaagaa ggtggagttc aaaatagaca tcgtggtgct   5640
agcttgataa atcgattagc ccgggtaccg tcgacctcta gctagagctt ggcgtaatca   5700
tggtcatagc tgtttcctgt gtgaaattgt tatccgctca caattccaca acatacga    5760 gccggaagca taaagtgtaa agcctggggt gcctaatgag tgagctaact cacattaatt   5820
gcgttgcgct cactgcccgc tttccagtcg ggaaacctgt cgtgccagct gcattaatga   5880
atcggccaac gcgcgggag aggcggtttg cgtattgggc gctcttccgc ttcctcgctc    5940
actgactcgc tgcgctcggt cgttcggctg cggcgagcgg tatcagctca ctcaaaggcg   6000
gtaatacggt tatccacaga atcaggggat aacgcaggaa agaacatgtg agcaaaaggc   6060
cagcaaaagg ccaggaaccg taaaaaggcc gcgttgctgg cgtttttcca taggctccgc   6120 cccctgacg agcatcacaa aaatcgacgc tcaagtcaga ggtggcgaaa cccgacagga    6180
ctataaagat accaggcgtt ccccctgga agctccctcg tgcgctctcc tgttccgacc    6240
ctgccgctta ccggatacct gtccgccttt ctcccttcgg gaagcgtggc gctttctcat   6300
agctcacgct gtaggtatct cagttcggtg taggtcgttc gctccaagct gggctgtgtg   6360 cacgaaccc ccgttcagcc cgaccgctgc gccttatccg gtaactatcg tcttgagtcc    6420
aacccggtaa gacacgactt atcgccactg gcagcagcca ctggtaacag gattagcaga   6480
gcgaggtatg taggcggtgc tacagagttc ttgaagtggt ggcctaacta cggctacact   6540
agaagaacag tatttggtat ctgcgctctg ctgaagccag ttaccttcgg aaaaagagtt   6600
ggtagctctt gatccggcaa acaaaccacc gctggtagcg tggtttttt tgtttgcaag    6660 cagcagatta cgcgcagaaa aaaggatct caagaagatc ctttgatctt ttctacgggg    6720
tctgacgctc agtggaacga aaactcacgt taagggattt tggtcatgag attatcaaaa   6780
aggatcttca cctagatcct tttaaattaa aaatgaagtt ttaaatcaat ctaaagtata   6840
tatgagtaaa cttggtctga cagttaccaa tgcttaatca gtgaggcacc tatctcagcg   6900
atctgtctat ttcgttcatc catagttgcc tgactccccg tcgtgtagat aactacgata   6960
cgggagggct taccatctgg ccccagtgct gcaatgatac cgcgagaccc acgctcaccg   7020
gctccagatt tatcagcaat aaaccagcca gccggaaggg ccgagcgcag aagtggtcct   7080
gcaactttat ccgcctccat ccagtctatt aattgttgcc gggaagctag agtaagtagt   7140
tcgccagtta atagtttgcg caacgttgtt gccattgcta caggcatcgt ggtgtcacgc   7200
tcgtcgtttg gtatggcttc attcagctcc ggttcccaac gatcaaggcg agttacatga   7260
tcccccatgt tgtgcaaaaa agcggttagc tccttcggtc ctccgatcgt tgtcagaagt   7320
aagttggccg cagtgttatc actcatggtt atggcagcac tgcataattc tcttactgtc   7380
atgccatccg taagatgctt ttctgtgact ggtgagtact caaccaagtc attctgagaa   7440
tagtgtatgc ggcgaccgag ttgctcttgc ccggcgtcaa tacgggataa taccgcgcca   7500
catagcagaa ctttaaaagt gctcatcatt ggaaaacgtt cttcggggcg aaaactctca   7560
aggatcttac cgctgttgag atccagttcg atgtaaccca ctcgtgcacc caactgatct   7620
tcagcatctt ttactttcac cagcgtttct gggtgagcaa aaacaggaag gcaaaatgcc   7680
gcaaaaaagg gaataagggc gacacggaaa tgttgaatac tcatactctt cctttttcaa   7740
tattattgaa gcatttatca gggttattgt ctcatgagcg gatacatatt tgaatgtatt   7800
tagaaaaata aacaaatagg ggttccgcgc acatttcccc gaaaagtgcc acctgacgtc   7860
gacggatcgg gagatctccc gatccctat ggtgcactct cagtacaatc tgctctgatg   7920
```

```
ccgcatagtt aagccagtat ctgctccctg cttgtgtgtt ggaggtcgct gagtagtgcg    7980
cgagcaaaat ttaagctaca acaaggcaag gcttgaccga caattgcatg aagaatctgc    8040
ttagg                                                                8045
```

<210> SEQ ID NO 98
<211> LENGTH: 9823
<212> TYPE: DNA
<213> ORGANISM: Artificial Sequence
<220> FEATURE:
<223> OTHER INFORMATION: Synthetic: pAM3473

<400> SEQUENCE: 98

```
gttaggcgtt ttgcgctgct tcgcgatgta cgggccagat atacgcgttg acattgatta      60
ttgactagtt attaatagta atcaattacg gggtcattag ttcatagccc atatatggag     120
ttccgcgtta cataacttac ggtaaatggc ccgcctggct gaccgcccaa cgaccccccgc    180
ccattgacgt caataatgac gtatgttccc atagtaacgc caatagggac tttccattga    240
cgtcaatggg tggagtattt acggtaaact gcccacttgg cagtacatca agtgtatcat    300
atgccaagta cgccccctat tgacgtcaat gacggtaaat ggcccgcctg gcattatgcc    360
cagtacatga ccttatggga ctttcctact tggcagtaca tctacgtatt agtcatcgct    420
attaccatgg tgatgcggtt ttggcagtac atcaatgggc gtggatagcg gtttgactca    480
cggggatttc caagtctcca ccccattgac gtcaatggga gtttgttttg gcaccaaaat    540
caacgggact ttccaaaatg tcgtaacaac tccgccccat tgacgcaaat gggcggtagg    600
cgtgtacggt gggaggtcta tataagcaga gctcgtttag tgaaccgtca gatcgcctgg    660
agacgccatc cacgctgttt tgacctccat agaagacacc gggaccgatc cagcctccgg    720
agcggccgcc accatgggca gcccatccc taacccctg ttggggctgg acagcaccgc    780
tcccaaaaag aaaaggaagg tgggcattca cggcgtgcct gcggccgaca aaaagtacag    840
catcggcctt gatatcggca ccaatagcgt gggctgggcc gttatcacag acgaatacaa    900
ggtacccagc aagaagttca aggtgctggg gaatacagac aggcactcta tcaagaaaaa    960
ccttatcggg gctctgctgt ttgactcagg cgagaccgcc gaggccacca ggttgaagag   1020
gaccgcaagg cgaaggtaca cccggaggaa gaacaggatc tgctatctgc aggagatctt   1080
cagcaacgag atggccaagg tggacgacag cttcttccac aggctggagg agagcttcct   1140
tgtcgaggag gataagaagc acgaacgaca ccccatcttc ggcaacatag tcgacgaggt   1200
cgcttatcac gagaagtacc caccatcta ccacctgcga aagaaattgg tggatagcac   1260
cgataaagcc gacttgcgac ttatctactt ggctctggcg cacatgatta agttcagggg   1320
ccacttcctg atcgagggcg accttaaccc cgacaacagt gacgtagaca aattgttcat   1380
ccagcttgta cagacctata accagctgtt cgaggaaaac cctattaacg ccagcggggt   1440
ggatgcgaag gccatactta gcgccaggct gagcaaaagc aggcgcttgg agaacctgat   1500
agcccagctg cccggtgaaa agaagaacgg cctcttcggt aatctgattg ccctgagcct   1560
gggcctgacc cccaacttca gagcaacttc gacctggca gaagatgcca agctgcagtt   1620
gagtaaggac acctatgacg acgacttgga caatctgctc gcccaaatcg gcgaccagta   1680
cgctgacctg ttcctcgccg ccaagaacct ttctgacgca atcctgctta gcgatatcct   1740
tagggtgaac acagagatca ccaaggcccc cctgagcgcc agcatgatca agaggtacga   1800
cgagcaccat caggacctga cccttctgaa ggccctggtg aggcagcaac tgcccgaaaa   1860
gtacaaggag atcttttccg accagagcaa gaacggctac gccggctaca tcgacggcgg   1920
```

```
agccagccaa gaggagttct acaagttcat caagcccatc ctggagaaga tggatggcac    1980
cgaggagctg ctggtgaagc tgaacaggga agatttgctc cggaagcaga ggacctttga    2040
caacggtagc atcccccacc agatccacct gggcgagctg cacgcaatac tgaggcgaca    2100
ggaggatttc tacccttcc tcaaggacaa tagggagaaa atcgaaaaga ttctgacctt     2160
caggatcccc tactacgtgg gccctcttgc caggggcaac agccgattcg cttggatgac    2220
aagaaagagc gaggagacca tcaccccctg gaacttcgag aagtggtgg acaaaggagc     2280
aagcgcgcag tctttcatcg aacggatgac caatttcgac aaaaacctgc ctaacgagaa    2340
ggtgctgccc aagcacagcc tgctttacga gtacttcacc gtgtacaacg agctcaccaa    2400
ggtgaaatat gtgaccgagg gcatgcgaaa acccgctttc ctgagcggcg agcagaagaa    2460
ggccatcgtg gacctgctgt tcaagaccaa caggaaggtg accgtgaagc agctgaagga    2520
ggactacttc aagaagatcg agtgcttga tagcgtggaa ataagcggcg tggaggacag     2580
gttcaacgcc agcctgggca cctaccacga cttgttgaag ataatcaaag acaaggattt    2640
cctggataat gaggagaacg aggatatact cgaggacatc gtgctgactt tgaccctgtt    2700
tgaggaccga gagatgattg aagaaggct caaaacctac gcccaccgtgt tcgacgacaa    2760
agtgatgaaa caactgaaga cgcaagata caccggctgg ggcagactgt ccaggaagct     2820
catcaacggc attagggaca gcagagcgg caagaccatc ctggatttcc tgaagtccga    2880
cggcttcgcc aaccgaaact tcatgcagct gattcacgat acagcttga ccttcaagga    2940
ggacatccag aaggcccagg ttagcggcca gggcgactcc ctgcacgaac atattgcaaa    3000
cctggcaggc tcccctgcga tcaagaaggg catactgcag accgttaagg ttgtggacga    3060
attggtcaag gtcatgggca ggcacaagcc cgaaaacata gttatagaga tggccagaga    3120
gaaccagacc acccaaaagg gccagaagaa cagccgggag cgcatgaaaa ggatcgagga    3180
gggtatcaag gaactcggaa gccagatcct caaagagcac cccgtggaga ataccccagct   3240
ccagaacgag aagctgtacc tgtactacct gcagaacggc agggacatgt acgttgacca    3300
ggagttggac atcaacaggc tttcagacta tgacgtggat cacatagtgc cccagagctt    3360
tcttaaagac gatagcatcg acaacaaggt cctgacccgc tccgacaaaa acaggggcaa    3420
aagcgacaac gtgccaagcg aagaggtggt taaaagatg aagaactact ggaggcaact     3480
gctcaacgcg aaattgatca cccagagaaa gttcgataac ctgaccaagg ccgagagggg    3540
cggactctcc gaacttgaca aagcgggctt cataaagagg cagctggtcg agaccccgaca   3600
gatcacgaag cacgtggccc aaatcctcga cagcagaatg aataccaagt acgatgagaa    3660
tgacaaactc atcagggaag tgaaagtgat taccctgaag agcaagttgg tgtccgactt    3720
tcgcaaagat ttccagttct acaaggtgag ggagatcaac aactaccacc atgcccacga    3780
cgcatacctg aacgccgtgg tcggcaccgc cctgattaag aagtatccaa agctggagtc    3840
cgaatttgtc tacggcgact acaaagttta cgatgtgagg aagatgatcg ctaagagcga    3900
acaggagatc ggcaaggcca ccgctaagta tttcttctac agcaacatca tgaacttttt    3960
caagaccgag atcacacttg ccaacggcga atcaggaag aggccgctta tcgagaccaa     4020
cggtgagacc ggcgagatcg tgtgggacaa gggcaggac ttcgccaccg tgaggaaagt     4080
cctgagcatg ccccaggtga atattgtgaa aaaaactgag gtgcagacag gcggctttag    4140
caaggaatcc atcctgccca gaggaacag cgacaagctg atcgcccgga agaaggactg     4200
ggaccctaag aagtatggag gcttcgacag ccccaccgta gcctacagcg tgctggtggt    4260
cgcgaaggta gagaagggga agagcaagaa actgaagagc gtgaaggagc tgctcggcat    4320
```

```
aaccatcatg gagaggtcca gctttgagaa gaaccccatt gacttttttgg aagccaaggg    4380 ctacaaagag gtcaaaaagg acctgatcat caaactcccc aagtactccc tgtttgaatt    4440
ggagaacggc agaaagagga tgctggcgag cgctgggaa ctgcaaaagg caacgaact    4500 ggcgctgccc agcaagtacg tgaattttct gtacctggcg tcccactacg aaaagctgaa    4560
aggcagcccc gaggacaacg agcagaagca gctgttcgtg gagcagcaca agcattacct    4620
ggacgagata tcgagcaaa tcagcgagtt cagcaagagg gtgattctgg ccgacgcgaa    4680
cctggataag gtcctcagcg cctacaacaa gcaccgagac aaacccatca gggagcaggc    4740
cgagaatatc atacacctgt tcaccctgac aaatctgggc gcacctgcgg cattcaaata    4800
cttcgatacc accatcgaca ggaaaaggta cactagcact aaggaggtgc tggatgccac    4860
cttgatccac cagtccatta ccggcctgta tgagaccagg atcgacctga ccagcttgg    4920 aggcgactct agggcggacc caaaaaagaa aaggaaggtg gaattctcta gaggcagtgg    4980
agagggcaga ggaagtctgc taacatgcgg tgacgtcgag gagaatcctg gcccaatgaa    5040 ccgggagtc ccttttaggc acttgcttct ggtgctgcaa ctggcgctcc tcccagcagc    5100
cactcaggga aagaaagtgg tgctgggcaa aaaaggggat acagtggaac tgacctgtac    5160
agcttcccag aagaagagca tacaattcca ctggaaaaac tccaaccaga taagagttct    5220
gggaaatcag ggctccttct taactaaagg tccatccaag ctgaatgatc gcgctgactc    5280
aagaagaagc ctttgggacc aaggaaactt ccccctgatc atcaagaatc ttaagataga    5340
agactcagat acttacatct gtgaagtgga ggaccagaag gaggaggtgc aattgctagt    5400
gttcggattg actgccaact ctgacaccca cctgcttcag gggcagagcc tgaccctgac    5460
cttggagagc ccccctggta gtagcccctc agtgcaatgt aggagtccaa ggggtaaaaa    5520
catacagggg gggaagaccc tctccgtgtc tcagctggag ctccaggata gtggcacctg    5580
gacatgcact gtcttgcaga accagaagaa ggtggagttc aaaatagaca tcgtggtgct    5640 agcttttccag aaggcctcca gcatagtcta taagaaagag ggggaacagg tggagttctc    5700
cttcccactc gcctttacag ttgaaaagct gacgggcagt ggcgagctgt ggtggcaggc    5760
ggagagggct tcctcctcca gtcttggat caccttttgac ctgaagaaca aggaagtgtc    5820
tgtaaaacgg gttacccagg accctaagct ccagatgggc aagaagctcc cgctccacct    5880
caccctgccc caggccttgc ctcagtatgc tggctctgga aacctcaccc tggcccttga    5940
agcgaaaaca ggaaagttgc atcaggaagt gaacctggtg gtgatgagag ccactcagct    6000
ccagaaaaat ttgacctgtg aggtgtgggg acccacctcc cctaagctga tgctgagctt    6060
gaaactggag aacaaggagg caaaggtctc gaagcgggag aaggcggtgt gggtgctgaa    6120
ccctgaggcg gggatgtggc agtgtctgct gagtgactcg ggacaggtcc tgctggaatc    6180
caacatcaag gttctgccca tggtcgac cccggtgcag ccaatggccc tgattgtgct    6240 gggggcgtc gccggcctcc tgcttttcat tgggctaggc atcttcttct gtgtcaggtg    6300
ccggcacacc ggttagtaat gagtttaaac ggggagggct aactgaaaca cggaaggaga    6360
caataccgga aggaacccgc gctatgacgg caataaaaag acagaataaa acgcacgggt    6420
gttgggtcgt ttgttcataa acgcggggtt cggtcccagg gctggcactc tgtcgatacc    6480
ccaccgagac cccattgggg ccaatacgcc cgcgtttctt ccttttcccc accccacccc    6540
ccaagttcgg gtgaaggccc agggctcgca gccaacgtcg gggcggcagg ccctgccata    6600
gcagatctgc gcagctgggg gctctagggg tatcccccacg cgccctgtag cggcgcatta    6660
agcgcggcgg gtgtggtggt tacgcgcagc gtgaccgcta cacttgccag cgccctagcg    6720
```

```
cccgctcctt tcgctttctt cccttcctttt ctcgccacgt tcgccggctt tccccgtcaa    6780
gctctaaatc gggggctccc tttagggttc cgatttagtg ctttacggca cctcgacccc    6840
aaaaaacttg attagggtga tggttcacgt agtgggccat cgccctgata gacggttttt    6900
cgcccttttga cgttggagtc cacgttcttt aatagtggac tcttgttcca aactggaaca    6960
acactcaacc ctatctcggt ctattctttt gatttataag ggattttgcc gatttcggcc    7020
tattggttaa aaaatgagct gatttaacaa aaatttaacg cgaattaatt aaggtcgggc    7080
aggaagaggg cctatttccc atgattcctt catatttgca tatacgatac aaggctgtta    7140
gagagataat tagaattaat ttgactgtaa acacaaagat attagtacaa aatacgtgac    7200
gtagaaagta ataatttctt gggtagtttg cagttttaaa attatgtttt aaaatggact    7260
atcatatgct taccgtaact tgaaagtatt tcgatttctt ggctttatat atcttgtgga    7320
aaggacgaaa caccgggggc cactagggac aggatgtttt agagctagaa atagcaagtt    7380
aaaataaggc tagtccgtta tcaacttgaa aaagtggcac cgagtcggtg cttttttcta    7440
gtataccgtc gacctctagc tagagcttgg cgtaatcatg gtcatagctg tttcctgtgt    7500
gaaattgtta tccgctcaca attccacaca acatacgagc cggaagcata agtgtaaag    7560
cctggggtgc ctaatgagtg agctaactca cattaattgc gttgcgctca ctgcccgctt    7620
tccagtcggg aaacctgtcg tgccagctgc attaatgaat cggccaacgc gcggggagag    7680
gcggtttgcg tattgggcgc tcttccgctt cctcgctcac tgactcgctg cgctcggtcg    7740
ttcggctgcg gcgagcggta tcagctcact caaaggcggt aatacggtta tccacagaat    7800
caggggataa cgcaggaaag aacatgtgag caaaaggcca gcaaaaggcc aggaaccgta    7860
aaaaggccgc gttgctggcg tttttccata ggctccgccc ccctgacgag catcacaaaa    7920
atcgacgctc aagtcagagg tggcgaaacc cgacaggact ataaagatac caggcgtttc    7980
cccctggaag ctccctcgtg cgctctcctg ttccgaccct gccgcttacc ggatacctgt    8040
ccgcctttct cccttcggga agcgtggcgc tttctcatag ctcacgctgt aggtatctca    8100
gttcggtgta ggtcgttcgc tccaagctgg gctgtgtgca cgaaccccc gttcagcccg    8160
accgctgcgc cttatccggt aactatcgtc ttgagtccaa cccggtaaga cacgacttat    8220
cgccactggc agcagccact ggtaacagga ttagcagagc gaggtatgta ggcggtgcta    8280
cagagttctt gaagtggtgg cctaactacg gctacactag aagaacagta tttggtatct    8340
gcgctctgct gaagccagtt accttcggaa aaagagttgg tagctcttga tccggcaaac    8400
aaaccaccgc tggtagcggt ggtttttttg tttgcaagca gcagattacg cgcagaaaaa    8460
aaggatctca agaagatcct ttgatctttt ctacggggtc tgacgctcag tggaacgaaa    8520
actcacgtta agggattttg gtcatgagat tatcaaaaag gatcttcacc tagatccttt    8580
taaattaaaa atgaagtttt aaatcaatct aaagtatata tgagtaaact tggtctgaca    8640
gttaccaatg cttaatcagt gaggcaccta tctcagcgat ctgtctattt cgttcatcca    8700
tagttgcctg actccccgtc gtgtagataa ctacgatacg ggagggctta ccatctggcc    8760
ccagtgctgc aatgataccg cgagacccac gctcaccggc tccagattta tcagcaataa    8820
accagccagc cggaagggcc gagcgcagaa gtggtcctgc aactttatcc gcctccatcc    8880
agtctattaa ttgttgccgg gaagctagag taagtagttc gccagttaat agtttgcgca    8940
acgttgttgc cattgctaca ggcatcgtgg tgtcacgctc gtcgtttggt atggcttcat    9000
tcagctccgg ttcccaacga tcaaggcgag ttacatgatc cccatgttg tgcaaaaaag    9060
cggttagctc cttcggtcct ccgatcgttg tcagaagtaa gttggccgca gtgttatcac    9120
```

| | |
|---|---:|
| tcatggttat ggcagcactg cataattctc ttactgtcat gccatccgta agatgctttt | 9180 |
| ctgtgactgg tgagtactca accaagtcat tctgagaata gtgtatgcgg cgaccgagtt | 9240 |
| gctcttgccc ggcgtcaata cgggataata ccgcgccaca tagcagaact ttaaaagtgc | 9300 |
| tcatcattgg aaaacgttct cggggcgaaa actctcaag gatcttaccg ctgttgagat | 9360 |
| ccagttcgat gtaacccact cgtgcaccca actgatcttc agcatctttt actttcacca | 9420 |
| gcgtttctgg gtgagcaaaa acaggaaggc aaaatgccgc aaaaaaggga ataagggcga | 9480 |
| cacggaaatg ttgaatactc atactcttcc ttttcaata ttattgaagc atttatcagg | 9540 |
| gttattgtct catgagcgga tacatatttg aatgtattta gaaaaataaa caaatagggg | 9600 |
| ttccgcgcac atttccccga aaagtgccac ctgacgtcga cggatcggga gatctcccga | 9660 |
| tcccctatgg tgcactctca gtacaatctg ctctgatgcc gcatagttaa gccagtatct | 9720 |
| gctccctgct tgtgtgttgg aggtcgctga gtagtgcgcg agcaaaattt aagctacaac | 9780 |
| aaggcaaggc ttgaccgaca attgcatgaa gaatctgctt agg | 9823 |

<210> SEQ ID NO 99
<211> LENGTH: 3296
<212> TYPE: DNA
<213> ORGANISM: Artificial Sequence
<220> FEATURE:
<223> OTHER INFORMATION: Synthetic: pAM3514

<400> SEQUENCE: 99

| | |
|---|---:|
| ggtcgttcgg ctgcggcgag cggtatcagc tcactcaaag gcggtaatac ggttatccac | 60 |
| agaatcaggg gataacgcag gaaagaacat gtgagcaaaa ggccagcaaa aggccaggaa | 120 |
| ccgtaaaaag gccgcgttgc tggcgttttt ccataggctc cgcccccctg acgagcatca | 180 |
| caaaaatcga cgctcaagtc agaggtggcg aaacccgaca ggactataaa gataccaggc | 240 |
| gtttccccct ggaagctccc tcgtgcgctc tcctgttccg accctgccgc ttaccggata | 300 |
| cctgtccgcc tttctccctt cgggaagcgt ggcgctttct catagctcac gctgtaggta | 360 |
| tctcagttcg gtgtaggtcg ttcgctccaa gctgggctgt gtgcacgaac cccccgttca | 420 |
| gcccgaccgc tgcgccttat ccggtaacta tcgtcttaag tccaacccgg taagacacga | 480 |
| cttatcgcca ctggcagcag ccactggtaa caggattagc agagcgaggt atgtaggcgg | 540 |
| tgctacagag ttcttgaagt ggtggcctaa ctacggctac actagaagaa cagtatttgg | 600 |
| tatctgcgct ctgctgaagc cagttacctt cggaaaaaga gttggtagct cttgatccgg | 660 |
| caaacaaacc accgctggta gcggtggttt ttttgtttgc aagcagcaga ttacgcgcag | 720 |
| aaaaaaagga tctcaagaag atcctttgat cttttctacg gggtctgacg ctcagtggaa | 780 |
| cgaaaactca cgttaaggga ttttggtcat gagattatca aaaaggatct tcacctagat | 840 |
| ccttttaaat taaaaatgaa gttttaaatc aatctaaagt atatatgagt aaactggtcg | 900 |
| catgcttacc aatgcttaat cagtgaggca cctatctcag cgatctgtct atttcgttca | 960 |
| tccatagttg cctgactgcc cgtcgtgtag ataactacga tacgggaggg cttaccatct | 1020 |
| ggccccagtg ctgcaatgat accgcgagac ccacgctcac cggctccaga tttatcagca | 1080 |
| ataaaccagc cagccggaag ggccgagcgc agaagtggtc ctgcaacttt atccgcctcc | 1140 |
| atccagtcta ttaattgttg ccgggaagct agagtaagta gttcgccagt taatagtttg | 1200 |
| cgcaacgttg ttgccattgc tacaggcatc gtggtgtcac gctcgtcgtt tggtatggct | 1260 |
| tcattcagct ccggttccca acgatcaagg cgagttacat gatcccccat gttgtgcaaa | 1320 |
| aaagcggtta gctccttcgg tcctccgatc gttgtcagaa gtaagttggc cgcagtgtta | 1380 |

```
tcactcatgg ttatggcagc actgcataat tctcttactg tcatgccatc cgtaagatgc    1440
ttttctgtga ctggtgagta ctcaaccaag tcattctgag aatagtgtat gcggcgaccg    1500
agttgctctt gcccggcgtc aatacgggat aataccgcgc cacatagcag aactttaaaa    1560
gtgctcatca ttggaaaacg ttcttcgggg cgaaaactct caaggatctt accgctgttg    1620
agatccagtt cgatgtaacc cactcgtgca cccaactgat cttcagcatc ttttactttc    1680
accagcgttt ctgggtgagc aaaaacagga aggcaaaatg ccgcaaaaaa gggaataagg    1740
gcgacacgga aatgttgaat actcatcaat tgccttttc aatattattg aagcatttat    1800
cagggttatt gtctcatgag cggttacata tttgaatgta tttagaaaaa taaacaaata    1860
ggggttccgc gcacatttcc ccgaaaagtg ccacctgacg tctaagaaac cattattatc    1920
atgacattaa cctataaaaa taggcgtatc acgaggccct ttcatctcgc gcgtttcggt    1980
gatgacggtg aaaacctctg acacatgcag ctcccggaga cagtcacagc ttgtctgtaa    2040
gcggatgccg ggagcagaca gcccgtcag ggcgcgtcag cgggtgttgg cgggtgtcgg    2100
ggctggtaaa acgacggcca gtattaaccc tcactaaagg gaactcgagg ctcttcagac    2160
ggcacggcca cgcgtttaaa ccgccagttt tccacacgga cacccccctc ctcaccacag    2220
ccctgccagg acggggctgg ctactggcct tatctcacag gtaaaactga cgcacggagg    2280
aacaatataa attggggact agaaaggtga agagccaaag ttagaactca ggaccaactt    2340
attctgattt tgttttttca aactgcttct cctcttggga agtgtaagga agctgcagca    2400
ccaggatcag tgaaacgcac cagacggccg cgtcagagca gctcaggttc tgggagaggg    2460
tagcgcaggg tggccactga gaaccgggca ggtcacgcat ccccccttc cctcccaccc    2520 cctgccaagc tctccctccc aggatcctct ctggctccat cgtaagcaaa ccttagaggt    2580
tctggcaagg agagagatgg ctccaggaaa tgggggtgtg tcaccagata aggaatctgc    2640
ctaacaggag gtgggggtta gacccaatat caggagacta ggaaggagga ggcctaagga    2700
tggggctttt ctgtcagaat tcactgtggg gtggagggga cagataaaag tacccagaac    2760
cagagccaca ttaaccggcc ctgggaatat aaggtggtcc cagctcgggg acacaggatc    2820
cctggaggca gcaaacatgc tgtcctgaag tggacatagg ggccgggtt ggaggaagaa    2880 gactagctga gctctcggac ccctggaaga tgccatgaca gggggctgga agagctagca    2940
cagactagag aggtaagggg ggtaggggag ctgcccaaat gaaaggagtg agaggtgacc    3000
cgaatccaca ggagaacggg gtgtccaggc aaagaaagca agaggatgga gaggtggcta    3060
aagccaggga gacggggtac tttggggttg tccagaaaaa cggtgatgat gcaggcctac    3120
aagaagggga ggcgggacgc aagggagaca tccgtcggag aaggccatcc taagaaacga    3180
gagatggcac aggccccaga aggagaagga aaagggaacg tgttaaac cccagcgcct    3240 ggcgggtgaa gagcgagctc ccgctgagca ataactagcg tcatagctgt ttcctg       3296
```

<210> SEQ ID NO 100
<211> LENGTH: 5068
<212> TYPE: DNA
<213> ORGANISM: Artificial Sequence
<220> FEATURE:
<223> OTHER INFORMATION: Synthetic: pAM3515

<400> SEQUENCE: 100

```
ggtcgttcgg ctgcggcgag cggtatcagc tcactcaaag gcggtaatac ggttatccac      60
agaatcaggg gataacgcag gaaagaacat gtgagcaaaa ggccagcaaa aggccaggaa     120
ccgtaaaaag gccgcgttgc tggcgttttt ccataggctc cgcccccctg acgagcatca     180
```

```
caaaaatcga cgctcaagtc agaggtggcg aaacccgaca ggactataaa gataccaggc    240
gtttccccct ggaagctccc tcgtgcgctc tcctgttccg accctgccgc ttacccgata    300
cctgtccgcc tttctccctt cgggaagcgt ggcgctttct catagctcac gctgtaggta    360
tctcagttcg gtgtaggtcg ttcgctccaa gctgggctgt gtgcacgaac cccccgttca    420
gcccgaccgc tgcgccttat ccggtaacta tcgtcttaag tccaacccgg taagacacga    480
cttatcgcca ctggcagcag ccactggtaa caggattagc agagcgaggt atgtaggcgg    540
tgctacagag ttcttgaagt ggtggcctaa ctacggctac actagaagaa cagtatttgg    600
tatctgcgct ctgctgaagc cagttacctt cggaaaaaga gttggtagct cttgatccgg    660
caaacaaacc accgctggta gcggtggttt ttttgtttgc aagcagcaga ttacgcgcag    720
aaaaaaagga tctcaagaag atcctttgat cttttctacg gggtctgacg ctcagtggaa    780
cgaaaactca cgttaaggga ttttggtcat gagattatca aaaaggatct tcacctagat    840
ccttttaaat taaaaatgaa gttttaaatc aatctaaagt atatatgagt aaactggtcg    900
catgcttacc aatgcttaat cagtgaggca cctatctcag cgatctgtct atttcgttca    960
tccatagttg cctgactgcc cgtcgtgtag ataactacga tacgggaggg cttaccatct   1020
ggccccagtg ctgcaatgat accgcgagac ccacgctcac cggctccaga tttatcagca   1080
ataaaccagc cagccggaag ggccgagcgc agaagtggtc ctgcaacttt atccgcctcc   1140
atccagtcta ttaattgttg ccgggaagct agagtaagta gttcgccagt taatagtttg   1200
cgcaacgttg ttgccattgc tacaggcatc gtggtgtcac gctcgtcgtt tggtatggct   1260
tcattcagct ccggttccca acgatcaagg cgagttacat gatcccccat gttgtgcaaa   1320
aaagcggtta gctccttcgg tcctccgatc gttgtcagaa gtaagttggc cgcagtgtta   1380
tcactcatgg ttatggcagc actgcataat tctcttactg tcatgccatc cgtaagatgc   1440
ttttctgtga ctggtgagta ctcaaccaag tcattctgag aatagtgtat gcggcgaccg   1500
agttgctctt gcccggcgtc aatacggat aataccgcgc cacatagcag aactttaaaa   1560
gtgctcatca ttggaaaacg ttcttcgggg cgaaaactct caaggatctt accgctgttg   1620
agatccagtt cgatgtaacc cactcgtgca cccaactgat cttcagcatc ttttactttc   1680
accagcgttt ctgggtgagc aaaaacagga aggcaaaatg ccgcaaaaaa gggaataagg   1740
gcgacacgga aatgttgaat actcatcaat tgccttttc aatattattg aagcatttat   1800
cagggttatt gtctcatgag cggttacata tttgaatgta tttagaaaaa taaacaaata   1860
ggggttccgc gcacatttcc ccgaaaagtg ccacctgacg tctaagaaac cattattatc   1920
atgacattaa cctataaaaa taggcgtatc acgaggccct ttcatctcgc gcgtttcggt   1980
gatgacggtg aaaacctctg acacatgcag ctcccggaga cagtcacagc ttgtctgtaa   2040
gcggatgccg ggagcagaca agcccgtcag gcgcgtcag cgggtgttgg cgggtgtcgg   2100
ggctggtaaa acgacggcca gtattaaccc tcactaaagg gaactcgagg ctcttcagac   2160
ggcacggcca cgcgtttaaa ccgccataca gtggaactga cctgtacagc ttcccagaag   2220
aagagcatac aattccactg gaaaaactcc aaccagataa agattctggg aaatcagggc   2280
tccttcttaa ctaaaggtcc atccaagctg aatgatcgcg ctgactcaag aagaagcctt   2340
tgggaccaag gaaacttccc cctgatcatc aagaatctta agatagaaga ctcagatact   2400
tacatctgtg aagtggagga ccagaaggag gaggtgcaat tgctagtgtt cggattgact   2460
gccaactctg acacccacct gcttcagggg cagagcctga ccctgacctt ggagagcccc   2520
cctggtagta gccccctcagt gcaatgtagg agtccaaggg gtaaaaacat acaggggggg   2580
```

```
aagaccctct ccgtgtctca gctggagctc caggatagtg gcacctggac atgcactgtc    2640
ttgcagaacc agaagaaggt ggagttcaaa atagacatcg tggtgctagc tttccagaag    2700
gcctccagca tagtctataa gaaagagggg gaacaggtgg agttctcctt cccactcgcc    2760
tttacagttg aaaagctgac gggcagtggc gagctgtggt ggcaggcgga gagggcttcc    2820
tcctccaagt cttggatcac cttttgacctg aagaacaagg aagtgtctgt aaaacgggtt    2880
acccaggacc ctaagctcca gatgggcaag aagctcccgc tccacctcac cctgccccag    2940
gccttgcctc agtatgctgg ctctggaaac ctcaccctgg cccttgaagc gaaaacagga    3000
aagttgcatc aggaagtgaa cctggtggtg atgagagcca ctcagctcca gaaaaatttg    3060
acctgtgagg tgtggggacc cacctcccct aagctgatgc tgagcttgaa actggagaac    3120
aaggaggcaa aggtctcgaa gcgggagaag gcggtgtggg tgctgaaccc tgaggcgggg    3180
atgtggcagt gtctgctgag tgactcggga caggtcctgc tggaatccaa catcaaggtt    3240
ctgcccacat ggtcgacccc ggtgcagcca atggccctga ttgtgctggg gggcgtcgcc    3300
ggcctcctgc ttttcattgg gctaggcatc ttcttctgtg tcaggtgccg gcacaccggt    3360
tagtaatgag tttaaacggg ggaggctaac tgaaacacgg aaggagacaa taccggaagg    3420
aacccgcgct atgacggcaa taaaagaca gaataaaacg cacgggtgtt gggtcgtttg    3480
ttcataaacg cggggttcgg tcccagggct ggcactctgt cgataccca ccgagacccc    3540 attgggccca atacgcccgc gtttcttcct ttccccacc ccaccccca gttcgggtg    3600 aaggcccagg gctcgcagcc aacgtcgggg cggcaggccc tgccatagca gatctgcgca    3660 gctgggctc taggggtat ccccacgcgc cctgtagcgg cgcattaagc gcggcggtg    3720 tggtggttac gcgcagcgtg accgctacac ttgccagcgc cctagcgccc gctcctttcg    3780
ctttcttccc ttcctttctc gccacgttcg ccggctttcc ccgtcaagct ctaaatcggg    3840
ggctcccttt agggttccga tttagtgctt tacggcacct cgaccccaaa aaacttgatt    3900
agggtgatgg ttcacgtagt gggccatcgc cctgatagac ggtttttcgc cctttgacgt    3960
tggagtccac gttctttaat agtggactct tgttccaaac tggaacaaca ctcaaccta    4020 tctcggtcta ttcttttgat ttataaggga ttttgccgat ttcggcctat tggttaaaaa    4080
atgagctgat ttaacaaaaa tttaacgcga attaattaag gtcgggcagg aagagggcct    4140
atttcccatg attccttcat atttgcatat acgatacaag gctgttagag agataattag    4200
aattaatttg actgtaaaca caaagatatt agtacaaaat acgtgacgta gaaagtaata    4260
atttcttggg tagtttgcag ttttaaaatt atgtttaaa atggactatc atatgcttac    4320
cgtaacttga aagtatttcg atttcttggc tttatatat ttgtggaaag gacgaaacac    4380
cgggggccac tagggacagg atgttttaga gctagaaata gcaagttaaa ataaggctag    4440
tccgttatca acttgaaaaa gtggcaccga gtcggtgctt ttttctagta taccgtcgac    4500
ctctagctag agcttggcgt aatcatggtc atagctgttt cctgtgtgaa attgttatcc    4560
gctcacaatt ccacacaaca tacgagccgg aagcataaag tgtaaagcct ggggtgccta    4620
atgagtgagc taactcacat taattgcgtt gcgctcactg cccgctttcc agtcgggaaa    4680
cctgtcgtgc cagctgcatt aatgaatcgg ccaacgcgcg gggagaggcg gtttgcgtat    4740
tgggcgctct tccgcttcct cgctcactga ctcgctgcgc tcggtcgttc ggctgcggcg    4800
agcggtatca gctcactcaa aggcggtaat acggttatcc acagaatcag gggataacgc    4860
aggaaagaac atgtgagcaa aaggccagca aaaggccagg aaccgtaaaa aggccgcgtt    4920
gctggcgttt ttccataggc tccgcccccc tgacgagcat cacaaaaatc gacgctcaag    4980
```

```
tcagaggtgg cggtgtttaa accccagcgc ctggcgggtg aagagcgagc tcccgctgag    5040
caataactag cgtcatagct gtttcctg                                       5068

<210> SEQ ID NO 101
<211> LENGTH: 4224
<212> TYPE: DNA
<213> ORGANISM: Artificial Sequence
<220> FEATURE:
<223> OTHER INFORMATION: Synthetic: pAM3516

<400> SEQUENCE: 101
ggtcgttcgg ctgcggcgag cggtatcagc tcactcaaag gcggtaatac ggttatccac      60
agaatcaggg gataacgcag gaaagaacat gtgagcaaaa ggccagcaaa aggccaggaa     120
ccgtaaaaag gccgcgttgc tggcgttttt ccataggctc cgcccccctg acgagcatca     180
caaaaatcga cgctcaagtc agaggtggcg aaacccgaca ggactataaa gataccaggc     240
gtttccccct ggaagctccc tcgtgcgctc tcctgttccg accctgccgc ttacccgata     300
cctgtccgcc tttctccctt cgggaagcgt ggcgctttct catagctcac gctgtaggta     360
tctcagttcg gtgtaggtcg ttcgctccaa gctgggctgt gtgcacgaac cccccgttca     420
gcccgaccgc tgcgccttat ccggtaacta tcgtcttaag tccaacccgg taagacacga     480
cttatcgcca ctggcagcag ccactggtaa caggattagc agagcgaggt atgtaggcgg     540
tgctacagag ttcttgaagt ggtggcctaa ctacggctac actagaagaa cagtatttgg     600
tatctgcgct ctgctgaagc cagttacctt cggaaaaaga gttggtagct cttgatccgg     660
caaacaaacc accgctggta gcggtggttt ttttgtttgc aagcagcaga ttacgcgcag     720
aaaaaaagga tctcaagaag atcctttgat cttttctacg gggtctgacg ctcagtggaa     780
cgaaaactca cgttaaggga ttttggtcat gagattatca aaaaggatct tcacctagat     840
ccttttaaat taaaaatgaa gttttaaatc aatctaaagt atatatgagt aaactggtcg     900
catgcttacc aatgcttaat cagtgaggca cctatctcag cgatctgtct atttcgttca     960
tccatagttg cctgactgcc cgtcgtgtag ataactacga tacgggaggg cttaccatct    1020
ggccccagtg ctgcaatgat accgcgagac ccacgctcac cggctccaga tttatcagca    1080
ataaaccagc cagccggaag ggccgagcgc agaagtggtc ctgcaacttt atccgcctcc    1140
atccagtcta ttaattgttg ccgggaagct agagtaagta gttcgccagt taatagtttg    1200
cgcaacgttg ttgccattgc tacaggcatc gtggtgtcac gctcgtcgtt tggtatggct    1260
tcattcagct ccggttccca acgatcaagg cgagttacat gatcccccat gttgtgcaaa    1320
aaagcggtta gctccttcgg tcctccgatc gttgtcagaa gtaagttggc cgcagtgtta    1380
tcactcatgg ttatggcagc actgcataat tctcttactg tcatgccatc cgtaagatgc    1440
ttttctgtga ctggtgagta ctcaaccaag tcattctgag aatagtgtat gcggcgaccg    1500
agttgctctt gcccggcgtc aatacgggat aataccgcgc cacatagcag aactttaaaa    1560
gtgctcatca ttggaaaacg ttcttcgggg cgaaaactct caaggatctt accgctgttg    1620
agatccagtt cgatgtaacc cactcgtgca cccaactgat cttcagcatc ttttactttc    1680
accagcgttt ctgggtgagc aaaaacagga aggcaaaatg ccgcaaaaaa gggaataagg    1740
gcgacacgga aatgttgaat actcatcaat tgccttttc aatattattg aagcatttat    1800
cagggttatt gtctcatgag cggttacata tttgaatgta tttagaaaaa taaacaaata    1860
ggggttccgc gcacatttcc ccgaaaagtg ccacctgacg tctaagaaac cattattatc    1920
```

```
atgacattaa cctataaaaa taggcgtatc acgaggccct ttcatctcgc gcgtttcggt    1980
gatgacggtg aaaacctctg acacatgcag ctcccggaga cagtcacagc ttgtctgtaa    2040
gcggatgccg ggagcagaca agcccgtcag ggcgcgtcag cgggtgttgg cgggtgtcgg    2100
ggctggtaaa acgacggcca gtattaaccc tcactaaagg gaactcgagg ctcttcagac    2160
ggcacggcca cgcgtttaaa ccgccataca gtggaactga cctgtacagc ttcccagaag    2220
aagagcatac aattccactg gaaaaactcc aaccagataa agattctggg aaatcagggc    2280
tccttcttaa ctaaaggtcc atccaagctg aatgatcgcg ctgactcaag aagaagcctt    2340
tgggaccaag gaaacttccc cctgatcatc aagaatctta agatagaaga ctcagatact    2400
tacatctgtg aagtggagga ccagaaggag gaggtgcaat tgctagtgtt cggattgact    2460
gccaactctg acacccacct gcttcagggg cagagcctga ccctgacctt ggagagcccc    2520
cctggtagta gcccctcagt gcaatgtagg agtccaaggg gtaaaaacat acagggggg    2580
aagaccctct ccgtgtctca gctggagctc caggatagtg gcacctggac atgcactgtc    2640
ttgcagaacc agaagaaggt ggagttcaaa atagacatcg tggtgctagc tttccagaag    2700
gcctccagca tagtctataa gaaagagggg gaacaggtgg agttctcctt cccactcgcc    2760
tttacagttg aaaagctgac gggcagtggc gagctgtggt ggcaggcgga gagggcttcc    2820
tcctccaagt cttggatcac cttgacctg aagaacaagg aagtgtctgt aaaacgggtt    2880
acccaggacc ctaagctcca gatgggcaag aagctcccgc tccacctcac cctgccccag    2940
gccttgcctc agtatgctgg ctctggaaac ctcaccctgg cccttgaagc gaaaacagga    3000
aagttgcatc aggaagtgaa cctggtggtg atgagagcca ctcagctcca gaaaatttg    3060
acctgtgagg tgtggggacc cacctcccct aagctgatgc tgagcttgaa actggagaac    3120
aaggaggcaa aggtctcgaa gcgggagaag gcggtgtggg tgctgaaccc tgaggcgggg    3180
atgtggcagt gtctgctgag tgactcggga caggtcctgc tggaatccaa catcaaggtt    3240
ctgcccacat ggtcgacccc ggtgcagcca atggccctga ttgtgctggg ggcgtcgcc    3300
ggcctcctgc ttttcattgg gctaggcatc ttcttctgtg tcaggtgccg gcacaccggt    3360
tagtaatgag tttaaacggg ggaggctaac tgaaacacgg aaggagacaa taccggaagg    3420
aacccgcgct atgacggcaa taaaaagaca gaataaaacg cacgggtgtt gggtcgtttg    3480
ttcataaacg cggggttcgg tcccagggct ggcactctgt cgatacccca ccgagacccc    3540
attggggcca atacgcccgc gtttcttcct tttccccacc ccaccccca gttcgggtg    3600
aaggcccagg gctcgcagcc aacgtcgggg cggcaggccc tgccatagcc gtcgacctct    3660
agctagagct tggcgtaatc atggtcatag ctgtttcctg tgtgaaattg ttatccgctc    3720
acaattccac acaacatacg agccggaagc ataaagtgta aagcctgggg tgcctaatga    3780
gtgagctaac tcacattaat tgcgttgcgc tcactgcccg ctttccagtc gggaaacctg    3840
tcgtgccagc tgcattaatg aatcggccaa cgcgcgggga gaggcggttt gcgtattggg    3900
cgctcttccg cttcctcgct cactgactcg ctgcgctcgg tcgttcggct gcggcgagcg    3960
gtatcagctc actcaaaggc ggtaatacgg ttatccacag aatcagggga taacgcagga    4020
aagaacatgt gagcaaaagg ccagcaaaag gccaggaacc gtaaaaaggc cgcgttgctg    4080
gcgttttccc ataggctccg ccccctgac gagcatcaca aaaatcgacg ctcaagtcag    4140
aggtggcggt gtttaaaccc cagcgcctgg cgggtgaaga gcgagctccc gctgagcaat    4200
aactagcgtc atagctgttt cctg                                          4224
```

<210> SEQ ID NO 102
<211> LENGTH: 9467
<212> TYPE: DNA
<213> ORGANISM: Artificial Sequence
<220> FEATURE:
<223> OTHER INFORMATION: Synthetic: pAM15068

<400> SEQUENCE: 102

```
gttaggcgtt ttgcgctgct tcgcgatgta cgggccagat atacgcgttg acattgatta      60
ttgactagtt attaatagta atcaattacg gggtcattag ttcatagccc atatatggag     120
ttccgcgtta cataacttac ggtaaatggc ccgcctggct gaccgcccaa cgacccccgc     180
ccattgacgt caataatgac gtatgttccc atagtaacgc caatagggac tttccattga     240
cgtcaatggg tggagtattt acggtaaact gcccacttgg cagtacatca agtgtatcat     300
atgccaagta cgccccctat tgacgtcaat gacggtaaat ggcccgcctg gcattatgcc     360
cagtacatga ccttatggga ctttcctact tggcagtaca tctacgtatt agtcatcgct     420
attaccatgg tgatgcggtt ttggcagtac atcaatgggc gtggatagcg gtttgactca     480
cggggatttc caagtctcca ccccattgac gtcaatggga gtttgttttg gcaccaaaat     540
caacgggact ttccaaaatg tcgtaacaac tccgccccat tgacgcaaat gggcggtagg     600
cgtgtacggt gggaggtcta tataagcaga gctcgtttag tgaaccgtca gatcgcctgg     660
agacgccatc cacgctgttt tgacctccat agaagacacc gggaccgatc cagcctccgg     720
agcggccgcc accatgggca gcccatccc taaccccctg ttggggctgg acagcaccgc     780
tcccaaaaag aaaaggaagg tgggcattca cggcgtgcct gcggccgaca aaagtacag     840
catcggcctt gatatcggca ccaatagcgt gggctgggcc gttatcacag acgaatacaa     900
ggtacccagc aagaagttca aggtgctggg gaatacagac aggcactcta tcaagaaaaa     960
ccttatcggg gctctgctgt ttgactcagg cgagaccgcc gaggccacca ggttgaagag    1020
gaccgcaagg cgaaggtaca cccggaggaa gaacaggatc tgctatctgc aggagatctt    1080
cagcaacgag atggccaagg tggacgacag cttcttccac aggctggagg agagcttcct    1140
tgtcgaggag gataagaagc acgaacgaca ccccatcttc ggcaacatag tcgacgaggt    1200
cgcttatcac gagaagtacc ccaccatcta ccacctgcga aagaaattgg tggatagcac    1260
cgataaagcc gacttgcgac ttatctactt ggctctggcg cacatgatta agttcagggg    1320
ccacttcctg atcgagggcg accttaaccc cgacaacagt gacgtagaca aattgttcat    1380
ccagcttgta cagacctata accagctgtt cgaggaaaac cctattaacg ccagcggggt    1440
ggatgcgaag gccatactta gcgccaggct gagcaaaagc aggcgcttgg agaacctgat    1500
agcccagctg cccggtgaaa agaagaacgg cctcttcggt aatctgattg ccctgagcct    1560
gggcctgacc cccaacttca gagcaactt cgacctggca gaagatgcca agctgcagtt    1620
gagtaaggac acctatgacg acgacttgga caatctgctc gcccaaatcg cgaccagta    1680
cgctgacctg ttcctcgccg ccaagaacct ttctgacgca atcctgctta gcgatatcct    1740
tagggtgaac acagagatca ccaaggcccc cctgagcgcc agcatgatca agaggtacga    1800
cgagcaccat caggacctga cccttctgaa ggccctggtg aggcagcaac tgcccgagaa    1860
gtacaaggag atcttttcg accagagcaa gaacggctac gccggctaca tcgacggcgg    1920
agccagccaa gaggagttct acaagttcat caagcccatc ctggagaaga tggatggcac    1980
cgaggagctg ctggtgaagc tgaacaggga agatttgctc cggaagcaga ggaccctgta    2040
caacggtagc atccccccacc agatccacct gggcgagctg cacgcaatac tgaggcgaca    2100
```

-continued

```
ggaggatttc taccccttcc tcaaggacaa tagggagaaa atcgaaaaga ttctgacctt   2160
caggatcccc tactacgtgg gccctcttgc caggggcaac agccgattcg cttggatgac   2220
aagaaagagc gaggagacca tcaccccctg aacttcgag gaagtggtgg acaaaggagc    2280
aagcgcgcag tctttcatcg aacggatgac caatttcgac aaaaacctgc ctaacgagaa   2340
ggtgctgccc aagcacagcc tgctttacga gtacttcacc gtgtacaacg agctcaccaa   2400
ggtgaaatat gtgaccgagg gcatgcgaaa acccgctttc ctgagcggcg agcagaagaa   2460
ggccatcgtg gacctgctgt tcaagaccaa caggaaggtg accgtgaagc agctgaagga   2520
ggactacttc aagaagatcg agtgctttga tagcgtggaa ataagcggcg tggaggacag   2580
gttcaacgcc agcctgggca cctaccacga cttgttgaag ataatcaaag acaaggattt   2640
cctggataat gaggagaacg aggatatact cgaggacatc gtgctgactt tgaccctgtt   2700
tgaggaccga gagatgattg aagaaggct caaaacctac gcccacctgt tcgacgacaa    2760
agtgatgaaa caactgaaga gacgaagata caccggctgg ggcagactgt ccaggaagct   2820
catcaacggc attagggaca gcagagcgg caagaccatc ctggatttcc tgaagtccga    2880
cggcttcgcc aaccgaaact tcatgcagct gattcacgat gacagcttga ccttcaagga   2940
ggacatccag aaggcccagg ttagcggcca gggcgactcc ctgcacgaac atattgcaaa   3000
cctggcaggc tcccctgcga tcaagaaggg catactgcag accgttaagg ttgtggacga   3060
attggtcaag gtcatgggca ggcacaagcc cgaaaacata gttatagaga tggccagaga   3120
gaaccagacc acccaaaagg ccagaagaa cagccgggag cgcatgaaaa ggatcgagga   3180
gggtatcaag gaactcggaa gccagatcct caaagagcac cccgtggaga tacccagct   3240
ccagaacgag aagctgtacc tgtactacct gcagaacggc agggacatgt acgttgacca   3300
ggagttggac atcaacaggc tttcagacta tgacgtggat cacatagtgc cccagagctt   3360
tcttaaagac gatagcatcg acaacaaggt cctgacccgc tccgacaaaa cagggggcaa   3420
aagcgacaac gtgccaagcg aagaggtggt taaaaagatg aagaactact ggaggcaact   3480
gctcaacgcg aaattgatca cccagagaaa gttcgataac ctgaccaagg ccgagagggg   3540
cggactctcc gaacttgaca aagcgggctt cataaagagg cagctggtcg agacccgaca   3600
gatcacgaag cacgtggccc aaatcctcga cagcagaatg aataccaagt acgatgagaa   3660
tgacaaactc atcagggaag tgaaagtgat taccctgaag agcaagttgg tgtccgactt   3720
tcgcaaagat ttccagttct acaaggtgag ggagatcaac aactaccacc atgcccacga   3780
cgcatacctg aacgccgtgg tcggcaccgc cctgattaag aagtatccaa agctggagtc   3840
cgaatttgtc tacggcgact acaaagttta cgatgtgagg aagatgatcg ctaagagcga   3900
acaggagatc ggcaaggcca ccgctaagta tttcttctac agcaacatca tgaactttt    3960
caagaccgag atcacacttg ccaacggcga aatcaggaag aggccgctta tcgagaccaa   4020
cggtgagacc ggcgagatcg tgtgggacaa gggcagggac ttcgccaccg tgaggaaagt   4080
cctgagcatg cccaggtga atattgtgaa aaaaactgag gtgcagacag gcggctttag   4140
caaggaatcc atcctgccca agaggaacag cgacaagctg atcgcccgga gaaggactg    4200
ggaccctaag aagtatggag gcttcgacag cccccaccgt agcctacagcg tgctggtggt   4260
cgcgaaggta gagaagggga agagcaagaa actgaagagc gtgaaggagc tgctcggcat   4320
aaccatcatg gagaggtcca gctttgagaa gaaccccatt gactttttgg aagccaaggg   4380
ctacaaagag gtcaaaaagg acctgatcat caaactcccc aagtactccc tgtttgaatt   4440
ggagaacggc agaaagagga tgctggcgag cgctgggaa ctgcaaaagg gcaacgaact   4500
```

-continued

```
ggcgctgccc agcaagtacg tgaattttct gtacctggcg tcccactacg aaaagctgaa    4560
aggcagcccc gaggacaacg agcagaagca gctgttcgtg gagcagcaca agcattacct    4620
ggacgagata atcgagcaaa tcagcgagtt cagcaagagg gtgattctgg ccgacgcgaa    4680
cctggataag gtcctcagcg cctacaacaa gcaccgagac aaacccatca gggagcaggc    4740
cgagaatatc atacacctgt tcaccctgac aaatctgggc gcacctgcgg cattcaaata    4800
cttcgatacc accatcgaca ggaaaaggta cactagcact aaggaggtgc tggatgccac    4860
cttgatccac cagtccatta ccggcctgta tgagaccagg atcgacctga ccagcttgg    4920 aggcgactct agggcggacc caaaaaagaa aaggaaggtg gaattctcta gaggcagtgg    4980
agagggcaga ggaagtctgc taacatgcgg tgacgtcgag gagaatcctg cccaatgaa     5040 ccggggagtc ccttttaggc acttgcttct ggtgctgcaa ctggcgctcc tcccagcagc    5100
cactcaggga aagaaagtgg tgctgggcaa aaaaggggat acagtggaac tgacctgtac    5160
agcttcccag aagaagagca taaattcca ctggaaaaac tccaaccaga taaagattct    5220
gggaaatcag ggctccttct taactaaagg tccatccaag ctgaatgatc gcgctgactc    5280
aagaagaagc ctttgggacc aaggaaactt ccccctgatc atcaagaatc ttaagataga    5340
agactcagat acttacatct gtgaagtgga ggaccagaag gaggagtgc aattgctagt    5400 gttcggattg actgccaact ctgacaccca cctgcttcag gggcagagcc tgaccctgac    5460
cttggagagc ccccctggta gtagcccctc agtgcaatgt aggagtccaa ggggtaaaaa    5520
catacagggg gggaagaccc tctccgtgtc tcagctggag ctccaggata gtggcacctg    5580
gacatgcact gtcttgcaga accagaagaa ggtggagttc aaaatagaca tcgtggtgct    5640
agctttccag aaggcctcca gcatagtcta taagaaagag ggggaacagg tggagttctc    5700
cttcccactc gcctttacag ttgaaaagct gacgggcagt ggcgagctgt ggtggcaggc    5760
ggagagggct tcctcctcca agtcttggat caccctttgac ctgaagaaca aggaagtgtc    5820
tgtaaaacgg gttacccagg accctaagct ccagatgggc aagaagctcc cgctccacct    5880
caccctgccc caggccttgc ctcagtatgc tggctctgga aacctcaccc tggcccttga    5940
agcgaaaaca ggaaagttgc atcaggaagt gaacctggtg gtgatgagag ccactcagct    6000
ccagaaaaat ttgacctgtg aggtgtgggg acccacctcc cctaagctga tgctgagctt    6060
gaaactggag aacaaggagg caaaggtctc gaagcgggag aaggcggtgt gggtgctgaa    6120
ccctgaggcg gggatgtggc agtgtctgct gagtgactcg ggacaggtcc tgctggaatc    6180
caacatcaag gttctgccca catggtcgac cccggtgcag ccaatggccc tgattgtgct    6240 gggggggcgtc gccggcctcc tgcttttcat tgggctaggc atcttcttct gtgtcaggtg    6300
ccggcacacc ggttagtaat gagtttaaac ggggaggct aactgaaaca cggaaggaga    6360
caataccgga aggaacccgc gctatgacgg caataaaaag acagaataaa acgcacgggt    6420
gttgggtcgt ttgttcataa acgcggggtt cggtccagg gctggcactc tgtcgatacc    6480
ccaccgagac cccattgggg ccaatacgcc cgcgtttctt ccttttcccc accccacccc    6540
ccaagttcgg gtgaaggccc agggctcgca gccaacgtcg gggcggcagg ccctgccata    6600
gcagatctgc gcagctgggg ctctaggggg tatccccacg cgccctgtag cggcgcatta    6660
agcgcggcgg gtgtggtggt tacgcgcagc gtgaccgcta cacttgccag cgccctagcg    6720
cccgctcctt tcgctttctt cccttccttt ctcgccacgt tcgccggctt tccccgtcaa    6780
gctctaaatc gggggctccc tttagggttc cgatttagtg ctttacggca cctcgacccc    6840
aaaaaacttg attagggtga tggttcacgt agtgggccat cgccctgata gacggttttt    6900
```

```
cgcccttga cgttggagtc cacgttcttt aatagtggac tcttgttcca aactggaaca    6960
acactcaacc ctatctcggt ctattctttt gatttataag ggattttgcc gatttcggcc    7020
tattggttaa aaaatgagct gatttaacaa aaatttaacg cgaattaatt aagcggccgc    7080
gtgcatatac cgtcgacctc tagctagagc ttggcgtaat catggtcata gctgtttcct    7140
gtgtgaaatt gttatccgct cacaattcca cacaacatac gagccggaag cataaagtgt    7200
aaagcctggg gtgcctaatg agtgagctaa ctcacattaa ttgcgttgcg ctcactgccc    7260
gctttccagt cgggaaacct gtcgtgccag ctgcattaat gaatcggcca acgcgcgggg    7320
agaggcggtt tgcgtattgg gcgctcttcc gcttcctcgc tcactgactc gctgcgctcg    7380
gtcgttcggc tgcggcgagc ggtatcagct cactcaaagg cggtaatacg ttatccaca    7440 gaatcagggg ataacgcagg aaagaacatg tgagcaaaag gccagcaaaa ggccaggaac    7500
cgtaaaaagg ccgcgttgct ggcgtttttc cataggctcc gcccccctga cgagcatcac    7560
aaaaatcgac gctcaagtca gaggtggcga acccgacag gactataaag ataccaggcg    7620
tttccccctg gaagctccct cgtgcgctct cctgttccga ccctgccgct taccggatac    7680
ctgtccgcct ttctcccttc gggaagcgtg gcgctttctc atagctcacg ctgtaggtat    7740
ctcagttcgg tgtaggtcgt tcgctccaag ctgggctgtg tgcacgaacc ccccgttcag    7800
cccgaccgct gcgccttatc cggtaactat cgtcttgagt ccaacccggt aagacacgac    7860
ttatcgccac tggcagcagc cactggtaac aggattagca gagcgaggta tgtaggcggt    7920
gctacagagt tcttgaagtg gtggcctaac tacggctaca ctagaagaac agtatttggt    7980
atctgcgctc tgctgaagcc agttaccttc ggaaaaagag ttggtagctc ttgatccggc    8040
aaacaaacca ccgctggtag cggtggtttt tttgtttgca agcagcagat tacgcgcaga    8100
aaaaaaggat ctcaagaaga tcctttgatc ttttctacgg ggtctgacgc tcagtggaac    8160
gaaaactcac gttaagggat tttggtcatg agattatcaa aaaggatctt cacctagatc    8220
cttttaaatt aaaaatgaag ttttaaatca atctaaagta tatatgagta aacttggtct    8280
gacagttacc aatgcttaat cagtgaggca cctatctcag cgatctgtct atttcgttca    8340
tccatagttg cctgactccc cgtcgtgtag ataactacga tacgggaggg cttaccatct    8400
ggccccagtg ctgcaatgat accgcgagac ccacgctcac cggctccaga tttatcagca    8460
ataaccagcc agccggaag ggccgagcgc agaagtggtc ctgcaacttt atccgcctcc    8520
atccagtcta ttaattgttg ccgggaagct agagtaagta gttcgccagt taatagtttg    8580
cgcaacgttg ttgccattgc tacaggcatc gtggtgtcac gctcgtcgtt tggtatggct    8640
tcattcagct ccggttccca acgatcaagg cgagttacat gatccccat gttgtgcaaa    8700 aaagcggtta gctccttcgg tcctccgatc gttgtcagaa gtaagttggc cgcagtgtta    8760
tcactcatgg ttatggcagc actgcataat tctcttactg tcatgccatc cgtaagatgc    8820
ttttctgtga ctggtgagta ctcaaccaag tcattctgag aatagtgtat gcggcgaccg    8880
agttgctctt gcccggcgtc aatacgggat aataccgcgc cacatagcag aactttaaaa    8940
gtgctcatca ttggaaaacg ttcttcgggg cgaaaactct caaggatctt accgctgttg    9000
agatccagtt cgatgtaacc cactcgtgca cccaactgat cttcagcatc ttttactttc    9060
accagcgttt ctgggtgagc aaaaacagga aggcaaaatg ccgcaaaaaa gggaataagg    9120
gcgacacgga aatgttgaat actcatactc ttcctttttc aatattattg aagcatttat    9180
cagggttatt gtctcatgag cggatacata tttgaatgta tttagaaaaa taaacaaata    9240
ggggttccgc gcacatttcc ccgaaaagtg ccacctgacg tcgacggatc gggagatctc    9300
```

```
ccgatcccct atggtgcact ctcagtacaa tctgctctga tgccgcatag ttaagccagt   9360
atctgctccc tgcttgtgtg ttggaggtcg ctgagtagtg cgcgagcaaa atttaagcta   9420
caacaaggca aggcttgacc gacaattgca tgaagaatct gcttagg                9467
```

<210> SEQ ID NO 103
<211> LENGTH: 27
<212> TYPE: DNA
<213> ORGANISM: Artificial Sequence
<220> FEATURE:
<223> OTHER INFORMATION: Synthetic: CUT1214

<400> SEQUENCE: 103

```
ctagcttgat aaatcgatta gcccggg                                         27
```

<210> SEQ ID NO 104
<211> LENGTH: 23
<212> TYPE: DNA
<213> ORGANISM: Artificial Sequence
<220> FEATURE:
<223> OTHER INFORMATION: Synthetic: CUT1215

<400> SEQUENCE: 104

```
cccgggctaa tcgatttatc aag                                             23
```

<210> SEQ ID NO 105
<211> LENGTH: 25
<212> TYPE: DNA
<213> ORGANISM: Artificial Sequence
<220> FEATURE:
<223> OTHER INFORMATION: Synthetic: CUT1216

<400> SEQUENCE: 105

```
ggggccacta gggacaggat gtttt                                           25
```

<210> SEQ ID NO 106
<211> LENGTH: 25
<212> TYPE: DNA
<213> ORGANISM: Artificial Sequence
<220> FEATURE:
<223> OTHER INFORMATION: Synthetic: CUT1217

<400> SEQUENCE: 106

```
atcctgtccc tagtggcccc cggtg                                           25
```

<210> SEQ ID NO 107
<211> LENGTH: 53
<212> TYPE: DNA
<213> ORGANISM: Artificial Sequence
<220> FEATURE:
<223> OTHER INFORMATION: Synthetic: CUT1220

<400> SEQUENCE: 107

```
gacggcacgg ccacgcgttt aaaccgccat acagtggaac tgacctgtac agc           53
```

<210> SEQ ID NO 108
<211> LENGTH: 49
<212> TYPE: DNA
<213> ORGANISM: Artificial Sequence
<220> FEATURE:
<223> OTHER INFORMATION: Synthetic: CUT1221

<400> SEQUENCE: 108

```
cccgccaggc gctggggttt aaacaccgcc acctctgact tgagcgtcg                 49
```

```
<210> SEQ ID NO 109
<211> LENGTH: 40
<212> TYPE: DNA
<213> ORGANISM: Artificial Sequence
<220> FEATURE:
<223> OTHER INFORMATION: Synthetic: CUT1224

<400> SEQUENCE: 109
ggggcttttc tgtcagaatt cactgtgggg tggaggggac                              40

<210> SEQ ID NO 110
<211> LENGTH: 52
<212> TYPE: DNA
<213> ORGANISM: Artificial Sequence
<220> FEATURE:
<223> OTHER INFORMATION: Synthetic: CUT1227

<400> SEQUENCE: 110
cccgccaggc gctgggtttt aaacaccgtt ccctttcct tctccttctg gg                 52

<210> SEQ ID NO 111
<211> LENGTH: 38
<212> TYPE: DNA
<213> ORGANISM: Artificial Sequence
<220> FEATURE:
<223> OTHER INFORMATION: Synthetic: CUT1252

<400> SEQUENCE: 111
gctctagcta gaggtcgacg gctatggcag ggcctgcc                                38

<210> SEQ ID NO 112
<211> LENGTH: 43
<212> TYPE: DNA
<213> ORGANISM: Artificial Sequence
<220> FEATURE:
<223> OTHER INFORMATION: Synthetic: CUT1253

<400> SEQUENCE: 112
gcggcaggcc ctgccatagc cgtcgacctc tagctagagc ttg                          43

<210> SEQ ID NO 113
<211> LENGTH: 18
<212> TYPE: DNA
<213> ORGANISM: Artificial Sequence
<220> FEATURE:
<223> OTHER INFORMATION: Synthetic: CUT1254

<400> SEQUENCE: 113
taagcggccg ctgcagta                                                      18

<210> SEQ ID NO 114
<211> LENGTH: 20
<212> TYPE: DNA
<213> ORGANISM: Artificial Sequence
<220> FEATURE:
<223> OTHER INFORMATION: Synthetic: CUT1255

<400> SEQUENCE: 114
tactgcagcg gccgcttaat                                                    20

<210> SEQ ID NO 115
<211> LENGTH: 20
<212> TYPE: DNA
<213> ORGANISM: Artificial Sequence
<220> FEATURE:
<223> OTHER INFORMATION: Synthetic: CUT1294
```

```
<400> SEQUENCE: 115
cctggcttta gccacctctc                                                    20

<210> SEQ ID NO 116
<211> LENGTH: 20
<212> TYPE: DNA
<213> ORGANISM: Artificial Sequence
<220> FEATURE:
<223> OTHER INFORMATION: Synthetic: CUT1297

<400> SEQUENCE: 116
cctggtgaac acctaggacg                                                    20

<210> SEQ ID NO 117
<211> LENGTH: 28
<212> TYPE: DNA
<213> ORGANISM: Artificial Sequence
<220> FEATURE:
<223> OTHER INFORMATION: Synthetic: RYSE0

<400> SEQUENCE: 117
gacggcacgg ccacgcgttt aaaccgcc                                           28

<210> SEQ ID NO 118
<211> LENGTH: 28
<212> TYPE: DNA
<213> ORGANISM: Artificial Sequence
<220> FEATURE:
<223> OTHER INFORMATION: Synthetic: RYSE19

<400> SEQUENCE: 118
cccgccaggc gctggggttt aaacaccg                                           28

<210> SEQ ID NO 119
<211> LENGTH: 48
<212> TYPE: DNA
<213> ORGANISM: Artificial Sequence
<220> FEATURE:
<223> OTHER INFORMATION: Synthetic: CUT1226

<400> SEQUENCE: 119
gacggcacgg ccacgcgttt aaaccgccag ttttccacac ggacaccc                     48

<210> SEQ ID NO 120
<211> LENGTH: 30
<212> TYPE: DNA
<213> ORGANISM: Artificial Sequence
<220> FEATURE:
<223> OTHER INFORMATION: Synthetic: CUT1223

<400> SEQUENCE: 120
gaattctgac agaaaagccc catccttagg                                         30

<210> SEQ ID NO 121
<211> LENGTH: 18
<212> TYPE: DNA
<213> ORGANISM: Artificial Sequence
<220> FEATURE:
<223> OTHER INFORMATION: Synthetic: I-SceI

<400> SEQUENCE: 121
tagggataac agggtaat                                                      18
```

```
<210> SEQ ID NO 122
<211> LENGTH: 31
<212> TYPE: DNA
<213> ORGANISM: Artificial Sequence
<220> FEATURE:
<223> OTHER INFORMATION: Synthetic: VDE (PI-SceI)

<400> SEQUENCE: 122
tatgtcgggt gcggagaaag aggtaatgaa a                                      31

<210> SEQ ID NO 123
<211> LENGTH: 24
<212> TYPE: DNA
<213> ORGANISM: Artificial Sequence
<220> FEATURE:
<223> OTHER INFORMATION: Synthetic: F-CphI

<400> SEQUENCE: 123
gatgcacgag cgcaacgctc acaa                                              24

<210> SEQ ID NO 124
<211> LENGTH: 24
<212> TYPE: DNA
<213> ORGANISM: Artificial Sequence
<220> FEATURE:
<223> OTHER INFORMATION: Synthetic: PI-MgaI

<400> SEQUENCE: 124
gcgtagctgc ccagtatgag tcag                                              24

<210> SEQ ID NO 125
<211> LENGTH: 40
<212> TYPE: DNA
<213> ORGANISM: Artificial Sequence
<220> FEATURE:
<223> OTHER INFORMATION: Synthetic: PI-MtuII

<400> SEQUENCE: 125
acgtgcacta cgtagagggt cgcaccgcac cgatctacaa                             40
```